US011648213B2

(12) United States Patent
Mohr et al.

(10) Patent No.: US 11,648,213 B2
(45) Date of Patent: May 16, 2023

(54) TRANSDERMAL THERAPEUTIC SYSTEM CONTAINING ASENAPINE

(71) Applicant: LTS LOHMANN THERAPIE-SYSTEME AG, Andernach (DE)

(72) Inventors: Patrick Mohr, Bad Breisig (DE); René Rietscher, Neuwied (DE); René Eifler, Koblenz (DE); Olga Bourquain, Dürrholz (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 0 days.

(21) Appl. No.: 17/250,163

(22) PCT Filed: Jun. 19, 2019

(86) PCT No.: PCT/EP2019/066270
§ 371 (c)(1),
(2) Date: Dec. 7, 2020

(87) PCT Pub. No.: WO2019/243452
PCT Pub. Date: Dec. 26, 2019

(65) Prior Publication Data
US 2021/0251915 A1 Aug. 19, 2021

(30) Foreign Application Priority Data
Jun. 20, 2018 (EP) .................................. 18178876

(51) Int. Cl.
| A61K 9/70 | (2006.01) |
| A61K 31/407 | (2006.01) |
| A61K 47/02 | (2006.01) |
| A61K 47/14 | (2017.01) |
| A61K 47/22 | (2006.01) |
| A61K 47/32 | (2006.01) |

(52) U.S. Cl.
CPC .......... *A61K 9/7061* (2013.01); *A61K 31/407* (2013.01); *A61K 47/02* (2013.01); *A61K 47/14* (2013.01); *A61K 47/22* (2013.01); *A61K 47/32* (2013.01)

(58) Field of Classification Search
CPC .... A61K 9/7061; A61K 31/407; A61K 47/02; A61K 47/14; A61K 47/22; A61K 47/32; A61P 25/18; A61P 25/24; A61P 25/28
See application file for complete search history.

(56) References Cited

U.S. PATENT DOCUMENTS

| 4,145,434 A | 3/1979 | Van |
| 4,158,059 A | 6/1979 | Der |
| 5,112,842 A | 5/1992 | Zierenberg et al. |
| 5,446,070 A | 8/1995 | Mantelle |
| 5,656,286 A | 8/1997 | Miranda et al. |
| 5,763,476 A | 6/1998 | Delbressine et al. |
| 5,830,497 A | 11/1998 | Yamanaka et al. |
| 6,190,690 B1 | 2/2001 | Park et al. |
| 6,235,306 B1 | 5/2001 | Miranda et al. |
| 6,620,429 B1 | 9/2003 | Mueller |
| 6,638,528 B1 | 10/2003 | Kanios |
| 6,669,953 B1 | 12/2003 | Kamiyama |
| 6,797,280 B1 | 9/2004 | Kitazono et al. |
| 6,964,962 B2 | 11/2005 | Wong et al. |
| 7,641,703 B2 | 1/2010 | Guerin et al. |
| 7,650,848 B2 | 1/2010 | Brennan et al. |
| 7,744,918 B2 | 6/2010 | Yamaguchi et al. |
| 7,875,729 B2 | 1/2011 | Zhu et al. |
| 7,884,096 B2 | 2/2011 | Buntinx |
| 7,956,202 B2 | 6/2011 | Kemperman et al. |
| 7,964,739 B2 | 6/2011 | Kemperman |
| 7,973,043 B2 | 7/2011 | Migaly |
| 7,988,991 B2 | 8/2011 | Tateishi et al. |
| 8,022,228 B2 | 9/2011 | Heeres |
| 8,173,637 B2 | 5/2012 | Liu et al. |
| 8,202,525 B2 | 6/2012 | Crain et al. |
| 8,227,623 B2 | 7/2012 | Kemperman et al. |
| 8,288,564 B2 | 10/2012 | Wang et al. |
| 8,304,431 B2 | 11/2012 | Buntinx |
| 8,309,120 B2 | 11/2012 | Koch et al. |

(Continued)

FOREIGN PATENT DOCUMENTS

| CN | 1121854 C | 9/2003 |
| CN | 102746209 A | 10/2012 |

(Continued)

OTHER PUBLICATIONS

Kharkevich, D. A., ed., "Pharmacology," 10th Revised and Extended Edition, Textbook, pp. 72-73, GEOTAR—Media, Russia (2010).
Office Action dated Apr. 1, 2021, in U.S. Appl. No. 16/470,322, Mohr, P. et al., § 371(c), dated Jun. 17, 2019 (Int'l filing date: Dec. 19, 2017), 7 pages.
Office Action dated Nov. 20, 2018, in U.S. Appl. No. 15/847,360, Inventor Mohr, Patrick et al., filed Dec. 19, 2017, 8 pages.
Voloshinets, V.A., "Effect of Alkyl substituents on the reactivity of alkyl acrylic monomers inradical copolymerization," The Sixth All-Russian Kargin Conference: "Polymers—2014," vol. 11, Collection of theses of poster presentation in 2 parts. Partone, Moscow, Jan. 27-Jan. 31, 2014, p. 334 (Jan. 2014).
Health Canada, "A Report on Mental Illnesses in Canada," Health Canada Editorial Board Mental Illnesses, Canada, pp. 1-91 (Oct. 2002).

(Continued)

*Primary Examiner* — Robert A Wax
*Assistant Examiner* — Quanglong N Truong
(74) *Attorney, Agent, or Firm* — Sterne, Kessler, Goldstein & Fox P.L.L.C.

(57) ABSTRACT

The present invention relates to transdermal therapeutic systems (TTS) for the transdermal administration of asenapine comprising a self-adhesive layer structure containing a therapeutically effective amount of asenapine, such asenapine TTS for use in a method of treatment, processes of manufacture of such TTS as well as asenapine and transdermal therapeutic systems containing asenapine for use in a method of treatment and to a method of treating a human patient by transdermal administration of asenapine.

20 Claims, 23 Drawing Sheets

(56) References Cited

U.S. PATENT DOCUMENTS

| | | |
|---|---|---|
| 8,318,813 B2 | 11/2012 | Sanfilippo |
| 8,372,414 B2 | 2/2013 | Crain et al. |
| 8,409,609 B2 | 4/2013 | Inosaka et al. |
| 8,420,117 B2 | 4/2013 | Chono et al. |
| 8,426,610 B2 | 4/2013 | Kemperman et al. |
| 8,431,552 B2 | 4/2013 | Chen |
| 8,512,742 B2 | 8/2013 | Amano et al. |
| 8,580,281 B2 | 11/2013 | Morimoto et al. |
| 8,580,972 B2 | 11/2013 | Bosch, I et al. |
| 8,591,941 B2 | 11/2013 | Kanios et al. |
| 8,614,274 B2 | 12/2013 | Jackson et al. |
| 8,617,577 B2 | 12/2013 | Crain et al. |
| 8,624,052 B2 | 1/2014 | Johnson et al. |
| 8,632,802 B2 | 1/2014 | Kanios |
| 8,652,776 B2 | 2/2014 | Lavedan et al. |
| 8,653,280 B2 | 2/2014 | Dalmases et al. |
| 8,658,687 B2 | 2/2014 | Faassen et al. |
| 8,703,175 B2 | 4/2014 | Kanios et al. |
| 8,741,319 B2 | 6/2014 | Crain et al. |
| 8,779,161 B2 | 7/2014 | Katkam et al. |
| 8,846,093 B2 | 9/2014 | Govil et al. |
| 8,933,114 B2 | 1/2015 | Ventimiglia et al. |
| 8,945,063 B2 | 2/2015 | Wotton et al. |
| 8,986,677 B2 | 3/2015 | Altschul et al. |
| 9,011,910 B2 | 4/2015 | Schwarz |
| 9,017,737 B2 | 4/2015 | Kikuchi et al. |
| 9,050,348 B2 | 6/2015 | Kydonieus et al. |
| 9,073,890 B2 | 7/2015 | Suzuki et al. |
| 9,095,516 B2 | 8/2015 | Middelbeek et al. |
| 9,119,794 B2 | 9/2015 | Middelbeek et al. |
| 9,145,421 B2 | 9/2015 | Aryan et al. |
| 9,169,262 B2 | 10/2015 | Blatter et al. |
| 9,180,191 B2 | 11/2015 | Sheehan et al. |
| 9,198,877 B2 | 12/2015 | Jackson et al. |
| 9,205,060 B2 | 12/2015 | Kamakura et al. |
| 9,226,902 B2 | 1/2016 | Tang |
| 9,267,151 B2 | 2/2016 | Guerrero et al. |
| 9,295,726 B2 | 3/2016 | Kulakofsky et al. |
| 9,303,036 B2 | 4/2016 | Blatter et al. |
| 9,328,387 B2 | 5/2016 | Lavedan et al. |
| 9,370,495 B2 | 6/2016 | Toshimitsu et al. |
| 9,393,367 B2 | 7/2016 | Wotton et al. |
| 9,421,178 B2 | 8/2016 | Fogel et al. |
| 9,427,420 B2 | 8/2016 | Fogel et al. |
| 9,447,066 B2 | 9/2016 | Okumura et al. |
| 9,447,109 B2 | 9/2016 | Frigoli et al. |
| 9,457,014 B2 | 10/2016 | Lawton et al. |
| 9,457,018 B2 | 10/2016 | Scheel-Krüger et al. |
| 9,486,453 B2 | 11/2016 | Javitt |
| 9,499,816 B2 | 11/2016 | Mann |
| 9,500,642 B2 | 11/2016 | Blackman et al. |
| 9,505,771 B2 | 11/2016 | Bertran et al. |
| 9,511,051 B2 | 12/2016 | Suzuki et al. |
| 9,526,718 B2 | 12/2016 | Lee et al. |
| 9,533,994 B2 | 1/2017 | Solà et al. |
| 9,844,515 B2 | 12/2017 | Fleschhut et al. |
| 10,071,090 B2 | 9/2018 | Stinchcomb et al. |
| 10,806,705 B2 | 10/2020 | Yasukochi et al. |
| 10,898,449 B2 | 1/2021 | Mohr et al. |
| 10,980,753 B2 | 4/2021 | Mohr et al. |
| 11,033,512 B2 | 6/2021 | Mohr et al. |
| 11,337,932 B2 | 5/2022 | Mohr et al. |
| 2003/0109546 A1 | 6/2003 | Fenton |
| 2003/0228354 A1 | 12/2003 | Muraoka et al. |
| 2004/0033254 A1 | 2/2004 | Song et al. |
| 2004/0202704 A1 | 10/2004 | Sharma et al. |
| 2005/0004106 A1 | 1/2005 | Romano |
| 2005/0171086 A1 | 8/2005 | Brodney et al. |
| 2005/0209250 A1 | 9/2005 | Romano |
| 2005/0215571 A1 | 9/2005 | Romano |
| 2005/0245539 A1 | 11/2005 | Mendla et al. |
| 2005/0256112 A1 | 11/2005 | Brodney et al. |
| 2006/0019969 A1 | 1/2006 | Baeyens |
| 2006/0084692 A1 | 4/2006 | Erik et al. |
| 2006/0128688 A1 | 6/2006 | Tonnaer |
| 2006/0150989 A1 | 7/2006 | Migaly |
| 2006/0177493 A1 | 8/2006 | Altenschopfer et al. |
| 2006/0204486 A1 | 9/2006 | Pyke et al. |
| 2006/0229299 A1 | 10/2006 | Bruinvels |
| 2006/0286160 A1 | 12/2006 | Satoda et al. |
| 2006/0292210 A1 | 12/2006 | Inosaka et al. |
| 2007/0015763 A1 | 1/2007 | Romano |
| 2007/0148218 A1 | 6/2007 | Gordon |
| 2007/0191350 A1 | 8/2007 | Field et al. |
| 2007/0203119 A1 | 8/2007 | Danjou et al. |
| 2007/0259952 A1 | 11/2007 | Svensson |
| 2008/0020028 A1 | 1/2008 | Shevchuk et al. |
| 2008/0045512 A1 | 2/2008 | Duplantier et al. |
| 2008/0090892 A1 | 4/2008 | Casteel et al. |
| 2008/0103155 A1 | 5/2008 | Mendla et al. |
| 2008/0131490 A1 | 6/2008 | Hanatani et al. |
| 2008/0138388 A1 | 6/2008 | Aida et al. |
| 2008/0226697 A1 | 9/2008 | Yamaguchi et al. |
| 2008/0226698 A1 | 9/2008 | Tang et al. |
| 2008/0306133 A1 | 12/2008 | Van et al. |
| 2009/0004255 A1 | 1/2009 | Uchida et al. |
| 2009/0042950 A1 | 2/2009 | Pandya |
| 2009/0075974 A1 | 3/2009 | Yamaguchi et al. |
| 2009/0111837 A1 | 4/2009 | Cox et al. |
| 2009/0148504 A1 | 6/2009 | Kamiyama et al. |
| 2009/0169605 A1 | 7/2009 | Maeda et al. |
| 2009/0209608 A1 | 8/2009 | Czarnik |
| 2010/0004259 A1 | 1/2010 | Liu et al. |
| 2010/0178323 A1 | 7/2010 | Kydonieus et al. |
| 2010/0234288 A1 | 9/2010 | Jain et al. |
| 2010/0297181 A1 | 11/2010 | Hanada et al. |
| 2011/0105519 A1 | 5/2011 | Mendla et al. |
| 2011/0106006 A1 | 5/2011 | Martin et al. |
| 2011/0166194 A1 | 7/2011 | Blumberg et al. |
| 2011/0178068 A1 | 7/2011 | Almarsson et al. |
| 2011/0262442 A1 | 10/2011 | Hamilton et al. |
| 2011/0269777 A1 | 11/2011 | Bachurin et al. |
| 2011/0306596 A1 | 12/2011 | Rao et al. |
| 2012/0010242 A1 | 1/2012 | Buntinx |
| 2012/0122793 A1 | 5/2012 | Johnson et al. |
| 2012/0157420 A1 | 6/2012 | Schneider |
| 2012/0201804 A1 | 8/2012 | Williams et al. |
| 2012/0237561 A1 | 9/2012 | Faassen et al. |
| 2012/0315318 A1 | 12/2012 | Toshimitsu et al. |
| 2013/0053357 A1 | 2/2013 | Kuma et al. |
| 2013/0071412 A1 | 3/2013 | Leighton et al. |
| 2013/0143867 A1 | 6/2013 | Fogel et al. |
| 2013/0203766 A1 | 8/2013 | Mendla et al. |
| 2013/0217681 A1 | 8/2013 | Weizman et al. |
| 2013/0224110 A1 | 8/2013 | Bynoe |
| 2013/0245004 A1 | 9/2013 | Fogel et al. |
| 2013/0245253 A1 | 9/2013 | Marx et al. |
| 2013/0274466 A1 | 10/2013 | Gorin et al. |
| 2013/0344125 A1 | 12/2013 | Govender et al. |
| 2014/0018348 A1 | 1/2014 | Javitt |
| 2014/0037710 A1 | 2/2014 | Hashimoto et al. |
| 2014/0080911 A1 | 3/2014 | Stefanelli et al. |
| 2014/0121202 A1 | 5/2014 | Johnson et al. |
| 2014/0163083 A1 | 6/2014 | Blatter et al. |
| 2014/0206667 A1 | 7/2014 | Gallagher |
| 2014/0221742 A1 | 8/2014 | Bandy et al. |
| 2014/0221942 A1 | 8/2014 | Scasso et al. |
| 2014/0271866 A1 | 9/2014 | Ryoo |
| 2014/0271923 A1 | 9/2014 | Reid |
| 2014/0276478 A1 | 9/2014 | Liao et al. |
| 2014/0276479 A1 | 9/2014 | Nguyen et al. |
| 2014/0287529 A1 | 9/2014 | Leider |
| 2014/0315886 A1 | 10/2014 | Suzuki et al. |
| 2014/0336391 A1 | 11/2014 | Sharma et al. |
| 2014/0350064 A1 | 11/2014 | Chen |
| 2014/0350081 A1 | 11/2014 | Hill et al. |
| 2015/0037335 A1 | 2/2015 | Westbrook |
| 2015/0099015 A1 | 4/2015 | Tsai |
| 2015/0099741 A1 | 4/2015 | Li et al. |
| 2015/0111834 A1 | 4/2015 | Cheng et al. |
| 2015/0141274 A1 | 5/2015 | Friedman et al. |
| 2015/0202183 A1 | 7/2015 | Suzuki et al. |
| 2015/0224120 A1 | 8/2015 | Clelland et al. |
| 2015/0231154 A1 | 8/2015 | Theobald et al. |

(56) References Cited

U.S. PATENT DOCUMENTS

| | | |
|---|---|---|
| 2015/0231250 A1 | 8/2015 | Sonobe et al. |
| 2015/0250716 A1 | 9/2015 | Watkins |
| 2015/0272946 A1 | 10/2015 | Sato et al. |
| 2015/0292014 A1 | 10/2015 | Zhu et al. |
| 2015/0320739 A1 | 11/2015 | Mendla et al. |
| 2015/0328163 A1 | 11/2015 | Gujjar et al. |
| 2015/0329497 A1 | 11/2015 | Pinkerton et al. |
| 2015/0343144 A1 | 12/2015 | Altschul et al. |
| 2015/0359566 A1 | 12/2015 | Sillender |
| 2016/0022571 A1 | 1/2016 | Schwarz et al. |
| 2016/0024011 A1 | 1/2016 | Zeid et al. |
| 2016/0030362 A1 | 2/2016 | Liao et al. |
| 2016/0101075 A1 | 4/2016 | Fogel et al. |
| 2016/0199313 A1 | 7/2016 | LeDONNE et al. |
| 2016/0235677 A1 | 8/2016 | Hoerr et al. |
| 2016/0303102 A1 | 10/2016 | Albayrak |
| 2016/0310502 A1 | 10/2016 | Vanover et al. |
| 2016/0317465 A1 | 11/2016 | Shinoda et al. |
| 2017/0007537 A1 | 1/2017 | Reddy et al. |
| 2017/0079932 A1 | 3/2017 | Emgenbroich et al. |
| 2017/0202830 A1 | 7/2017 | Stinchcomb et al. |
| 2018/0028461 A1 | 2/2018 | Singh et al. |
| 2018/0028464 A1 | 2/2018 | Komoda et al. |
| 2018/0193283 A1 | 7/2018 | Mohr et al. |
| 2018/0207108 A1 | 7/2018 | Sonobe et al. |
| 2019/0336454 A1 | 11/2019 | Mohr et al. |
| 2020/0085759 A1 | 3/2020 | Mohr et al. |
| 2020/0179298 A1 | 6/2020 | Mohr et al. |
| 2020/0188317 A1 | 6/2020 | Mohr et al. |
| 2021/0251914 A1 | 8/2021 | Mohr et al. |
| 2021/0330601 A1 | 10/2021 | Mohr et al. |

FOREIGN PATENT DOCUMENTS

| | | |
|---|---|---|
| CN | 102858372 A | 1/2013 |
| CN | 102952144 A | 3/2013 |
| CN | 102976929 A | 3/2013 |
| CN | 102976998 A | 3/2013 |
| CN | 103113379 A | 5/2013 |
| CN | 103120688 A | 5/2013 |
| CN | 101851242 B | 7/2013 |
| CN | 103183680 A | 7/2013 |
| CN | 102229613 B | 8/2013 |
| CN | 102657635 B | 8/2013 |
| CN | 103254202 A | 8/2013 |
| CN | 103760258 A | 4/2014 |
| CN | 103760280 A | 4/2014 |
| CN | 103772400 A | 5/2014 |
| CN | 103772401 A | 5/2014 |
| CN | 103772402 A | 5/2014 |
| CN | 103864802 A | 6/2014 |
| CN | 103893139 A | 7/2014 |
| CN | 103083284 B | 8/2014 |
| CN | 103099799 B | 8/2014 |
| CN | 103965206 A | 8/2014 |
| CN | 104000800 A | 8/2014 |
| CN | 104098580 A | 10/2014 |
| CN | 104133010 A | 11/2014 |
| CN | 104133012 A | 11/2014 |
| CN | 104297366 A | 1/2015 |
| CN | 104447770 A | 3/2015 |
| CN | 104447771 A | 3/2015 |
| CN | 104487072 A | 4/2015 |
| CN | 104507472 A | 4/2015 |
| CN | 103342707 B | 9/2015 |
| CN | 104974167 A | 10/2015 |
| CN | 104974168 A | 10/2015 |
| CN | 105377245 A | 3/2016 |
| CN | 103254201 B | 4/2016 |
| CN | 103351393 B | 4/2016 |
| CN | 104098580 B | 4/2016 |
| CN | 105566336 A | 5/2016 |
| CN | 105693735 A | 6/2016 |
| CN | 105813636 A | 7/2016 |
| CN | 103864802 B | 8/2016 |

| | | |
|---|---|---|
| EP | 0569096 A1 | 11/1993 |
| EP | 0730865 B1 | 12/2001 |
| EP | 1547650 A1 | 6/2005 |
| EP | 1181935 B1 | 9/2005 |
| EP | 1576985 A1 | 9/2005 |
| EP | 1684681 A1 | 8/2006 |
| EP | 1765310 A2 | 3/2007 |
| EP | 2236138 A1 | 10/2010 |
| EP | 2468750 A1 | 6/2012 |
| EP | 2154134 B1 | 10/2012 |
| EP | 2599847 A1 | 6/2013 |
| EP | 2878298 A1 | 6/2015 |
| EP | 3020782 A1 | 5/2016 |
| EP | 3031458 A1 | 6/2016 |
| EP | 3329914 A1 | 6/2018 |
| EP | 3329915 A1 | 6/2018 |
| EP | 3338768 A1 | 6/2018 |
| JP | 5301190 B2 | 9/2013 |
| JP | 2014214109 A | 11/2014 |
| JP | 2016056142 A | 4/2016 |
| JP | 2017178799 A | 10/2017 |
| KR | 20130120648 A | 11/2013 |
| KR | 20160107610 A | 9/2016 |
| KR | 20160108258 A | 9/2016 |
| RU | 2352336 C2 | 4/2009 |
| RU | 2450805 C2 | 5/2012 |
| WO | WO-8600806 A1 | 2/1986 |
| WO | WO-9518603 A1 | 7/1995 |
| WO | WO-9854186 A1 | 12/1998 |
| WO | WO-9932108 A1 | 7/1999 |
| WO | WO-0064418 A2 | 11/2000 |
| WO | WO-03013482 A1 | 2/2003 |
| WO | WO-03066039 A1 | 8/2003 |
| WO | WO-2004017941 A2 | 3/2004 |
| WO | WO-2004039322 A2 | 5/2004 |
| WO | WO-2005084654 A2 | 9/2005 |
| WO | WO-2006000222 A2 | 1/2006 |
| WO | WO-2006023497 A2 | 3/2006 |
| WO | WO-2006079547 A2 | 8/2006 |
| WO | WO-200610613 5 A1 | 10/2006 |
| WO | WO-2006106136 A1 | 10/2006 |
| WO | WO-2007017750 A1 | 2/2007 |
| WO | WO-2007046554 A1 | 4/2007 |
| WO | WO-2007124757 A2 | 11/2007 |
| WO | WO-2007137224 A2 | 11/2007 |
| WO | WO-2007145996 A2 | 12/2007 |
| WO | WO-2007137224 A3 | 1/2008 |
| WO | WO-2008003460 A1 | 1/2008 |
| WO | WO-2008066180 A1 | 6/2008 |
| WO | WO-2008078482 A1 | 7/2008 |
| WO | WO-2008141438 A1 | 11/2008 |
| WO | WO-2009000890 A2 | 12/2008 |
| WO | WO-2009017453 A1 | 2/2009 |
| WO | WO-2009102962 A2 | 8/2009 |
| WO | WO-2009135091 A1 | 11/2009 |
| WO | WO-2010011232 A1 | 1/2010 |
| WO | WO-2010060742 A1 | 6/2010 |
| WO | WO-2010073326 A1 | 7/2010 |
| WO | WO-2010074182 A1 | 7/2010 |
| WO | WO-2010074183 A1 | 7/2010 |
| WO | WO-2010080757 A2 | 7/2010 |
| WO | WO-2010110914 A2 | 9/2010 |
| WO | WO-2010112530 A1 | 10/2010 |
| WO | WO-2010119455 A2 | 10/2010 |
| WO | WO-2010124187 A2 | 10/2010 |
| WO | WO-2010127674 A1 | 11/2010 |
| WO | WO-2011012654 A2 | 2/2011 |
| WO | WO-2011047341 A2 | 4/2011 |
| WO | WO-2011085188 A1 | 7/2011 |
| WO | WO-2011087755 A2 | 7/2011 |
| WO | WO-2011101799 A1 | 8/2011 |
| WO | WO-2011107855 A2 | 9/2011 |
| WO | WO-2011143755 A1 | 11/2011 |
| WO | WO-2012038975 A2 | 3/2012 |
| WO | WO-2012065102 A2 | 5/2012 |
| WO | WO-2012066565 A2 | 5/2012 |
| WO | WO-2012114325 A1 | 8/2012 |
| WO | WO-2012123325 A1 | 9/2012 |
| WO | WO-2012163665 A1 | 12/2012 |

(56) References Cited

FOREIGN PATENT DOCUMENTS

| | | |
|---|---|---|
| WO | WO-2013024492 A2 | 2/2013 |
| WO | WO-2013027052 A1 | 2/2013 |
| WO | WO-2013035109 A1 | 3/2013 |
| WO | WO-2013041435 A1 | 3/2013 |
| WO | WO-2013041604 A1 | 3/2013 |
| WO | WO-2013061247 A1 | 5/2013 |
| WO | WO-2013114400 A2 | 8/2013 |
| WO | WO-2013150032 A1 | 10/2013 |
| WO | WO-2013190481 A1 | 12/2013 |
| WO | WO-2014064076 A1 | 5/2014 |
| WO | WO-2014078377 A1 | 5/2014 |
| WO | WO-2014079573 A1 | 5/2014 |
| WO | WO-2014080378 A1 | 5/2014 |
| WO | WO-2014084401 A1 | 6/2014 |
| WO | WO-2014127786 A1 | 8/2014 |
| WO | WO-2014152965 A2 | 9/2014 |
| WO | WO-2014160026 A2 | 10/2014 |
| WO | WO-2014160155 A2 | 10/2014 |
| WO | WO-2014160167 A1 | 10/2014 |
| WO | WO-2014207664 A2 | 12/2014 |
| WO | WO-2015027342 A1 | 3/2015 |
| WO | WO-2014207664 A3 | 4/2015 |
| WO | WO-2015071831 A1 | 5/2015 |
| WO | WO-2015120317 A1 | 8/2015 |
| WO | WO-2015127416 A1 | 8/2015 |
| WO | WO-2015127556 A1 | 9/2015 |
| WO | WO-2015127557 A1 | 9/2015 |
| WO | WO-2015127558 A1 | 9/2015 |
| WO | WO-2015154025 A1 | 10/2015 |
| WO | WO-2015154030 A1 | 10/2015 |
| WO | WO-2015177212 A1 | 11/2015 |
| WO | WO-2015191554 A1 | 12/2015 |
| WO | WO-2016009063 A1 | 1/2016 |
| WO | WO-2016020573 A1 | 2/2016 |
| WO | WO-2016023658 A1 | 2/2016 |
| WO | WO-2016060564 A1 | 4/2016 |
| WO | WO-2016062285 A1 | 4/2016 |
| WO | WO-2016089737 A1 | 6/2016 |
| WO | WO-2016090228 A1 | 6/2016 |
| WO | WO-2016114655 A1 | 7/2016 |
| WO | WO-2016130408 A1 | 8/2016 |
| WO | WO-2016138138 A1 | 9/2016 |
| WO | WO-2016140087 A1 | 9/2016 |
| WO | WO-2016166679 A1 | 10/2016 |
| WO | WO-2016170102 A1 | 10/2016 |
| WO | WO-2016176519 A1 | 11/2016 |
| WO | WO-2016207466 A1 | 12/2016 |
| WO | WO-2016209982 A1 | 12/2016 |
| WO | WO-2017018321 A1 | 2/2017 |
| WO | WO-2017018322 A1 | 2/2017 |
| WO | WO-2017131034 A1 | 8/2017 |
| WO | WO-2018115010 A1 | 6/2018 |
| WO | WO-2019243432 A1 | 12/2019 |

OTHER PUBLICATIONS

Health Canada, "A Report on Mental Illnesses in Canada," Health Canada Editorial Board Mental Illnesses, Canada, pp. 92-111 (Oct. 2002).

Acosta, F.J., et al., "Medication Adherence in Schizophrenia," World Journal of Psychiatry 2(5):74-82, Baishideng Publishing Group, United States (Oct. 2012).

Amato, D., et al., "Neuroadaptations to Antipsychotic Drugs: Insights From Pre-clinical and Human Post-mortem Studies," Neuroscience and Biobehavioral Reviews 76 (Pt B):317-335, Pergamon Press, United States (May 2017).

Andree, B., et al., "Central 5-HT2A and D2 Dopamine Receptor Occupancy After Sublingual Administration of ORG 5222 in Healthy Men," Psychopharmacology 131:339-345, Springer-Verlag, Germany (1997).

"Saphris®/Sycrest® (asenapine) Bipolar I disorder, MSD," Monograph, 2011, 58 Pages.

"Asenapine maleate," Sicherheitsdatenblatt, Sigma-Aldrich, 2014, 7 Pages.

"Australian Public Assessment Report for Asenapine," Australian Government, Department of Health and Aging, Apr. 2011, 154 pages.

Balaraman, R., and Gandhi, H., "Asenapine, a New Sublingual Atypical Antipsychotic," Journal of Pharmacology & Pharmacotherapeutics 1(1):60-61, Medknow Publications and Media, India (Jan. 2010).

Bartlett, J.A., and Maarschalk, K., "Understanding the Oral Mucosal Absorption and Resulting Clinical Pharmacokinetics of Asenapine," AAPS PharmSciTech 13(4): 1110-1115, Springer, United States (Dec. 2012).

Benson, H.A.E., and Watkinson, A.C., eds., "Transdermal and Topical Drug Delivery: Principles and Practice," 448 pages, John Wiley & Sons, Inc., United States (2012).

National Institute for Health and Care Excellence, "Bipolar disorder: assessment and management—clinical guideline," Published: Sep. 24, 2014, 46 Pages.

Bishara D and Taylor D., "Asenapine Monotherapy in the Acute Treatment of Both Schizophrenia and Bipolar I Disorder," Neuropsychiatric Disease and Treatment, 5:483-490, Dove Medical Press, New Zealand (2009).

Brisch R., et al., "The Role of Dopamine in Schizophrenia From a Neurobiological and Evolutionary Perspective: Old Fashioned, but Still in Vogue," Frontiers in Psychiatry, 5:47, Frontiers Research Foundation, Switzerland (May 2014).

Broekkamp, C.L., et al., "Behavioural Pharmacology of Trans-5-chloro-2-methyl-2,3,3a,12b-tetrahydro-1h-dibenz[2,3:6,7]oxepino-[4,5-c]pyrrolidine Maleate, a Compound Interacting With Dopaminergic and Serotonergic Receptors," Drug Discovery, 40 (5):544-549, Editio Cantor, Germany (May 1990).

Buchanan R.W., et al., "Asenapine Versus Olanzapine in People With Persistent Negative Symptoms of Schizophrenia," Journal of Clinical Psychopharmacology, 32(1):36-45, Williams And Wilkins, United States (Feb. 2012).

Byers A., et al., "Asenapine Versus Placebo for Schizophrenia," The Cochrane Database of Systematic Reviews, 2015 (11):CD011458, Wiley, United Kingdom (Nov. 2015).

Caresano C., et al., "Cost-effectiveness of Asenapine in the Treatment of Patients With Bipolar I Disorder With Mixed Episodes in an Italian Context," Advances in Therapy, 31 (8):873-890, Springer Healthcare Communications, United States (Aug. 2014).

Cazorla P., et al., "Safety and Tolerability of Switching to Asenapine From Other Antipsychotic Agents: Pooled Results From Two Randomized Multicenter Trials in Stable Patients With Persistent Negative Symptoms in Schizophrenia," Neuropsychiatric Disease and Treatment, 8:247-257, Dove Medical Press, New Zealand (2012).

Chapel S., et al., "Exposure-response Analysis in Patients With Schizophrenia to Assess the Effect of Asenapine on QTc Prolongation," Journal of Clinical Pharmacology, 49(11):1297-1308, Wiley, United Kingdom (Nov. 2009).

Cipriani, A., et al., "Comparative Efficacy and Acceptability of Antimanic Drugs in Acute Mania: a Multiple-treatments Meta-analysis," Lancet, 378(9799): 1306-1315, Elsevier, United Kingdom (Oct. 2011).

Chrome L., "Asenapine for Schizophrenia and Bipolar Disorder: a Review of the Efficacy and Safety Profile for This Newly Approved Sublingually Absorbed Second-generation Antipsychotic," International Journal of Clinical Practice, 63 (12):1762-1784, Wiley, United Kingdom (Dec. 2009).

Chrome L., "Asenapine Review, Part I: Chemistry, Receptor Affinity Profile, Pharmacokinetics and Metabolism," Expert Opinion on Drug Metabolism & Toxicology, 10 (6):893-903, Informa Healthcare, United Kingdom (Jun. 2014).

Chrome L., "Asenapine Review, Part II: Clinical Efficacy, Safety and Tolerability," Expert Opinion on Drug Safety, 13 (6):803-830, Taylor & Francis, United Kingdom (Jun. 2014).

Chrome L., "Role of Sublingual Asenapine in Treatment of Schizophrenia," Neuropsychiatric Disease and Treatment, 7:325-339, Dove Medical Press, New Zealand (2011).

NCT01549041, "Once-Daily Asenapine for Schizophrenia," ClinicalTrials.gov, 3 pages.

(56) References Cited

OTHER PUBLICATIONS

Correll C.U., et al., "Cardiometabolic Risk of Second-generation Antipsychotic Medications During First-time Use in Children and Adolescents," JAMA, 302 (16):1765-1773, American Medical Association, United States (Oct. 2009).
Correll C.U., et al., "Lower Risk for Tardive Dyskinesia Associated With Second-generation Antipsychotics: a Systematic Review of 1-year Studies," The American Journal of Psychiatry, 161 (3):414-425, American Psychiatric Association, United States (Mar. 2004).
Correll C.U., et al., "What Are We Looking for in New Antipsychotics?," The Journal of Clinical Psychiatry, 72( Suppl 1):9-13, Physicians Postgraduate Press, United States (2011).
Costall, B., et al., "Actions of Org 5222 as a Novel Psychotropic Agent," Pharmacology Biochemistry and Behavior, 35(3):607-615, Elsevier, United States (Mar. 1990).
Cramer J.A and Rosenheck R., "Compliance With Medication Regimens for Mental and Physical Disorders," Psychiatric Services 49 (2):196-201, American Psychiatric Association, United States (Feb. 1998).
Davidson M., et al., "Cognitive Effects of Antipsychotic Drugs in First-episode Schizophrenia and Schizophreniform Disorder: a Randomized, Open-label Clinical Trial (EUFEST)," The American Journal of Psychiatry, 166 (6):675-682, American Psychiatric Association, United States (Jun. 2009).
De Hert M., et al., "Metabolic and Cardiovascular Adverse Effects Associated With Antipsychotic Drugs," Nature Reviews Endocrinology, 8(2):114-126, Nature Publishing Group, United Kingdom (Oct. 2011).
Dogterom, P., et al., "Asenapine Safety, Tolerability, and Pharmacokinetics After Single and Multiple Doses in Healthy Volunteers," Clinical Pharmacology in Drug Development, 1(4):131-143, Wiley, United States (Oct. 2012).
Dogterom, P., et al., "The Effect of Food on the High Clearance Drug Asenapine After Sublingual Administration to Healthy Male Volunteers," European Journal of Clinical Pharmacology, 71(1):65-74, Springer, Germany (Jan. 2015).
"Draft Guidance on Asenapine Maleate—Contains Nonbinding Recommendations," 4 pages (2013).
Dubovsky S.L., et al., "Short-term Safety and Pharmacokinetic Profile of Asenapine in Older Patients With Psychosis," International Journal of Geriatric Psychiatry, 27(5):472-482, John Wiley, United Kingdom (May 2012).
"Evaluation of Medicines for Human Use," European Medicine Agency, An agency of the European Union, 2010, 88 pages.
Fagiolini, A., et al., "Asenapine for the Treatment of Manic and Mixed Episodes Associated With Bipolar I Disorder: From Clinical Research to Clinical Practice," Expert Opinion on Pharmacotherapy, 14(4):489-504, Informa Healthcare, United Kingdom (Mar. 2013).
Findling R.L., et al., "Long-term Safety of Asenapine in Pediatric Patients Diagnosed With Bipolar I Disorder: a 50-week Open-label, Flexible-dose Trial," Paediatric Drugs, 18 (5):367-378, Springer International, Switzerland (Oct. 2016).
Fleischhacker W.W., et al., "Schizophrenia—time to Commit to Policy Change," Schizophrenia Bulletin, 40 (Suppl 3):S165-S194, Oxford University Press, United Kingdom (Apr. 2014).
Fleming, K., et al., "P.3.c.073 Effects of Asenapine on Cognitive Function in Acute Schizophrenia: a Placebo- and Risperidone-controlled Trial," European Neuropsychopharmacology, 17(4):S466-S467, Elsevier, Netherlands (Oct. 2007).
Fountoulakis K.N., et al., "The International College of Neuropsychopharmacology (CINP) Treatment Guidelines for Bipolar Disorder in Adults (CINP-BD-2017), Part 1: Background and Methods of the Development of Guidelines," International Journal of Neuropsychopharmacology, 20(2):98-120, Oxford University Press, United Kingdom (2017).
Fountoulakis K.N., et al., "The International College of Neuro-Psychopharmacology (CINP) Treatment Guidelines for Bipolar Disorder in Adults (CINP-BD-2017), Part 3: The Clinical Guidelines," The International Journal of Neuropsychopharmacology, 20(2):180-195, Oxford University Press, United Kingdom (Feb. 2017).
Franberg, O., et al., "Asenapine, a Novel Psychopharmacologic Agent: Preclinical Evidence for Clinical Effects in Schizophrenia," Psychopharmacology, 196(3):417-429, Springer-Verlag, Germany (Feb. 2008).
Friberg, L.E., et al., "Modeling and Simulation of the Time Course of Asenapine Exposure Response and Dropout Patterns in Acute Schizophrenia," Clinical Pharmacology & Therapeutics, 86(1):84-91, Wiley, United States (Jul. 2009).
Geddes J., et al., "Atypical Antipsychotics in the Treatment of Schizophrenia: Systematic Overview and Meta-regression Analysis," BMJ (Clinical research ed.), 321 (7273): 1371-1376, British Medical Association, United Kingdom (Dec. 2000).
Gerrits, M., et al., "Effect of Absorption Site on the Pharmacokinetics of Sublingual Asenapine in Healthy Male Subjects," Biopharmaceutics & Drug Disposition, 31(5-6):351-357, Wiley, United Kingdom (Jul. 2010).
Gerrits, M.G., et al., "Valproate Reduces the Glucuronidation of Asenapine Without Affecting Asenapine Plasma Concentrations," The Journal of Clinical Pharmacology, 52(5):757-765, Wiley, United Kingdom (May 2012).
Goodwin G.M., et al., "Evidence-based Guidelines for Treating Bipolar Disorder: Revised Second Edition—recommendations From the British Association for Psychopharmacology," Journal of Psychopharmacology ,23(4):346-388, Sage Publications, United States (Jun. 2009).
Grunder, G., et al., "Therapeutic Plasma Concentrations of Antidepressants and Antipsychotics: Lessons From PET Imaging," Pharmacopsychiatry, 44(6):236-248, Georg Thieme Verlag, Germany (Sep. 2011).
Grunze H., et al., "The World Federation of Societies of Biological Psychiatry (Wfsbp) Guidelines for the Biological Treatment of Bipolar Disorders: Update 2012 on the Long-term Treatment of Bipolar Disorder," The World Journal of Biological Psychiatry, 14 (3):154-219, Informa Healthcare, United Kingdom (Apr. 2013).
Hagg S., et al., "Associations Between Venous Thromboembolism and Antipsychotics. A Study of the Who Database of Adverse Drug Reactions," Drug Safety, 31 (8):685-694, Springer International, New Zealand (2008).
Hiemke C., et al., "AGNP Consensus Guidelines for Therapeutic Drug Monitoring in Psychiatry: Update 2011.," Pharmacopsychiatry, 44 (6):195-235, Georg Thieme Verlag, Germany (Sep. 2011).
Hirschfeld, R.M, "Differential Diagnosis of Bipolar Disorder and Major Depressive Disorder," Journal of Affective Disorders, 169 Suppl 1:S12-S16, Elsevier/North-Holland Biomedical Press, Netherlands (Dec. 2014).
International Search Report and Written Opinion for International Application No. PCT/EP2018/066950, European Patent Office, Netherlands, dated Aug. 27, 2018, 9 pages.
Jones P.B., et al., "Randomized Controlled Trial of the Effect on Quality of Life of Second- Vs First-generation Antipsychotic Drugs in Schizophrenia: Cost Utility of the Latest Antipsychotic Drugs in Schizophrenia Study (Cutlass 1)," Archives of General Psychiatry, 63 (10):1079-1087, American Medical Association, United States (Oct. 2006).
Judd L.L and Akiskal H.S., "The Prevalence and Disability of Bipolar Spectrum Disorders in the Us Population: Re-analysis of the ECA Database Taking Into Account Subthreshold Cases," Journal of Affective Disorders, 73 (1-2):123-131, Elsevier/North-Holland Biomedical Press, Netherlands (Jan. 2003).
Kahn, R.S., et al., "Schizophrenia," Nature Reviews Disease Primers, 1:1-23, Nature Publishing Group, United Kingdom (Nov. 2015).
Kaminsky, B.M., et al., "Alternate Routes of Administration of Antidepressant and Antipsychotic Medications," Annals of Pharmacotherapy, 49(7):2 pages, Sage, United States (Jul. 2015).
Kane J.M., et al., "Efficacy and Safety of Asenapine in a Placebo- and Haloperidol-controlled Trial in Patients With Acute Exacerbation of Schizophrenia," Journal of Clinical Psychopharmacology, 30(2):106-115, Williams And Wilkins, United States (Apr. 2010).

(56) References Cited

OTHER PUBLICATIONS

Kane, J.M., et al., "Non-adherence to Medication in Patients with Psychotic Disorders: Epidemiology, Contributing Factors and Management Strategies," World Psychiatry, 12(3):216-226, Masson Italy, Italy (Oct. 2013).
Kapil R.P., et al., "Once-weekly Transdermal Buprenorphine Application Results in Sustained and Consistent Steady-state Plasma Levels," Journal of Pain and Symptom Management, 46 (1):65-75, Elsevier, United States (Jul. 2013).
"Asenapin," KBV, Wirkstoff Aktuell, 4 pages (2013).
Kemp, D.E., et al., "Weight Change and Metabolic Effects of Asenapine in Patients With Schizophrenia and Bipolar Disorder," The Journal of Clinical Psychiatry, 75(3):238-245, Physicians Postgraduate Press, United States (Mar. 2014).
Kessler R.C., et al., "Prevalence, Severity, and Comorbidity of 12-month Dsm-iv Disorders in the National Comorbidity Survey Replication," Archives of General Psychiatry, 62 (6):617-627, American Medical Association, United States (Jun. 2005).
Ketter T. A., et al., "Long-term Safety and Tolerability of Asenapine: a Double-blind, Uncontrolled, Long-term Extension Trial in Adults With an Acute Manic or Mixed Episode Associated With Bipolar I Disorder," Journal of Affective Disorders, 207:3 84-3 92, Elsevier/North-Holland Biomedical Press, Netherlands (Jan. 2017).
Kikkert, M.J., et al., "Medication Adherence in Schizophrenia: Exploring Patients', Carers' and Professionals' Views," Schizophrenia Bulletin, 32(4):786-794, Oxford University Press, United States (Oct. 2006).
Kinoshita, T., et al., "Efficacy and Safety of Asenapine in Asian Patients With an Acute Exacerbation of Schizophrenia: a Multicentre, Randomized, Double-blind, 6-week, Placebo-controlled Study," Psychopharmacology, 233(14):2663-2674, Springer-Verlag, Germany (Jul. 2016).
Lachaine J., et al., "Cost-effectiveness of asenapine in the treatment of bipolar disorder in Canada," BMC Psychiatry, 14:16, (2014).
Lachaine J., et al., "Cost-effectiveness of asenapine in the treatment of schizophrenia in Canada," Journal of Medical Economics, 17 (4):296-304, Taylor & Francis, United Kingdom (2014).
Landbloom R., et al., "Asenapine for the Treatment of Adults With an Acute Exacerbation of Schizophrenia: Results From a Randomized, Double-blind, Fixed-dose, Placebo-controlled Trial With Olanzapine as an Active Control," CNS Spectrums, 22 (4):333-341, Cambridge University Press, United Kingdom (Aug. 2017).
Landbloom, R.L., et al., "Asenapine: Efficacy and Safety of 5 and 10mg Bid in a 3-week, Randomized, Double-blind, Placebo-controlled Trial in Adults With a Manic or Mixed Episode Associated With Bipolar I Disorder," Journal of Affective Disorders, 190:103-110, Elsevier/North-Holland Biomedical Press, Netherlands (Jan. 2016).
Lehman A.F., et al., "Practice Guideline for the Treatment of Patients With Schizophrenia," Second Edition, Work Group on Schizophrenia, APA Practice Guidelines, 2010, 184 pages.
Leucht S., et al., "Comparative Efficacy and Tolerability of 15 Antipsychotic Drugs in Schizophrenia: a Multiple-treatments Meta-analysis," Lancet 382 (9896):951-962, Elsevier, United Kingdom (Sep. 2013).
Leucht S., et al., "New Generation Antipsychotics Versus Low-potency Conventional Antipsychotics: a Systematic Review and Meta-analysis," Lancet 361 (9369):1581-1589, Elsevier, United Kingdom (May 2003).
Lieberman J.A., et al., "Effectiveness of Antipsychotic Drugs in Patients With Chronic Schizophrenia," The New United Kingdom Journal of Medicine, 353 (12):1209-1223, Massachusetts Medical Society, United States (Sep. 2005).
Lincoln, M.J., "Asenepine for schizophrenia and bipolar 1 disorder," Bipolar Disorders 8(12):1-6, Dec. 2009.
Makdisi J., et al., "Pityriasis Rosea-like Drug Reaction to Asenapine," Journal of Drugs in Dermatology: JDD, 12 (9):1050-1051, Physicians Continuing Education Corporation, United States (Sep. 2013).

Maletic, V., et al., "Integrated Neurobiology of Bipolar Disorder," Frontiers in Psychiatry, 5:98, Frontiers Research Foundation, Switzerland (2014).
Mutalik, S., "Nano-Carrier Based Transdermal Formulation of an Antipsychotic Drug: Development and In Vitro and In Vivo Evaluations," Conference: AAPS Annual Meeting and Exposition, Oct. 2015, 1 page.
Martin-Blanco, A., et al., "Asenapine in the Treatment of Borderline Personality Disorder: an Atypical Antipsychotic Alternative," International Clinical Psychopharmacology, 29(2):120-123, Lippincott Williams And Wilkins, United Kingdom (Mar. 2014).
Mauri M.C., et al., "Clinical Pharmacology of Atypical Antipsychotics: an Update," EXCLI Journal, 13:1163-1191, University of Mainz, Germany (Oct. 2014).
Mccormick, U., et al., "Diagnosis and Treatment of Patients With Bipolar Disorder: a Review for Advanced Practice Nurses," Journal of the American Association of Nurse Practitioners, 27(9):530-542, Wolters Kluwer, United States (Sep. 2015).
Mcgrath J., et al., "Schizophrenia: a Concise Overview of Incidence, Prevalence, and Mortality," Epidemiologic Reviews, 30:67-76, Oxford University Press on Behalf of Johns Hopkins Bloomberg School of Public Health, United States (2008).
Mcintyre R.S and Wong R., "Asenapine: a Synthesis of Efficacy Data in Bipolar Mania and Schizophrenia," Clinical Schizophrenia & Related Psychoses, 5 (4):217-220, Walsh Medical Media, United States (Jan. 2012).
Mcintyre, R.S., et al., "A 3-week, Randomized, Placebo-controlled Trial of Asenapine in the Treatment of Acute Mania in Bipolar Mania and Mixed States," Bipolar Disorder, 11(7):1-15, Wiley-Blackwell Munksgaard, Denmark , (Nov. 2009).
Mcintyre, R.S., et al., "Asenapine in the Treatment of Acute Mania in Bipolar I Disorder: a Randomized, Double-blind, Placebo-controlled Trial," Journal of Affective Disorders, 122(1-2):27-38, Elsevier/North-Holland Biomedical Press, Netherlands (Apr. 2010).
Meltzer, H.Y., "Chapter 58: Mechamsm of Action of Atypical Antipsychotic Drugs," 2002, 14 pages.
Merikangas K.R., et al., "Lifetime and 12-month Prevalence of Bipolar Spectrum Disorder in the National Comorbidity Survey Replication," Archives of General Psychiatry, 64 (5):543-552, American Medical Association, United States (May 2007).
Merikangas K.R., et al., "Prevalence and Correlates of Bipolar Spectrum Disorder in the World Mental Health Survey Initiative," Archives of General Psychiatry, 68 (3):241-251, American Medical Association, United States (Mar. 2011).
Meyer J.M., "Understanding Depot Antipsychotics: an Illustrated Guide to Kinetics," CNS Spectrums, 18 (Suppl 1):58-67, Cambridge University Press, United Kingdom (Dec. 2013).
Minassian A and Young J.W., "Evaluation of the Clinical Efficacy of Asenapine in Schizophrenia," Expert Opinion on Pharmacotherapy, 11 (12):2107-2115, Informa Healthcare, United Kingdom (Aug. 2010).
Miyake, N., et al., "New Serotonin/Dopamine Antagonists for the Treatment of Schizophrenia," Clinical Schizophrenia & Related Psychoses, 6(3):122-133, (Oct. 2012).
Mura G., et al., "Schizophrenia: from Epidemiology to Rehabilitation," Clinical Practice and Epidemiology in Mental Health: CP & EMH, 8:52-66, Bentham Open, United Arab Emirates, (2012).
"Sycrest® (Asenapin)," Neue Arzneimittel, 2011, 2 pages.
Nivoli A.M., et al., "New Treatment Guidelines for Acute Bipolar Mania: a Critical Review," Journal of Affective Disorders, 140 (2):125-141, Elsevier/North-Holland Biomedical Press, Netherlands (Oct. 2012).
Office Action dated Aug. 15, 2019, in U.S. Appl. No. 15/847,360, inventor MOHR, Patrick et al., filed Dec. 19, 2017, 20 pages.
Peeters, P., et al., "Asenapine Pharmacokinetics in Hepatic and Renal Impairment," Clinical Pharmacokinetics, 50(7):471-481, Adis, part of Springer Science+Business Media, Switzerland (Jul. 2011).
"5.5 Pharmacokinetics—Sublingual: 5.5.1 Single Dose Pharmacokinetics," 2008, 279 pages.
Picchioni, M.M., "Schizophrenia," The BMJ 335:91-95, Clinical Review (Jul. 2007).

(56) References Cited

OTHER PUBLICATIONS

Pompili M., et al., "The Role of Asenapine in the Treatment of Manic or Mixed States Associated With Bipolar I Disorder," Neuropsychiatric Disease and Treatment, 7:259-265, Dove Medical Press, New Zealand (2011).
Potkin, S., et al., "Asenapine in Schizophrenia: an Overview of Clinical Trials in the Olympia Program," Schizophrenia Research, 102(1):258-258, Elsevier B.V., Netherlands (Jun. 2008).
Potkin S.G., et al., "Efficacy and Tolerability of Asenapine in Acute Schizophrenia: a Placebo- and Risperidone-controlled Trial," The Journal of Clinical Psychiatry, 68(10):1492-1500, Physicians Postgraduate Press, United States (Oct. 2007).
Potkin, S.G., et al., "Long-term Effects of Asenapine or Olanzapine in Patients With Persistent Negative Symptoms of Schizophrenia: a Pooled Analysis," Schizophrenia Research, 150(2-3):442-449, Elsevier Science Publisher B.V., Netherlands (Nov. 2013).
Rado, J and Janicak, P.G, "Pharmacological and Clinical Profile of Recently Approved Second-generation Antipsychotics: Implications for Treatment of Schizophrenia in Older Patients," Drugs Aging, 29(10):783-791, Springer International, New Zealand (Oct. 2012).
"Receptor Binding Profiles of Atypical Antipsychotics: Mechanisms of Therapeutic Actions and Adverse Side Effects," Presented at the 2012 NEI Global Psychopharmacology Congress, 1 page.
Regier D.A., et al., "The De Facto Us Mental and Addictive Disorders Service System. Epidemiologic Catchment Area Prospective 1-year Prevalence Rates of Disorders and Services," Archives of General Psychiatry, 50 (2):85-94, American Medical Association, United States (Feb. 1993).
Reynolds G.P., "Receptor Mechanisms of Antipsychotic Drug Action in Bipolar Disorder—Focus on Asenapine," Therapeutic Advances in Psychopharmacology, 1 (6):197-204, Sage, United Kingdom (Dec. 2011).
Ross, C.A., et al., "Neurobiology of Schizophrenia," Neuron, 52(1):139-153, Cell Press, United States (Oct. 2006).
"Product Information Saphris® (asenapine maleate)," 25 pages.
"SAPHRIS® (asenapine) 2.5 mg Sublingual Tablets for the Acute Treatment of Manic or Mixed Episodes of Bipolar I Disorder in Pediatric Patients (ages 10-17) Now Available in Pharmacies throughout the U.S," accessed from PRNewswire, 2015, 8 pages.
Saphris (asenapine) Sublingual Tablets, Jul. 30, 2009 PDAC, Briefing Book, vol. 1, U.S. Food and Drug Administration, 1068 Pages.
"Product Monograph Saphris® (asenapine sublingual tablets)—Antypsychotic," 2016, 49 Pages.
Sawy Er, L., et al., "Cost-effectiveness of Asenapine in the Treatment of Bipolar I Disorder Patients With Mixed Episodes," Journal of Medical Economics, 17(7):508-519, Taylor & Francis, United Kingdom (Jul. 2014).
Scheidemantel, T., et al., "Asenapine for Bipolar Disorder," Neuropsychiatric Disease and Treatment, 11:3007-3017, Dove Medical Press, New Zealand (2015).
"Schizophrenia: Core Interventions in the Treatment and Management of Schizophrenia in Adults in Primary and Secondary Care (update)," NICE guideline, Draft for consultation, Sep. 2008, 39 Pages.
Schoemaker, J., et al., "Long-Term Assessment of Asenapine vs. Olanzapine in Patients with Schizoaffective Disorder," Pharmacopsychiatry, 43(4):e1-e10, Georg Thieme Verlag KG, Germany (2010).
Shahid, M., et al., "Asenapine: a Novel Psychopharmacologic Agent With a Unique Human Receptor Signature," Journal of Psychopharmacology, 23(1):2 pages, Sage Publications, United States (Feb. 2008).
Shreya, A.B., et al., "Nano-transfersomal Formulations for Transdermal Delivery of Asenapine Maleate: in Vitro and in Vivo Performance Evaluations," Journal of Liposome Research, 26(3):221-232, Informa Healthcare, United Kingdom (Sep. 2016).
Simeone J.C., et al., "An Evaluation of Variation in Published Estimates of Schizophrenia Prevalence From 1990-2013: A Systematic Literature Review," BMC Psychiatry, 15:193, BioMed Central, United Kingdom (Aug. 2015).
Smith E.N., et al., "Asenapine Augmentation and Treatment-resistant Schizophrenia in the High-secure Hospital Setting," Therapeutic Advances in Psychopharmacology, 4 (5):193-197, Sage, United Kingdom (Oct. 2014).
Smyth A.M., et al., "The Neuroimmunology of Schizophrenia," Clinical Psychopharmacology and Neuroscience, 11(3):107-117, Korean College of Neuropsychopharmacology, Korea, (Dec. 2013).
"Stellenwert Von Asenapin (Sycrest®) in Der Behandlung Von Bipolaren Storungen—Clinical Experience Program (CEP): Erste Praktische Erfahrungen in Der Schweiz," Aug. 2013, 12 pages.
"Sycrest® 10 mg Sublingualtabletten," Fachinformation (zusammenfassung der merkmale des arzneimittels, 2012, 6 pages.
Szegedi A., et al., "Effects of Asenapine on Depressive Symptoms in Patients With Bipolar I Disorder Experiencing Acute Manic or Mixed Episodes: a Post Hoc Analysis of Two 3-week Clinical Trials," BMC Psychiatry, 11:101, BioMed Central, United Kingdom (Jun. 2011).
Tarazi, F.I and Stahl, S.M, "Iloperidone, Asenapine and Lurasidone: a Primer on Their Current Status," Expert Opinion on Pharmacotherapy, 13(13):1911-1922, Informa Healthcare, United Kingdom (Sep. 2012).
Tiihonen J., et al., "11-year Follow-up of Mortality in Patients With Schizophrenia: a Population-based Cohort Study (Fin11 Study)," Lancet (London, United Kingdom), 374 (9690):620-627, Elsevier, United Kingdom (Aug. 2009).
Van De Wetering-Krebbers S.F., et al., "Metabolism and Excretion of Asenapine in Healthy Male Subjects," Drug Metabolism and Disposition: the Biological Fate of Chemicals, 39 (4):580-590, American Society for Pharmacology and Experimental Therapeutics, United States (Apr. 2011).
Weber, J and Mccormack, P.L, "Asenapine," CNS Drugs, 23(9):781-792, Springer, Germany (Sep. 2009).
"Zusammenfassung Der Merkmale Des Arzneimittels," 1 Anhang I, 2010, 44 pages.
Office Action dated Jan. 31, 2020, in U.S. Appl. No. 15/847,360, inventor Mohr, Patrick et al., filed Dec. 19, 2017, 22 pages.
Office Action dated Sep. 20, 2019, in U.S. Appl. No. 16/445,582, inventor Mohr, Patrick et al., filed Jun. 19, 2019, 15 pages.
Final Office Action dated Feb. 20, 2020, in U.S. Appl. No. 16/445,582, inventor Mohr, Patrick et al., filed Jun. 19, 2019, 25 pages.
Office Action dated Jul. 8, 2020, in U.S. Appl. No. 16/445,582, inventor Mohr, Patrick et al., filed Jun. 19, 2019, 25 pages.
Final Office Action dated Sep. 2, 2020, in U.S. Appl. No. 16/445,582, inventor Mohr, Patrick et al., filed Jun. 19, 2019, 34 pages.
Office Action dated Jun. 9, 2020, in U.S. Appl. No. 16/788,128, inventor Mohr, Patrick et al., filed Feb. 11, 2020, 18 pages.
Final Office Action dated Aug. 19, 2020, in U.S. Appl. No. 16/788,128, inventor Mohr, Patrick et al., filed Feb. 11, 2020, 26 pages.
International Preliminary Report on Patentability for International Application No. PCT/EP2017/083640, The International Bureau of WIPO, dated Jun. 25, 2019, 8 pages.
International Search Report and Written Opinion for International Application No. PCT/EP2017/083640, European Patent Office, Netherlands, dated Mar. 26, 2018, 10 pages.
International Search Report and Written Opinion for International Application No. PCT/EP2019/066226, European Patent Office, Netherlands, dated Sep. 18, 2019, 11 pages.
Co-pending U.S. Appl. No. 17/250,162, inventors Mohr, P., et al., International Filing Date: Jun. 19, 2019 (Not yet Published).
Co-pending U.S. Appl. No. 17/195,267, inventors Mohr, P., et al., filed Mar. 8, 2021 (Not yet Published).
Office Action dated Dec. 2, 2022 in U.S. Appl. No. 17/250,162, Mohr, P., et al., § 371(c) dated Dec. 7, 2020, 8 pages.

TRANSDERMAL THERAPEUTIC SYSTEM CONTAINING ASENAPINE

TECHNICAL FIELD OF THE INVENTION

The present invention relates to a transdermal therapeutic system (TTS) for the transdermal administration of asenapine to the systemic circulation, and processes of manufacture, method of treatments and uses thereof.

BACKGROUND OF THE INVENTION

The active agent asenapine (3aRS,12bRS)-rel-5-chloro-2,3,3a,12b-tetrahydro-2-methyl-1H-dibenz[2,3:6,7]oxepino[4,5-c]pyrrole) is an atypical antipsychotic belonging to the dibenzo-oxepino pyrrole family, the tetracyclic structure of which is unrelated to those of other antipsychotics such as Olanzapine, Quetiapine or Clozapine (tricyclic structure), Risperidone, Ziprasidone or Aripiprazole (bicyclic structure). Asenapine is an antagonist at the dopamine D2 and serotonin 5-HT2A receptors with high affinity to the latter and has been developed by Schering-Plough/Organon for the treatment of schizophrenia and acute mania associated with bipolar disorder.

Currently, asenapine is commercially available in the form of sublingual tablets, which is administered in dosage strengths of 2.5 mg, 5 mg or 10 mg twice daily (BID) under the brand names Sycrest (Swissmedic) and Saphris (Schering-Plough).

The sublingual administration route avoids the first-pass metabolism of an oral administration in order to increase bioavailability, which is at 35% when taken sublingually and <2% if ingested. However, sublingual administration is associated with bitter or unpleasant taste as well as tongue/oral mucosal numbness induced by a local anesthetic effect, nausea and headaches. Further, eating, drinking and smoking are not allowed immediately after sublingual dosing for 10 min. These inconveniences may lead to reduced patient compliance and improper administration such as dose reduction, dose skipping, irregular drug intake or a complete abstinence from the intended asenapine intake. Sublingual administration is also difficult to monitor in institutionalized psychiatric patients and may not be suitable for children, elderly and other patients with difficulty in swallowing, or for those not capable of taking medication on their own.

Asenapine shows side effects which are not unusual for a neuroleptic drug. Somnolence and anxiety are very common (observed in ≥10% of the patients). Other common (≥1% to <10% of the patients) adverse effects include weight gain and increased appetite, nervous system disorders such as dystonia, akathisia, dyskinesia, parkinsonism, sedation, dizziness, dysgeusia; gastrointestinal disorders such as oral hypoesthesia, nausea, increased salivation; increases in alanine aminotransferase (ALT), muscle rigidity, and fatigue (tiredness).

Asenapine is metabolized hepatically, mainly via CYP1A2 and UGT1A4 (glucuronidation). The clinical relevance of the main human metabolites N-desmethyl-asenapine and asenapine N+ glucuronide remain controversial. It at least appears that the metabolites would not substantially participate in the therapeutic effect. Thus, a decrease in the amount of these metabolites appears generally desirable.

Following sublingual administration, asenapine is rapidly absorbed with peak blood plasma concentrations occurring within 0.5 to 1.5 hours and (in therapeutic doses) exhibits 2-compartment pharmacokinetics with a rapid initial distribution phase with a half-life of several hours, followed by a longer terminal disposition half-life of around 1 day or longer. The blood plasma concentration thus exhibits a certain degree of fluctuation with peaks about 1 hour post-dose, followed by a concentration decrease resulting in a low point just before the next dose, even in steady state. The relatively rapid concentration decrease also inevitably leads to multiple daily doses (currently twice daily), which are associated with poor patient compliance, in particular in chronic conditions.

Such fluctuation could be avoided, or at least reduced by transdermal administration of asenapine, which prevents plasma concentration decrease between two doses to some extent by providing an extended release of the active. Transdermal delivery of asenapine has been investigated, but it appears that passive transdermal delivery of asenapine, and in particular a constant release over an extended period of time, is challenging. Passive transport of active agents from a transdermal therapeutic system (TTS) through the skin makes use of the driving force based on the concentration gradient between the concentration of active agent in the transdermal system and on the outer surface of the skin and the concentration in the blood stream. Such passive transport is advantageous in view of complexity of the TTS and the convenience of administration compared to TTS making use of active transportation such as iontophoresis or microporation. Up to date, no commercial asenapine TTS is available.

The inventors have previously developed a transdermal therapeutic system for the transdermal administration of asenapine overcoming the above-mentioned disadvantages of current asenapine administration. In particular, a TTS was developed which is able to provide a permeation rate sufficient for achieving a therapeutically effective dose, which is adequate for a continuous administration of asenapine for administration periods of up to 7 days, e.g. 3.5 days, and which is also easy and cost-efficient to manufacture.

However, in terms of stability of the manufactured TTS, in particular with respect to the content of active and active degradation, initially as well as upon storage, the previously developed formulation still has room for improvement. There is thus a need for improved asenapine TTS formulations that provide better stability without impairing the advantageous skin permeation rates.

OBJECTS AND SUMMARY OF THE INVENTION

It is an object of the present invention to provide a TTS overcoming the above-mentioned disadvantages of current asenapine administration.

Thus, it is an object of the present invention to provide a TTS, and in particular a matrix-type TTS, for the transdermal administration of asenapine, with improved stability, and at the same time providing a permeation rate which is sufficient for achieving a therapeutically effective dose, in particular in a continuous administration, providing therapeutically effective amounts of asenapine for up to 7 days, during an administration period to the skin of the patient of up to 7 days (e.g. 3.5 days).

It is also an object of the present invention to provide a TTS, and in particular a matrix-type TTS, for the transdermal administration of asenapine, with improved stability, wherein the fluctuation in asenapine blood plasma concentration is reduced when compared to sublingual administration, in particular in steady state.

It is another object of the present invention to provide a TTS, and in particular a matrix-type TTS, for the transdermal administration of asenapine, with improved stability, and which complies with the needs of a convenient application in view of size and thickness and/or which is easy and cost-efficient to manufacture.

These objects and others are accomplished by the present invention, which according to one aspect relates to a transdermal therapeutic system for the transdermal administration of asenapine comprising a self-adhesive layer structure containing a therapeutically effective amount of asenapine, said self-adhesive layer structure comprising:

A) a backing layer;
B) an asenapine-containing matrix layer consisting of a matrix layer composition comprising:
  1. asenapine; and
  2. a polymer selected from acrylic polymers
  3. an additional polymer; and
  4. α-tocopherol in an amount of from 0.01 to 2% of the matrix layer composition and ascorbyl palmitate in an amount of at least 0.01% of the matrix layer composition as stabilizers According to certain embodiments of the invention, the transdermal therapeutic system according to the invention is for use in a method of treatment, preferably for use in a method of treating psychosis and more preferably for use in a method of treating one or more conditions selected from schizophrenia, bipolar disorder, posttraumatic stress disorder, major depressive disorder, dementia related psychosis, agitation and manic disorder, in particular during administration for an extended period of time.

Thus, according to certain embodiments of the invention, the transdermal therapeutic system according to the invention is for use in a method of treating schizophrenia and/or bipolar disorder during an administration period of about 24 hours to about 168 hours, or 1 to 7 days, and in particular for use in a method of treating schizophrenia and/or bipolar disorder during an administration period of about 24 hours, or 1 day, of about 48 hours, or 2 days, or of about 84 hours, or 3.5 days.

According to other embodiments, the present invention relates to a method of treatment, and in particular a method of treating psychosis and more preferably a method of treating one or more conditions selected from schizophrenia, bipolar disorder, posttraumatic stress disorder, major depressive disorder, dementia related psychosis, agitation and manic disorder, including applying a transdermal therapeutic system according to the invention to the skin of a patient for an extended period of time.

Thus, according to certain other embodiments, the invention relates to a method of treating schizophrenia and/or bipolar disorder including applying a transdermal therapeutic system according to the invention for about 24 hours to about 168 hours or for 1 to 7 days, or for about 24 hours, 48 hours or 84 hours, or for 1 day, 2 days or 3.5 days to the skin of a patient.

Such modes of administration require a once a day, once each two days, twice a week or a once a week exchange of the TTS in an around-the-clock treatment.

According to yet another specific aspect, the invention relates to a process of manufacture of a matrix layer for use in a transdermal therapeutic system comprising the steps of:

1) combining at least the components asenapine, acrylic polymer, additional polymer, α-tocopherol and ascorbyl palmitate, in a solvent to obtain a coating composition;
2) coating the coating composition onto a backing layer or a release liner or any intermediate liner; and
3) drying the coated coating composition to form the matrix layer.

According to certain embodiments the invention also relates to a transdermal therapeutic system for the transdermal administration of asenapine comprising a self-adhesive layer structure comprising:

A) a backing layer;
B) an asenapine-containing matrix layer consisting of a matrix layer composition comprising:
  1. asenapine included in the form of the free base;
  2. a copolymer based on vinyl acetate, 2-ethylhexyl-acrylate, 2-hydroxyethyl-acrylate and glycidyl-methacrylate or a copolymer based on vinyl acetate, 2-ethylhexyl-acrylate and 2-hydroxyethyl-acrylate;
  3. medium chain triglycerides in an amount of from 5 to 12% of the matrix layer composition;
  4. soluble polyvinylpyrrolidone in an amount of from 5 to 15% of the matrix layer composition; and
  5. α-tocopherol in an amount of from 0.025 to 0.1% of the matrix layer composition, ascorbyl palmitate in an amount of from 0.15 to 0.5% of the matrix layer composition, and sodium metabisulfite in an amount of from 0.05 to 0.15% of the matrix layer composition, as stabilizers;

Within the meaning of this invention, the term "transdermal therapeutic system" (TTS) refers to a system by which the active agent (asenapine) is administered to the systemic circulation via transdermal delivery and refers to the entire individual dosing unit that is applied to the skin of a patient, and which comprises a therapeutically effective amount of asenapine in a self-adhesive layer structure and optionally an additional adhesive overlay on top of the asenapine-containing self-adhesive layer structure. The self-adhesive layer structure may be located on a release liner (a detachable protective layer), thus, the TTS may further comprise a release liner. Within the meaning of this invention, the term "TTS" in particular refers to a system providing passive transdermal delivery excluding active transport as in methods including iontophoresis or microporation.

Within the meaning of this invention, the term "asenapine-containing self-adhesive layer structure" or "self-adhesive layer structure containing a therapeutically effective amount of asenapine" refers to the active agent-containing structure providing the area of release for asenapine during administration. The adhesive overlay adds to the overall size of the TTS but does not add to the area of release. The asenapine-containing self-adhesive layer structure comprises a backing layer and at least one asenapine-containing layer.

Within the meaning of this invention, the term "therapeutically effective amount" refers to a quantity of active agent in the TTS sufficient to provide, if administered by the TTS to a patient, asenapine blood levels of a similar range (e.g. of about 10% to about 1000% as measured as an AUC) when compared to blood levels obtained in steady state administration of twice daily 5 mg sublingual asenapine over a predefined extended period of time (e.g. 1, 3.5 and 7 days). A TTS usually contains more active in the system than is in fact provided to the skin and the systemic circulation. This excess amount of active agent is usually necessary to provide enough driving force for the passive transportation from the TTS to the systemic circulation.

Within the meaning of this invention, the terms "active", "active agent", and the like, as well as the term "asenapine" refer to asenapine in any pharmaceutically acceptable chemical and morphological form and physical state. These forms include without limitation asenapine in its free base form, protonated or partially protonated asenapine, asenapine salts and in particular acid addition salts formed by addition of an inorganic or organic acid such as asenapine hydrochloride or asenapine maleate, hydrates, complexes and so on, as well as asenapine in the form of particles which may be micronized, crystalline and/or amorphous, and any mixtures of the aforementioned forms. The asenapine, where contained in a medium such as a solvent, may be dissolved or dispersed or in part dissolved and in part dispersed.

When asenapine is mentioned to be used in a particular form in the manufacture of the TTS, this does not exclude interactions between this form of asenapine and other ingredients of the asenapine-containing self-adhesive layer structure, e.g. salt formation or complexation, in the final TTS. This means that, even if asenapine is included in its free base form, it may be present in the final TTS in protonated or partially protonated form or in the form of an acid addition salt, or, if it is included in the form of a salt, parts of it may be present as free base in the final TTS. Unless otherwise indicated, in particular the amount of asenapine in the self-adhesive layer structure relates to the amount of asenapine included in the TTS during manufacture of the TTS and is calculated based on asenapine in the form of the free base. E.g., when a) 0.1 mmol (equal to 28.6 mg) asenapine base or b) 0.1 mmol (equal to 40.2 mg) asenapine maleate is included in the TTS during manufacture, the amount of asenapine in the self-adhesive layer structure is, within the meaning of the invention, in both cases 0.1 mmol or 28.6 mg.

The asenapine starting material included in the TTS during manufacture of the TTS may be in the form of particles. Asenapine may e.g. be present in the self-adhesive layer structure in the form of particles and/or dissolved.

Within the meaning of this invention, the term "particles" refers to a solid, particulate material comprising individual particles, the dimensions of which are negligible compared to the material. In particular, the particles are solid, including plastic/deformable solids, including amorphous and crystalline materials.

Within the meaning of this invention, the term "dispersing" refers to a step or a combination of steps wherein a starting material (e.g. asenapine) is not totally dissolved. Dispersing in the sense of the invention comprises the dissolution of a part of the starting material (e.g. asenapine particles), depending on the solubility of the starting material (e.g. the solubility of asenapine in the coating composition).

There are two main types of TTS using passive active agent delivery, i.e. matrix-type TTS and reservoir-type TTS. In matrix-type TTS the active agent is included in a matrix, while in a reservoir-type TTS the active agent is included in a liquid or semi-liquid reservoir. The release of the active agent in a matrix-type TTS is mainly controlled by the matrix including the active agent itself. In contrast thereto, a reservoir-type TTS needs a rate-controlling membrane controlling the release of the active agent. Matrix-type TTS are advantageous in that, compared to reservoir type TTS, usually no rate determining membranes are necessary and no dose dumping can occur due to membrane rupture. In summary, matrix-type transdermal therapeutic systems (TTS) are less complex in manufacture and easy and convenient to use by patients.

Within the meaning of this invention, "matrix-type TTS" refers to a system or structure wherein the active is homogeneously dissolved and/or dispersed within a polymeric carrier, i.e. the matrix, which forms with the active agent and optionally remaining ingredients a matrix layer. In such a system, the matrix layer controls the release of the active agent from the TTS. A matrix-type TTS may also include a rate-controlling membrane.

TTS with a rate-controlling membrane and a liquid or semi-liquid active agent containing reservoir, wherein the release of the active agent from the TTS is controlled by the rate-controlling membrane, are referred to by the term "reservoir-type TTS". Reservoir-type TTS are not to be understood as being of matrix-type within the meaning of the invention. In particular, within the meaning of this invention, microreservoir-systems (biphasic systems having an inner active-containing phase in an outer matrix-phase), considered in the art to be a mixture between a matrix-type TTS and a reservoir-type TTS, are considered to be of matrix-type within the meaning of the invention. Matrix-type TTS may in particular be in the form of a "drug-in-adhesive"-type TTS referring to a system wherein the active is homogeneously dissolved and/or dispersed within a pressure-sensitive adhesive matrix.

Within the meaning of this invention, the term "matrix layer" refers to any layer containing the active homogeneously dissolved and/or dispersed within a polymeric carrier. Typically, a matrix layer is present in a matrix-type TTS as the active agent-containing layer. A reservoir-type TTS may comprise, in addition to a reservoir layer and a rate-controlling membrane, an additional adhesive layer which serves as a skin contact layer. In such a reservoir-type TTS, the additional adhesive layer often is manufactured as an active agent-free layer. However, due to the concentration gradient, the active agent will migrate from the reservoir to the additional adhesive layer over time, until an equilibrium is reached. Therefore, in such a reservoir-type TTS, after some time of equilibration, the additional adhesive layer contains the active agent and is to be regarded as a matrix layer in the sense of the present invention.

The matrix layer is the final, solidified layer e.g. obtained after coating and drying the solvent-containing coating composition. The matrix layer may also be manufactured by laminating two or more such solidified layers (e.g. dried layers) of the same composition to provide the desired area weight. The matrix layer may be self-adhesive (in the form of a pressure sensitive adhesive matrix) or the TTS may comprise an additional skin contact layer of a pressure sensitive adhesive for providing sufficient tack. In particular, the matrix layer is a pressure sensitive adhesive matrix.

Within the meaning of this invention, the term "pressure-sensitive adhesive" refers to a material that in particular adheres with finger pressure, is permanently tacky, exerts a strong holding force and should be removable from smooth surfaces without leaving a residue. A pressure sensitive adhesive layer, when in contact with the skin, is "self-adhesive", i.e. provides adhesion to the skin so that typically no further aid for fixation on the skin is needed. A "self-adhesive" layer structure includes a pressure sensitive adhesive layer for skin contact which may be provided in the form of a pressure sensitive adhesive matrix or in the form of an additional layer, i.e. a pressure sensitive adhesive skin contact layer. An adhesive overlay may still be employed to advance adhesion.

Within the meaning of this invention, the term "skin contact layer" refers to a layer included in the TTS to be in direct contact with the skin of the patient during administration. When the TTS comprises a skin contact layer, the other layers do not contact the skin and do not necessarily have self-adhesive properties. As outlined above, the skin contact layer may over time absorb parts of the active agent and then may be regarded as a matrix layer. The area of release is provided by the area of the matrix layer. A skin contact layer may be used to enhance adherence. The sizes of an additional skin contact layer and the matrix layer are usually coextensive and correspond to the area of release.

Within the meaning of this invention, the term "area weight" refers to the dry weight of a specific layer, e.g. of the matrix layer, provided in g/m². The area weight values are subject to a tolerance of ±10%, preferably ±7.5%, due to manufacturing variability.

If not indicated otherwise "%" refers to weight-%.

Within the meaning of this invention, the term "polymer" refers to any substance consisting of so-called repeating units obtained by polymerizing one or more monomers, and includes homopolymers which consist of one type of monomer and copolymers which consist of two or more types of monomers. Polymers may be of any architecture such as linear polymers, star polymer, comb polymers, brush polymers, of any monomer arrangements in case of copolymers, e.g. alternating, statistical, block copolymers, or graft polymers. The minimum molecular weight varies depending on the polymer type and is known to the skilled person. Polymers may e.g. have a molecular weight above 2,000, preferably above 5,000 and more preferably above 10,000 Dalton. Correspondingly, compounds with a molecular weight below 2,000, preferably below 5,000 or more preferably below 10,000 Dalton are usually referred to as oligomers.

Within the meaning of this invention, the term "functional groups" refers to hydroxy- and carboxylic acid groups.

Within the meaning of this invention, the term "cross-linking agent" refers to a substance which is able to cross-link functional groups contained within the polymer.

Within the meaning of this invention, the term "adhesive overlay" refers to a self-adhesive layer structure that is free of active agent and larger in area than the active agent-containing structure and provides additional area adhering to the skin, but no area of release of the active agent. It enhances thereby the overall adhesive properties of the TTS. The adhesive overlay comprises a backing layer and an adhesive layer.

Within the meaning of this invention, the term "backing layer" refers to a layer, which supports e.g. the asenapine-containing layer or forms the backing of the adhesive overlay. At least one backing layer in the TTS and usually the backing layer of the asenapine-containing layer is occlusive, i.e. substantially impermeable to the active agent contained in the layer during the period of storage and administration and thus prevents active loss or cross-contamination in accordance with regulatory requirements.

The TTS according to the present invention can be characterized by certain parameters as measured in an in vitro skin permeation test.

The in vitro permeation test is performed in a Franz diffusion cell, with human or animal skin and preferably with dermatomed split-thickness human skin with a thickness of 800 μm and an intact epidermis, and with phosphate buffer pH 5.5 or 7.4 as receptor medium (32° C. with 0.1% saline azide) with or without addition of a maximum of 40 vol-% organic solvent e.g. ethanol, acetonitrile, isopropanol, dipropylene glycol, PEG 400 so that a receptor medium may e.g. contain 60 vol-% phosphate buffer pH 5.5, 30 vol-% dipropylene glycol and 10 vol-% acetonitrile.

Where not otherwise indicated, the in vitro permeation test is performed with dermatomed split-thickness human skin with a thickness of 800 μm and an intact epidermis, and with phosphate buffer pH 5.5 as receptor medium (32° C. with 0.1% saline azide). The amount of active permeated into the receptor medium is determined in regular intervals using a validated HPLC method with a UV photometric detector by taking a sample volume. The receptor medium is completely or in part replaced by fresh medium when taking the sample volume, and the measured amount of active permeated relates to the amount permeated between the two last sampling points and not the total amount permeated so far.

Thus, within the meaning of this invention, the parameter "permeated amount" is provided in μg/cm² and relates to the amount of active permeated in a sample interval at certain elapsed time. E.g., in an in vitro permeation test as described above, wherein the amount of active permeated into the receptor medium has been e.g. measured at hours 0, 2, 4, 8, 12 and 24, the "permeated amount" of active can be given e.g. for the sample interval from hour 8 to hour 12 and corresponds to the measurement at hour 12.

The permeated amount can also be given as a "cumulative permeated amount", corresponding to the cumulated amount of active permeated at a certain point in time. E.g., in an in vitro permeation test as described above, wherein the amount of active permeated into the receptor medium has been e.g. measured at hours 0, 2, 4, 8, 12 and 24, the "cumulative permeated amount" of active at hour 12 corresponds to the sum of the permeated amounts from hour 0 to hour 2, hour 2 to hour 4, hour 4 to hour 8 and hour 8 to hour 12.

Within the meaning of this invention, the parameter "skin permeation rate" for a certain sample interval at certain elapsed time is provided in μg/(cm² h) and is calculated from the permeated amount in said sample interval as measured by in vitro permeation test as described above in μg/cm², divided by the hours of said sample interval. E.g. the skin permeation rate in an in vitro permeation test as described above, wherein the amount of active permeated into the receptor medium has been e.g. measured at hours 0, 2, 4, 8, 12 and 24, the "skin permeation rate" at hour 12 is calculated as the permeated amount in the sample interval from hour 8 to hour 12 divided by 4 hours.

A "cumulative skin permeation rate" can be calculated from the respective cumulative permeated amount by dividing the cumulative permeated amount by the elapsed time. E.g. in an in vitro permeation test as described above, wherein the amount of active permeated into the receptor medium has been e.g. measured at hours 0, 2, 4, 8, 12 and 24, the "cumulative skin permeation rate" at hour 12 is calculated as the cumulative permeated amount for hour 12 (see above) divided by 12 hours.

Within the meaning of this invention, the above parameters permeated amount and skin permeation rate (as well as cumulative permeated amount and cumulative skin permeation rate) refer to mean values calculated from 3 in vitro permeation test experiments.

The TTS according to the present invention can also be characterized by certain parameters as measured in an in vivo clinical study.

Within the meaning of this invention, the parameter "mean release rate" refers to the mean release rate in μg/h, in mg/h, in μg/24 h, in mg/24 h, in μg/day or in mg/day over the period of administration (e.g. 1 to 7 day(s)) by which the active agent is released through the human skin into the systemic circulation and is based on the AUC obtained over said period of administration in a clinical study. The mean release rate is a parameter used to identify the dose or the strength of a TTS. Since, in contrast to e.g. intravenous or oral administration and (as also described above) a TTS usually contains more active in the system than is in fact provided to the skin and the systemic circulation, the amount of active contained in the TTS is not meaningful as a parameter for the dose. This is why for a TTS the dose or strength is usually characterized by the mean release rate, which describes more accurately the amount of active delivered to the subject over time.

Within the meaning of this invention, the term "extended period of time" relates to a period of at least or about 24 hours, at least or about 48 hours, at least or about 84 hours, at least or about 168 hours, at least or about 1 day, at least or about 3.5 days, or at least or about 7 days, or to a period of about 24 hours to about 168 hours or 1 to 7 day(s), or about 24 hours to about 84 hours or 1 to 3.5 day(s).

For a continuous drug treatment, the frequency of drug administration is preferably kept sufficiently high so as to maintain a therapeutically effective blood plasma concentration. In other words, the interval between two dosage form administrations, also called dosing interval, needs to be adapted accordingly. Within the meaning of the present invention, the term "dosing interval" refers to the period of time between two consecutive TTS administrations, i.e. the interval between two consecutive points in time a TTS is applied to the skin of the patient. Once applied, the TTS is usually maintained on the skin of the patient for the entire dosing interval and only removed at the end of the dosing interval, at which time a new TTS is applied to the skin. E.g., if the dosing interval is 168 hours or 7 days, the TTS is applied to and maintained on the skin of the patient for 168 hours or 7 days. After 168 hours or 7 days, the TTS is removed from the skin and a new TTS is applied. Thus, a dosing interval of 168 hours or 7 days allows a once-a-week TTS exchange mode in an around-the-clock treatment.

Within the meaning of this invention, the term "room temperature" refers to the unmodified temperature found indoors in the laboratory where the experiments are conducted and usually lies within 15 to 35° C., preferably about 18 to 25° C.

Within the meaning of this invention, the term "patient" refers to a subject who has presented a clinical manifestation of a particular symptom or symptoms suggesting the need for treatment, who is treated preventatively or prophylactically for a condition, or who has been diagnosed with a condition to be treated.

Within the meaning of this invention the term "pharmacokinetic parameters" refers to parameters describing the blood plasma curve, e.g. $C_{max}$, $C_t$ and $AUC_{t1-t2}$ obtained in a clinical study, e.g. by single-dose, multi-dose or steady state administration of the active agent TTS, e.g. the asenapine TTS to healthy human subjects. The pharmacokinetic parameters of the individual subjects are summarized using arithmetic and geometric means, e.g. a mean $C_{max}$, a mean $AUC_t$ and a mean $AUC_{INF}$, and additional statistics such as the respective standard deviations and standard errors, the minimum value, the maximum value, and the middle value when the list of values is ranked (Median). In the context of the present invention, pharmacokinetic parameters, e.g. the $C_{max}$, $C_t$ and $AUC_{t1-t2}$ refer to arithmetic or geometric mean values and preferably refer to geometric mean values. It cannot be precluded that the absolute mean values obtained for a certain TTS in a clinical study vary to a certain extent from study to study. To allow a comparison of absolute mean values between studies, a reference formulation, e.g. in the future any product based on the invention, may be used as internal standard. A comparison of the AUC per area of release of the respective reference product in the earlier and later study can be used to obtain a correction factor to take into account differences from study to study.

Clinical studies according to the present invention refer to studies performed in full compliance with the International Conference for Harmonization of Clinical Trials (ICH) and all applicable local Good Clinical Practices (GCP) and regulations.

Within the meaning of this invention, the term "healthy human subject" refers to a male or female subject with a body weight ranging from 55 kg to 100 kg and a body mass index (BMI) ranging from 18 to 29 and normal physiological parameters, such as blood pressure, etc. Healthy human subjects for the purposes of the present invention are selected according to inclusion and exclusion criteria which are based on and in accordance with recommendations of the ICH.

Within the meaning of this invention, the term "subject population" refers to at least ten individual healthy human subjects.

Within the meaning of this invention, the term "geometric mean" refers to the mean of the log transformed data back-transformed to the original scale.

Within the meaning of this invention, the term "arithmetic mean" refers to the sum of all values of observation divided by the total number of observations.

Within the meaning of this invention, the parameter "AUC" corresponds to the area under the plasma concentration-time curve. The AUC value is proportional to the amount of active agent absorbed into the blood circulation in total and is hence a measure for the bioavailability.

Within the meaning of this invention, the parameter "$AUC_{t1-t2}$" is provided in (ng/ml) h and relates to the area under the plasma concentration-time curve from hour t1 to t2 and is calculated by the linear trapezoidal method.

Within the meaning of this invention, the parameter "$C_{max}$" is provided in (ng/ml) and relates to the maximum observed blood plasma concentration of the active agent.

Within the meaning of this invention, the parameter "$C_t$" is provided in (ng/ml) and relates to the blood plasma concentration of the active agent observed at hour t.

Within the meaning of this invention, the parameter "$t_{max}$" is provided in h and relates to the time point at which the $C_{max}$ value is reached. In other words, $t_{max}$ is the time point of the maximum observed plasma concentration.

Within the meaning of this invention, the parameter "$t_{lag}$" is provided in h and relates to the delay between the time of administration (in case of a TTS the time when the TTS is first applied to the skin, i.e. t=0) and the time of appearance of measurable blood plasma concentration. The $t_{lag}$ can be calculated approximatively as the mean arithmetic value of the first point in time when a measurable (i.e. non-zero) active agent blood plasma concentration is obtained or represented by a median value.

Within the meaning of this invention, the term "mean plasma concentration" is provided in (ng/ml) and is a mean of the individual plasma concentrations of active agent, e.g. asenapine, at each point in time.

Within the meaning of this invention, the term "coating composition" refers to a composition comprising all components of the matrix layer in a solvent, which may be coated onto the backing layer or release liner to form the matrix layer upon drying.

Within the meaning of this invention, the term "dissolve" refers to the process of obtaining a solution, which is clear and does not contain any particles, as visible to the naked eye.

Within the meaning of this invention, the term "solvent" refers to any liquid substance, which preferably is a volatile organic liquid such as methanol, ethanol, isopropanol, acetone, ethyl acetate, methylene chloride, hexane, n-heptane, heptanes, toluene and mixtures thereof.

Within the meaning of this invention, and unless otherwise specified, the term "about" refers to an amount that is ±10% of the disclosed amount. In some embodiments, the term "about" refers to an amount that is ±5% of the disclosed amount. In some embodiments, the term "about" refers to an amount that is ±2% of the disclosed amount.

BRIEF DESCRIPTION OF THE DRAWINGS

FIG. 12d depicts the amount of asenapine base detected in a storage stability test at 25° C. and 60% RH initially and after 3 months for TTS prepared according to Reference Example 2d and Examples 9a, 12a, 12b and 12c, after 6 months for TTS prepared according to Examples 9a, 12a, 12b and 12c, and after 9 months for TTS prepared according to Reference Example 2d and Example 9a.

DETAILED DESCRIPTION

TTS Structure

Figure 1A:
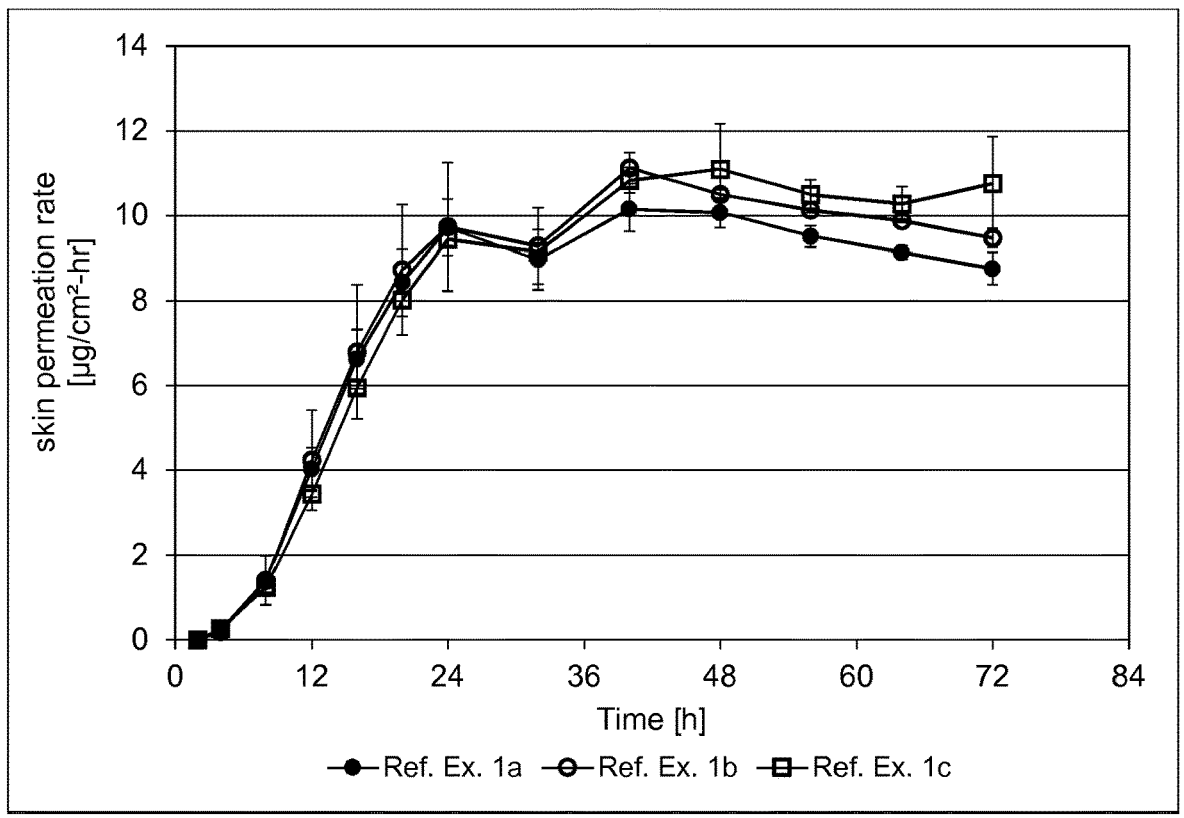
FIG. 1a depicts the asenapine skin permeation rate of TTS prepared according to Reference Examples 1a to 1c for hours 0 to 72.

The present invention is related to a transdermal therapeutic system for the transdermal administration of asenapine comprising a self-adhesive layer structure containing asenapine.

The self-adhesive layer structure contains therapeutically effective amounts of asenapine and comprises A) a backing layer, and B) an asenapine-containing matrix layer consisting of a matrix layer composition comprising 1. asenapine, 2. a polymer, 3. an additional polymer, and 4. α-tocopherol and ascorbyl palmitate as stabilizers.

Thus, the transdermal therapeutic system for the transdermal administration of asenapine comprises a self-adhesive layer structure containing a therapeutically effective amount of asenapine, said self-adhesive layer structure comprising:
  A) a backing layer;
  B) an asenapine-containing matrix layer consisting of a matrix layer composition comprising:
    1. asenapine;
    2. a polymer selected from acrylic polymers;
    3. an additional polymer; and
    4. α-tocopherol in an amount of from 0.01 to 2% of the matrix layer composition and ascorbyl palmitate in an amount of at least 0.01% of the matrix layer composition as stabilizers.

The backing layer is in particular substantially asenapine-impermeable.

The TTS according to the present invention may be a matrix-type TTS or a reservoir-type TTS, and preferably is a matrix-type TTS.

In such a matrix-type TTS, the asenapine, and preferably a therapeutically effective amount of asenapine, is included in the asenapine-containing matrix layer. The self-adhesive layer structure in such a matrix-type TTS can include one or more further layers such as a skin contact layer. In such a further layer, the active agent may be included or may not be included. As outlined above, a skin contact layer can, even if manufactured as an active agent-free layer, after equilibration, comprise asenapine and then may also be regarded as a (further) matrix layer. The further layer and the asenapine-containing matrix layer may comprise the same polymer or different polymers. Any of the asenapine-containing matrix layer and the further layer(s) may be directly contacting each other or separated by a membrane such as a rate controlling membrane. If an asenapine-containing layer is prepared by laminating two asenapine-containing matrix layers, which are of substantially the same composition, the resulting double layer is to be regarded as one matrix layer.

In certain embodiments, the self-adhesive layer structure comprises an additional reservoir layer which is located between the backing layer and the matrix layer, and a further rate controlling membrane which is located between the additional reservoir layer and the matrix layer.

In specific embodiments, the self-adhesive layer structure according to the invention comprises an additional skin contact layer. The additional skin contact layer is self-adhesive and provides for adhesion between the self-adhesive layer structure and the skin of the patient during administration.

In such embodiments, the self-adhesive layer structure may or may not comprise a membrane, which is located between the matrix layer and the additional skin contact layer, wherein the membrane is preferably a rate controlling membrane.

In another embodiment, the self-adhesive layer structure according to the invention does not comprise an additional skin contact layer. Sufficient adhesion between the self-adhesive layer structure and the skin of the patient during administration is then provided for by other means, e.g. an asenapine-containing matrix layer and/or an adhesive layer.

Thus, according to certain embodiments of the invention, the TTS may further comprise an adhesive overlay or does not comprise an adhesive overlay, and preferably does not comprise an adhesive overlay. This adhesive overlay is in particular larger than the asenapine-containing self-adhesive layer structure and is attached thereto for enhancing the adhesive properties of the overall transdermal therapeutic system. Said adhesive overlay comprises also a backing layer. The area of said adhesive overlay adds to the overall size of the TTS but does not add to the area of release. The adhesive overlay comprises a self-adhesive polymer or a self-adhesive polymer mixture selected from the group of acrylic polymers, polyisobutylenes, styrene-isoprene-styrene copolymers, polysiloxanes, and mixtures thereof, which may be identical to or different from any polymer or polymer mixture included in the active agent-containing self-adhesive layer structure.

The self-adhesive layer structure according to the invention is normally located on a detachable protective layer (release liner) from which it is removed immediately before application to the surface of the patient's skin. Thus, the TTS may further comprise a release liner. A TTS protected this way is usually stored in a seam-sealed pouch. The packaging may be child resistant and/or senior friendly.

Matrix Layer and Matrix Layer Composition

As outlined in more detail above, the TTS of the present invention comprises a self-adhesive layer structure comprising an asenapine-containing matrix layer consisting of a matrix layer composition.

The matrix layer composition comprises:
1. asenapine;
2. a polymer selected from acrylic polymers;
3. an additional polymer; and
4. α-tocopherol in an amount of from 0.01 to 2% of the matrix layer composition and ascorbyl palmitate in an amount of at least 0.01% of the matrix layer composition as stabilizers.

In a specific embodiment of the invention, the matrix layer composition comprises asenapine and a polymer selected from acrylic polymers, wherein the transdermal therapeutic system has an area of release of from 5 to 100 $cm^2$.

In certain embodiments of the invention, the area of release ranges from 5 to 100 $cm^2$, preferably from 5 to 80 $cm^2$, and more preferably from 10 to 50 $cm^2$ or from 50 to 80 $cm^2$, from 10 to 40 $cm^2$ or from 10 to 30 $cm^2$ or from 55 to 65 $cm^2$, i.e. the transdermal therapeutic system has an area of release of from 5 to 100 $cm^2$, preferably from 5 to 80 $cm^2$, and more preferably from 10 to 50 $cm^2$ or from 50 to 80 $cm^2$, from 10 to 40 $cm^2$ or from 10 to 30 $cm^2$ or from 55 to 65 $cm^2$.

In certain embodiments of the invention, the area weight of the matrix layer ranges from 90 to 230 $g/m^2$, preferably from 110 to 210 $g/m^2$, and most preferably from 120 to 170 $g/m^2$.

Without wishing to be bound by theory, it is believed that the good in vitro skin permeation is inter alia achieved by the amount of asenapine contained in the TTS, which can be controlled two-way by adjusting concentration and/or the area weight of the asenapine-containing layers such as the matrix layer.

Thus, in certain embodiments of the invention, the transdermal therapeutic system contains at least 0.70 $mg/cm^2$, preferably at least 0.80 $mg/cm^2$, more preferably at least 0.82 $mg/cm^2$ and most preferably at least 0.83 $mg/cm^2$ asenapine per area of release. In certain further embodiments of the invention, the transdermal therapeutic system contains at least 0.90 $mg/cm^2$, at least 1.00 $mg/cm^2$, at least 1.2 $mg/cm^2$, at least 1.5 $mg/cm^2$ or at least 2.0 $mg/cm^2$ asenapine per area of release.

In particular, the transdermal therapeutic system contains from 0.70 $mg/cm^2$ to 4.0 $mg/cm^2$, preferably from 0.80 $mg/cm^2$ to 3.0 $mg/cm^2$, more preferably from 0.82 $mg/cm^2$ to 2.0 $mg/cm^2$ and most preferably from 0.83 $mg/cm^2$ to 1.7 $mg/cm^2$ asenapine.

In certain embodiments of the invention, the matrix layer composition is a pressure-sensitive adhesive composition. The matrix layer composition may comprise a second polymer or may comprise two or more further polymers.

According to certain embodiments of the invention, the total polymer content in the matrix layer composition ranges from 60 to 95%, preferably from 70 to 90% and more preferably from 75 to 85% of the matrix layer composition. In any event does the matrix layer include sufficient amounts of polymer to provide sufficient cohesion.

According to certain embodiments, the amount of asenapine contained in the TTS, in particular in the matrix layer of the TTS, ranges from 5 to 100 mg, preferably from 10 to 80 mg, and most preferably from 15 to 60 mg.

In certain embodiments, the transdermal therapeutic system has an area of release of from 5 to 100 $cm^2$, and the amount of asenapine contained in the TTS ranges from 5 to 100 mg.

In certain embodiments of the invention, the asenapine-containing matrix layer does not comprise isopropyl palmitate in an amount of 10% of the matrix layer composition, preferably does not comprise isopropyl palmitate in an amount of 5-15% of the matrix layer composition and most preferably does not comprise isopropyl palmitate.

In certain embodiments of the invention, the asenapine-containing matrix layer does not comprise isopropyl myristate in an amount of 5% of the matrix layer composition, preferably does not comprise isopropyl myristate in an amount of 1-10% of the matrix layer composition and most preferably does not comprise isopropyl myristate.

In certain embodiments of the invention, the asenapine-containing matrix layer does not comprise ethyl cellulose in an amount of 10-20% of the matrix layer composition and preferably does not comprise ethyl cellulose.

In certain embodiments of the invention, the asenapine-containing matrix layer does not comprise hydrogen chloride.

In certain embodiments of the invention, the asenapine-containing matrix layer does not comprise sodium acetate or sodium diacetate. In yet another embodiment, the asenapine-containing layer does not comprise a dicarboxylic acid alkali salt. In yet another embodiment, the asenapine-containing layer does not comprise a maleic acid alkali salt.

In certain embodiments of the invention, the matrix layer composition does not comprise any of polysiloxanes and polyisobutylenes in an amount of more than 50% of the matrix layer composition.

In certain embodiments, the asenapine-containing matrix layer is obtainable by drying a coated coating composition wherein no hydrochloric acid has been included in the coating composition.

In certain embodiments of the invention, the asenapine-containing matrix layer does not comprise toluene.

In certain embodiments of the invention, the asenapine-containing matrix layer is obtainable by drying a coated coating composition comprising no toluene.

Asenapine

In accordance with the invention, the self-adhesive layer structure contains asenapine in a therapeutically effective amount, and the self-adhesive layer structure comprises an asenapine-containing matrix layer consisting of a matrix layer composition comprising asenapine.

While in accordance with the present invention, the active agent may be present in the TTS in protonated or in free base form, the free base form is preferred.

Thus, in certain embodiments, the asenapine in the matrix layer composition is included in the form of the free base.

In certain embodiments, the matrix layer composition is obtainable by incorporating the asenapine in the form of the free base.

In particular, at least 90 mol %, preferably at least 95 mol %, more preferably at least 98 mol % and most preferably at least 99 mol % of the asenapine in the matrix layer is present in the form of the free base.

The asenapine in the matrix layer may be completely dissolved, or the matrix layer composition may contain asenapine particles, preferably constituted of asenapine free base.

As outlined above, the amount of asenapine in the TTS is believed to be important for a good release of the active, and can be e.g. adjusted by the asenapine concentration. Thus, in certain embodiments, the amount of asenapine in the matrix layer composition ranges from 2 to 20%, preferably from 3 to 15% and more preferably from 4 to 12% of the matrix layer composition.

In certain embodiments, the asenapine has a purity of at least 95%, preferably of at least 98% and more preferably of at least 99% as determined by quantitative HPLC. Quantitative HPLC may be performed with Reversed-Phase-HPLC with UV detection. In particular, the following conditions can be used if HPLC is performed isocratically:
Column: Octadecyl phase acc. Ph. Eur. 2.2.29 (USP phase L1)
Kromasil C18 125 mm×4.0 mm; 5 µm or equivalent
Mobile phase: 0.05 molar $KH_2PO_4$ Buffer/Methanol/TEA (45:55:0.1; v:v:v); pH 2.5±0.05
(TEA=triethylamine)
Gradient: isocratic
Flux: 1.0 ml
Injection volume: 30 µl
Column temperature: 40° C.
Wavelength: 225 nm, 270 nm and 3-D-field; Evaluation is performed at 270 nm
Run time: 10 min
Furthermore, the following conditions can be used if HPLC is performed with a gradient:
Column: Octadecyl phase acc. Ph. Eur. 2.2.29 (USP phase L1)
Kinetex C18 EVO 100 mm×4.6 mm; 2.1 µm or equivalent
Mobile phase: A: 0.02 molar $KH_2PO_4$ Buffer/Methanol/TEA (70:30:0.1; v:v:v) adj. to pH 2.5
B: 0.02 molar $KH_2PO_4$ Buffer/Methanol/TEA (30:70:0.1; v:v:v); adj. to pH 2.5 (TEA=triethylamine)
Flux: 0.7 ml
Injection volume: 30 µl
Column temperature: 40° C.
Wavelength: 225 nm, 270 nm and 3-D-field; Evaluation is performed at 225 nm
Run time: 32 min
Gradient profile: 0.00 min: A: 100% B: 0%
12.00 min: A: 40% B: 60%
18.00 min: A: 0% B: 100%
27.00 min: A: 0% B: 100%
27.01 min: A: 100% B: 0%
32.00 min: A: 100% B: 0%

Polymer

As outlined above, the TTS according to the present invention comprises a self-adhesive layer structure comprising an asenapine-containing matrix layer consisting of a matrix layer composition, wherein the matrix layer composition comprises a polymer.

This polymer provides for sufficient cohesion of the matrix layer. According to certain embodiments the polymer may also provide for sufficient adhesion. In those embodiments the polymer is selected from pressure sensitive adhesive polymers.

In a preferred embodiment, the polymer is selected from pressure-sensitive adhesive polymers.

Polymers which are suitable as the polymer in accordance with the invention are acrylic polymers.

Corresponding commercial products are available e.g. under the brand name Duro-Tak™ (see below for details).

The acrylic polymers comprise or do not comprise functional groups.

Corresponding commercial products are available e.g. under the brand names Duro-Tak™ 387-2287 (an acrylic copolymer comprising hydroxyl groups), Duro-Tak™ 87-4287 (an acrylic copolymer comprising hydroxyl groups), Duro-Tak™ 387-2516 (an acrylic copolymer comprising hydroxyl groups), Duro-Tak™ 387-2051 (an acrylic copolymer comprising carboxylic acid groups), Duro-Tak™ 387-2353 (an acrylic copolymer comprising carboxylic acid groups), Duro-Tak™ 387-4098 (an acrylic copolymer comprising no functional groups) and Duro-Tak™ 387-9301 (an acrylic copolymer comprising no functional groups).

In certain embodiments, the polymer is selected from acrylic polymers comprising functional groups wherein the functional groups are selected from hydroxyl groups, carboxylic acid groups, neutralized carboxylic acid groups and mixtures thereof. Preferably, the functional groups are limited to hydroxyl groups.

In certain embodiments, the polymer is selected from acrylic polymers, which do not comprise carboxylic acid groups or neutralized carboxylic acid groups or both groups, and preferably the polymer is selected from acrylic polymers which do not comprise acidic groups.

In further preferred embodiments, the polymer is selected from acrylic polymers comprising hydroxyl groups and no carboxylic acid groups, and more preferably, the polymer is a copolymer based on vinyl acetate, 2-ethylhexyl-acrylate, 2-hydroxyethyl-acrylate and glycidyl-methacrylate or a copolymer based on vinyl acetate, 2-ethylhexyl-acrylate and 2-hydroxyethyl-acrylate.

Such a copolymer based on vinyl acetate, 2-ethylhexyl-acrylate, 2-hydroxyethyl-acrylate and glycidyl-methacrylate is commercially available under the brand names Duro-Tak™ 387-2287 (provided as a solution in ethyl acetate without cross-linking agent) and Duro-Tak™ 387-2516 (provided as a solution in ethyl acetate, ethanol, heptanes and methanol with a titanium cross-linking agent). A copolymer based on vinyl acetate, 2-ethylhexyl-acrylate and 2-hydroxyethyl-acrylate (provided as a solution in ethyl acetate without cross-linking agent) is commercially available under the brand name Duro-Tak™ 387-4287. Thus, depending on the type of commercially available acrylic polymer used and depending on whether a cross-linking agent is added to the coating composition, the polymer in the finalized matrix layer is cross-linked (and preferably is cross-linked by an aluminium and/or a titanium cross-linking agent) or is not cross-linked by a cross-linking agent.

In certain other embodiments, the polymer is selected from acrylic polymers comprising no hydroxyl groups and no carboxylic acid groups, and preferably, the polymer is selected from acrylic polymers comprising no functional groups.

In further preferred embodiments, the polymer is a copolymer based on methyl acrylate, 2-ethylhexyl acrylate and t-octyl acrylamide, and which is commercially available under the brand name Duro-Tak™ 387-9301 (provided as a solution in ethyl acetate).

In further preferred embodiments, the polymer is a copolymer based on 2-ethylhexyl-acrylate and vinyl acetate, which is commercially available under the brand name Duro-Tak™ 387-4098 (provided as a solution in ethyl acetate).

In certain preferred embodiments, the amount of the polymer ranges from 50 to 90%, preferably from 60 to 85% and more preferably from 65 to 80% of the matrix layer composition.

Additional Polymer

As outlined above, in the TTS according to the present invention, the matrix layer composition comprises an additional polymer.

Of particular interests are polymers with an enhanced ability to absorb water, as higher water and/or moisture absorption assists in maintaining/improving the adhesive properties of the matrix layer.

Thus, in certain embodiments, the matrix layer composition comprises an additional polymer selected from polymers, which provide for an improved water and/or moisture absorption of the matrix layer. Such polymers are well known in the art. Of those, particularly suitable and preferred are polyvinylpyrrolidones, and in particular soluble polyvinylpyrrolidones.

The term "soluble polyvinylpyrrolidone" refers to polyvinylpyrrolidone, also known as povidone, which is soluble with more than 10% in at least ethanol, preferably also in water, diethylene glycol, methanol, n-propanol, 2-propanol, n-butanol, chloroform, methylene chloride, 2-pyrrolidone, macrogol 400, 1,2 propylene glycol, 1,4 butanediol, glycerol, triethanolamine, propionic acid and acetic acid. Examples of polyvinylpyrrolidones which are commercially available include Kollidon® 12 PF, Kollidon® 17 PF, Kollidon® 25, Kollidon® 30 and Kollidon® 90 F supplied by BASF, or povidone K90F. The different grades of Kollidon® are defined in terms of the K-Value reflecting the average molecular weight of the polyvinylpyrrolidone grades. Kollidon® 12 PF is characterized by a K-Value range of 10.2 to 13.8, corresponding to a nominal K-Value of 12. Kollidon® 17 PF is characterized by a K-Value range of 15.3 to 18.4, corresponding to a nominal K-Value of 17. Kollidon® 25 is characterized by a K-Value range of 22.5 to 27.0, corresponding to a nominal K-Value of 25, Kollidon® 30 is characterized by a K-Value range of 27.0 to 32.4, corresponding to a nominal K-Value of 30. Kollidon® 90 F is characterized by a K-Value range of 81.0 to 97.2, corresponding to a nominal K-Value of 90. Preferred Kollidon® grades are Kollidon® 12 PF, Kollidon® 30 and Kollidon® 90 F. For all grades and types of polyvinylpyrrolidone, it is preferred that the amount of peroxides is within certain limits, in particular, the peroxide amount is equal to or less than 500 ppm, more preferably equal to or less than 150 ppm, and most preferably equal to or less than 100 ppm.

Within the meaning of this invention, the term "K-Value" refers to a value calculated from the relative viscosity of polyvinylpyrrolidone in water according to the European Pharmacopoeia (Ph.Eur.) and USP monographs for "Povidone".

Thus, in certain embodiments, the matrix layer composition comprises an additional polymer, wherein the additional polymer is a polyvinylpyrrolidone having a K-Value within a range selected from the group of ranges consisting of 9 to 15, and preferably 10.2 to 13.8,
15 to 20, and preferably 15.3 to 18.4,
20 to 27, and preferably 22.5 to 27.0,
27 to 35, and preferably 27.0 to 32.4, and
75 to 110, and preferably 81.0 to 97.2, or any mixtures thereof, and more preferably is a polyvinylpyrrolidone having a K-Value within a range of 27.0 to 32.4 or of 81.0 to 97.2, and any mixtures thereof, and most preferably is a polyvinylpyrrolidone having a K-Value within range of 27.0 to 32.4.

The additional polymer, e.g. polyvinylpyrrolidones, and preferably soluble polyvinylpyrrolidones, may be present for example in an amount of from 0 to 20% of the matrix layer composition, preferably of from 5 to 15% of the matrix layer composition and more preferably in an amount of about 10% of the matrix layer composition.

The matrix layer composition may e.g. comprise one of the aforementioned polymers as additional polymer(s). Other additional polymers and additives may also be added to enhance cohesion and/or adhesion.

Other polymers in particular reduce the cold flow and are thus also suitable as additional polymer. A polymeric matrix may show a cold flow, since such polymer compositions often exhibit, despite a very high viscosity, the ability to flow very slowly. Thus, during storage, the matrix may flow to a certain extent over the edges of the backing layer. This is a problem with storage stability and can be prohibited by the addition of certain polymers. A basic acrylate polymer (e.g. Eudragit E100 which is a copolymer based on dimethylaminoethyl methacrylate, butyl methacrylate and methyl methacrylate) may e.g. be used to reduce the cold flow. Thus, in certain embodiments, the matrix layer composition comprises additionally a basic polymer, in particular an amine-functional acrylate as e.g. Eudragit E100.

According to certain embodiments, the total polymer content in the matrix layer composition ranges from 60 to 95%, preferably from 70 to 90% and more preferably from 75 to 85% of the matrix layer composition.

Stabilizers

As outlined above, the TTS according to the present invention comprises a self-adhesive layer structure comprising an asenapine-containing matrix layer consisting of a matrix layer composition, wherein the matrix layer composition comprises α-tocopherol and ascorbyl palmitate.

The α-tocopherol and ascorbyl palmitate are included as stabilizers. The inventors have surprisingly found that the stability of the inventive formulations in terms of asenapine content and degradation is improved by a synergistic combination of α-tocopherol and ascorbyl palmitate, in particular in certain specific amounts.

Thus, the matrix layer composition comprises α-tocopherol in an amount of from 0.01 to 2% of the matrix layer composition and ascorbyl palmitate in an amount of at least 0.01% of the matrix layer composition as stabilizers.

The inventors have further found that the advantageous effect on stability can be further improved by addition of sodium metabisulfite. Thus, preferably, the matrix layer composition further comprises sodium metabisulfite in an amount of from 0 to 0.5%, preferably from 0.01 to 0.2%, and more preferably from 0.05 to 0.15% of the matrix layer composition as stabilizer. Particularly preferably, the matrix layer composition further comprises sodium metabisulfite in an amount of about 0.1% of the matrix layer composition as stabilizer. Where the present application is referring to sodium metabisulfite, any other sulfite or disulfite is considered to be included as an alternative embodiment.

In terms of the amount of α-tocopherol and ascorbyl palmitate, certain ranges have a particularly favorable effect on the stability.

Thus, the matrix layer composition preferably comprises α-tocopherol at least 0.025% of the matrix layer composition, and/or in an amount of up to 1.5% or 0.75%, preferably up to 0.5%, and more preferably up to 0.1% of the matrix layer composition, and most preferably in an amount of about 0.05% of the matrix layer composition.

The matrix layer composition may further comprise ascorbyl palmitate in an amount of at least 0.02% of the matrix layer composition, preferably at least 0.08% of the matrix layer composition, and more preferably at least 0.15% of the matrix layer composition, and/or in an amount of up to 2.0 or 1.0%, preferably up to 0.6% of the matrix layer composition, and more preferably in an amount of from 0.2 to 0.4% of the matrix layer composition.

In certain embodiments, the matrix layer composition may comprise one or more further stabilizers selected from ascorbic acid and ester derivatives thereof, butylated hydroxytoluene, tocopherol ester derivatives such as tocopheryl acetate and tocopheryl linoleate, carboxylic acids, and in particular branched or linear alkyl mono-, di- or tri-carboxylic acids, preferably a branched or linear C4 to C16-monocarboxylic acid and more preferably isononanoic acid or heptanoic acid, and most preferably 3,5,5-trimethylhexanoic acid, as well as any combination thereof.

The TTS according to the present invention advantageously show an improved stability in terms of the asenapine content as well as asenapine degradation.

Thus, in certain embodiments, the matrix layer contains initially (i.e. shortly after manufacture e.g. within one week) an amount of asenapine of at least 95%, preferably of at least 96%, more preferably of at least 97% and even more preferably of at least 98% of the theoretical amount of asenapine included in the matrix layer. The theoretical amount of asenapine is calculated from the asenapine amount used for the coating composition and the (actual) area weight of the coated and dried matrix layer of the tested TTS.

The matrix layer may also contain initially a total amount of asenapine-related degradation substances of less than 0.7%, preferably of less than 0.5%, more preferably of less than 0.3% and even more preferably of less than 0.2%.

In certain other embodiments, the TTS according to the present invention are stable upon storage, i.e. they may maintain the initial asenapine content values or present low amounts of degradation products, as follows:

In one of such embodiments, the matrix layer contains, after having been stored at 25° C. and 60% relative humidity for at least 2 months, preferably at least 3 months, an amount of asenapine of at least 90%, preferably of at least 92%, more preferably of at least 94% and even more preferably of at least 95% of the theoretical amount of asenapine included in the matrix layer.

The matrix layer may also contain, after having been stored at 25° C. and 60% relative humidity for at least 2 months, preferably at least 3 months, a total amount of asenapine-related degradation substances of less than 1.0%, preferably of less than 0.7%, more preferably of less than 0.5% and even more preferably of less than 0.4%.

In another of such embodiments the matrix layer contains, after having been stored at 40° C. and 75% relative humidity for at least 2 months, preferably at least 3 months, an amount of asenapine of at least 88%, preferably of at least 90%, more preferably of at least 91% and even more preferably of at least 92% of the theoretical amount of asenapine included in the matrix layer.

The matrix layer may also contain, after having been stored at 40° C. and 75% relative humidity for at least 2 months, preferably at least 3 months, a total amount of asenapine-related degradation substances of less than 3.0%, preferably of less than 2.0%, more preferably of less than 1.5% and even more preferably of less than 0.7%.

For determining the asenapine content and the total amount of asenapine-related degradation substances, a TTS sample is extracted with an appropriate extraction solvent and the amount of asenapine base, as well as various possible degradation substances is determined by a quantitative HPLC method with a UV photometric detector. The amount of asenapine is determined based on an asenapine standard. The total amount of asenapine-related degradation substances (expressed in %) is the sum of the peak areas of all degradation substances, each multiplied by a response factor, which is 0.33 for tetradehydro asenapine and is 1 for all other substances, divided by the peak area of asenapine of the tested sample, and multiplied by 100%.

Further Additives

The matrix layer composition of the TTS according to the invention may comprise further excipients or additives selected from the group consisting of additional polymers (see above), cross-linking agents, solubilizers, fillers, tackifiers, plasticizers, stabilizers, softeners, substances for skincare, permeation enhancers, i.e. substances which influence the barrier properties of the stratum corneum in the sense of increasing the active agent permeability, pH regulators, and preservatives. Particularly preferred additives are tackifiers and stabilizers. Such additives may be present in the asenapine-containing layer in an amount of from 0.001% to 15% of the matrix layer composition per additive. In a certain embodiment, the total amount of all additives is from 0.001% to 25% of the matrix layer composition. Hereinafter, where a range for an amount of a specific additive is given, such a range refers to the amount per individual additive.

It should be noted that in pharmaceutical formulations, the formulation components are categorized according to their physicochemical and physiological properties, and in accordance with their function. This means in particular that a substance or a compound falling into one category is not excluded from falling into another category of formulation component. E.g. a certain polymer can be a crystallization inhibitor but also a tackifier. Some substances may e.g. be a typical softener but at the same time act as a permeation enhancer. The skilled person is able to determine based on his general knowledge in which category or categories of formulation component a certain substance or compound belongs to. In the following, details on the excipients and additives are provided which are, however, not to be understood as being exclusive. Other substances not explicitly listed in the present description may be as well used in accordance with the present invention, and substances and/or compounds explicitly listed for one category of formulation component are not excluded from being used as another formulation component in the sense of the present invention.

The cross-linking agent may be selected from the group consisting of aluminium and titanium cross-linking agents such as aluminium acetylacetonate, titanium acetylacetonate or polybutyltitanate, and preferably is a titanium cross-linking agent. The amount of cross-linking agent may range from 0.005 to 1%, and preferably from 0.01 to 0.1% of the matrix layer composition. The matrix layer composition may also comprise a polymer which is self-crosslinking, i.e. comprises a cross-linking functional group such as glycidyl groups, which reacts upon heating. According to a further specific embodiment, the matrix layer composition comprises a cross-linking agent as above and a self-crosslinking polymer.

In one embodiment, the matrix layer composition further comprises a solubilizer. The solubilizer preferably improves the solubility of the asenapine in the asenapine-containing layer. Preferred solubilizers include, e.g., glycerol-, polyglycerol-, propylene glycol- and polyoxyethylene-esters of medium chain and/or long chain fatty acids, such as glyceryl mono linoleate, medium chain glycerides and medium chain triglycerides, non-ionic solubilizers made by reacting castor oil with ethylene oxide, and any mixtures thereof which may further contain fatty acids or fatty alcohols; cellulose and methylcellulose and derivatives thereof such as hydroxypropylcellulose and hypromellose acetate succinate; various cyclodextrins and derivatives thereof; non-ionic tri-block copolymers having a central hydrophobic chain of polyoxypropylene flanked by two hydrophilic chains of polyoxyethylene known as poloxamers; a polyethylene glycol, polyvinyl acetate and polyvinylcaprolactame-based graft copolymer, also abbreviated as PVAc-PVCap-PEG and known as Soluplus®; purified grades of naturally derived castor oil, of polyethylene glycol 400, of polyoxyethylene sorbitan monooleate (such as polysorbate 80) or of propylene glycols; diethylene glycol monoethyl ether; as well as any of the below mentioned soluble polyvinylpyrrolidones but also insoluble/cross-linked polyvinylpyrrolidones also known as crospovidones such as Kollidon® CL, Kollidon® CL-M and Kollidon® CL-SF, and polyvinylpyrrolidone-polyvinyl acetate copolymers, also known as copovidones, such as Kollidon® VA64.

However, also the permeation enhancers mentioned below can act as solubilizers. Furthermore, also crystallization inhibitors may act as solubilizers.

Fillers such as silica gels, titanium dioxide and zinc oxide may be used in conjunction with the polymer in order to influence certain physical parameters, such as cohesion and bond strength, in the desired way.

In case the matrix layer is required to have self-adhesive properties and one or more polymers is/are selected which does/do not provide sufficient self-adhesive properties, a tackifier is added. The tackifier may be selected from triglycerides, polyethylene glycols, dipropylene glycol, resins, resin esters, terpenes and derivatives thereof, ethylene vinyl acetate adhesives, dimethylpolysiloxanes and polybutenes, and mixtures thereof. In certain embodiments, the matrix layer composition comprises a tackifier in an amount of from 5 to 15% of the matrix layer composition.

In certain embodiments, the matrix layer composition comprises medium chain triglycerides. Such medium chain triglycerides are included as a tackifier and provide for improved adhesion of the matrix layer to the skin. In certain embodiments, a sufficient amount of medium chain triglycerides can be added to asenapine-containing matrix layer compositions comprising acrylic polymers without impairing the skin permeation performance.

In such embodiments, the matrix layer composition may comprise medium chain triglycerides in an amount of from 0.1 to 14% of the matrix layer composition, preferably from 1 to 13% of the matrix layer composition, more preferably from 3 to 12% of the matrix layer composition, even more preferably from 5 to 12% of the matrix layer composition, and most preferably in an amount of about 10% of the matrix layer composition. In terms of adhesion, high amounts of medium chain triglycerides are preferable, but the cohesive properties may become insufficient at too high concentrations.

Medium chain triglycerides are esters derived from glycerol and three medium chain fatty acids. The properties of triglycerides depend on the fatty acid composition, i.e. the composition based on all fatty acid-derived moieties present in the medium chain triglycerides (which means that the fatty acid composition of 3 molecules of triglycerides based on one octanoid acid, one decanoic acid and one dodecanoic acid each is the same as the fatty acid composition of a mixture of a first triglyceride based only on octanoic acid, a second triglyceride based only on decanoic acid, and a third triglyceride based only on dodecanoic acid).

In certain embodiments, the fatty acid composition of the medium chain triglycerides consists of one or more of
 (i) Hexanoic acid,
 (ii) Octanoic acid,
 (iii) Decanoic acid,
 (iv) Dodecanoic acid, and
 (v) Tetradecanoic acid.

In certain preferred embodiments, the fatty acid composition of the medium chain triglycerides consists of
 (i) 0 to 5% hexanoic acid,
 (ii) 40.0 to 90.0% octanoic acid,
 (iii) 10.0 to 55.0% decanoic acid,
 (iv) 0 to 5% dodecanoic acid, and
 (v) 0 to 2% tetradecanoic acid.

Preferably, the fatty acid composition of the medium chain triglycerides consists of
 (i) 0 to 2% hexanoic acid,
 (ii) 50.0 to 80.0% octanoic acid,
 (iii) 20.0 to 45.0% decanoic acid,
 (iv) 0 to 2% dodecanoic acid, and
 (v) 0 to 1% tetradecanoic acid.

In certain of the above embodiments, the fatty acid composition of the medium chain triglycerides consists of
 (i) 0 to 2% hexanoic acid,
 (ii) 50.0 to 65.0% octanoic acid,
 (iii) 30.0 to 45.0% decanoic acid, (iv) 0 to 2% dodecanoic acid, and
(v) 0 to 1% tetradecanoic acid, In certain other of the above embodiments, the fatty acid composition of the medium chain triglycerides consists of
(i) 0 to 2% hexanoic acid,
(ii) 65.0 to 80.0% octanoic acid,
(iii) 20.0 to 35.0% decanoic acid,
(iv) 0 to 2% dodecanoic acid, and
(v) 0 to 1% tetradecanoic acid.

The medium chain triglycerides further may present certain acid values, peroxide values and/or hydroxyl values.

I.e., in certain embodiments, the acid value of the medium chain triglycerides is 0.5 mg KOH/g or less, preferably 0.2 mg KOH/g or less and most preferably 0.1 mg KOH/g or less.

In certain other embodiments, the peroxide value of the medium chain triglycerides is 5.0 mequi O/kg or less, preferably 2.0 mequi O/kg or less and most preferably 1.0 mequi O/kg or less.

In yet other embodiments, the hydroxyl value of the medium chain triglycerides is 10 mg KOH/g or less, preferably 8.0 mg KOH/g or less and most preferably 5.0 mg KOH/g or less.

In one embodiment, the matrix layer composition further comprises a softener/plasticizer. Exemplary softeners/plasticizers include linear or branched, saturated or unsaturated alcohols having 6 to 20 carbon atoms, triglycerides and polyethylene glycols.

In certain embodiments, the matrix layer composition comprises a permeation enhancer selected from diethylene glycol monoethyl ether, diisopropyl adipate, isopropyl myristate, isopropyl palmitate, lauryl lactate, dimethylpropylene urea and a mixture of propylene glycol monoesters and diesters of fatty acids. Such a mixture of propylene glycol monoesters and diesters of fatty acids is commercially available e.g. under the brand name Capryol, which is a propylene glycol monocaprylate (type II), a mixture of propylene glycol monoesters and diesters of fatty acids with a ratio of >90% monoesters and <10% diesters, wherein the fatty acids mainly consist of caprylic acid.

In certain other embodiments, the matrix layer composition does not comprise a permeation enhancer selected from oleic acids, oleic alcohols, and mixtures thereof, and in particular the matrix layer composition does not comprise a permeation enhancer at all. In another embodiment, the matrix layer composition does not comprise sodium acetate or sodium diacetate. In yet another embodiment, the asenapine-containing layer does not comprise a dicarboxylic acid alkali salt. In yet another embodiment, the matrix layer composition does not comprise a maleic acid alkali salt.

The matrix layer composition according to the invention may comprise a pH regulator. Preferably, the pH regulator is selected from amine derivatives, inorganic alkali derivatives, polymers with basic and acidic functionality, respectively.

Release Characteristics

The TTS in accordance with the invention are designed for transdermally administering asenapine to the systemic circulation for a predefined extended period of time.

In one aspect, the TTS according to the invention provide a mean release rate of 0.5 to 20 mg/day, 0.5 to 20 mg/24 h, 500 to 20,000 µg/day, 500 to 20,000 µg/24 h, 0.021 to 0.833 mg/h or 21 to 833 µg/h, preferably of 1.0 to 15 mg/day, 1.0 to 15 mg/24 h, 1,000 to 15,000 µg/day, 1,000 to 15,000 µg/24 h, 0.042 to 0.625 mg/h or 42 to 625 µg/h, and more preferably of 2.0 to 10 mg/day, 2.0 to 10 mg/24 h, 2,000 to 10,000 µg/day, 2,000 to 10,000 µg/24 h, 0.083 to 0.417 mg/h or 83 to 417 µg/h over at least 24 hours of administration, preferably over at least 48 hours of administration, more preferably over at least 72 hours of administration, and most preferably over at least 84 hours of administration.

According to certain embodiments, the TTS according to the invention provide a cumulative skin permeation rate of asenapine at hour 48 or at hour 72 as measured in a Franz diffusion cell with dermatomed human skin of 1 µg/(cm$^2$ h) to 20 µg/(cm$^2$ h), preferably of 2 µg/(cm$^2$ h) to 15 µg/(cm$^2$ h) and more preferably of 4 µg/(cm$^2$ h) to 12 µg/(cm$^2$ h).

In specific embodiments of the invention, the TTS according to the invention as described above provides a skin permeation rate of asenapine as measured in a Franz diffusion cell with dermatomed human skin of
0 µg/(cm$^2$ h) to 10 µg/(cm$^2$ h) in the first 8 hours,
2 µg/(cm$^2$ h) to 20 µg/(cm$^2$ h) from hour 8 to hour 24,
3 µg/(cm$^2$ h) to 20 µg/(cm$^2$ h) from hour 24 to hour 32,
3 µg/(cm$^2$ h) to 20 µg/(cm$^2$ h) from hour 32 to hour 48,
2 µg/(cm$^2$ h) to 15 µg/(cm$^2$ h) from hour 48 to hour 72.

In certain embodiments, the transdermal therapeutic system according to the invention provides a cumulative permeated amount of asenapine as measured in a Franz diffusion cell with dermatomed human skin of 0.05 mg/cm$^2$ to 1.0 mg/cm$^2$, preferably of 0.1 mg/cm$^2$ to 0.7 mg/cm$^2$ over a time period of 48 hours.

In certain embodiments, the transdermal therapeutic system according to the invention provides a cumulative permeated amount of asenapine as measured in a Franz diffusion cell with dermatomed human skin of 0.1 mg/cm$^2$ to 2.0 mg/cm$^2$, preferably 0.2 mg/cm$^2$ to 1.0 mg/cm$^2$ over a time period of 72 hours.

Method of Treatment/Medical Use

In accordance with a specific aspect of the present invention, the TTS according to the invention is for use in a method of treatment, and in particular in a method of treating a human patient.

In certain embodiments, the TTS according to the invention is preferably for use in a method of treating psychosis, and more preferably for use in a method of treating one or more conditions selected from schizophrenia, bipolar disorder, posttraumatic stress disorder, major depressive disorder, dementia related psychosis, agitation and manic disorder, in particular for use in a method of treating schizophrenia and/or bipolar disorder in a human patient, and in particular for use in a method of treating acute manic or mixed episodes of bipolar disorder in a human patient.

In certain embodiments, the TTS according to the invention is for use in a method of treating acute manic or mixed episodes of bipolar disorder in an adult or a pediatric patient 10 to 17 years of age. In certain embodiments, the TTS according to the invention is for use as an adjunctive treatment to lithium or valproate in a method of treating bipolar disorder in a human patient, in particular an adult. In certain embodiments, the TTS according to the invention is for use as a maintenance monotherapy treatment in a method of treating bipolar disorder in a human patient, in particular an adult.

The TTS may be further for use in a method of treatment with a dosing interval of at least 24 hours or 1 day, at least 48 hours or 2 days, or at least 72 hours or 3 days, and/or with a dosing interval of up to 168 hours or 7 days, up to 120 hours or 5 days, or up to 96 hours or 4 days. The dosing interval may in particular be 24 hours or 1 day, 48 hours or 2 days, or 84 hours or 3.5 days.

Accordingly the invention is also related to TTS for use in a method of treatment, and in particular for use in a method of treating schizophrenia and/or bipolar disorder, and in particular acute manic or mixed episodes of bipolar disorder, in an around-the-clock treatment with a once-a-day TTS exchange mode (dosing interval of 24 hours or 1 day), a twice-a-week TTS exchange mode (dosing interval of 84 hours or 3.5 days) or a once-a-week TTS exchange mode (dosing interval of 168 hours, or 7 days).

The TTS according to the invention is further preferably for use in a method of treating a patient, wherein the transdermal therapeutic system provides a reduction in at least one asenapine-related side effect relative to an equivalent dose of sublingual asenapine.

Relative to an equivalent dose of sublingual asenapine should be understood as a comparison in the incidence and intensity of side effects in a clinical study when using a dose of transdermal and sublingual asenapine that leads substantially to the same blood plasma exposure of asenapine.

In another embodiment, the TTS according to the invention may also be for use in a method of reducing, in a patient, at least one asenapine-related side effect relative to an equivalent dose of sublingual asenapine.

In such a method of treating a patient or in such a method of reducing at least one asenapine-related side effect, but also in all the transdermal therapeutic systems for use in a method of treatment, the transdermal therapeutic systems for use in a method of reducing at least one asenapine-related side effect as well as the methods of treatment and methods of reducing at least one asenapine-related side effect, the following may generally further apply:

(i) The at least one asenapine-related side effect is in particular fatigue, somnolence, dizziness, oral hypoaesthesia, or any combination thereof.

(ii) As these side effects are reduced, in one embodiment, the inventive methods and transdermal therapeutic systems for use in the methods are in particular suitable for a human patient already suffering from such a condition, i.e. suffering from fatigue, somnolence, dizziness, or any combination thereof.

(iii) Further, the incidence of the at least one asenapine-related side effect relative to an equivalent dose of sublingual asenapine may be reduced by at least about 30%, at least about 40%, at least about 70% or at least about 80%, and/or the intensity of the at least one asenapine-related side effect relative to an equivalent dose of sublingual asenapine may be reduced. The intensity of a side effect can be determined e.g. by classifying the side effects on a scale indicating "mild", "moderate" or "severe" intensity, and a reduction of the intensity can be quantified by comparing the median intensity.

(iv) In such embodiments, the at least one asenapine-related side effect may be fatigue and the incidence of fatigue relative to an equivalent dose of sublingual asenapine may be reduced by at least about 30% or at least about 40% and/or the intensity of fatigue relative to an equivalent dose of sublingual asenapine may be reduced.

(v) alternatively, the at least one asenapine-related side effect may be dizziness, and the incidence of dizziness relative to an equivalent dose of sublingual asenapine may be reduced by at least about 30%, at least about 40%, at least about 70% or at least about 80%.

As concerns the type of side effects, it should be noted that fatigue and somnolence, while designating clinically different conditions, have common and/or similar symptoms and may be therefore difficult to distinguish, in particular if not followed on a long term.

In accordance with another specific aspect, the present invention is also related to a method of treatment, and in particular a method of treating a human patient.

The invention is in particular related to a method of treating psychosis, and in particular to a method of treating one or more conditions selected from schizophrenia, bipolar disorder, posttraumatic stress disorder, major depressive disorder, dementia related psychosis, agitation and manic disorder, and preferably to a method of treating schizophrenia and/or bipolar disorder in a human patient, and in particular acute manic or mixed episodes of bipolar disorder including applying a transdermal therapeutic system according to the invention to the skin of a human patient.

In certain embodiments, the invention is also related to a method of treating acute manic or mixed episodes of bipolar disorder in an adult or a pediatric patient 10 to 17 years of age. In certain embodiments, the invention is also related to a method of treating bipolar disorder in a human patient, in particular an adult, as an adjunctive treatment to lithium or valproate. In certain embodiments, the invention is also related to a maintenance monotherapy treatment in a method of treating bipolar disorder in a human patient, in particular an adult.

The invention is also related to a method of treatment by applying a transdermal therapeutic system according to the invention for at least 24 hours or 1 day, at least 48 hours or 2 days, or at least 72 hours or 3 days, and/or for up to 168 hours or 7 days, up to 120 hours or 5 days, or up to 96 hours or 4 days to the skin of a human patient. The transdermal therapeutic system according to the invention may in particular be applied for 24 hours or 1 day, 48 hours or 2 days, or 84 hours or 3.5 days to the skin of a human patient.

Accordingly the invention is also related to a method of treatment in an around-the-clock treatment with a once-a-day TTS exchange mode (dosing interval of 24 hours or 1 day), a twice-a-week TTS exchange mode (dosing interval of 84 hours or 3.5 days) or a once-a-week TTS exchange mode (dosing interval of 168 hours, or 7 days).

In such a method, as previously outlined, the transdermal therapeutic system may provide a reduction in at least one asenapine-related side effect relative to an equivalent dose of sublingual asenapine.

In another embodiment, the present invention is also related to a method of reducing, in a patient, at least one asenapine-related side effect relative to an equivalent dose of sublingual asenapine, the method comprising administering a transdermal therapeutic system according to the invention.

The invention is also related to a method of reducing at least one asenapine-related side effect in a patient being treated with sublingual asenapine therapy, the method comprising
  a) discontinuing sublingual asenapine therapy; and
  b) administering a transdermal therapeutic system according to the invention to the skin of the patient, wherein the transdermal therapeutic system provides a reduction in at least one asenapine-related side effect relative to an equivalent dose of sublingual asenapine.

In such a method, the transdermal therapeutic system may deliver an amount of asenapine equivalent to the amount of asenapine originally provided by the sublingual asenapine therapy.

The relatively constant asenapine blood plasma concentration can be described by several pharmacokinetic parameters as obtained in an in vivo clinical study on human subjects.

Thus, in certain embodiments, the transdermal therapeutic system of the present invention:

provides by transdermal delivery a mean release rate of 0.5 to 20 mg/day, 0.5 to 20 mg/24 h, 500 to 20,000 µg/day, 500 to 20,000 µg/24 h, 0.021 to 0.833 mg/h or 21 to 833 µg/h, preferably 1.0 to 15 mg/day, 1.0 to 15 mg/24 h, 1,000 to 15,000 µg/day, 1,000 to 15,000 µg/24 h, 0.042 to 0.625 mg/h or 42 to 625 µg/h, more preferably of 2.0 to 10 mg/day, 2.0 to 10 mg/24 h, 2,000 to 10,000 µg/day, 2,000 to 10,000 µg/24 h, 0.083 to 0.417 mg/h or 83 to 417 µg/h over at least 48 hours or 2 days of administration, or provides by transdermal delivery a mean release rate of 0.5 to 20 mg/day, 0.5 to 20 mg/24 h, 500 to 20,000 µg/day, 500 to 20,000 µg/24 h, 0.021 to 0.833 mg/h or 21 to 833 µg/h, preferably 1.0 to 15 mg/day, 1.0 to 15 mg/24 h, 1,000 to 15,000 µg/day, 1,000 to 15,000 µg/24 h, 0.042 to 0.625 mg/h or 42 to 625 µg/h, more preferably of 2.0 to 10 mg/day, 2.0 to 10 mg/24 h, 2,000 to 10,000 µg/day, 2,000 to 10,000 µg/24 h, 0.083 to 0.417 mg/h or 83 to 417 µg/h over at least 72 hours or 3 days of administration, or provides by transdermal delivery a mean release rate of 0.5 to 20 mg/day, 0.5 to 20 mg/24 h, 500 to 20,000 µg/day, 500 to 20,000 µg/24 h, 0.021 to 0.833 mg/h or 21 to 833 µg/h, preferably 1.0 to 15 mg/day, 1.0 to 15 mg/24 h, 1,000 to 15,000 µg/day, 1,000 to 15,000 µg/24 h, 0.042 to 0.625 mg/h or 42 to 625 µg/h, more preferably of 2.0 to 10 mg/day, 2.0 to 10 mg/24 h, 2,000 to 10,000 µg/day, 2,000 to 10,000 µg/24 h, 0.083 to 0.417 mg/h or 83 to 417 µg/h over at least 84 hours or 3.5 days of administration.

Further, in certain embodiments, the transdermal therapeutic system of the present invention:

provides by transdermal delivery an $AUC_{0-48}$ from 20 to 300 (ng/ml) h or from more than 300 to 450 (ng/ml) h and preferably from 30 to 200 (ng/ml) h, or provides by transdermal delivery an $AUC_{0-72}$ from 30 to 400 (ng/ml) h or from more than 400 to 600 (ng/ml) h and preferably from 50 to 300 (ng/ml) h, or provides by transdermal delivery an $AUC_{0-84}$ from 35 to 450 (ng/ml) h or from more than 450 to 700 (ng/ml) h and preferably from 60 to 350 (ng/ml) h.

Still further, in certain embodiments, the transdermal therapeutic system of the present invention:

provides by transdermal delivery a $C_{max}$ to $C_{48}$ ratio of less than 2.0, preferably of less than 1.5 and more preferably of less than 1.3, or provides by transdermal delivery a $C_{max}$ to $C_{72}$ ratio of less than 3.0, preferably of less than 2.5 and more preferably of less than 2.0, or provides by transdermal delivery a $C_{max}$ to $C_{84}$ ratio of less than 3.5, preferably of less than 3.0, more preferably of less than 2.5 and most preferably of less than 2.0.

Still further, in certain embodiments, the transdermal therapeutic system of the present invention:

provides by transdermal delivery a $C_{max}$ value of from 0.5 to 10 ng/ml and preferably of from 1 to 8 ng/ml.

In all such embodiments, as previously described, the TTS may be for use in a method of treating a human patient, wherein the transdermal therapeutic system provides a reduction in at least one asenapine-related side effect relative to an equivalent dose of sublingual asenapine.

Process of Manufacture

The invention further relates to a process of manufacture of a matrix layer for use in a transdermal therapeutic system and a corresponding matrix layer structure and a corresponding TTS.

In accordance with the invention, the process of manufacture of a matrix layer for use in a transdermal therapeutic system comprises the steps of:

1) combining at least the components asenapine, acrylic polymer, additional polymer, α-tocopherol and ascorbyl palmitate, in a solvent to obtain a coating composition;
2) coating the coating composition onto a backing layer or a release liner or any intermediate liner; and
3) drying the coated coating composition to form the matrix layer.

In certain embodiments, in step 1), at least the components asenapine, acrylic polymer, additional polymer, α-tocopherol, ascorbyl palmitate and sodium metabisulfite are combined in a solvent to obtain the coating composition.

In this process of manufacture, preferably in step 1) the asenapine is dissolved to obtain a coating composition.

In the above described process preferably the solvent is selected from alcoholic solvents, in particular methanol, ethanol, isopropanol and mixtures thereof, and from non-alcoholic solvents, in particular ethyl acetate, hexane, n-heptane, heptanes, petroleum ether, toluene, and mixtures thereof, and more preferably is selected from ethanol and ethyl acetate.

In certain embodiments, the polymer in the above process is an acrylic polymer and preferably a copolymer based on vinyl acetate, 2-ethylhexyl-acrylate, 2-hydroxyethyl-acrylate and glycidyl-methacrylate or a copolymer based on vinyl acetate, 2-ethylhexyl-acrylate and 2-hydroxyethyl-acrylate, which is provided as a solution and preferably as a solution in ethyl acetate, n-heptane, heptanes, methanol, ethanol or any mixture thereof with a solids content of from 30 to 60% by weight.

In certain preferred embodiments, the polymer is an acrylic polymer and the polymer is cross-linked. As outlined in detail above, commercially available acrylic polymers may be provided as a solution with or without a cross-linking agent. In addition, an additional cross-linking agent (i.e. a cross-linking agent which does not come with the polymer) can be added in step 1) of the process of manufacture.

Thus, in certain embodiments, an additional cross-linking agent is used in step 1) to obtain the coating composition, wherein the cross-linking agent preferably is an aluminium or a titanium cross-linking agent. In alternative embodiments, no additional cross-linking agent is used in step 1) to obtain the coating composition.

If a polymer solution with cross-linking agent is used and/or if an additional cross-linking agent is used in step 1), the polymer is cross-linked. In alternative embodiments, the polymer is an acrylic polymer and the polymer is not cross-linked.

In step 3), drying is performed preferably in one or more cycles at room temperature and/or at a temperature of from 65 to 100° C., more preferably from 70 to 90° C.

EXAMPLES

The present invention will now be more fully described with reference to the accompanying examples. It should be understood, however, that the following description is illustrative only and should not be taken in any way as a restriction of the invention. Numerical values provided in the examples regarding the amount of ingredients in the composition or the area weight may vary slightly due to manufacturing variability.

Reference Examples 1A-C

Coating Composition

The formulations of the asenapine-containing coating compositions of Reference Examples 1a to 1c are summarized in Table 1.1 below. The formulations are based on weight percent, as also indicated in Table 1.1.

TABLE 1.1

| Ingredient (Trade Name) | Ref. Ex. 1a Amt [g] | Ref. Ex. 1a Solids [%] | Ref. Ex. 1b Amt [g] | Ref. Ex. 1b Solids [%] | Ref. Ex. 1c Amt [g] | Ref. Ex. 1c Solids [%] |
|---|---|---|---|---|---|---|
| Asenapine base | 1.00 | 9.9 | 15.0 | 10.0 | 15.0 | 10.0 |
| Acrylic adhesive in ethyl acetate, ethanol, heptanes and methanol, with a titanium cross-linking agent. Solids content of about 42.5% (Ref. Ex. 1a) or 41.5% (Ref. Ex. 1b and 1c) by weight (Duro-Tak ™ 387-2516) | 16.5 | 69.7 | 287.7 | 79.5 | 287.7 | 79.5 |
| Polyvinylpyrrolidone (Povidone K90F) | — | — | 15.0 | 10.0 | 15.0 | 10.0 |
| Polyvinylpyrrolidone (Povidone K30) | 1.00 | 9.9 | — | — | — | — |
| α-Tocopherol | 0.05 | 0.50 | 0.76 | 0.50 | 0.76 | 0.50 |
| Medium chain triglycerides (Miglyol 812 N) | 1.01 | 10.00 | — | — | — | — |
| Ethanol denat. (1% (v/v) methyl ethyl ketone) | 4.72 | — | 43.5 | — | 43.5 | — |
| Total | 24.3 | 100.0 | 361.9 | 100.0 | 361.9 | 100.0 |
| Area weight [g/m$^2$] | 136.8 | | 151.5 | | 222.6 | |
| Asenapine content [mg/cm$^2$] | 1.357 | | 1.514 | | 2.224 | |

Preparation of the Coating Composition

For Reference Example 1a, a stainless steel vessel was loaded with the α-tocopherol. The medium chain triglycerides, the acrylic pressure sensitive adhesive Duro-Tak™ 387-2516 and the polyvinylpyrrolidone was added and the mixture was then stirred until a clear solution was obtained (about 40 min). The asenapine was added slowly and dissolved under stirring until a clear solution was obtained.

For Reference Examples 1b and 1c, a beaker was loaded with the α-tocopherol, the asenapine and the ethanol. The acrylic pressure sensitive adhesive Duro-Tak™ 387-2516 was added and the mixture was then stirred until a clear solution was obtained (about 10 min). The polyvinylpyrrolidone was added slowly while stirring and dissolved under stirring until a clear solution was obtained.

Coating of the Coating Composition of Reference Examples 1a and 1b

The resulting asenapine-containing coating composition was coated on a polyethylene terephthalate film (one side siliconized, 75 μm thickness, which may function as release liner) and dried for approx. 10 min at room temperature and 20 min. at 80° C. The coating thickness gave an area weight of 136.8 g/m$^2$ (Ref. Ex. 1a) and 151.5 (Ref. Ex. 1b), respectively. The dried film was laminated with a polyethylene terephthalate backing layer (23 μm thickness) to provide an asenapine-containing self-adhesive layer structure.

Coating of the Coating Composition, Reference Example 1c

The resulting asenapine-containing coating composition was coated on a polyethylene terephthalate film (siliconized, 100 μm thickness, which may function as release liner) and dried for approx. 10 min at room temperature and 20 min at 80° C. The coating thickness gave an area weight of the matrix layer of 111.3 g/m$^2$. A first part of the dried film was laminated with a polyethylene terephthalate backing layer (23 μm thickness). The polyethylene terephthalate film (siliconized, 100 mm thickness, which may function as a release liner) of this first part was then removed and the adhesive site of the first part was laminated on the adhesive site of a second, unmodified part of the dried film (comprising a release liner but not a backing layer). This results in an asenapine-containing self-adhesive layer structure with an area weight of the matrix layer of 222.6 g/m$^2$, with a backing layer and a release liner.

Preparation of the TTS (Concerning all Examples)

The individual systems (TTS) were then punched out from the asenapine-containing self-adhesive layer structure. In specific embodiments, a TTS as described above can be provided with a further self-adhesive layer of larger surface area, preferably with rounded corners, comprising a pressure-sensitive adhesive matrix layer which is free of active agent. This is of advantage when the TTS, on the basis of its physical properties alone, does not adhere sufficiently to the skin and/or when the asenapine-containing matrix layer, for the purpose of avoiding waste, has pronounced corners (square or rectangular shapes). The TTS are then punched out and sealed into pouches of the primary packaging material as conventional in the art, i.e. under protective atmosphere, by flushing with nitrogen gas.

Measurement of Skin Permeation Rate

The permeated amount and the corresponding skin permeation rates of TTS prepared according to Example 1a as well as Reference Examples 1b and 1c were determined by in vitro experiments in accordance with the OECD Guideline (adopted Apr. 13, 2004) carried out with a 7.0 ml Franz diffusion cell. Split thickness human skin from cosmetic surgeries (female abdomen, date of birth 1955) was used. A dermatome was used to prepare skin to a thickness of 800 μm, with an intact epidermis for all TTS. Diecuts with an area of 1.151 cm$^2$ were punched from the TTS. The asenapine permeated amount in the receptor medium of the Franz cell (phosphate buffer solution pH 5.5 with 0.1% saline azide as antibacteriological agent) at a temperature of 32±1° C. was measured and the corresponding skin permeation rate calculated. The results are shown in Table 1.2 and FIG. 1a.

TABLE 1.2

Skin permeation rate with SD [μg/(cm$^2$ h)]

| Elapsed time [h] | Ref. Ex. 1a (n = 3) Rate | Ref. Ex. 1a (n = 3) SD | Ref. Ex. 1b (n = 2) Rate | Ref. Ex. 1b (n = 2) SD | Ref. Ex. 1c (n = 3) Rate | Ref. Ex. 1c (n = 3) SD |
|---|---|---|---|---|---|---|
| 2 | 0.00 | 0.00 | 0.00 | 0.00 | 0.00 | 0.00 |
| 4 | 0.23 | 0.03 | 0.20 | 0.20 | 0.27 | 0.07 |
| 8 | 1.40 | 0.17 | 1.41 | 0.58 | 1.25 | 0.13 |
| 12 | 4.03 | 0.50 | 4.24 | 1.18 | 3.44 | 0.08 |
| 16 | 6.62 | 0.70 | 6.79 | 1.58 | 5.95 | 0.14 |
| 20 | 8.42 | 0.79 | 8.73 | 1.53 | 8.02 | 0.14 |
| 24 | 9.72 | 0.67 | 9.74 | 1.51 | 9.45 | 0.15 |
| 32 | 8.96 | 0.71 | 9.29 | 0.90 | 9.15 | 0.21 |
| 40 | 10.15 | 0.53 | 11.12 | 0.37 | 10.84 | 0.30 |

TABLE 1.2-continued

| | Skin permeation rate with SD [µg/(cm² h)] | | | | | |
|---|---|---|---|---|---|---|
| | Ref. Ex. 1a (n = 3) | | Ref. Ex. 1b (n = 2) | | Ref. Ex. 1c (n = 3) | |
| Elapsed time [h] | Rate | SD | Rate | SD | Rate | SD |
| 48 | 10.07 | 0.35 | 10.50 | 0.11 | 11.10 | 1.07 |
| 56 | 9.51 | 0.25 | 10.12 | 0.05 | 10.49 | 0.35 |
| 64 | 9.14 | 0.17 | 9.88 | 0.04 | 10.27 | 0.41 |
| 72 | 8.76 | 0.38 | 9.47 | 0.23 | 10.75 | 1.11 |

*: Standard deviation in this Example was, as in all other Examples, calculated based on the n-method.

Utilization of Asenapine

Figure 1B:
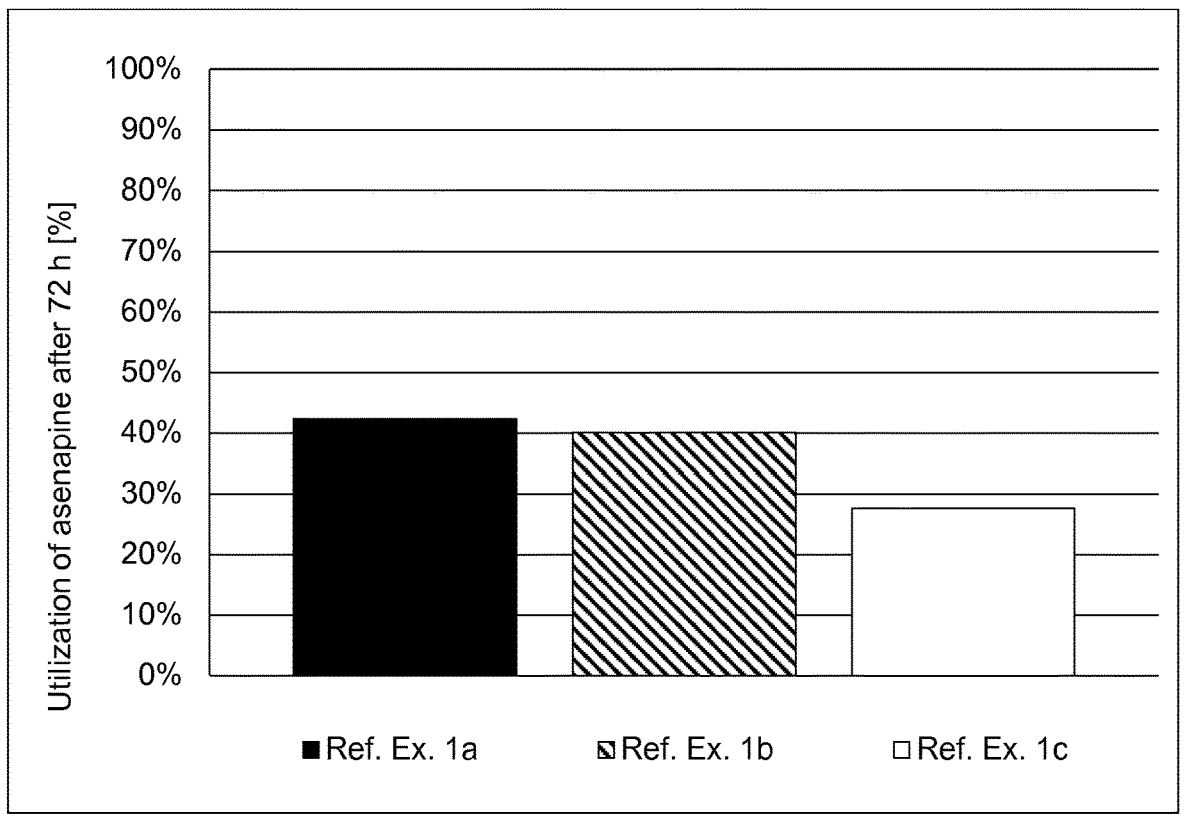
FIG. 1b depicts the utilization of asenapine of TTS prepared according to Reference Examples 1a to 1c after 72 hours.

The utilization of asenapine at 72 hours was calculated based on the cumulative permeated amount at 72 hours and the initial asenapine content. The results are shown in Table 1.3 and in FIG. 1b.

TABLE 1.3

| Utilization of asenapine after 72 hours [%] | | |
|---|---|---|
| Ref. Example 1a (n = 3) | Ref. Example 1b (n = 2) | Ref. Example 1c (n = 3) |
| 42.4 | 40.1 | 27.6 |

The in vitro experiments show the good skin permeation rate as well as the utilization of asenapine of the previously developed reference formulations (Ref Ex. 1b and 1c). Ref. Examples 1b and 1c correspond to the formulation of Ref. Example 2d (except that the area weight is higher), for which a successful in vivo clinical study has been conducted (see below).

Examples 2a, 2B and Reference Examples 2C, 2D

Coating Composition

The formulations of the asenapine-containing coating compositions of Examples 2a and 2b as well as Reference Examples 2b and 2d are summarized in Table 2.1 below. The formulations are based on weight percent, as also indicated in Table 2.1.

TABLE 2.1

| Ingredient (Trade Name) | Ex. 2a Amt [g] | Ex. 2a Solids [%] | Ex. 2b Amt [g] | Ex. 2b Solids [%] | Ref. Ex. 2c Amt [g] | Ref. Ex. 2c Solids [%] | Ref. Ex. 2d Amt [g] | Ref. Ex. 2d Solids [%] |
|---|---|---|---|---|---|---|---|---|
| Asenapine base | 30.0 | 10.0 | 1.00 | 10.0 | 54.0 | 6.0 | 135 | 10.0 |
| Acrylic adhesive in ethyl acetate, ethanol, heptanes and methanol, with a titanium cross-linking agent. Solids content of about 42.9% (Ex. 2a), 42.8% (Ex. 2b) or 41.5% (Ref. Ex. 2c and 2d) by weight (Duro-Tak™ 387-2516) | 487.2 | 69.6 | 16.3 | 69.5 | 1820 | 83.5 | 2580 | 79.5 |
| Polyvinylpyrrolidone (Povidone K90F) | 30.0 | 10.0 | — | — | 90.0 | 10.0 | 135 | 10.0 |
| Polyvinylpyrrolidone (Povidone K30) | — | — | 1.00 | 10.0 | — | — | — | — |
| α-Tocopherol | 0.15 | 0.05 | 0.01 | 0.10 | 4.50 | 0.5 | 6.75 | 0.5 |
| Ascorbyl palmitate | 0.60 | 0.20 | 0.02 | 0.21 | — | — | — | — |
| Sodium metabisulfite (30% aq. solution) | 1.12 | 0.11 | 0.04 | 0.12 | — | — | — | — |
| Medium chain triglycerides (Miglyol 812 N) | 30.0 | 10.0 | 1.01 | 10.1 | — | — | — | — |
| Ethanol denat. (1% (v/v) methyl ethyl ketone) | 143.8 | — | 4.74 | — | 211.8 | — | 414.2 | — |
| Total | 722.9 | 100.0 | 24.1 | 100.0 | 2180.3 | 100.0 | 3271.0 | 100.0 |
| Area weight [g/m²] | 140.2-143.8 | | 133.0 | | 140* | | 140* | |
| Asenapine content [mg/cm²] | 1.40-1.44 | | 1.33 | | 0.88 | | 1.47 | |

*Label area weight

Preparation of the Coating Composition

For Example 2a, a beaker was loaded with α-tocopherol. The ascorbyl palmitate, the medium chain triglycerides and the sodium metabisulfite solution were added. The acrylic pressure sensitive adhesive Duro-Tak™ 387-2516 was added and the mixture was then stirred until a clear solution was obtained. The polyvinylpyrrolidone was added slowly while stirring and dissolved under stirring until a clear solution was obtained. About 100 g of the ethanol were added and the resulting solution was stirred. The asenapine was transferred to the beaker and the mixture stirred. The remainder of the ethanol was added and the solution stirred.

For Example 2b, a beaker was loaded with the asenapine. The α-tocopherol, the ascorbyl palmitate, the medium chain triglycerides, the sodium metabisulfite solution, the acrylic pressure sensitive adhesive Duro-Tak™ 387-2516, the polyvinylpyrrolidone and the ethanol were added in this order to the asenapine. The resulting mixture was stirred.

For Reference Examples 2c and 2d, a stainless steel vessel was loaded with α-tocopherol. The acrylic pressure sensitive adhesive Duro-Tak™ 387-2516 was added and the mixture was then stirred until a clear solution was obtained. The polyvinylpyrrolidone was added slowly while stirring and dissolved under stirring until a clear solution was obtained. The asenapine was suspended in the ethanol and transferred to the stainless steel vessel. After addition of the asenapine, the mixture was stirred until a clear, slightly yellow colored solution was obtained.

Coating of the Coating Composition, Examples 2a and 2b

See Reference Example 1a and Reference Example 1b for the coating process. The coating thickness gave an area weight of 133.0 for Example 2b. For Example 2a, different films with an area weight of between 140.2 and 143.8 g/m$^2$ were produced. The dried film was laminated with a polyethylene terephthalate backing layer (23 μm thickness) to provide an asenapine-containing self-adhesive layer structure.

Coating of the Coating Composition of Reference Examples 2c and 2d

The resulting asenapine-containing coating composition was coated on a polyethylene terephthalate film (one side siliconized, 75 μm thickness, which may function as release liner) and dried for approx. 15 min at 80° C. The coating thickness gave an area weight of about 140 g/m$^2$ in accordance with the label requirements (hereinafter, where reference is made to a label value, it is understood that the actual value is within a tolerance of ±7.5% of the label value). The dried film was laminated with a polyethylene terephthalate backing layer (23 μm thickness) to provide an asenapine-containing self-adhesive layer structure. Residual solvents amounts fulfilled the requirement the ICH guideline Q3C (R3), i.e. methanol ≤3,000 ppm, ethanol ≤5,000 ppm, ethyl acetate ≤5,000 ppm and n-heptane ≤5,000 ppm.

Preparation of the TTS

See Example 1 for Examples 2a and 2b. For Reference Examples 2c and 2d, individual systems (TTS) of 10 cm$^2$ (Ref. Ex. 2c) as well as 15 cm$^2$ (Ref. Ex. 2d) were punched out from the asenapine-containing self-adhesive layer structure.

Stability Measurements

Figure 2A:
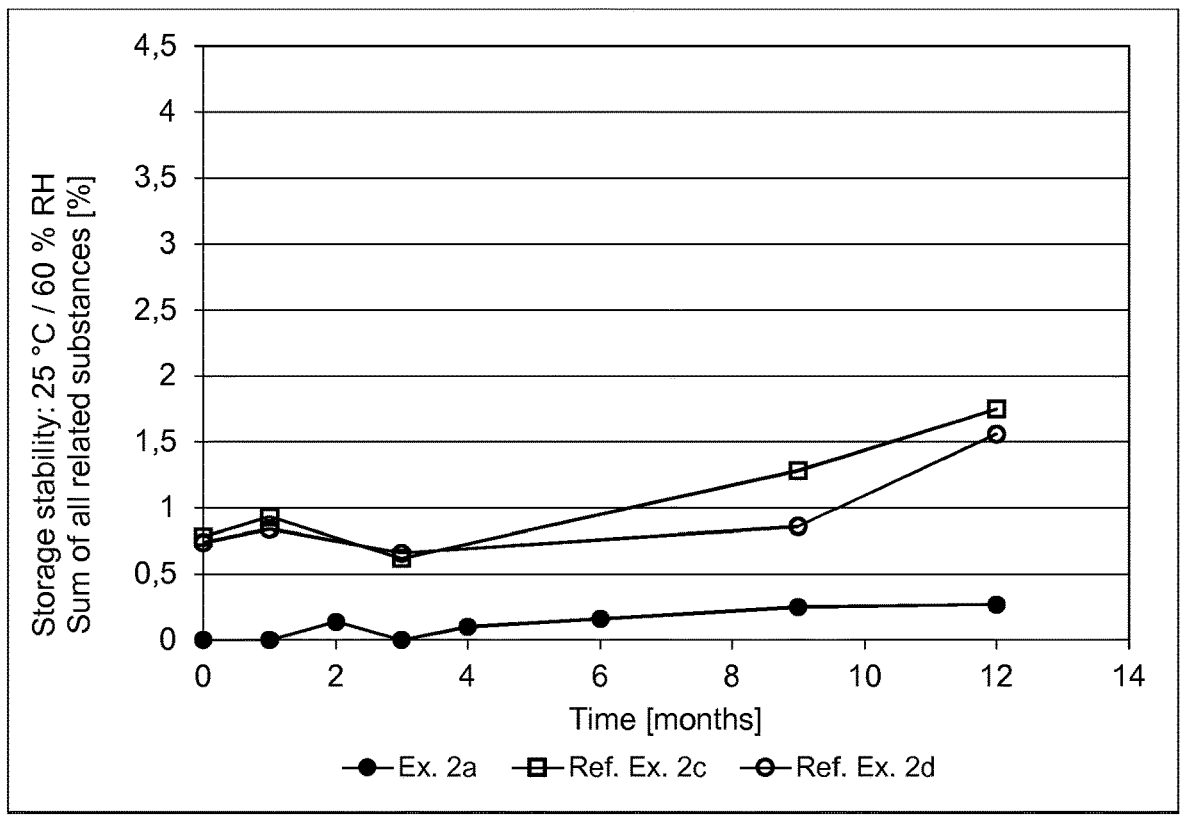
FIG. 2a depicts the sum of all related (i.e. possible degradation product) substances detected in a storage stability test at 25° C. and 60% relative humidity (RH) over 0 to 12 months for TTS prepared according to Example 2a and Reference Examples 2c and 2d.
Figure 2B:
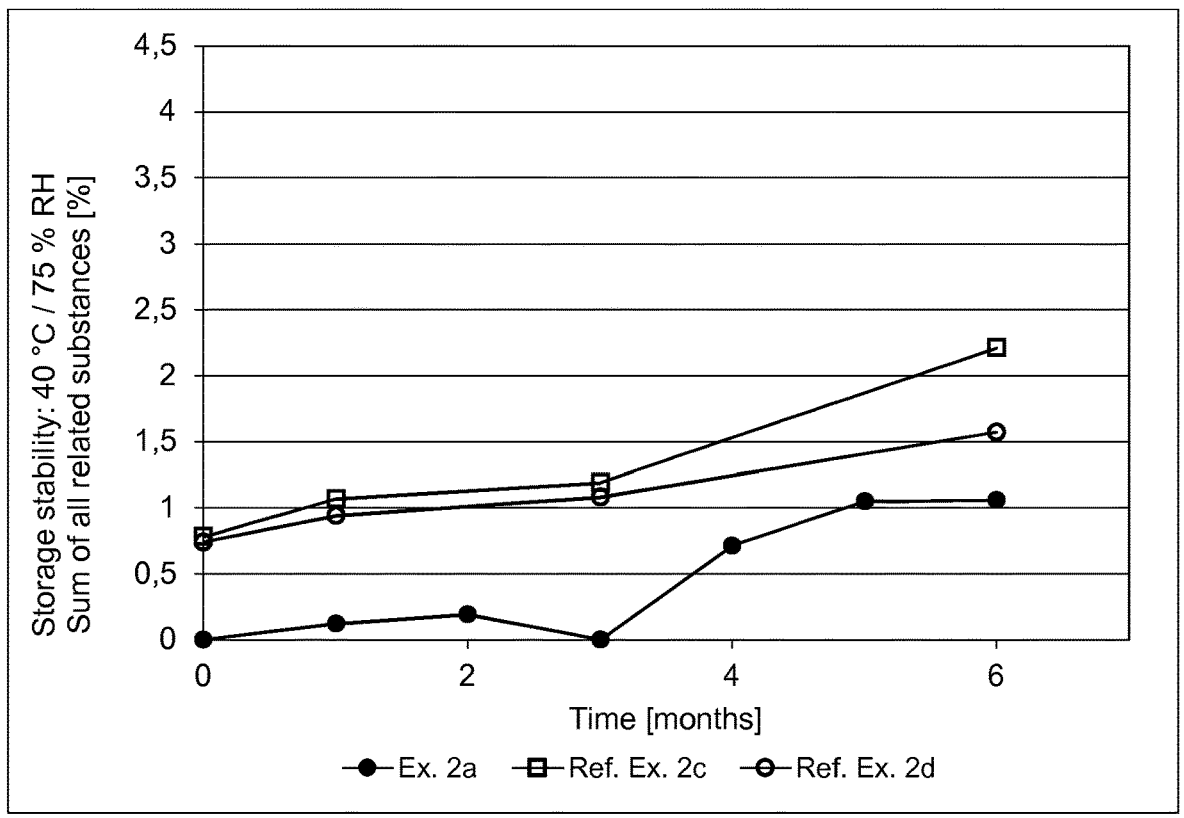
FIG. 2b depicts the sum of all related (i.e. possible degradation product) substances detected in a storage stability test at 40° C. and 75% RH over 0 to 6 months for TTS prepared according to Example 2a and Reference Examples 2c and 2d.

A long term storage stability test was conducted for Examples 2a as well as Reference Examples 2c and 2d under different test conditions, i.e. storage at 25° C. and 60% relative humidity (RH), and at 40° C. and 75% RH. All stability measurements disclosed herein (i.e. concerning all Examples and Reference Examples) were conducted in accordance with the ICH stability guideline Q1A (R2). At different time points, samples were taken from the TTS, extracted with an appropriate extraction solvent and the amount of asenapine base, as well as various possible degradation substances was determined by a specific quantitative HPLC method with a UV photometric detector, based on the asenapine content calculated from the (actual) area weight of the tested TTS. The amount of other related substances is presented in accordance with the ICH stability guideline Q1A (R2) throughout the whole description. The results are shown in Tables 2.2 to 2.7. A plot of the sum of all related (i.e. possible degradation product) substances is shown in FIGS. 2a and 2b.

TABLE 2.2

| Ex. 2a - 25° C./60% RH | Detected amounts [%] | | | | | | | |
|---|---|---|---|---|---|---|---|---|
| | Initial | 1 month | 2 months | 3 months | 4 months | 6 months | 9 months | 12 months |
| Asenapine base | 98 | 96 | 96 | 97 | 97 | 97 | 96 | 95 |
| Asenapine N-Oxide (Cis) | <LOR | <LOR | <LOR | <LOR | n.d. | <LOR | <LOR | 0.11 |
| Asenapine N-Oxide (Trans) | <LOR | <LOR | <LOR | <LOR | n.d. | <LOR | <LOR | <LOR |
| Deschloro Asenapine | n.d. | n.d. | n.d. | n.d. | n.d. | n.d. | n.d. | n.d. |
| Cis-Asenapine | n.d. | n.d. | n.d. | n.d. | n.d. | n.d. | n.d. | n.d. |
| Tetradehydro Asenapine | n.d. | <LOR | 0.14 | n.d. | 0.10 | 0.16 | 0.10 | <LOR |
| Other related substances | n.d. | n.d. | n.d. | n.d. | n.d. | n.d. | 0.15 | 0.16 |
| Sum of all related substances | 0.00 | 0.00 | 0.14 | 0.00 | 0.10 | 0.16 | 0.25 | 0.27 |

* n.d. = not detected, LOR = Limit of Reporting (0.1%)

TABLE 2.3

| Ex. 2a - 40° C./75% RH | Detected amounts [%] | | | | | | |
|---|---|---|---|---|---|---|---|
| | Initial | 1 month | 2 months | 3 months | 4 months | 5 months | 6 months |
| Asenapine base | 98 | 95 | 95 | 95 | 95 | 95 | 94 |
| Asenapine N-Oxide (Cis) | <LOR | <LOR | <LOR | <LOR | 0.26 | 0.42 | 0.36 |
| Asenapine N-Oxide (Trans) | <LOR | <LOR | <LOR | <LOR | 0.24 | 0.37 | 0.32 |
| Deschloro Asenapine | n.d. | n.d. | n.d. | n.d. | n.d. | n.d. | n.d. |
| Cis-Asenapine | n.d. | <LOR | <LOR | n.d. | n.d. | n.d. | n.d. |
| Tetradehydro Asenapine | n.d. | 0.12 | 0.19 | <LOR | 0.21 | 0.26 | 0.26 |
| Other related substances | n.d. | <LOR | <LOR | n.d. | <LOR | <LOR | 0.12 |
| Sum of all related substances | 0.00 | 0.12 | 0.19 | 0.00 | 0.71 | 1.05 | 1.06 |

* n.d. = not detected, LOR = Limit of Reporting (0.1%)

TABLE 2.4

| Ref. Ex. 2c - 25° C./60% RH | Detected amounts [%] | | | | |
|---|---|---|---|---|---|
| | Initial† | 1 month† | 3 months | 9 months | 12 months |
| Asenapine base | 92 | 92 | 94 | 88 | 88 |
| Asenapine N-Oxide (Cis) | 0.38 | 0.45 | 0.18 | 0.51 | 0.67 |
| Asenapine N-Oxide (Trans) | 0.40 | 0.48 | 0.19 | 0.49 | 0.62 |
| Deschloro Asenapine | n.d. | n.d. | n.d. | n.d. | n.d. |
| Cis-Asenapine | n.d. | n.d. | n.d. | n.d. | n.d. |
| Tetradehydro Asenapine | n.d. | n.d. | n.d. | 0.10 | 0.30 |
| Other related substances** | n.d. | n.d. | 0.25 | 0.17 | 0.16 |
| Sum of all related substances | 0.78 | 0.93 | 0.62 | 1.28 | 1.75 |

* n.d. = not detected, LOR = Limit of Reporting (0.1%)
†Due to a systematic error in the HPLC analysis (artefact peaks), the initial and 1 month values are too high and not reliable

TABLE 2.5

| Ref. Ex. 2c - 40° C./75% RH | Detected amounts [%] | | | |
|---|---|---|---|---|
| | Initial† | 1 month† | 3 months | 6 months |
| Asenapine base | 92 | 93 | 93 | 85 |
| Asenapine N-Oxide (Cis) | 0.38 | 0.52 | 0.46 | 0.93 |
| Asenapine N-Oxide (Trans) | 0.40 | 0.55 | 0.46 | 0.87 |
| Deschloro Asenapine | n.d. | n.d. | n.d. | n.d. |
| Cis-Asenapine | n.d. | n.d. | n.d. | n.d. |
| Tetradehydro Asenapine | n.d. | n.d. | 0.10 | 0.23 |
| Other related substances** | n.d. | n.d. | 0.17 | 0.17 |
| Sum of all related substances | 0.78 | 1.07 | 1.19 | 2.21 |

* n.d. = not detected, LOR = Limit of Reporting (0.1%)
†Due to a systematic error in the HPLC analysis (artefact peaks), the initial and 1 month values are too high and not reliable

TABLE 2.7

| Ref. Ex. 2d - 40° C./75% RH | Detected amounts [%] | | | |
|---|---|---|---|---|
| | Initial† | 1 month† | 3 months | 6 months |
| Asenapine base | 96 | 95 | 96 | 90 |
| Asenapine N-Oxide (Cis) | 0.36 | 0.46 | 0.41 | 0.72 |
| Asenapine N-Oxide (Trans) | 0.38 | 0.48 | 0.40 | 0.67 |
| Deschloro Asenapine | n.d. | n.d. | n.d. | n.d. |
| Cis-Asenapine | n.d. | n.d. | n.d. | n.d. |
| Tetradehydro Asenapine | n.d. | n.d. | 0.13 | 0.18 |
| Other related substances | n.d. | n.d. | 0.14 | n.d. |
| Sum of all related substances | 0.74 | 0.94 | 1.08 | 1.57 |

* n.d. = not detected, LOR = Limit of Reporting (0.1%)
†Due to a systematic error in the HPLC analysis (artefact peaks), the initial and 1 month values are too high and not reliable

TABLE 2.6

| Ref. Ex. 2d - 25° C./60% RH | Detected amounts [%] | | | | |
|---|---|---|---|---|---|
| | Initial† | 1 month† | 3 months | 9 months | 12 months |
| Asenapine base | 96 | 98 | 97 | 93 | 93 |
| Asenapine N-Oxide (Cis) | 0.36 | 0.41 | 0.22 | 0.37 | 0.59 |
| Asenapine N-Oxide (Trans) | 0.38 | 0.43 | 0.23 | 0.35 | 0.55 |
| Deschloro Asenapine | n.d. | n.d. | n.d. | n.d. | n.d. |
| Cis-Asenapine | n.d. | n.d. | n.d. | n.d. | n.d. |
| Tetradehydro Asenapine | n.d. | n.d. | <LOR | <LOR | 0.29 |
| Other related substances | n.d. | n.d. | 0.21 | 0.14 | 0.13 |
| Sum of all related substances | 0.74 | 0.84 | 0.66 | 0.86 | 1.56 |

* n.d. = not detected, LOR = Limit of Reporting (0.1%)
†Due to a systematic error in the HPLC analysis (artefact peaks), the initial and 1 month values are too high and not reliable The stability data show that, in certain embodiments of the invention, the initial stability as well as storage stability have been substantially improved when compared to the previously developed reference formulations (Ref. Ex. 2c and 2d), both in terms of the amount of asenapine base (in particular with respect to the amount of asenapine base remaining after storage) as well as the sum of all related (i.e. possible degradation product) substances.

Examples 3A-E

Coating Composition

The formulations of the asenapine-containing coating compositions of Examples 3a-e are summarized in Table 3.1 below. The formulations are based on weight percent, as also indicated in Table 3.1.

and the polyvinylpyrrolidone were added in this order and the mixture was then stirred. The asenapine was added and the mixture stirred. The ethanol was added while stirring (Ex. 3d) or the aluminium acetylacetonate was dissolved in the ethanol and added while stirring (Ex. 3e).

Coating of the Coating Composition

See Reference Example 1a and Reference Example 1b for the coating process. The coating thickness gave an area weight of the matrix layer of 149.7 $g/m^2$ (Example 3d) and 146.8 $g/m^2$ (Example 3e), respectively. For Examples 3a, 3b and 3c, different films with an area weight of between 135.9 and 147.0 $g/m^2$, 144.2 and 150.1 $g/m^2$, and 143.1 and 150.7 $g/m^2$ were produced, respectively. The dried film was laminated with a polyethylene terephthalate backing layer (23 μm thickness) to provide an asenapine-containing self-adhesive layer structure.

TABLE 3.1

| Ingredient (Trade Name) | Ex. 3a Amt [g] | Ex. 3a Solids [%] | Ex. 3b Amt [g] | Ex. 3b Solids [%] | Ex. 3c Amt [g] | Ex. 3c Solids [%] | Ex. 3d Amt [g] | Ex. 3d Solids [%] | Ex. 3e Amt [g] | Ex. 3e Solids [%] |
|---|---|---|---|---|---|---|---|---|---|---|
| Asenapine base | 30.0 | 10.0 | 30.0 | 10.0 | 30.0 | 10.0 | 4.00 | 10.0 | 4.00 | 10.0 |
| Acrylic adhesive in ethyl acetate, ethanol, heptanes and methanol, with a titanium cross-linking agent. Solids content ~42.8% by wt. (Duro-Tak ™ 387-2516) | 488.0 | 69.7 | — | — | — | — | — | — | — | — |
| Acrylic adhesive in ethyl acetate. Solids content ~51.5% by wt. (Duro-Tak ™ 387-2287) | — | — | 406.1 | 69.7 | 403.6 | 69.3 | — | — | — | — |
| Acrylic adhesive in ethyl acetate. Solids content ~38.6% by wt. (Duro-Tak ™ 387-4287) | — | — | — | — | — | — | 72.3 | 69.7 | 71.7 | 69.2 |
| Aluminium acetylacetonate | — | — | — | — | 1.38 | 0.46 | — | — | 0.18 | 0.46 |
| Polyvinylpyrrolidone (Povidone K30) | 30.0 | 10.0 | 30.0 | 10.0 | 30.0 | 10.0 | 4.00 | 10.0 | 4.00 | 10.0 |
| α-Tocopherol | 0.15 | 0.05 | 0.15 | 0.05 | 0.15 | 0.05 | 0.02 | 0.05 | 0.02 | 0.05 |
| Ascorbyl palmitate | 0.60 | 0.20 | — | — | — | — | — | — | — | — |
| Ascorbyl palmitate (10.0% in ethanol) | — | — | 6.16 | 0.21 | 6.01 | 0.21 | 0.80 | 0.20 | 0.80 | 0.20 |
| Sodium metabisulfite (30% aq. sol.) | 0.56 | 0.056 | 0.59 | 0.06 | 0.56 | 0.06 | 0.08 | 0.06 | 0.08 | 0.06 |
| Medium chain triglycerides (Miglyol 812 N) | 30.1 | 10.0 | 30.0 | 10.0 | 30.0 | 10.0 | 4.01 | 10.0 | 4.01 | 10.0 |
| Ethanol denat. (1% (v/v) methyl ethyl ketone) | 143.2 | — | 220.3 | — | 221.9 | — | 11.5 | — | 12.1 | — |
| Total | 722.6 | 100.0 | 723.3 | 100.0 | 723.6 | 100.0 | 96.7 | 100.0 | 96.9 | 100.0 |
| Area weight [$g/m^2$] | 135.9-147.0 | | 144.2-150.1 | | 143.1-150.7 | | 149.7 | | 146.8 | |
| Asenapine content [$mg/cm^2$] | 1.36-1.47 | | 1.44-1.50 | | 1.43-1.51 | | 1.50 | | 1.47 | |

Preparation of the Coating Composition

The coating composition of Example 3a was prepared as described in Example 2a.

For Examples 3b and 3c, a beaker was loaded with α-tocopherol. The medium chain triglycerides, the sodium metabisulfite solution and the acrylic pressure sensitive adhesive Duro-Tak™ 387-2287 were added in this order and the mixture was then stirred. The ascorbyl palmitate solution was added dropwise under stirring, the polyvinylpyrrolidone was added thereafter while stirring, and, for Example 3c, the aluminium acetylacetonate was added. The asenapine was transferred to the mixture with the ethanol in several portions, and the resulting mixture was stirred.

For Examples 3d and 3e, a beaker was loaded with α-tocopherol. The medium chain triglycerides, the sodium metabisulfite solution, the acrylic pressure sensitive adhesive Duro-Tak™ 387-4287, the ascorbyl palmitate solution Preparation of the TTS See Example 1.

Stability Measurements

Figure 3A:
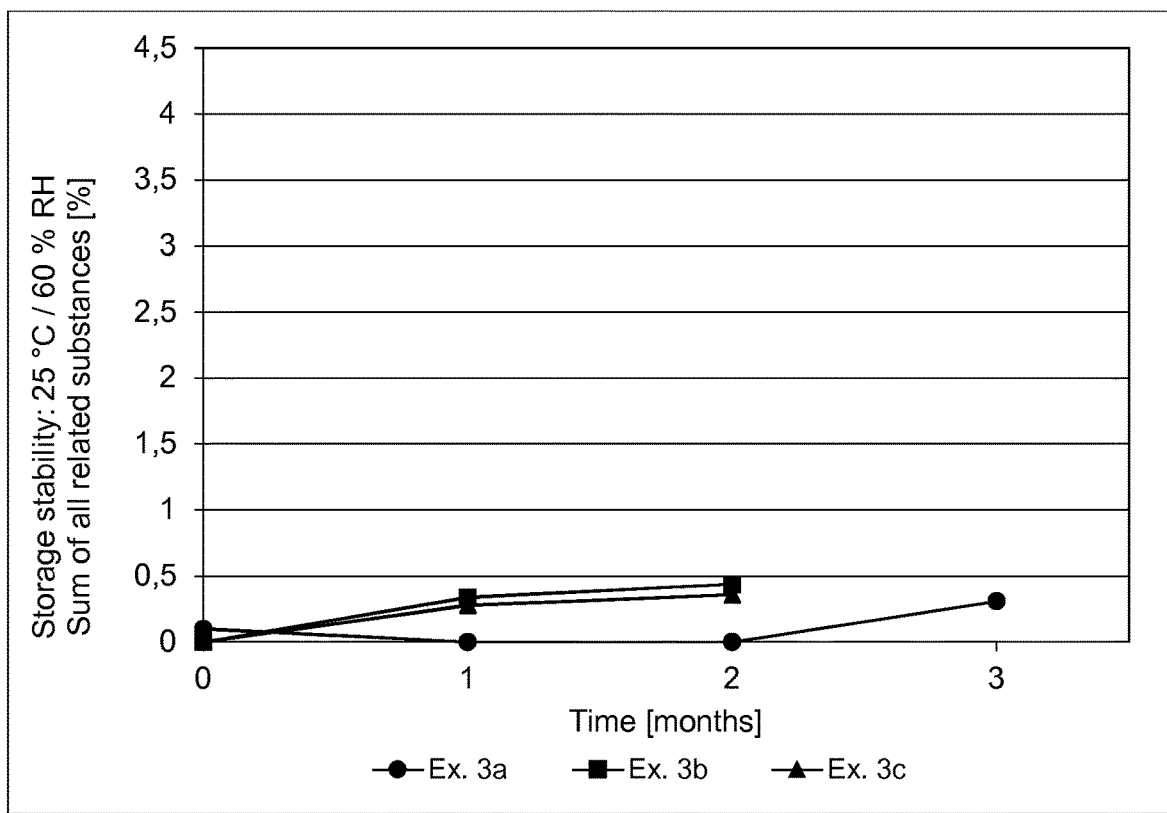
FIG. 3a depicts the sum of all related (i.e. possible degradation product) substances detected in a storage stability test at 25° C. and 60% RH over 0 to 3 months for TTS prepared according to Example 3a and over 0 to 2 months for TTS prepared according to Examples 3b and 3c.
Figure 3B:
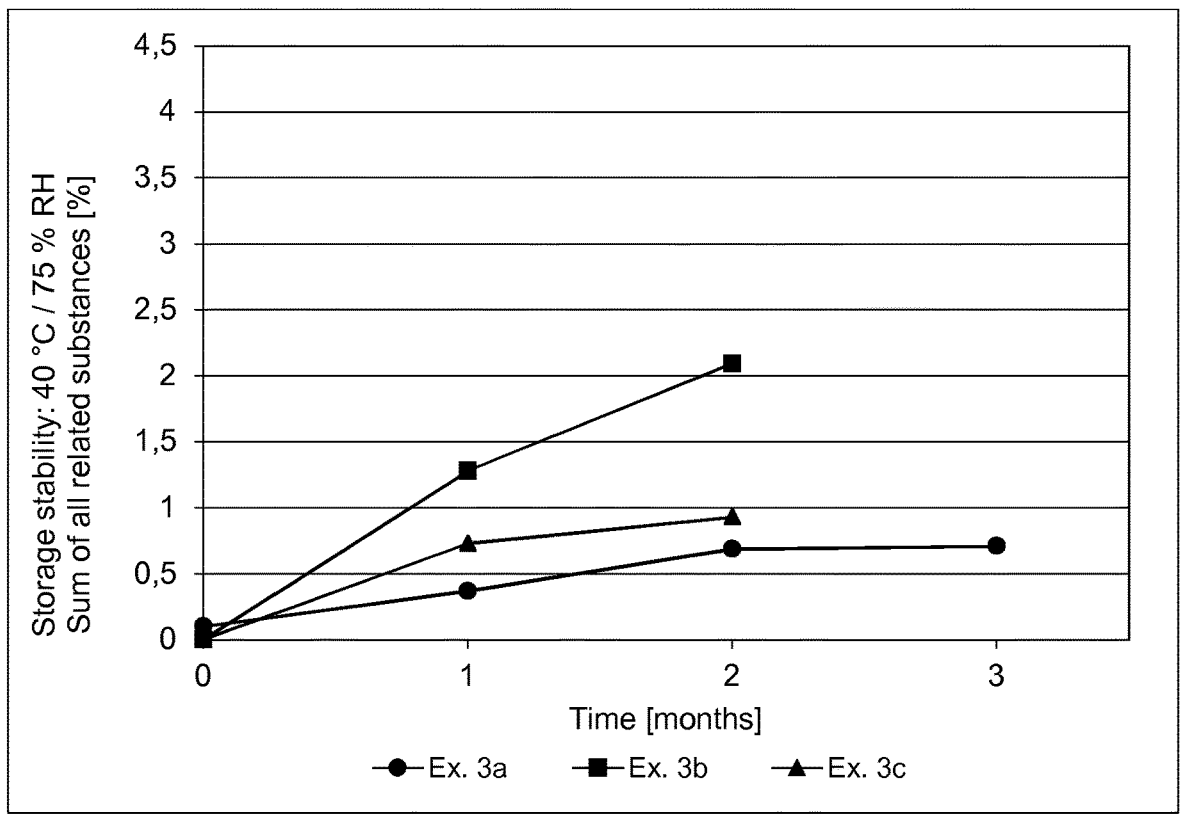
FIG. 3b depicts the sum of all related (i.e. possible degradation product) substances detected in a storage stability test at 40° C. and 75% RH over 0 to 3 months for TTS prepared according to Example 3a and over 0 to 2 months for TTS prepared according to Examples 3b and 3c.

A long term storage stability test was conducted for Examples 3a to 3c under different test conditions, i.e. storage at 25° C. and 60% relative humidity (RH), and at 40° C. and 75% RH. At different time points, samples were taken from the TTS, extracted with an appropriate extraction solvent and the amount of asenapine base, as well as various possible degradation substances was determined by a specific quantitative HPLC method with a UV photometric detector, based on the asenapine content calculated from the (actual) area weight of the tested TTS. The results are shown in Tables 3.2 to 3.7. A plot of the sum of all related (i.e. possible degradation product) substances is shown in FIGS. 3a and 3b.

Figure 3C:
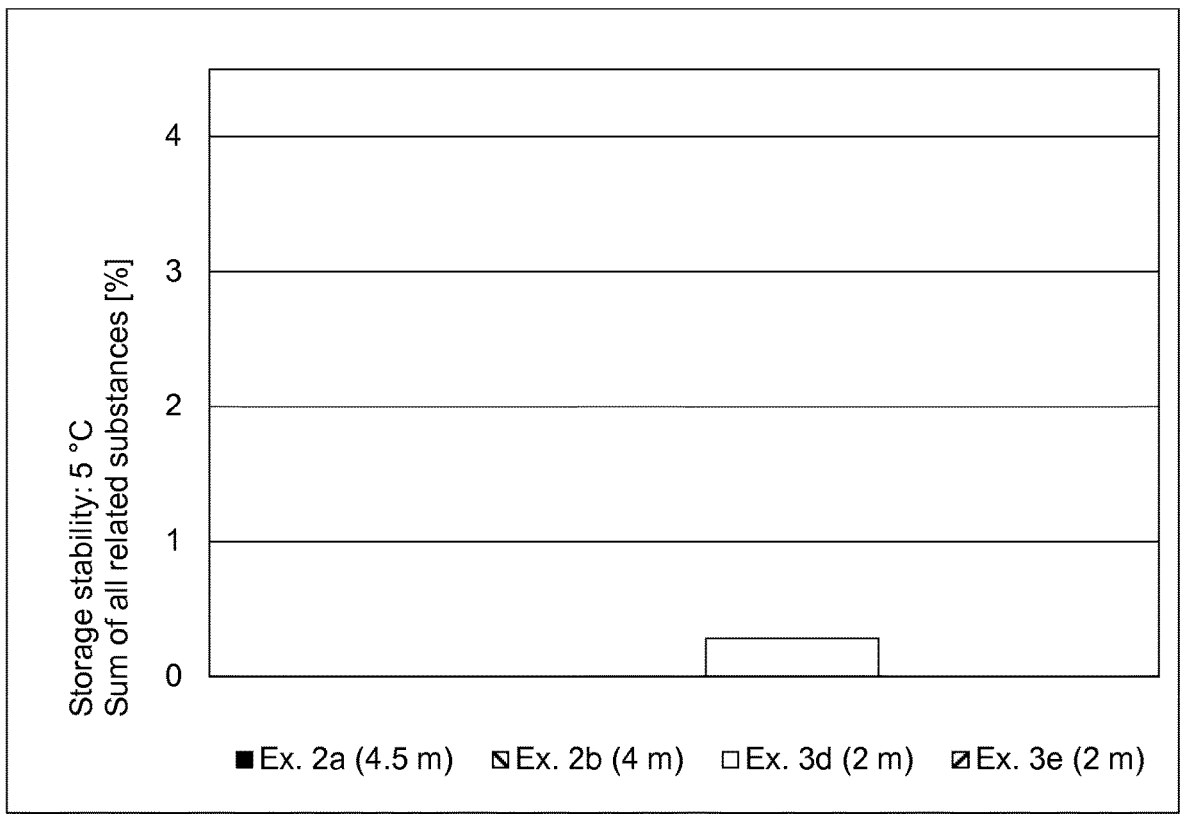
FIG. 3c depicts the sum of all related (i.e. possible degradation product) substances detected in a storage stability test at 5° C. after 4.5 months for a TTS prepared according to Example 2a, after 4 months for a TTS prepared according to Example 2b, and after 2 months for TTS prepared according to Examples 3d and 3e.

Further, in the same way, the amount of asenapine base, as well as various possible degradation substances was determined for TTS of Examples 2a, 2b, 3d and 3e, stored at 5° C. (packaged under $N_2$ atmosphere as outlined above) for 4.5, 4, 2 and 2 months, respectively. The results are shown in Table 3.8 and in FIG. 3c.

TABLE 3.2

| Ex. 3a - 25° C./60% RH | Detected amounts [%] | | | |
|---|---|---|---|---|
| | Initial | 1 month | 2 months | 3 months |
| Asenapine base | 96 | 95 | 96 | 96 |
| Asenapine N-Oxide (Cis) | <LOR | <LOR | <LOR | 0.16 |
| Asenapine N-Oxide (Trans) | 0.10 | <LOR | <LOR | 0.15 |
| Deschloro Asenapine | n.d. | n.d. | n.d. | n.d. |
| Cis-Asenapine | n.d. | <LOR | n.d. | n.d. |
| Tetradehydro Asenapine | n.d. | n.d. | <LOR | <LOR |
| Other related substances | n.d. | n.d. | n.d. | n.d. |
| Sum of all related substances | 0.10 | 0.00 | 0.00 | 0.31 |

* n.d. = not detected, LOR = Limit of Reporting (0.1%)

TABLE 3.3

| Ex. 3a - 40° C./75% RH | Detected amounts [%] | | | |
|---|---|---|---|---|
| | Initial | 1 month | 2 months | 3 months |
| Asenapine base | 96 | 95 | 95 | 94 |
| Asenapine N-Oxide (Cis) | <LOR | 0.13 | 0.28 | 0.38 |
| Asenapine N-Oxide (Trans) | 0.10 | 0.13 | 0.25 | 0.33 |
| Deschloro Asenapine | n.d. | n.d. | n.d. | n.d. |
| Cis-Asenapine | n.d. | 0.11 | n.d. | n.d. |
| Tetradehydro Asenapine | n.d. | <LOR | 0.16 | <LOR |
| Other related substances | n.d. | <LOR | <LOR | n.d. |
| Sum of all related substances | 0.10 | 0.37 | 0.69 | 0.71 |

* n.d. = not detected, LOR = Limit of Reporting (0.1%)

TABLE 3.4

| Ex. 3b - 25° C./60% RH | Detected amounts [%] | | |
|---|---|---|---|
| | Initial | 1 month | 2 months |
| Asenapine base | 96 | 96 | 94 |
| Asenapine N-Oxide (Cis) | <LOR | 0.17 | 0.22 |
| Asenapine N-Oxide (Trans) | <LOR | 0.17 | 0.22 |
| Deschloro Asenapine | n.d. | n.d. | n.d. |
| Cis-Asenapine | n.d. | n.d. | n.d. |
| Tetradehydro Asenapine | n.d. | <LOR | <LOR |
| Other related substances | n.d. | <LOR | n.d. |
| Sum of all related substances | 0.00 | 0.34 | 0.44 |

* n.d. = not detected, LOR = Limit of Reporting (0.1%)

TABLE 3.5

| Ex. 3b - 40° C./75% RH | Detected amounts [%] | | |
|---|---|---|---|
| | Initial | 1 month | 2 months |
| Asenapine base | 96 | 95 | 92 |
| Asenapine N-Oxide (Cis) | <LOR | 0.41 | 0.90 |
| Asenapine N-Oxide (Trans) | <LOR | 0.40 | 0.91 |
| Deschloro Asenapine | n.d. | n.d. | n.d. |
| Cis-Asenapine | n.d. | 0.15 | n.d. |
| Tetradehydro Asenapine | n.d. | 0.11 | 0.13 |
| Other related substances | n.d. | 0.21 | 0.15 |
| Sum of all related substances | 0.00 | 1.28 | 2.09 |

* n.d.= not detected, LOR = Limit of Reporting (0.1%)

TABLE 3.6

| Ex. 3c - 25° C./60% RH | Detected amounts [%] | | |
|---|---|---|---|
| | Initial | 1 month | 2 months |
| Asenapine base | 96 | 99 | 96 |
| Asenapine N-Oxide (Cis) | <LOR | 0.14 | 0.18 |
| Asenapine N-Oxide (Trans) | <LOR | 0.14 | 0.18 |
| Deschloro Asenapine | n.d. | n.d. | n.d. |
| Cis-Asenapine | n.d. | <LOR | n.d. |
| Tetradehydro Asenapine | n.d. | <LOR | <LOR |
| Other related substances | n.d. | <LOR | n.d. |
| Sum of all related substances | 0.00 | 0.28 | 0.36 |

* n.d. = not detected, LOR = Limit of Reporting (0.1%)

TABLE 3.7

| Ex. 3c - 40° C./75% RH | Detected amounts [%] | | |
|---|---|---|---|
| | Initial | 1 month | 2 months |
| Asenapine base | 96 | 95 | 93 |
| Asenapine N-Oxide (Cis) | <LOR | 0.24 | 0.42 |
| Asenapine N-Oxide (Trans) | <LOR | 0.24 | 0.41 |
| Deschloro Asenapine | n.d. | n.d. | n.d. |
| Cis-Asenapine | n.d. | n.d. | n.d. |
| Tetradehydro Asenapine | n.d. | 0.11 | 0.10 |
| Other related substances | n.d. | 0.14 | <LOR |
| Sum of all related substances | 0.00 | 0.73 | 0.93 |

* n.d. = not detected, LOR = Limit of Reporting (0.1%)

TABLE 3.8

| TTS stored at 5° C. | Detected amounts [%] | | | |
|---|---|---|---|---|
| | Ex. 2a 4.5 months | Ex. 2b 4 months | Ex. 3d 2 months | Ex. 3e 2 months |
| Asenapine base | 96 | 97 | 96 | 96 |
| Asenapine N-Oxide (Cis) | <LOR | <LOR | 0.14 | <LOR |
| Asenapine N-Oxide (Trans) | <LOR | <LOR | 0.14 | <LOR |
| Deschloro Asenapine | n.d. | n.d. | n.d. | n.d. |
| Cis-Asenapine | n.d. | n.d. | n.d. | n.d. |
| Tetradehydro Asenapine | <LOR | <LOQ | <LOR | <LOR |
| Other related substances | <LOR | n.d. | n.d. | n.d. |
| Sum of all related substances | 0.00 | 0.00 | 0.28 | 0.00 |

* n.d. = not detected, LOR = Limit of reporting (0.1%)

The stability data show that, in certain embodiments of the invention, the TTS provide excellent initial as well as storage stability.

Examples 4A and B

Coating Composition

The formulations of the asenapine-containing coating compositions of Examples 4a and 4b are summarized in Table 4.1 below. The formulations are based on weight percent, as also indicated in Table 4.1.

TABLE 4.1

|  | Ex. 4a | | Ex. 4b | |
| --- | --- | --- | --- | --- |
| Ingredient (Trade Name) | Amt [g] | Solids [%] | Amt [g] | Solids [%] |
| Asenapine base | 1.00 | 10.0 | 1.00 | 10.0 |
| Acrylic adhesive in ethyl acetate, ethanol, heptanes and methanol, with a titanium cross-linking agent. Solids content ~42.9% by wt. (Duro-Tak ™ 387-2516) | 16.3 | 69.7 | — | — |
| Acrylic adhesive in ethyl acetate. Solids content ~51.8% by weight (Duro-Tak ™ 387-2287) | — | — | 13.4 | 68.9 |
| Aluminium acetylacetonate | — | — | 0.05 | 0.53 |
| Polyvinylpyrrolidone (Povidone K90F) | 1.00 | 10.0 | 1.01 | 10.1 |
| α-Tocopherol | 0.005 | 0.05 | 0.008 | 0.08 |
| Ascorbyl palmitate | 0.02 | 0.20 | 0.02 | 0.21 |
| Sodium metabisulfite (30% aq. sol.) | 0.02 | 0.07 | 0.02 | 0.07 |
| Medium chain triglycerides (Miglyol 812 N) | 1.00 | 10.0 | 1.02 | 10.1 |
| Ethanol denat. (1% (v/v) methyl ethyl ketone) | 4.79 | — | 7.73 | — |
| Total | 24.1 | 100.0 | 24.3 | 100.0 |
| Area weight [g/m$^2$] | 143.2 | | 144.2 | |
| Asenapine content [mg/cm$^2$] | 1.43 | | 1.44 | |

Preparation of the Coating Composition

The coating composition of Example 4a was prepared as described in Example 2b.

For Example 4b, a beaker was loaded with the asenapine. The α-tocopherol, the ascorbyl palmitate, the medium chain triglycerides, the sodium metabisulfite solution, the acrylic pressure sensitive adhesive Duro-Tak™ 387-2287 and the polyvinylpyrrolidone were added in this order to the asenapine and the resulting mixture was stirred. The aluminium acetylacetonate was dissolved in the ethanol and added to the mixture while stirring.

Coating of the Coating Composition

See Reference Example 1a and Reference Example 1b for the coating process. The coating thickness gave an area weight of the matrix layer of 143.2 g/m$^2$ (Example 4a) and 144.2 g/m$^2$ (Example 4b), respectively. The dried film was laminated with a polyethylene terephthalate backing layer (23 μm thickness) to provide an asenapine-containing self-adhesive layer structure.

Preparation of the TTS

See Example 1.

Measurement of Skin Permeation Rate

Figure 4A:
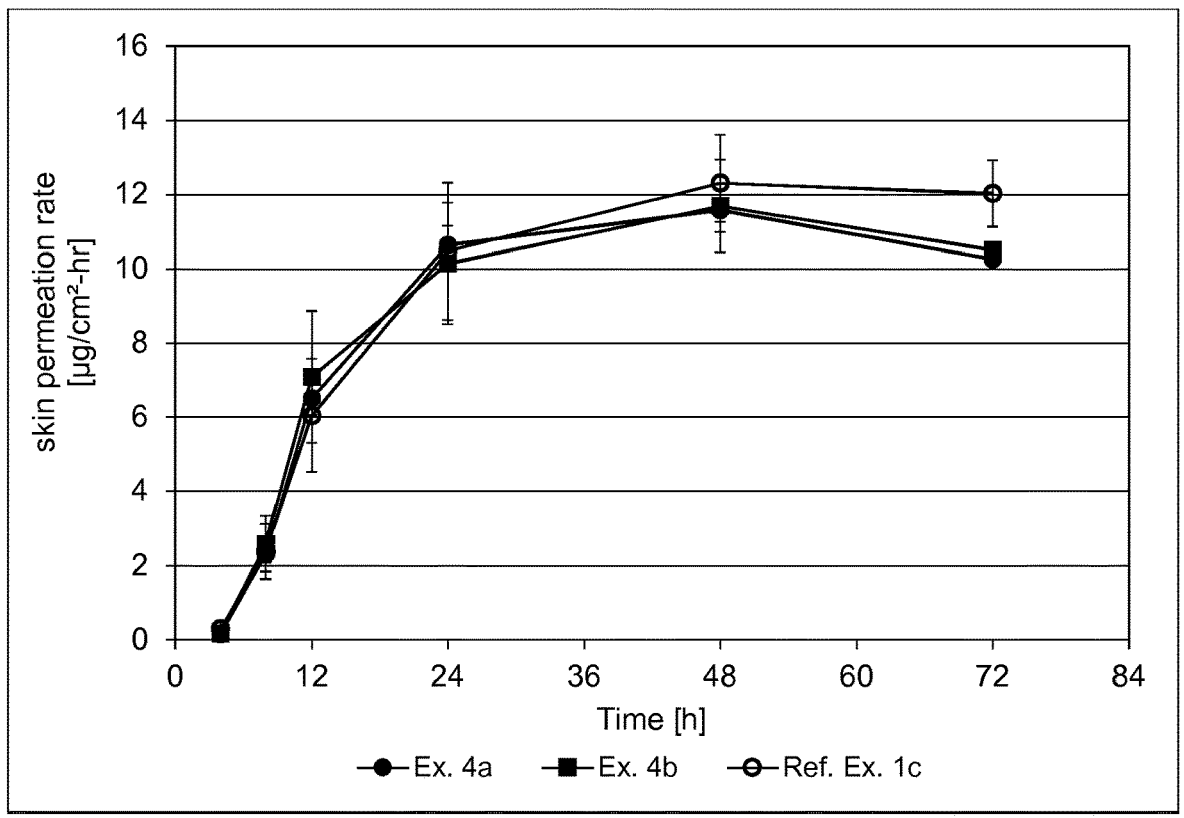
FIG. 4a depicts the asenapine skin permeation rate of TTS prepared according to Examples 4a and 4b as well as Reference Example 1c for hours 0 to 72.

The permeated amount and the corresponding skin permeation rates of TTS prepared according to Examples 4a and 4b as well as Reference Example 1c were determined by in vitro experiments in accordance with the OECD Guideline (adopted Apr. 13, 2004) carried out with a 7.0 ml Franz diffusion cell. Split thickness human skin from cosmetic surgeries (female abdomen, date of birth 1982) was used. A dermatome was used to prepare skin to a thickness of 800 μm, with an intact epidermis for all TTS. Diecuts with an area of 1.188 cm$^2$ were punched from the TTS. The asenapine permeated amount in the receptor medium of the Franz cell (phosphate buffer solution pH 5.5 with 0.1% saline azide as antibacteriological agent) at a temperature of 32±1° C. was measured and the corresponding skin permeation rate calculated. The results are shown in Table 4.2 and FIG. 4a.

TABLE 4.2

Skin permeation rate with SD [μg/(cm$^2$ h)]

| Elapsed time [h] | Ref. Ex. 1c (n = 3) | | Ex. 4a (n = 3) | | Ex. 4b (n = 3) | |
| --- | --- | --- | --- | --- | --- | --- |
| | Rate | SD | Rate | SD | Rate | SD |
| 4 | 0.30 | 0.20 | 0.16 | 0.01 | 0.18 | 0.06 |
| 8 | 2.39 | 0.74 | 2.31 | 0.22 | 2.59 | 0.75 |
| 12 | 6.05 | 1.53 | 6.52 | 0.46 | 7.09 | 1.78 |
| 24 | 10.47 | 1.84 | 10.64 | 0.52 | 10.15 | 1.63 |
| 48 | 12.30 | 1.31 | 11.57 | 0.31 | 11.69 | 1.25 |
| 72 | 12.03 | 0.90 | 10.26 | 0.13 | 10.51 | 0.12 |

*: Standard deviation in this Example was, as in all other Examples, calculated based on the n-method.

Utilization of Asenapine

Figure 4B:
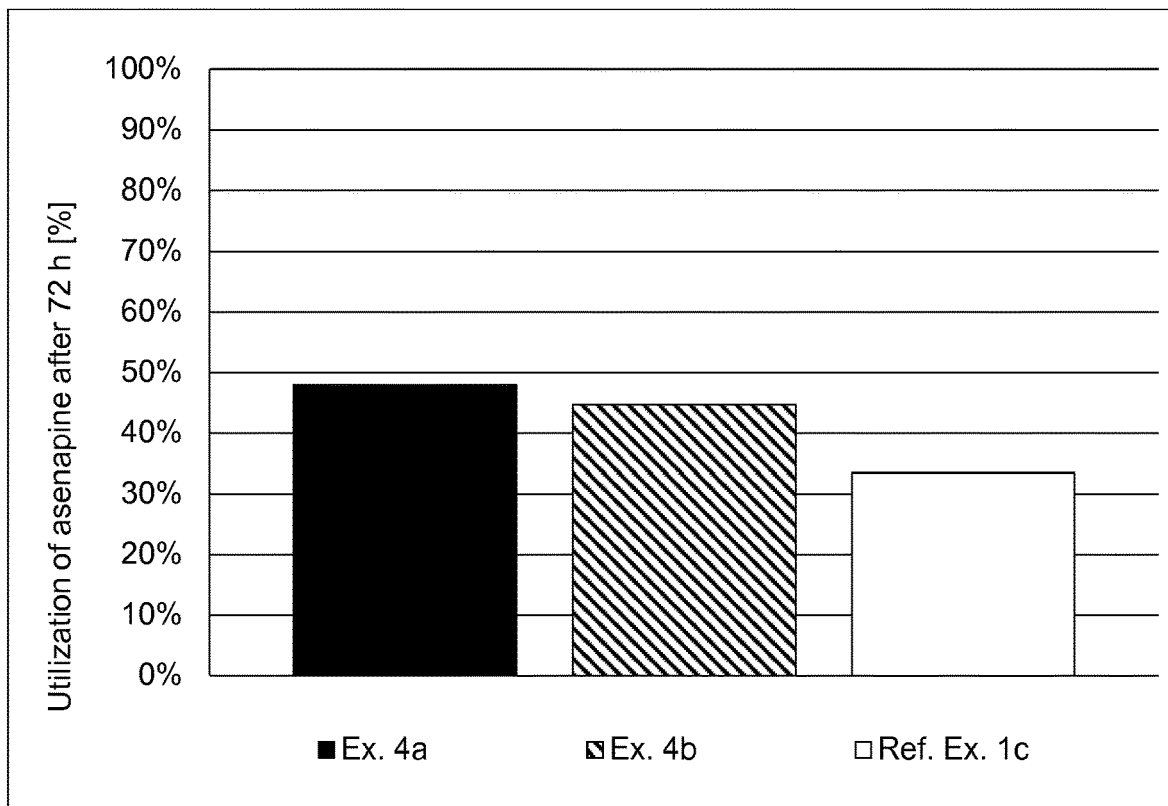
FIG. 4b depicts the utilization of asenapine of TTS prepared according to Examples 4a and 4b as well as Reference Example 1c after 72 hours.

The utilization of asenapine at 72 hours was calculated based on the cumulative permeated amount at 72 hours and the initial asenapine content. The results are shown in Table 4.3 and in FIG. 4b.

TABLE 4.3

Utilization of asenapine after 72 hours [%]

| Ref. Example 1c (n = 3) | Example 4a (n = 3) | Example 4b (n = 3) |
| --- | --- | --- |
| 33.5 | 47.9 | 44.7 |

The in vitro experiments show that the good skin permeation rate as well as the utilization of asenapine of the previously developed reference formulation (Ref. Ex. 1c) could be surprisingly maintained for formulations in accordance with certain embodiments of the present invention, comprising a considerable amount of medium chain triglycerides as tackifier as well as a specific combination of stabilizers. Reference Example 1c corresponds to the formulation of Reference Example 2d (except that the area weight is higher), for which a successful in vivo clinical study has been conducted (see below).

Reference Examples 5A-C

Coating Composition

The formulations of the asenapine-containing coating compositions of Reference Examples 5a, 5b and 5c are summarized in Table 5.1 below. The formulations are based on weight percent, as also indicated in Table 5.1.

TABLE 5.1

| Ingredient (Trade Name) | Ref. Ex. 5a Amt [g] | Ref. Ex. 5a Solids [%] | Ref. Ex. 5b Amt [g] | Ref. Ex. 5b Solids [%] | Ref. Ex. 5c Amt [g] | Ref. Ex. 5c Solids [%] |
|---|---|---|---|---|---|---|
| Asenapine base | 1.80 | 5.96 | 1.80 | 6.00 | 1.80 | 6.00 |
| Acrylic adhesive in ethyl acetate, ethanol, heptanes and methanol, with a titanium cross-linking agent. Solids content of about 41.3% by weight (Duro-Tak™ 387-2516) | 61.6 | 84.1 | 61.0 | 83.9 | 60.8 | 83.8 |
| Polyvinylpyrrolidone (Povidone K90F) | 3.00 | 9.93 | 3.00 | 10.0 | 3.00 | 10.0 |
| Ascorbyl palmitate | 0.003 | 0.01 | 0.03 | 0.10 | 0.06 | 0.20 |
| Ethanol denat. (1% (v/v) methyl ethyl ketone) | 6.49 | — | 6.48 | — | 6.46 | — |
| Total | 72.9 | 100.00 | 72.3 | 100.00 | 72.1 | 100.00 |
| Area weight [g/m²] | 150.9 | | 146.7 | | 146.2 | |
| Asenapine content [mg/cm²] | 0.90 | | 0.88 | | 0.88 | |

Preparation of the Coating Composition

A beaker was loaded with the ascorbyl palmitate. The acrylic pressure sensitive adhesive Duro-Tak™ 387-2516 was added, the mixture was stirred and the polyvinylpyrrolidone was added while stirring. The asenapine and the ethanol were added consecutively and the mixture was stirred until a clear solution was obtained.

Coating of the Coating Composition

See Reference Example 1a and Reference Example 1b for the coating process. The coating thickness gave an area weight of the matrix layer of 150.9 g/m² (Reference Example 5a), 146.7 g/m² (Reference Example 5b) and 146.2 g/m² (Reference Example 5c), respectively. The dried film was laminated with a polyethylene terephthalate backing layer (23 µm thickness) to provide an asenapine-containing self-adhesive layer structure.

Preparation of the TTS

See Example 1.

Stability Measurements

Figure 5A:
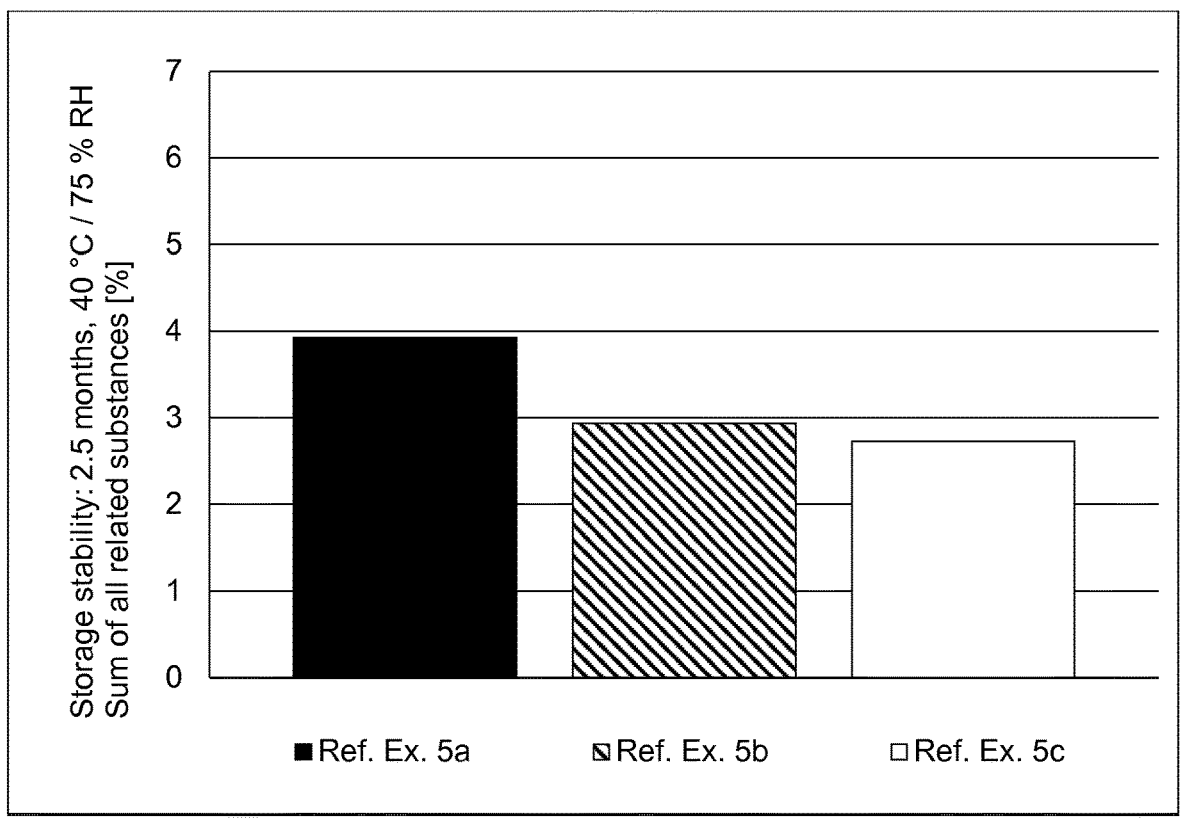
FIG. 5a depicts the sum of all related (i.e. possible degradation product) substances detected in a storage stability test at 40° C. and 75% RH after 2.5 months for TTS prepared according to Reference Examples 5a, 5b and 5c.
Figure 5B:
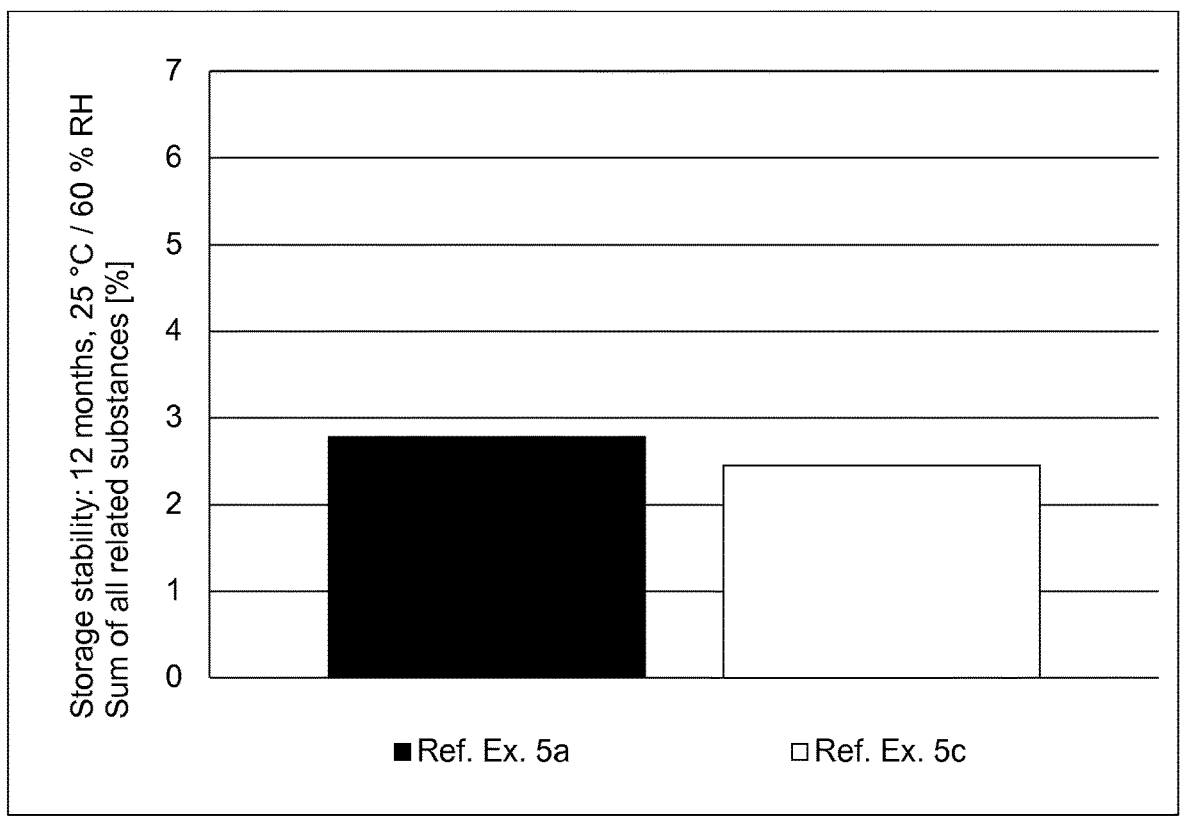
FIG. 5b depicts the sum of all related (i.e. possible degradation product) substances detected in a storage stability test at 25° C. and 60% RH after 12 months for TTS prepared according to Reference Examples 5a and 5c.

The stability of the TTS of Reference Examples 5a to 5c, stored at 40° C. and 75% RH for 2.5 months, as well as of the TTS of Reference Examples 5a and 5c, stored at 25° C. and 60% RH for 12 months was investigated. Samples were taken from the TTS, extracted with an appropriate extraction solvent and the amount of asenapine base, as well as various possible degradation substances was determined by a specific quantitative HPLC method with a UV photometric detector, based on the asenapine content calculated from the (actual) area weight of the tested TTS. The results are shown in Tables 5.2 and 5.3 as well as FIGS. 5a and 5b.

TABLE 5.2

| TTS stored at 40° C./75% RH For 2.5 months | Detected amounts [%] | | |
|---|---|---|---|
| | Ref. Ex. 5a | Ref. Ex. 5b | Ref. Ex. 5c |
| Asenapine base | 96 | 97 | 97 |
| Asenapine N-Oxide (Cis) | 1.08 | 0.80 | 0.80 |
| Asenapine N-Oxide (Trans) | 1.04 | 0.76 | 0.74 |
| Cis-Asenapine | <LOR | <LOR | 0.15 |

TABLE 5.2-continued

| TTS stored at 40° C./75% RH For 2.5 months | Detected amounts [%] | | |
|---|---|---|---|
| | Ref. Ex. 5a | Ref. Ex. 5b | Ref. Ex. 5c |
| Tetradehydro Asenapine | 1.62 | 1.27 | 0.94 |
| Other related substances | 0.19 | 0.11 | 0.10 |
| Sum of all related substances | 3.93 | 2.94 | 2.73 |

* LOR = Limit of Reporting (0.1%)

TABLE 5.3

| TTS stored at 25° C./60% RH For 12 months | Detected amounts [%] | |
|---|---|---|
| | Ref. Ex. 5a | Ref. Ex. 5c |
| Asenapine N-Oxide (Cis) | 1.24 | 1.15 |
| Asenapine N-Oxide (Trans) | 1.18 | 1.06 |
| Tetradehydro Asenapine | 0.25 | 0.24 |
| Other related substances | 0.11 | <LOR |
| Sum of all related substances | 2.78 | 2.45 |

* LOR = Limit of Reporting (0.1%)

The stability data of Reference Examples 5a-c show that the presence and certain higher amounts of ascorbyl palmitate have a positive influence on initial as well as storage stability of asenapine formulations comprising a matrix layer based on an acrylic adhesive and including an additional polymer (polyvinylpyrrolidone).

Reference Examples 6A-D

Coating Composition

The formulations of the asenapine-containing coating compositions of Reference Examples 6a, 6b, 6c and 6d are summarized in Table 6.1 below. The formulations are based on weight percent, as also indicated in Table 6.1.

TABLE 6.1

| Ingredient (Trade Name) | Ref. Ex. 6a Amt [g] | Ref. Ex. 6a Solids [%] | Ref. Ex. 6b Amt [g] | Ref. Ex. 6b Solids [%] | Ref. Ex. 6c Amt [g] | Ref. Ex. 6c Solids [%] | Ref. Ex. 6d Amt [g] | Ref. Ex. 6d Solids [%] |
|---|---|---|---|---|---|---|---|---|
| Asenapine base | 1.80 | 5.99 | 1.80 | 6.00 | 1.80 | 5.95 | 1.80 | 6.00 |
| Acrylic adhesive in ethyl acetate, ethanol, heptanes and methanol, with a titanium cross-linking agent. Solids content of about 41.3% by weight (Duro-Tak™ 387-2516) | 61.1 | 84.0 | 61.1 | 84.0 | 61.6 | 84.1 | 60.7 | 83.5 |
| α-Tocopherol | — | — | 0.002 | 0.006 | 0.02 | 0.05 | 0.15 | 0.5 |
| Polyvinylpyrrolidone (Povidone K90F) | 3.00 | 10.0 | 3.00 | 10.0 | 3.00 | 9.92 | 3.00 | 10.0 |
| Ethanol denat. (1% (v/v) methyl ethyl ketone) | 6.47 | — | 6.48 | — | 6.47 | — | 6.47 | — |
| Total | 72.4 | 100.0 | 72.4 | 100.0 | 72.9 | 100.0 | 72.1 | 100.0 |
| Area weight [g/m$^2$] | 144.2 | | 133.0 | | 149.0 | | 147.2 | |
| Asenapine content [mg/cm$^2$] | 0.86 | | 0.80 | | 0.89 | | 0.88 | |

Preparation of the Coating Composition

For Reference Example 6a, a beaker was loaded with the acrylic pressure sensitive adhesive Duro-Tak™ 387-2516. The polyvinylpyrrolidone was added while stirring. The asenapine and the ethanol were added consecutively and the mixture was stirred.

For Reference Examples 6b to 6d, a beaker was loaded with the α-Tocopherol. The acrylic pressure sensitive adhesive Duro-Tak™ 387-2516 was added, the mixture was stirred and the polyvinylpyrrolidone was added while stirring. The asenapine and the ethanol were added consecutively and the mixture was stirred until a clear solution was obtained.

Coating of the Coating Composition

See Reference Example 1a and Reference Example 1b for the coating process. The coating thickness gave an area weight of the matrix layer of 144.2 g/m$^2$ (Reference Example 6a), 133.0 g/m$^2$ (Reference Example 6b), 149.0 g/m$^2$ (Reference Example 6c) and 147.2 g/m$^2$ (Reference Example 6d), respectively. The dried film was laminated with a polyethylene terephthalate backing layer (23 μm thickness) to provide an asenapine-containing self-adhesive layer structure.

Preparation of the TTS

See Example 1.

Stability Measurements

Figure 6A:
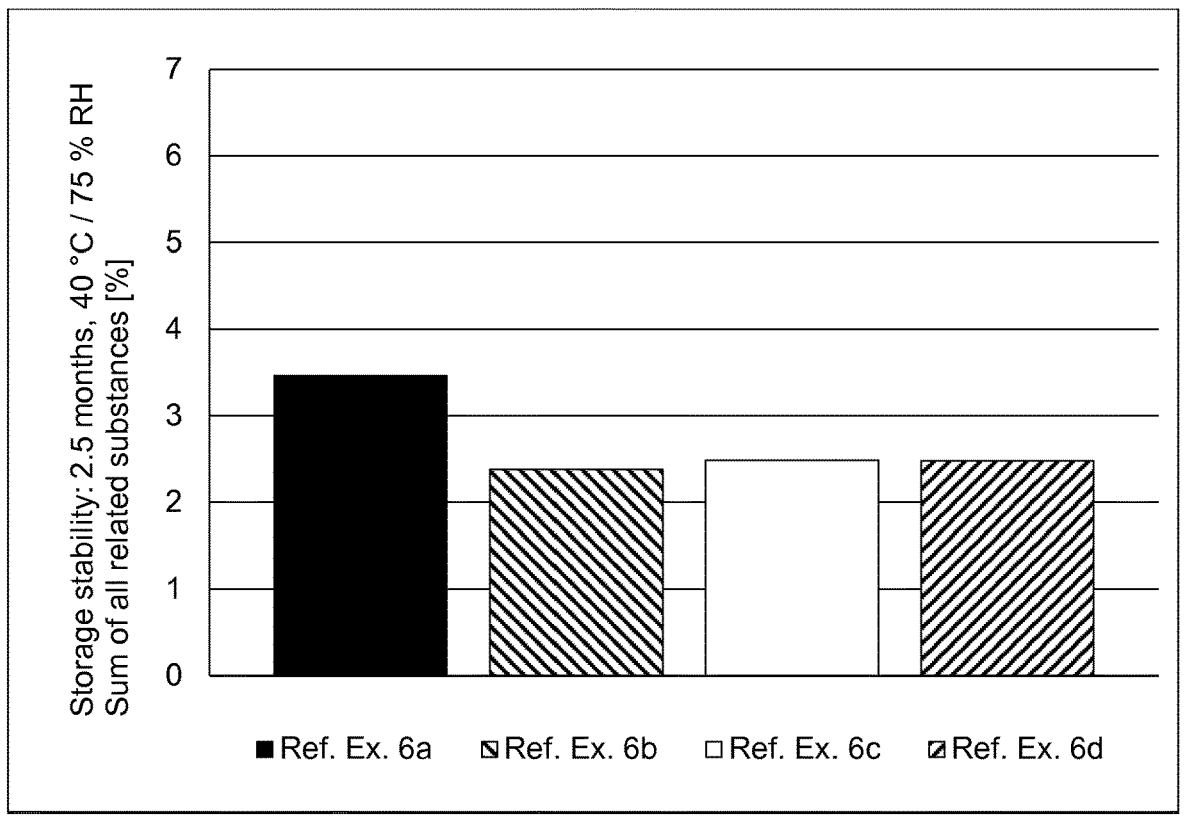
FIG. 6a depicts the sum of all related (i.e. possible degradation product) substances detected in a storage stability test at 40° C. and 75% RH after 2.5 months for TTS prepared according to Reference Examples 6a, 6b, 6c and 6d.
Figure 6B:
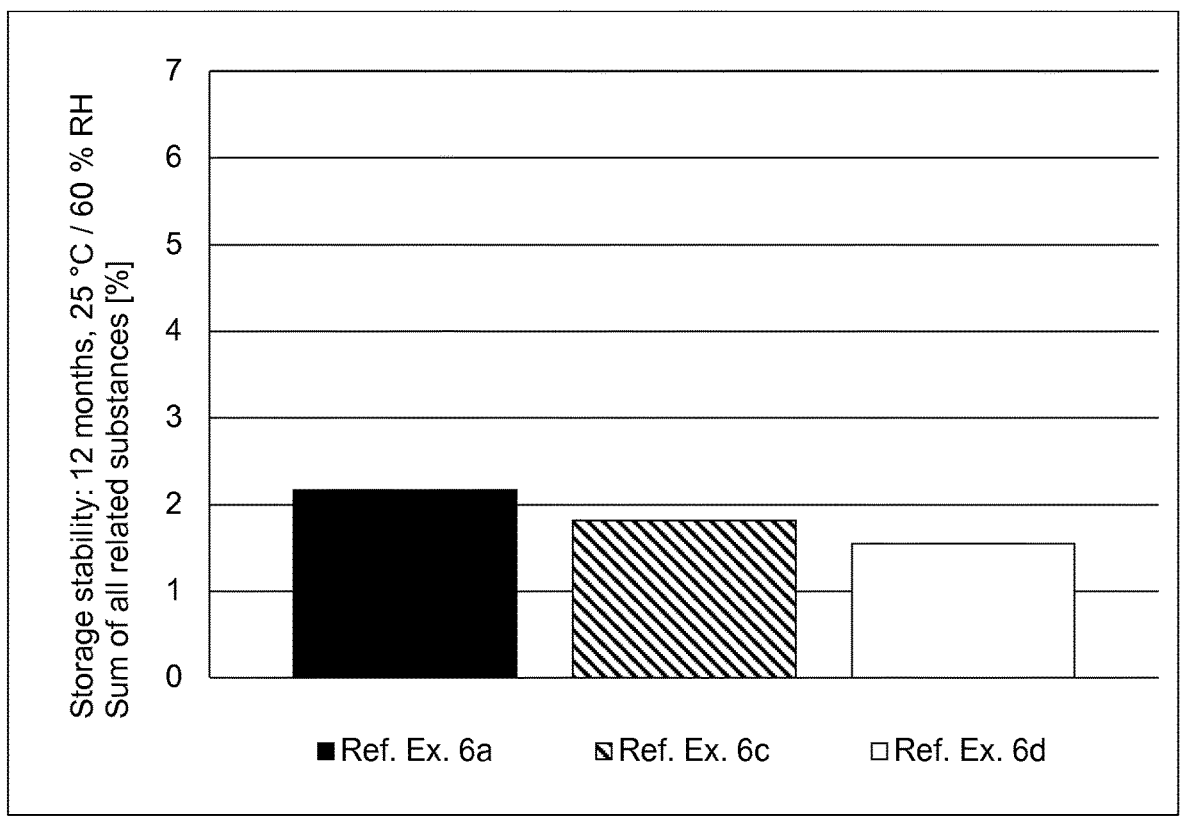
FIG. 6b depicts the sum of all related (i.e. possible degradation product) substances detected in a storage stability test at 25° C. and 60% RH after 12 months for TTS prepared according to Reference Examples 6a, 6c and 6d.

The stability of the TTS of Reference Examples 6a to 6d, stored at 40° C. and 75% RH for 2.5 months, as well as of the TTS of Reference Examples 6a, 6c and 6d, stored at 25° C. and 60% RH for 12 months was investigated. Samples were taken from the TTS, extracted with an appropriate extraction solvent and the amount of asenapine base, as well as various possible degradation substances was determined by a specific quantitative HPLC method with a UV photometric detector, based on the asenapine content calculated from the (actual) area weight of the tested TTS. The results are shown in Tables 6.2 and 6.3 as well as FIGS. 6a and 6b.

TABLE 6.2

| TTS stored at 40° C./75% RH | Detected amounts [%] | | | |
|---|---|---|---|---|
| For 2.5 months | Ref. Ex. 6a | Ref. Ex. 6b | Ref. Ex. 6c | Ref. Ex. 6d |
| Asenapine base | 97 | 98 | 97 | 98 |
| Asenapine N-Oxide (Cis) | 0.82 | 0.59 | 0.61 | 0.56 |
| Asenapine N-Oxide (Trans) | 0.84 | 0.61 | 0.59 | 0.54 |
| Cis-Asenapine | n.d. | <LOR | <LOR | n.d. |
| Tetradehydro Asenapine | 1.63 | 0.93 | 1.04 | 1.14 |
| Other related substances | 0.18 | 0.25 | 0.25 | 0.24 |
| Sum of all related substances | 3.47 | 2.38 | 2.49 | 2.48 |

* LOR = Limit of Reporting (0.1%)

TABLE 6.3

| TTS stored at 25° C./60% RH | Detected amounts [%] | | |
|---|---|---|---|
| For 12 months | Ref. Ex. 6a | Ref. Ex. 6c | Ref. Ex. 6d |
| Asenapine N-Oxide (Cis) | 0.95 | 0.77 | 0.64 |
| Asenapine N-Oxide (Trans) | 0.91 | 0.72 | 0.60 |
| Tetradehydro Asenapine | 0.20 | 0.18 | 0.16 |
| Other related substances | 0.11 | 0.15 | 0.15 |
| Sum of all related substances | 2.17 | 1.82 | 1.55 |

The stability data of Reference Examples 6a-d show that the presence and certain higher amounts of α-Tocopherol have a positive influence on initial as well as storage stability of asenapine formulations comprising a matrix layer based on an acrylic adhesive and including an additional polymer (polyvinylpyrrolidone).

Reference Examples 7A-D

Coating Composition

The formulations of the asenapine-containing coating compositions of Reference Examples 7a, 7b, 7c and 7d are summarized in Table 7.1 below. The formulations are based on weight percent, as also indicated in Table 7.1.

TABLE 7.1

| Ingredient (Trade Name) | Ref. Ex. 7a Amt [g] | Ref. Ex. 7a Solids [%] | Ref. Ex. 7b Amt [g] | Ref. Ex. 7b Solids [%] | Ref. Ex. 7c Amt [g] | Ref. Ex. 7c Solids [%] | Ref. Ex. 7d Amt [g] | Ref. Ex. 7d Solids [%] |
|---|---|---|---|---|---|---|---|---|
| Asenapine base | 1.80 | 5.89 | 1.80 | 5.99 | 1.80 | 6.00 | 1.80 | 5.97 |
| Acrylic adhesive in ethyl acetate, ethanol, heptanes and methanol, with a titanium cross-linking agent. Solids content of about 41.3% by weight (Duro-Tak™ 387-2516) | 62.4 | 84.3 | 61.1 | 84.0 | 60.9 | 84.0 | 61.4 | 84.0 |
| Sodium metabisulfite (30% aq. sol.) | — | — | 0.009 | 0.01 | 0.03 | 0.03 | 0.06 | 0.06 |
| Polyvinylpyrrolidone (Povidone K90F) | 3.00 | 9.81 | 3.00 | 9.99 | 3.00 | 10.0 | 3.00 | 9.94 |
| Ethanol denat. (1% (v/v) methyl ethyl ketone) | 6.48 | — | 6.48 | — | 6.47 | — | 6.47 | — |
| Purified water | 0.02 | — | — | — | — | — | — | — |
| Total | 73.7 | 100.0 | 72.4 | 100.0 | 72.2 | 100.0 | 72.7 | 100.0 |
| Area weight [g/m$^2$] | 147.7 | | 148.3 | | 147.6 | | 146.7 | |
| Asenapine content [mg/cm$^2$] | 0.87 | | 0.89 | | 0.89 | | 0.88 | |

Preparation of the Coating Composition

For Reference Example 7a, a beaker was loaded with the purified water and the acrylic pressure sensitive adhesive Duro-Tak™ 387-2516 was added. To this mixture, the polyvinylpyrrolidone was added while stirring. The asenapine and the ethanol were added consecutively and the mixture was stirred.

For Reference Examples 7b to 7d, a beaker was loaded with the sodium metabisulfite solution and the acrylic pressure sensitive adhesive Duro-Tak™ 387-2516 was added. The polyvinylpyrrolidone was added while stirring. The asenapine and the ethanol were added consecutively and the mixture was stirred until a clear solution was obtained.

Coating of the Coating Composition

See Reference Example 1a and Reference Example 1b for the coating process. The coating thickness gave an area weight of the matrix layer of 147.7 g/m$^2$ (Reference Example 7a), 148.3 g/m$^2$ (Reference Example 7b), 147.6 g/m$^2$ (Reference Example 7c) and 146.7 g/m$^2$ (Reference Example 7d), respectively. The dried film was laminated with a polyethylene terephthalate backing layer (23 μm thickness) to provide an asenapine-containing self-adhesive layer structure.

Preparation of the TTS

See Example 1.

Stability Measurements

Figure 7A:
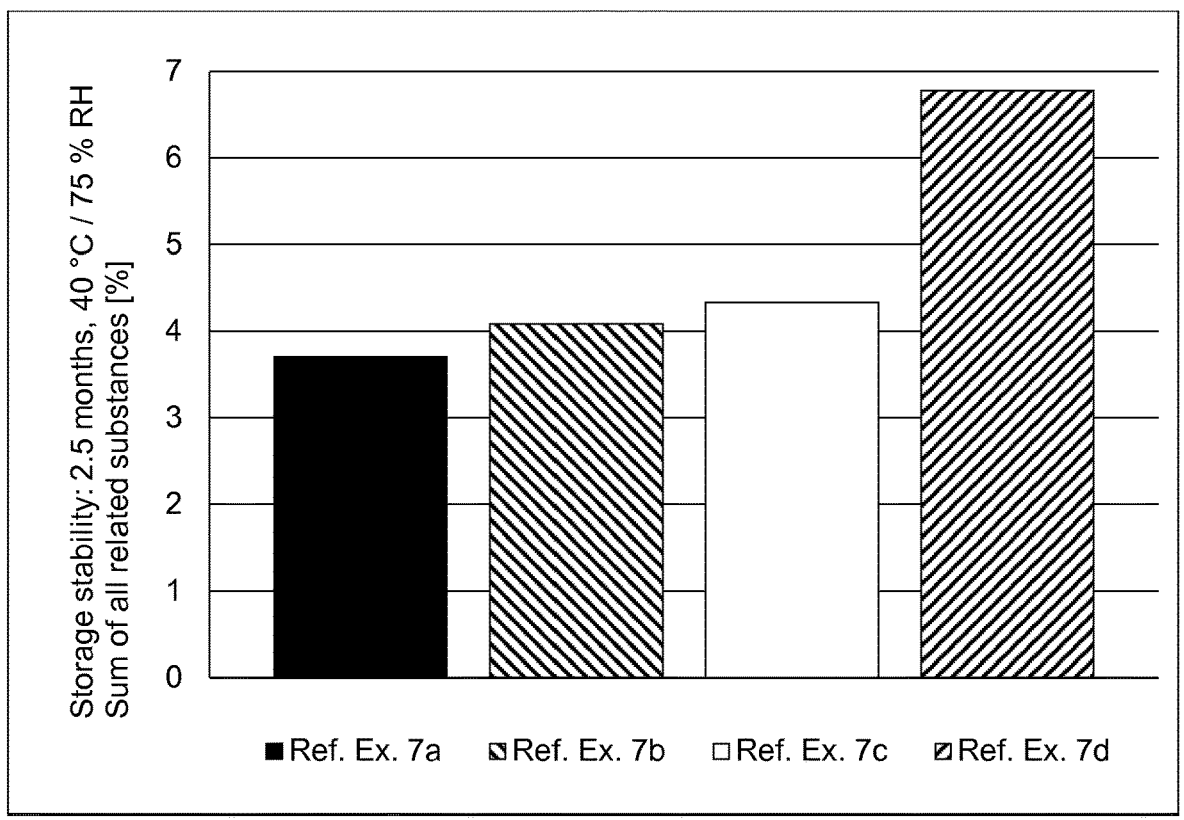
FIG. 7a depicts the sum of all related (i.e. possible degradation product) substances detected in a storage stability test at 40° C. and 75% RH after 2.5 months for TTS prepared according to Reference Examples 7a, 7b, 7c and 7d.

The stability of the TTS of Reference Examples 7a to 7d, stored at 40° C. and 75% RH for 2.5 months was investigated. Samples were taken from the TTS, extracted with an appropriate extraction solvent and the amount of asenapine base, as well as various possible degradation substances was determined by a specific quantitative HPLC method with a UV photometric detector, based on the asenapine content calculated from the (actual) area weight of the tested TTS. The results are shown in Table 7.2 and in FIG. 7a.

Figure 7B:
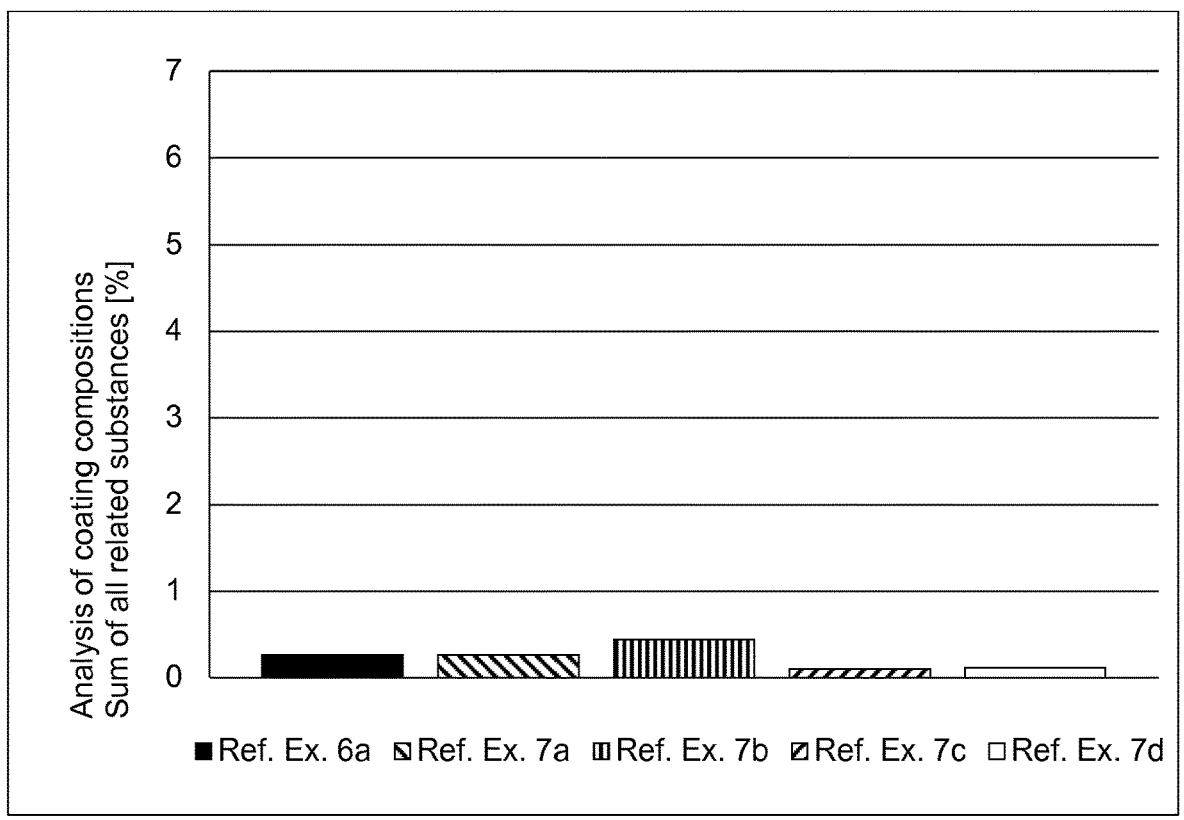
FIG. 7b depicts the sum of all related (i.e. possible degradation product) substances detected in an analysis of coating compositions (prior to coating) prepared according to Reference Examples 6a, 7a, 7b, 7c and 7d.

Further, the amount of asenapine base, as well as various possible degradation substances of the coating compositions of Reference Examples 6a as well as 7a to 7d was determined also by a specific quantitative HPLC method with a UV photometric detector few days after preparation of the coating compositions. The results are shown in Table 7.3 and in FIG. 7b.

TABLE 7.2

| TTS stored at 40° C./75% RH For 2.5 months | Detected amounts [%] | | | |
|---|---|---|---|---|
| | Ref. Ex. 7a | Ref. Ex. 7b | Ref. Ex. 7c | Ref. Ex. 7d |
| Asenapine base | 96 | 96 | 96 | 93 |
| Asenapine N-Oxide (Cis) | 0.88 | 0.94 | 0.87 | 1.51 |
| Asenapine N-Oxide (Trans) | 0.91 | 0.97 | 0.89 | 1.51 |
| Tetradehydro Asenapine | 1.71 | 2.00 | 2.46 | 3.76 |
| Other related substances | 0.21 | 0.18 | 0.12 | <LOR |
| Sum of all related substances | 3.71 | 4.09 | 4.34 | 6.78 |

* LOR = Limit of Reporting (0.1%)

TABLE 7.3

| Coating compositions (prior to coating) | Detected amounts [%] | | | | |
|---|---|---|---|---|---|
| | Ref. Ex. 6a | Ref. Ex. 7a | Ref. Ex. 7b | Ref. Ex. 7c | Ref. Ex. 7d |
| Asenapine base | 100 | 100 | 99 | 100 | 100 |
| Asenapine N-Oxide (Cis) | 0.12 | 0.12 | 0.21 | <LOR | n.a. |
| Asenapine N-Oxide (Trans) | 0.14 | 0.14 | 0.23 | 0.10 | n.a. |
| Deschloro Asenapine | <LOR | <LOR | <LOR | <LOR | <LOR |
| Tetradehydro Asenapine | n.a. | n.a. | n.a. | <LOR | 0.11 |
| Sum of all related substances | 0.26 | 0.26 | 0.44 | 0.10 | 0.11 |

* LOR = Limit of Reporting (0.1%)

The stability data of Reference Examples 7a-d show that the presence and certain higher amounts of sodium metabisulfite have a positive influence on initial stability of asenapine formulations comprising a matrix layer based on an acrylic adhesive and including an additional polymer (polyvinylpyrrolidone).

Examples 8A-E

Coating Composition

The formulations of the asenapine-containing coating compositions of Examples 8a to 8e are summarized in Table 8.1 below. The formulations are based on weight percent, as also indicated in Table 8.1.

TABLE 8.1

| Ingredient (Trade Name) | Ex. 8a Amt [g] | Ex. 8a Solids [%] | Ex. 8b Amt [g] | Ex. 8b Solids [%] | Ex. 8c Amt [g] | Ex. 8c Solids [%] | Ex. 8d Amt [g] | Ex. 8d Solids [%] | Ex. 8e Amt [g] | Ex. 8e Solids [%] |
|---|---|---|---|---|---|---|---|---|---|---|
| Asenapine base | 1.80 | 6.00 | 1.80 | 5.99 | 1.80 | 5.99 | 1.80 | 6.00 | 1.80 | 6.00 |
| Acrylic adhesive in ethyl acetate, ethanol, heptanes and methanol, with a titanium cross-linking agent. Solids content ~41.3% by wt. (Duro-Tak™ 387-2516) | 60.6 | 83.4 | 61.1 | 83.9 | 61.0 | 83.8 | 60.8 | 83.7 | 60.8 | 83.8 |
| Polyvinylpyrrolidone (Povidone K90F) | 3.00 | 10.0 | 3.00 | 9.99 | 3.00 | 9.98 | 3.00 | 10.0 | 3.00 | 10.0 |
| α-Tocopherol | 0.15 | 0.50 | 0.02 | 0.06 | 0.03 | 0.10 | 0.03 | 0.10 | 0.02 | 0.05 |
| Ascorbyl palmitate | 0.03 | 0.10 | 0.02 | 0.06 | 0.03 | 0.10 | 0.06 | 0.20 | 0.06 | 0.20 |
| Ethanol denat. (1% (v/v) methyl ethyl ketone) | 6.50 | — | 6.71 | — | 6.50 | — | 6.51 | — | 6.49 | — |
| Total | 72.1 | 100.0 | 72.7 | 100.0 | 72.4 | 100.0 | 72.2 | 100.0 | 72.2 | 100.0 |
| Area weight [g/m$^2$] | 144.7 | | 139.2 | | 147.5 | | 145.8 | | 144.8 | |
| Asenapine content [mg/cm$^2$] | 0.87 | | 0.83 | | 0.88 | | 0.88 | | 0.87 | |

Preparation of the Coating Composition

For Examples 8a to 8e, a beaker was loaded with the α-Tocopherol and the ascorbyl palmitate, the acrylic pressure sensitive adhesive Duro-Tak™ 387-2516 was added and the resulting mixture stirred. The polyvinylpyrrolidone was added while stirring. The asenapine and the ethanol were added consecutively and the mixture was stirred until a clear solution was obtained.

Coating of the Coating Composition

See Reference Example 1a and Reference Example 1b for the coating process. The coating thickness gave an area weight of the matrix layer of 144.7 g/m$^2$ (Example 8a), 139.2 g/m$^2$ (Example 8b), 147.5 g/m$^2$ (Example 8c), 145.8 g/m$^2$ (Example 8d) and 144.8 g/m$^2$ (Example 8e), respectively. The dried film was laminated with a polyethylene terephthalate backing layer (23 μm thickness) to provide an asenapine-containing self-adhesive layer structure.

Preparation of the TTS

See Example 1.

Stability Measurements

Figure 8A:
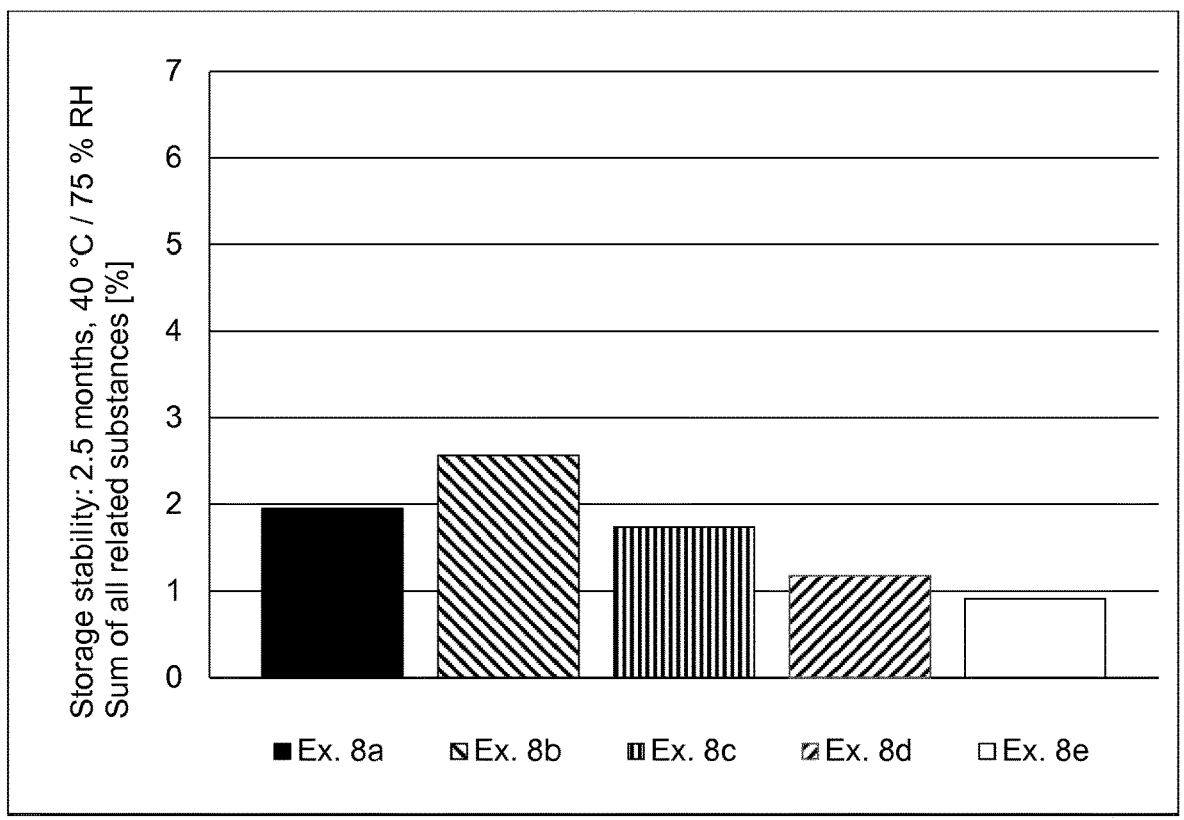
FIG. 8a depicts the sum of all related (i.e. possible degradation product) substances detected in a storage stability test at 40° C. and 75% RH after 2.5 months for TTS prepared according to Examples 8a, 8b, 8c, 8d and 8e.
Figure 8B:
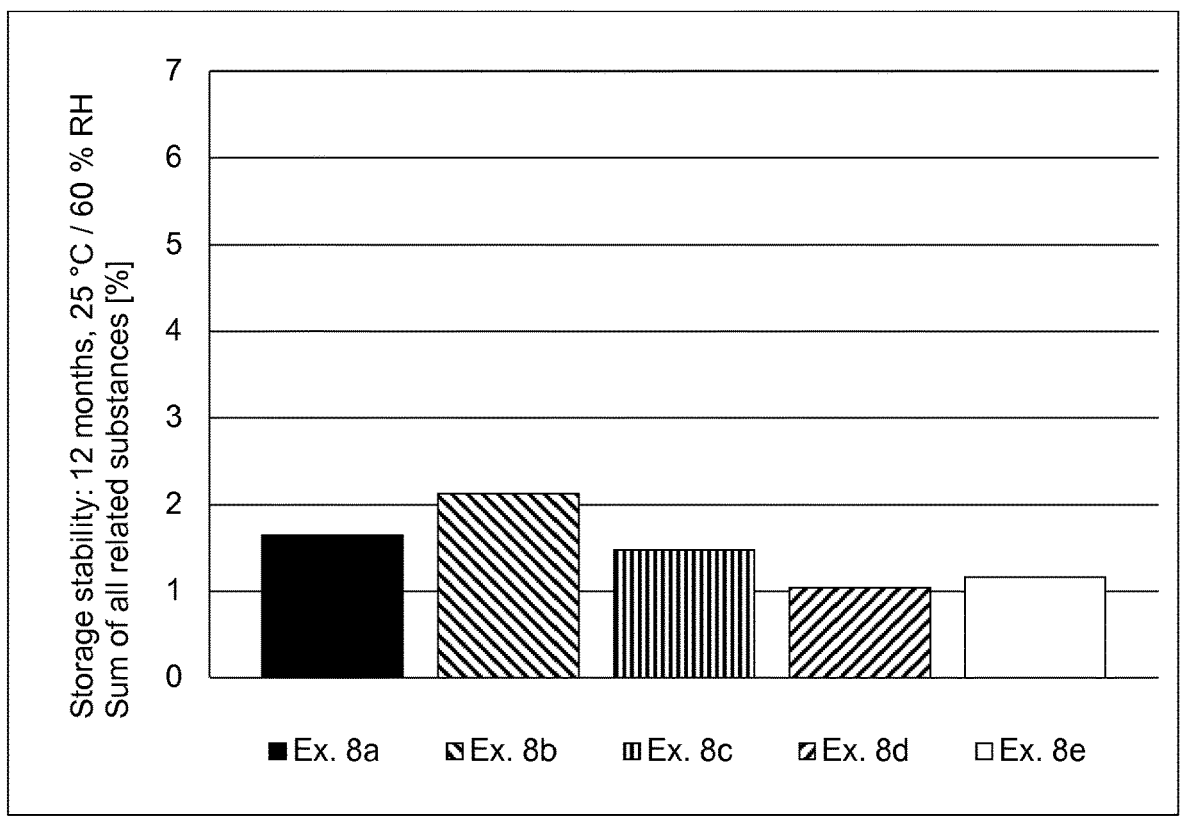
FIG. 8b depicts the sum of all related (i.e. possible degradation product) substances detected in a storage stability test at 25° C. and 60% RH after 12 months for TTS prepared according to Examples 8a, 8b, 8c, 8d and 8e.
Figure 9A:
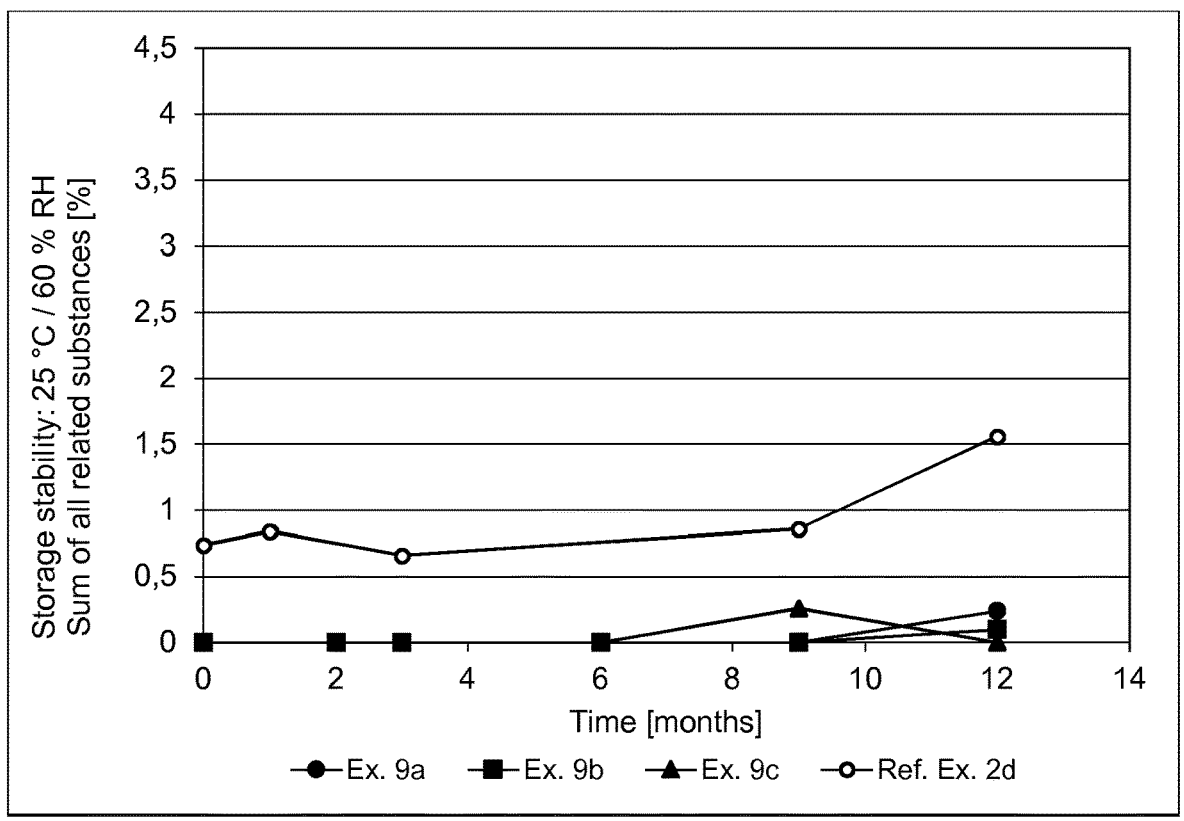
FIG. 9a depicts the sum of all related (i.e. possible degradation product) substances detected in a storage stability test at 25° C. and 60% RH over 0 to 12 months for TTS prepared according to Reference Example 2d and Examples 9a, 9b and 9c.
Figure 9B:
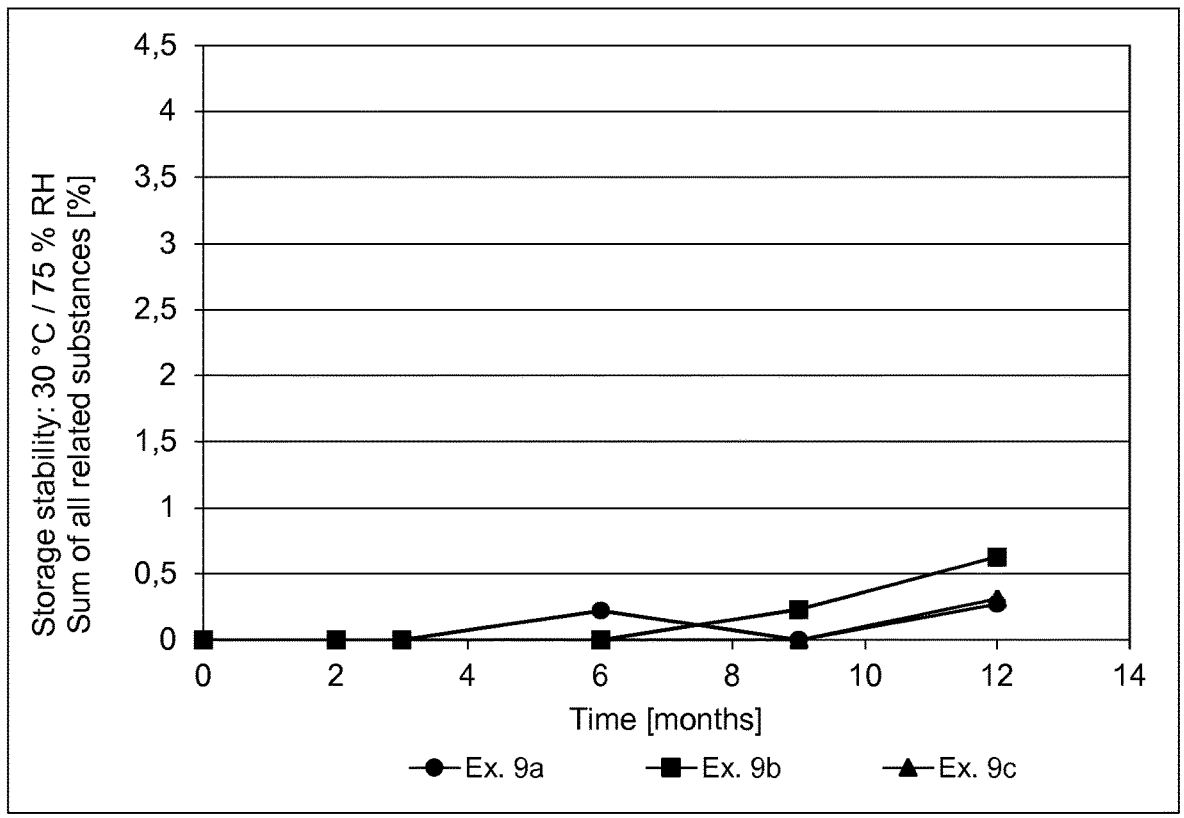
FIG. 9b depicts the sum of all related (i.e. possible degradation product) substances detected in a storage stability test at 30° C. and 75% RH over 0 to 12 months for TTS prepared according to Examples 9a, 9b and 9c.
Figure 9C:
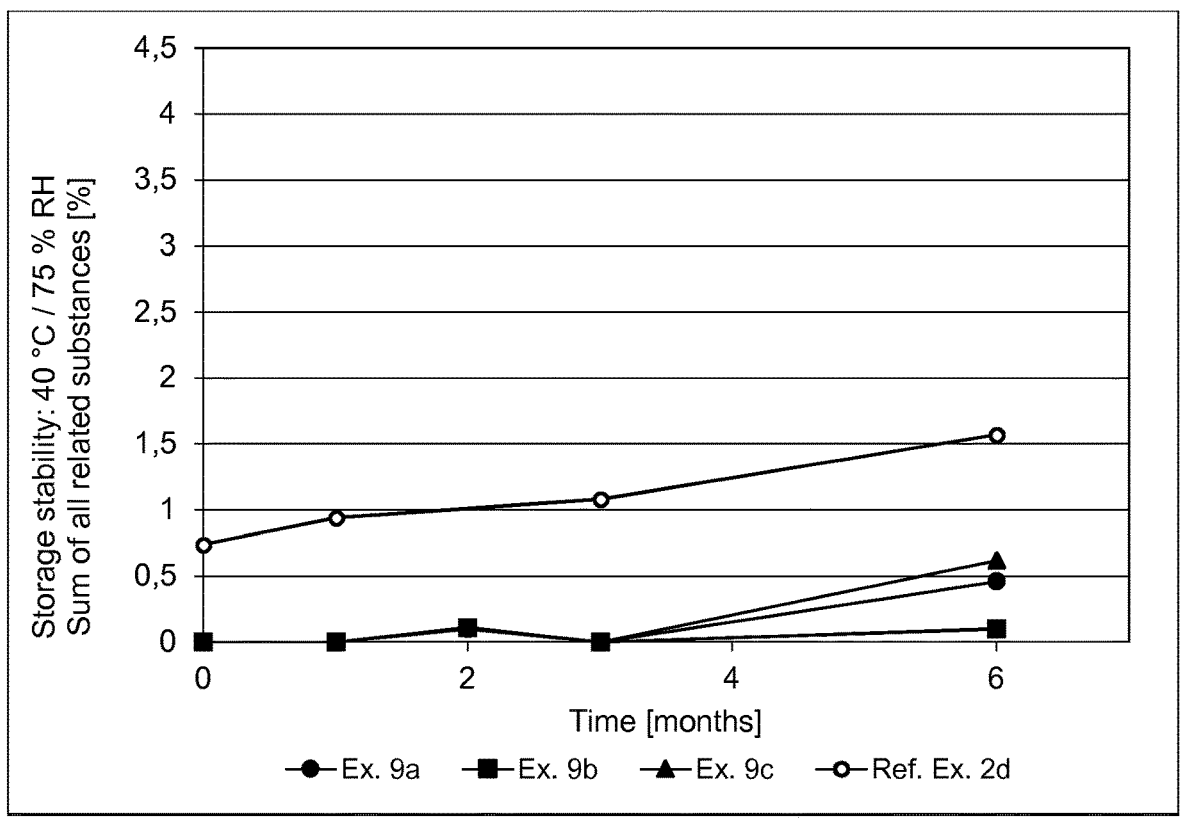
FIG. 9c depicts the sum of all related (i.e. possible degradation product) substances detected in a storage stability test at 40° C. and 75% RH over 0 to 6 months for TTS prepared according to Reference Example 2d and Examples 9a, 9b and 9c.
Figure 9D:
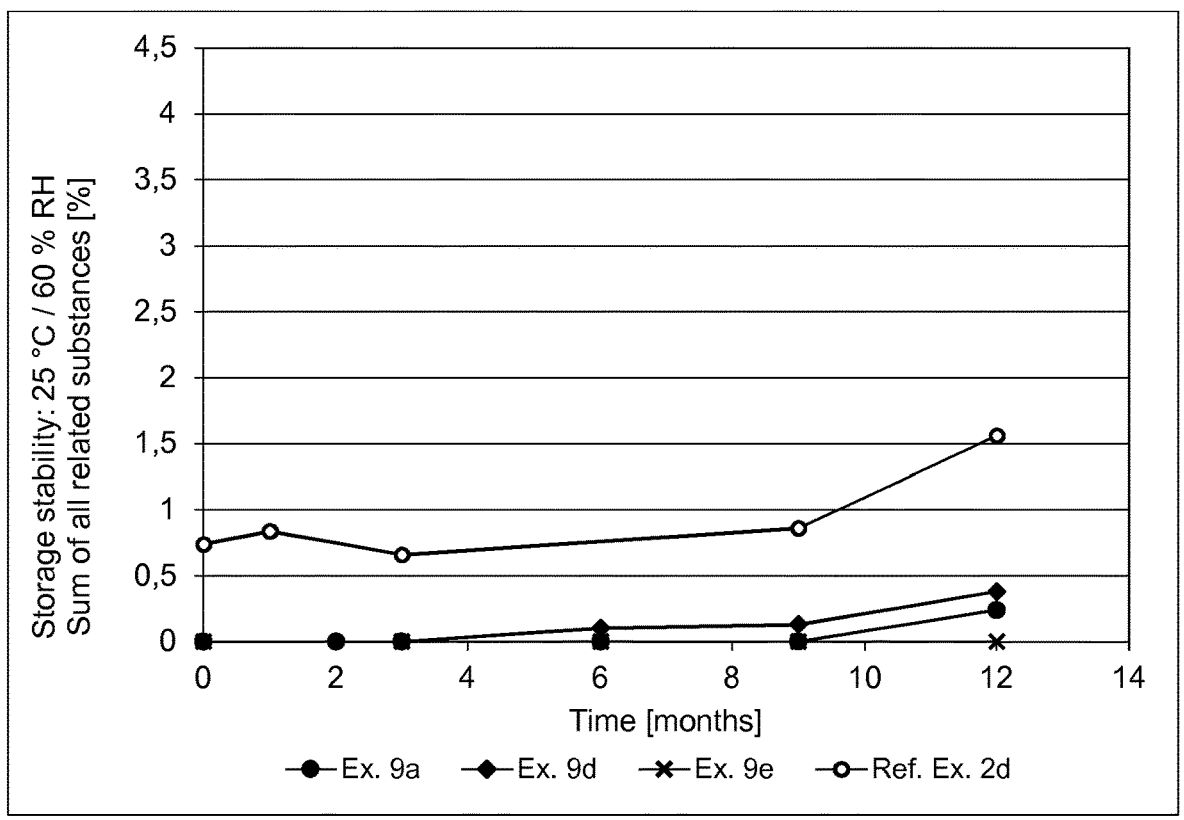
FIG. 9d depicts the sum of all related (i.e. possible degradation product) substances detected in a storage stability test at 25° C. and 60% RH over 0 to 12 months for TTS prepared according to Reference Example 2d and Examples 9a, 9d and 9e.
Figure 9E:
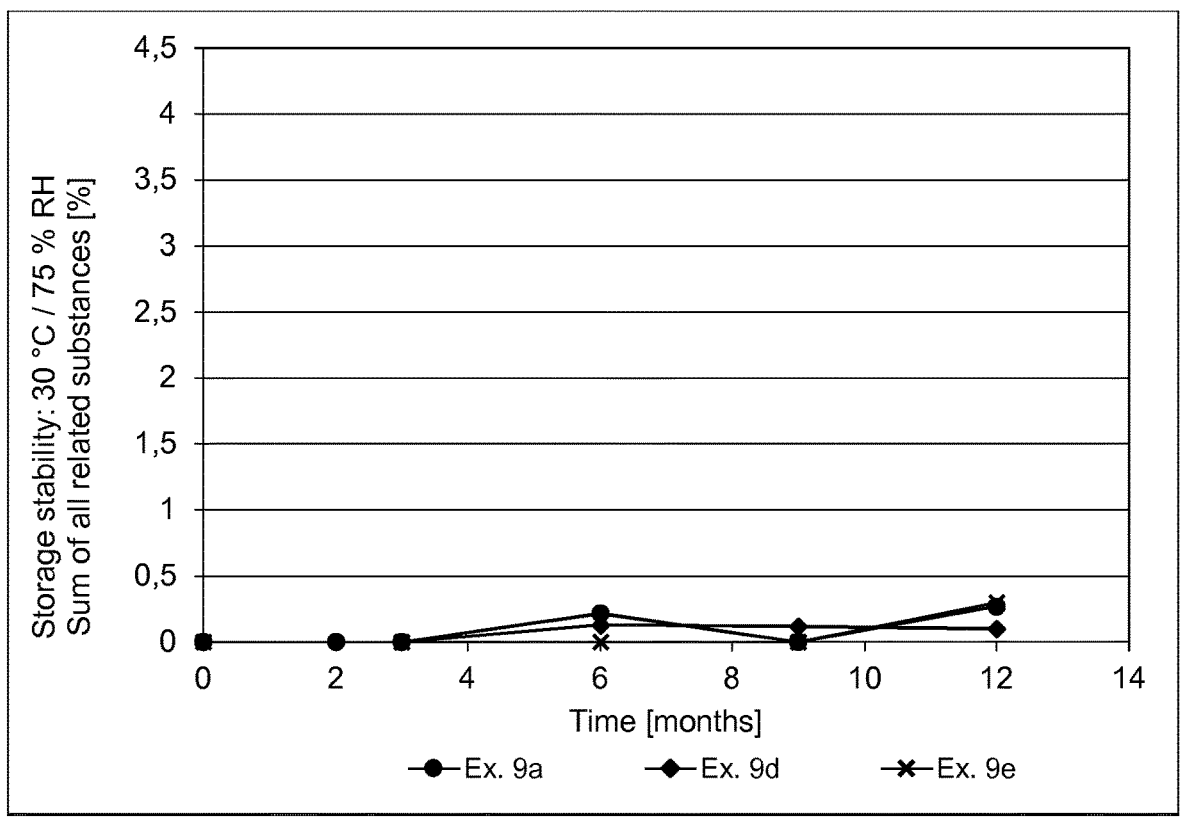
FIG. 9e depicts the sum of all related (i.e. possible degradation product) substances detected in a storage stability test at 30° C. and 75% RH over 0 to 12 months for TTS prepared according to Examples 9a, 9d and 9e.
Figure 9F:
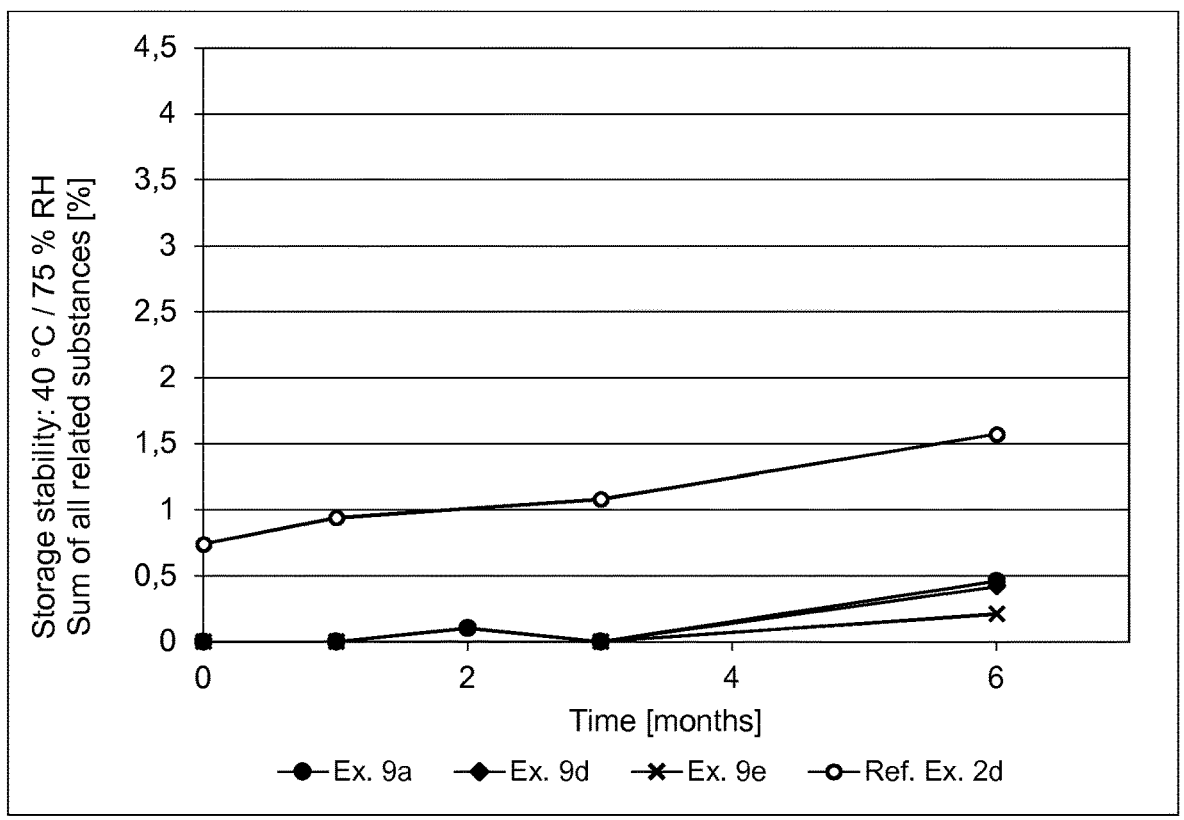
FIG. 9f depicts the sum of all related (i.e. possible degradation product) substances detected in a storage stability test at 40° C. and 75% RH over 0 to 6 months for TTS prepared according to Reference Example 2d and Examples 9a, 9d and 9e.

The stability of the TTS of Examples 8a to 8e, stored at 40° C. and 75% RH for 2.5 months, as well as at 25° C. and 60% RH for 12 months was investigated. Samples were taken from the TTS, extracted with an appropriate extraction solvent and the amount of asenapine base, as well as various possible degradation substances was determined by a specific quantitative HPLC method with a UV photometric detector, based on the asenapine content calculated from the (actual) area weight of the tested TTS. The results are shown in Tables 8.2 and 8.3 as well as FIGS. 8a and 8b.

TABLE 8.2

| TTS stored at For 2.5 months | Detected amounts [%] | | | | |
|---|---|---|---|---|---|
| 40° C./75% RH | Ex. 8a | Ex. 8b | Ex. 8c | Ex. 8d | Ex. 8e |
| Asenapine base | 98 | 97 | 98 | 99 | 99 |
| Asenapine N-Oxide (Cis) | 0.44 | 0.60 | 0.39 | 0.29 | 0.23 |

TABLE 8.2-continued

| TTS stored at For 2.5 months | Detected amounts [%] | | | | |
|---|---|---|---|---|---|
| 40° C./75% RH | Ex. 8a | Ex. 8b | Ex. 8c | Ex. 8d | Ex. 8e |
| Asenapine N-Oxide (Trans) | 0.43 | 0.60 | 0.39 | 0.28 | 0.23 |
| Cis-Asenapine | 0.14 | 0.15 | 0.10 | 0.10 | <LOR |
| Tetradehydro Asenapine | 0.74 | 1.01 | 0.70 | 0.37 | 0.33 |
| Other related substances | 0.20 | 0.21 | 0.16 | 0.14 | 0.13 |
| Sum of all related substances | 1.95 | 2.57 | 1.74 | 1.18 | 0.92 |

* LOR = Limit of Reporting (0.1%)

TABLE 8.3

| TTS stored at For 12 months | Detected amounts [%] | | | | |
|---|---|---|---|---|---|
| 25° C./60% RH | Ex. 8a | Ex. 8b | Ex. 8c | Ex. 8d | Ex. 8e |
| Asenapine N-Oxide (Cis) | 0.70 | 0.92 | 0.61 | 0.47 | 0.44 |
| Asenapine N-Oxide (Trans) | 0.65 | 0.85 | 0.57 | 0.43 | 0.42 |

TABLE 8.3-continued

| TTS stored at For 12 months | Detected amounts [%] | | | | |
|---|---|---|---|---|---|
| 25° C./60% RH | Ex. 8a | Ex. 8b | Ex. 8c | Ex. 8d | Ex. 8e |
| Tetradehydro Asenapine | 0.20 | 0.25 | 0.20 | 0.14 | 0.17 |
| Other related substances | 0.10 | 0.11 | 0.10 | <LOR | 0.13 |
| Sum of all related substances | 1.65 | 2.13 | 1.48 | 1.04 | 1.16 |

* LOR = Limit of Reporting (0.1%)

The stability data of Examples 8a-e show that positive influence of α-Tocopherol and ascorbyl palmitate on initial as well as storage stability of asenapine formulations comprising a matrix layer based on an acrylic adhesive and including an additional polymer (polyvinylpyrrolidone) is synergistic for certain amounts of α-Tocopherol and ascorbyl palmitate.

Examples 9A-E

Coating Composition

The formulations of the asenapine-containing coating compositions of Examples 9a to 9e are summarized in Table 9.1 below. The formulations are based on weight percent, as also indicated in Table 9.1.

Preparation of the Coating Composition

A stainless steel vessel (Examples 9a to 9c) or a beaker (Examples 9d and 9e) was loaded with a part of the ethanol, the sodium metabisulfite solution was added dropwise under stirring and the mixture stirred at least 10 min. The α-Tocopherol and the ascorbyl palmitate solution were added dropwise under stirring and the resulting mixture stirred for at least 20 min. After adding the medium chain triglycerides under stirring, polyvinylpyrrolidone was weighed in a beaker and added to the mixture under stirring. In case of Example 9e, the isononanoic acid was added and the mixture stirred for at least 10 min. before adding the polyvinylpyrrolidone. The acrylic pressure sensitive adhesive Duro-Tak™ 387-2516 was weighed into the reaction mixture, the resulting mixture was stirred and allowed to stand, after which the asenapine was weighed in a beaker and added to the mixture with the remaining part of the ethanol. The mixture was stirred until a clear solution was obtained.

Coating of the Coating Composition

See Reference Example 1a and Reference Example 1b for the coating process. The coating thickness gave an area weight of the matrix layer of 136.6 g/m² (Example 9d) and 135.1 g/m² (Example 9e), respectively. For Example 9a, different films with an area weight of between 140.2 and 148.7 g/m² were produced. For Example 9b, different films with an area weight of between 140.5 and 145.6 g/m² were produced. For Example 9c, different films with an area

TABLE 9.1

| Ingredient (Trade Name) | Ex. 9a Amt [g] | Ex. 9a Solids [%] | Ex. 9b Amt [g] | Ex. 9b Solids [%] | Ex. 9c Amt [g] | Ex. 9c Solids [%] | Ex. 9d Amt [g] | Ex. 9d Solids [%] | Ex. 9e Amt [g] | Ex. 9e Solids [%] |
|---|---|---|---|---|---|---|---|---|---|---|
| Asenapine base | 40.0 | 10.0 | 40.0 | 10.0 | 40.0 | 10.0 | 8.00 | 10.0 | 8.00 | 10.0 |
| Acrylic adhesive in ethyl acetate, ethanol, heptanes and methanol, with a titanium cross-linking agent. Solids content ~41.2% by wt. (Duro-Tak™ 387-2516) | 676.4 | 69.7 | 674.2 | 69.4 | 672.4 | 69.2 | 134.2 | 68.9 | 133.3 | 68.6 |
| Polyvinylpyrrolidone (Povidone K30) | 40.0 | 10.0 | 40.0 | 10.0 | 39.9 | 10.0 | 8.00 | 10.0 | 8.00 | 10.0 |
| α-Tocopherol | 0.21 | 0.05 | 0.20 | 0.05 | 0.21 | 0.05 | 0.13 | 0.17 | 0.06 | 0.07 |
| Ascorbyl palmitate (10% sol. in ethanol denat, containing 1% (v/v) methyl ethyl ketone) | 8.07 | 0.20 | 16.5 | 0.41 | 24.1 | 0.60 | 4.82 | 0.6 | 1.62 | 0.2 |
| Sodium metabisulfite (30% aq. sol.) | 1.51 | 0.11 | 1.51 | 0.11 | 1.51 | 0.11 | 0.29 | 0.11 | 0.33 | 0.12 |
| Medium chain triglycerides (Miglyol 812 N) | 40.0 | 10.0 | 40.0 | 10.0 | 40.1 | 10.0 | 8.23 | 10.3 | 8.00 | 10.0 |
| Isononanoic acid (3,5,5-Trimethylhexanoic acid, 97%) | — | — | — | — | — | — | — | — | 0.80 | 1.00 |
| Ethanol denat. (1% (v/v) methyl ethyl ketone) | 175.9 | — | 175.0 | — | 191.4 | — | 29.0 | — | 32.7 | — |
| Total | 982.1 | 100.0 | 987.4 | 100.0 | 1009.6 | 100.0 | 192.7 | 100.0 | 192.8 | 100.0 |
| Area weight [g/m²] | 140.2-148.7 | | 140.5-145.6 | | 137.0-148.9 | | 136.6 | | 135.1 | |
| Asenapine content [mg/cm²] | 1.402-1.487 | | 1.405-1.456 | | 1.370-1.489 | | 1.366 | | 1.351 | | weight of between 137.0 and 148.9 g/m² were produced. The dried film was laminated with a polyethylene terephthalate backing layer (23 μm thickness) to provide an asenapine-containing self-adhesive layer structure.

Preparation of the TTS

See Example 1.

Stability Measurements

A long term storage stability test was conducted for Examples 9a to 9e under different test conditions, i.e. storage at 25° C. and 60% relative humidity (RH), at 30° C. and 75% RH, and at 40° C. and 75% RH. At different time points, samples were taken from the TTS, extracted with an appropriate extraction solvent and the amount of asenapine base, as well as various possible degradation substances was determined by a specific quantitative HPLC method with a UV photometric detector, based on the asenapine content calculated from the (actual) area weight of the tested TTS. The results are shown in Tables 9.2 to 9.16. A plot of the sum of all related (i.e. possible degradation product) substances is shown in FIGS. 9a to 9f, in comparison to Reference Example 2d (for storage at 25° C. and 60% RH as well as at 40° C. and 75% RH).

TABLE 9.2

| Ex. 9a - 25° C./60% RH | Detected amounts [%] | | | | | |
|---|---|---|---|---|---|---|
| | Initial | 2 months | 3 months | 6 months | 9 months | 12 months |
| Asenapine base | 96 | 96 | 95 | 95 | 95 | 95 |
| Asenapine N-Oxide (Cis) | n.d. | n.d. | n.d. | <LOR | <LOR | 0.11 |
| Asenapine N-Oxide (Trans) | n.d. | n.d. | n.d. | <LOR | <LOR | 0.13 |
| Tetradhydro Asenapine | n.d. | <LOR | <LOR | <LOR | <LOR | <LOR |
| Other related substances | n.d. | n.d. | n.d. | <LOR | n.d. | <LOR |
| Sum of all related substances | 0.00 | 0.00 | 0.00 | 0.00 | 0.00 | 0.24 |

* n.d. = not detected, LOR = Limit of reporting (0.1%)

TABLE 9.3

| Ex. 9a - 30° C./75% RH | Detected amounts [%] | | | | | |
|---|---|---|---|---|---|---|
| | Initial | 2 months | 3 months | 6 months | 9 months | 12 months |
| Asenapine base | 96 | 96 | 95 | 96 | 95 | 95 |
| Asenapine N-Oxide (Cis) | n.d. | n.d. | n.d. | 0.11 | n.d. | 0.13 |
| Asenapine N-Oxide (Trans) | n.d. | n.d. | n.d. | 0.11 | n.d. | 0.14 |
| Tetradhydro Asenapine | n.d. | <LOR | <LOR | <LOR | <LOR | <LOR |
| Other related substances | n.d. | n.d. | n.d. | <LOR | n.d. | <LOR |
| Sum of all related substances | 0.00 | 0.00 | 0.00 | 0.22 | 0.00 | 0.27 |

* n.d. = not detected, LOR = Limit of reporting (0.1%)

TABLE 9.4

| Ex. 9a - 40° C./75% RH | Detected amounts [%] | | | | |
|---|---|---|---|---|---|
| | Initial | 1 month | 2 months | 3 months | 6 months |
| Asenapine base | 96 | 96 | 96 | 94 | 95 |
| Asenapine N-Oxide (Cis) | n.d. | n.d. | n.d. | <LOR | 0.17 |
| Asenapine N-Oxide (Trans) | n.d. | n.d. | n.d. | n.d. | 0.16 |
| Tetradhydro Asenapine | n.d. | <LOR | 0.10 | <LOR | <LOR |
| Other related substances | n.d. | n.d. | <LOR | n.d. | 0.13 |
| Sum of all related substances | 0.00 | 0.00 | 0.10 | 0.00 | 0.46 |

* n.d. = not detected, LOR = Limit of reporting (0.1%)

TABLE 9.5

| Ex. 9b - 25° C./60% RH | Detected amounts [%] | | | | | |
|---|---|---|---|---|---|---|
| | Initial | 2 months | 3 months | 6 months | 9 months | 12 months |
| Asenapine base | 96 | 96 | 95 | 95 | 95 | 95 |
| Asenapine N-Oxide (Cis) | n.d. | n.d. | n.d. | <LOR | n.d. | <LOR |
| Asenapine N-Oxide (Trans) | n.d. | n.d. | n.d. | <LOR | n.d. | 0.10 |
| Tetradhydro Asenapine | n.d. | <LOR | <LOR | <LOR | <LOR | <LOR |
| Other related substances | n.d. | n.d. | n.d. | <LOR | n.d. | <LOR |
| Sum of all related substances | 0.00 | 0.00 | 0.00 | 0.00 | 0.00 | 0.10 |

* n.d. = not detected, LOR = Limit of reporting (0.1%)

TABLE 9.6

| Ex. 9b - 30° C./75% RH | Detected amounts [%] | | | | | |
|---|---|---|---|---|---|---|
| | Initial | 2 months | 3 months | 6 months | 9 months | 12 months |
| Asenapine base | 96 | 95 | 95 | 95 | 94 | 94 |
| Asenapine N-Oxide (Cis) | n.d. | n.d. | n.d. | <LOR | 0.12 | 0.20 |
| Asenapine N-Oxide (Trans) | n.d. | n.d. | n.d. | <LOR | 0.11 | 0.20 |
| Tetradehydro Asenapine | n.d. | <LOR | <LOR | <LOR | <LOR | 0.13 |
| Other related substances | n.d. | n.d. | n.d. | <LOR | n.d. | 0.10 |
| Sum of all related substances | 0.00 | 0.00 | 0.00 | 0.00 | 0.23 | 0.63 |

* n.d. = not detected, LOR = Limit of reporting (0.1%)

TABLE 9.7

| Ex. 9b - 40° C./75% RH | Detected amounts [%] | | | | |
|---|---|---|---|---|---|
| | Initial | 1 month | 2 months | 3 months | 6 months |
| Asenapine base | 96 | 97 | 96 | 94 | 95 |
| Asenapine N-Oxide (Cis) | n.d. | n.d. | n.d. | n.d. | <LOR |
| Asenapine N-Oxide (Trans) | n.d. | n.d. | n.d. | n.d. | <LOR |
| Tetradehydro Asenapine | n.d. | <LOR | 0.11 | <LOR | <LOR |
| Other related substances | n.d. | n.d. | n.d. | n.d. | 0.10 |
| Sum of all related substances | 0.00 | 0.00 | 0.11 | 0.00 | 0.10 |

* n.d. = not detected, LOR = Limit of reporting (0.1%)

TABLE 9.8

| Ex. 9c - 25° C./60% RH | Detected amounts [%] | | | | | |
|---|---|---|---|---|---|---|
| | Initial | 2 months | 3 months | 6 months | 9 months | 12 months |
| Asenapine base | 96 | 97 | 94 | 95 | 94 | 94 |
| Asenapine N-Oxide (Cis) | n.d. | n.d. | <LOR | <LOR | 0.13 | <LOR |
| Asenapine N-Oxide (Trans) | n.d. | n.d. | <LOR | <LOR | 0.13 | <LOR |
| Tetradehydro Asenapine | <LOR | <LOR | <LOR | <LOR | <LOR | <LOR |
| Other related substances | n.d. | n.d. | <LOR | <LOR | n.d. | <LOR |
| Sum of all related substances | 0.00 | 0.00 | 0.00 | 0.00 | 0.26 | 0.00 |

* n.d. = not detected, LOR = Limit of reporting (0.1 %)

TABLE 9.9

| Ex. 9c - 30° C./75% RH | Detected amounts [%] | | | | | |
|---|---|---|---|---|---|---|
| | Initial | 2 months | 3 months | 6 months | 9 months | 12 months |
| Asenapine base | 96 | 95 | 94 | 95 | 94 | 94 |
| Asenapine N-Oxide (Cis) | n.d. | n.d. | n.d. | <LOR | <LOR | 0.10 |
| Asenapine N-Oxide (Trans) | n.d. | n.d. | n.d. | <LOR | <LOR | 0.10 |
| Tetradehydro Asenapine | <LOR | <LOR | <LOR | <LOR | <LOR | 0.11 |
| Other related substances | n.d. | n.d. | <LOR | <LOR | n.d. | <LOR |
| Sum of all related substances | 0.00 | 0.00 | 0.00 | 0.00 | 0.00 | 0.31 |

* n.d. = not detected, LOR = Limit of reporting (0.1%)

TABLE 9.10

| Ex. 9c - 40° C./75% RH | Detected amounts [%] | | | | |
|---|---|---|---|---|---|
| | Initial | 1 month | 2 months | 3 months | 6 months |
| Asenapine base | 96 | 96 | 95 | 93 | 94 |
| Asenapine N-Oxide (Cis) | n.d. | n.d. | n.d. | n.d. | 0.16 |
| Asenapine N-Oxide (Trans) | n.d. | n.d. | n.d. | n.d. | 0.14 |

TABLE 9.10-continued

| Ex. 9c - 40° C./75% RH | Detected amounts [%] | | | | |
| --- | --- | --- | --- | --- | --- |
| | Initial | 1 month | 2 months | 3 months | 6 months |
| Tetradehydro Asenapine | <LOR | <LOR | 0.11 | <LOR | 0.17 |
| Other related substances | n.d. | n.d. | <LOR | <LOR | 0.15 |
| Sum of all related substances | 0.00 | 0.00 | 0.11 | 0.00 | 0.62 |

* n.d. = not detected, LOR = Limit of reporting (0.1%)

TABLE 9.11

| Ex. 9d - 25° C./60% RH | Detected amounts [%] | | | | |
| --- | --- | --- | --- | --- | --- |
| | Initial | 3 months | 6 months | 9 months | 12 months |
| Asenapine base | 97 | 95 | 96 | 94 | 95 |
| Asenapine N-Oxide (Cis) | n.d. | n.d. | <LOR | <LOR | 0.13 |
| Asenapine N-Oxide (Trans) | n.d. | n.d. | <LOR | <LOR | 0.13 |
| Tetradehydro Asenapine | <LOR | <LOR | 0.10 | 0.13 | 0.12 |
| Other related substances | n.d. | n.d. | <LOR | n.d. | <LOR |
| Sum of all related substances | 0.00 | 0.00 | 0.10 | 0.13 | 0.38 |

* n.d. = not detected, LOR = Limit of reporting (0.1%)

TABLE 9.12

| Ex. 9d - 30° C./75% RH | Detected amounts [%] | | | | |
| --- | --- | --- | --- | --- | --- |
| | Initial | 3 months | 6 months | 9 months | 12 months |
| Asenapine base | 97 | 94 | 96 | 95 | 95 |
| Asenapine N-Oxide (Cis) | n.d. | n.d. | <LOR | <LOR | <LOR |
| Asenapine N-Oxide (Trans) | n.d. | n.d. | <LOR | <LOR | <LOR |
| Tetradehydro Asenapine | <LOR | <LOR | 0.13 | 0.12 | 0.10 |
| Other related substances | n.d. | <LOR | <LOR | n.d. | <LOR |
| Sum of all related substances | 0.00 | 0.00 | 0.13 | 0.12 | 0.10 |

* n.d. = not detected, LOR = Limit of reporting (0.1%)

TABLE 9.13

| Ex. 9d - 40° C./75% RH | Detected amounts [%] | | | |
| --- | --- | --- | --- | --- |
| | Initial | 1 month | 3 months | 6 months |
| Asenapine base | 97 | 96 | 94 | 95 |
| Asenapine N-Oxide (Cis) | n.d. | n.d. | n.d. | 0.10 |
| Asenapine N-Oxide (Trans) | n.d. | n.d. | n.d. | <LOR |
| Tetradehydro Asenapine | <LOR | <LOR | <LOR | 0.17 |
| Other related substances | n.d. | n.d. | <LOR | 0.15 |
| Sum of all related substances | 0.00 | 0.00 | 0.00 | 0.42 |

* n.d. = not detected, LOR = Limit of reporting (0.1%)

TABLE 9.14

| Ex. 9e - 25° C./60% RH | Detected amounts [%] | | | | |
|---|---|---|---|---|---|
| | Initial | 3 months | 6 months | 9 months | 12 months |
| Asenapine base | 97 | 96 | 97 | 96 | 96 |
| Asenapine N-Oxide (Cis) | n.d. | n.d. | <LOR | n.d. | <LOR |
| Asenapine N-Oxide (Trans) | n.d. | n.d. | <LOR | n.d. | <LOR |
| Tetradehydro Asenapine | n.d. | <LOR | <LOR | <LOR | <LOR |
| Other related substances | n.d. | n.d. | <LOR | n.d. | <LOR |
| Sum of all related substances | 0.00 | 0.00 | 0.00 | 0.00 | 0.00 |

* n.d. = not detected, LOR = Limit of reporting (0.1%)

TABLE 9.15

| Ex. 9e - 30° C./75% RH | Detected amounts [%] | | | | |
|---|---|---|---|---|---|
| | Initial | 3 months | 6 months | 9 months | 12 months |
| Asenapine base | 97 | 96 | 97 | 95 | 95 |
| Asenapine N-Oxide (Cis) | n.d. | n.d. | <LOR | <LOR | 0.15 |
| Asenapine N-Oxide (Trans) | n.d. | n.d. | <LOR | <LOR | 0.15 |
| Tetradehydro Asenapine | n.d. | <LOR | <LOR | <LOR | <LOR |
| Other related substances | n.d. | <LOR | n.d. | n.d. | <LOR |
| Sum of all related substances | 0.00 | 0.00 | 0.00 | 0.00 | 0.30 |

* n.d. = not detected, LOR = Limit of reporting (0.1%)

TABLE 9.16

| Ex. 9e - 40° C./75% RH | Detected amounts [%] | | | |
|---|---|---|---|---|
| | Initial | 1 month | 3 months | 6 months |
| Asenapine base | 97 | 97 | 95 | 96 |
| Asenapine N-Oxide (Cis) | n.d. | n.d. | n.d. | 0.10 |
| Asenapine N-Oxide (Trans) | n.d. | n.d. | n.d. | <LOR |
| Tetradehydro Asenapine | n.d. | <LOR | <LOR | <LOR |
| Other related substances | n.d. | n.d. | n.d. | 0.11 |
| Sum of all related substances | 0.00 | 0.00 | 0.00 | 0.21 |

* n.d. = not detected, LOR = Limit of reporting (0.1%)

The stability data show that, in certain embodiments of the invention, the initial stability as well as storage stability have been substantially improved when compared to the previously developed reference formulations (e.g. Ref. Ex. 2d), both in terms of the amount of asenapine base (in particular with respect to the amount of asenapine base remaining after storage) as well as the sum of all related (i.e. possible degradation product) substances.

Examples 10A and B

Coating Composition

The formulations of the asenapine-containing coating compositions of Examples 10a and 10b are summarized in Table 10.1 below. The formulations are based on weight percent, as also indicated in Table 10.1.

TABLE 10.1

| | Ex. 10a | | Ex. 10b | |
|---|---|---|---|---|
| Ingredient (Trade Name) | Amt [g] | Solids [%] | Amt [g] | Solids [%] |
| Asenapine base | 8.01 | 10.0 | 8.00 | 10.0 |
| Acrylic adhesive in ethyl acetate, ethanol, heptanes and methanol, with a titanium cross-linking agent. Solids content of 41.2% (Ex. 10a) or 41.9% (Ex. 10b) by weight (Duro-Tak ™ 387-2516) | 135.4 | 69.7 | 133.6 | 69.8 |
| Polyvinylpyrrolidone (Povidone K30) | 8.00 | 10.0 | 8.00 | 10.0 |
| α-Tocopherol | 0.07 | 0.09 | 0.04 | 0.05 |
| Ascorbyl palmitate (10% sol. in ethanol denat, containing 1% (v/v) methyl ethyl ketone) | 1.60 | 0.20 | 1.61 | 0.20 |
| Sodium metabisulfite (30% aq. sol.) | 0.08 | 0.03 | — | — |
| Medium chain triglycerides (Miglyol 812 N) | 8.01 | 10.0 | 8.01 | 10.0 |
| Ethanol denat. (1% (v/v) methyl ethyl ketone) | 32.4 | — | 34.3 | — |
| Total | 193.6 | 100.0 | 193.6 | 100.0 |
| Area weight [g/m²] | 135.9 | | 137.2 | |
| Asenapine content [mg/cm²] | 1.359 | | 1.372 | |

Preparation of the Coating Composition

For Example 10a, a beaker was loaded with a part of the ethanol, the sodium metabisulfite solution was added dropwise under stirring and the mixture stirred at least 10 min, before the α-Tocopherol was added dropwise under stirring. For Example 10b, a beaker was loaded with the α-Tocopherol as well as a part of the ethanol. To this mixture comprising α-Tocopherol (Example 10b) and sodium metabisulfite (Example 10a) in ethanol, the ascorbyl palmitate solution was added dropwise under stirring and the resulting mixture stirred for at least 20 min. After adding the medium chain triglycerides under stirring, polyvinylpyrrolidone was weighed in a beaker and added to the mixture under stirring. The acrylic pressure sensitive adhesive Duro-Tak™ 387-2516 was weighed into the reaction mixture, the resulting mixture was stirred and allowed to stand, after which the asenapine was weighed in a beaker and added to the mixture with the remaining part of the ethanol. The mixture was stirred until a clear solution was obtained.

Coating of the Coating Composition

See Reference Example 1a and Reference Example 1b for the coating process. The coating thickness gave an area weight of the matrix layer of 135.9 g/m$^2$ (Example 10a) and 137.2 g/m$^2$ (Example 11b), respectively. The dried film was laminated with a polyethylene terephthalate backing layer (23 μm thickness) to provide an asenapine-containing self-adhesive layer structure.

Preparation of the TTS

See Example 1.

Stability Measurements

Figure 10A:
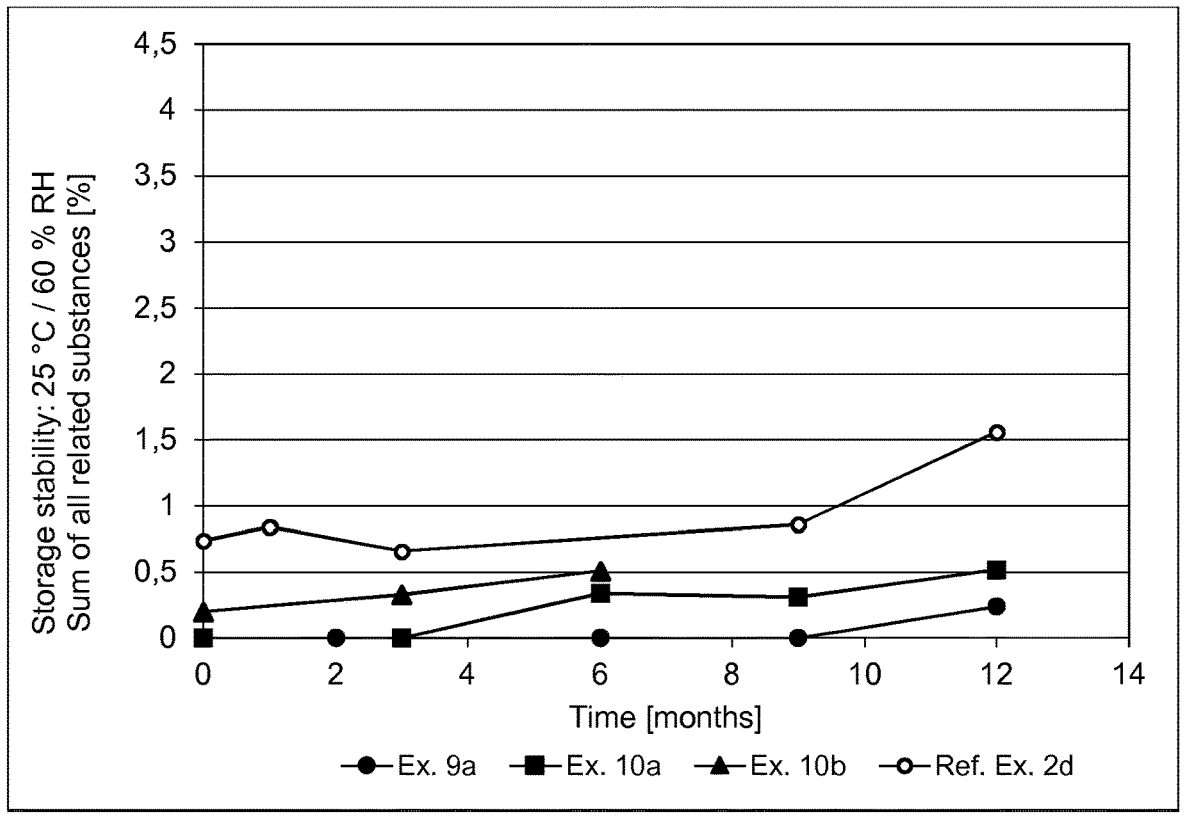
FIG. 10a depicts the sum of all related (i.e. possible degradation product) substances detected in a storage stability test at 25° C. and 60% RH over 0 to 12 months for TTS prepared according to Reference Example 2d and Examples 9a and 10a and over 0 to 6 months for TTS prepared according to Example 10b.
Figure 10B:
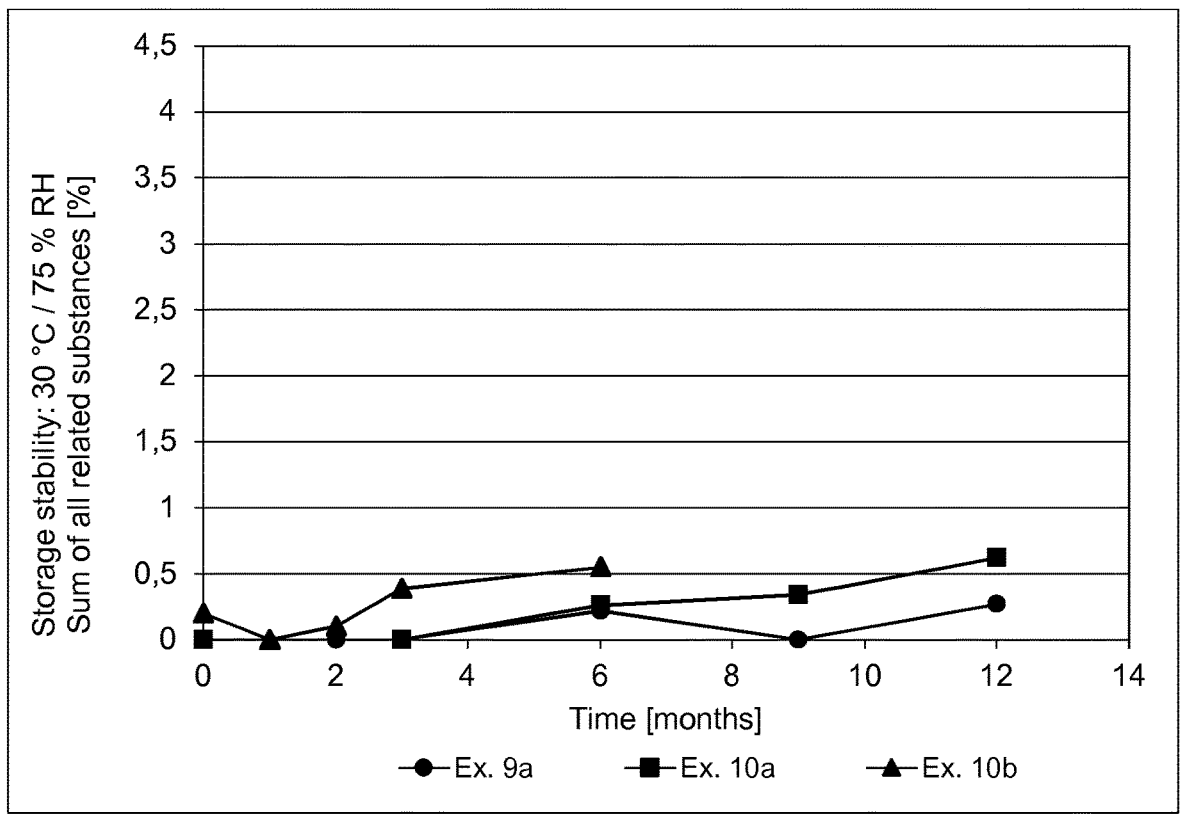
FIG. 10b depicts the sum of all related (i.e. possible degradation product) substances detected in a storage stability test at 30° C. and 75% RH over 0 to 12 months for TTS prepared according to Examples 9a and 10a and over 0 to 6 months for TTS prepared according to Example 10b.
Figure 10C:
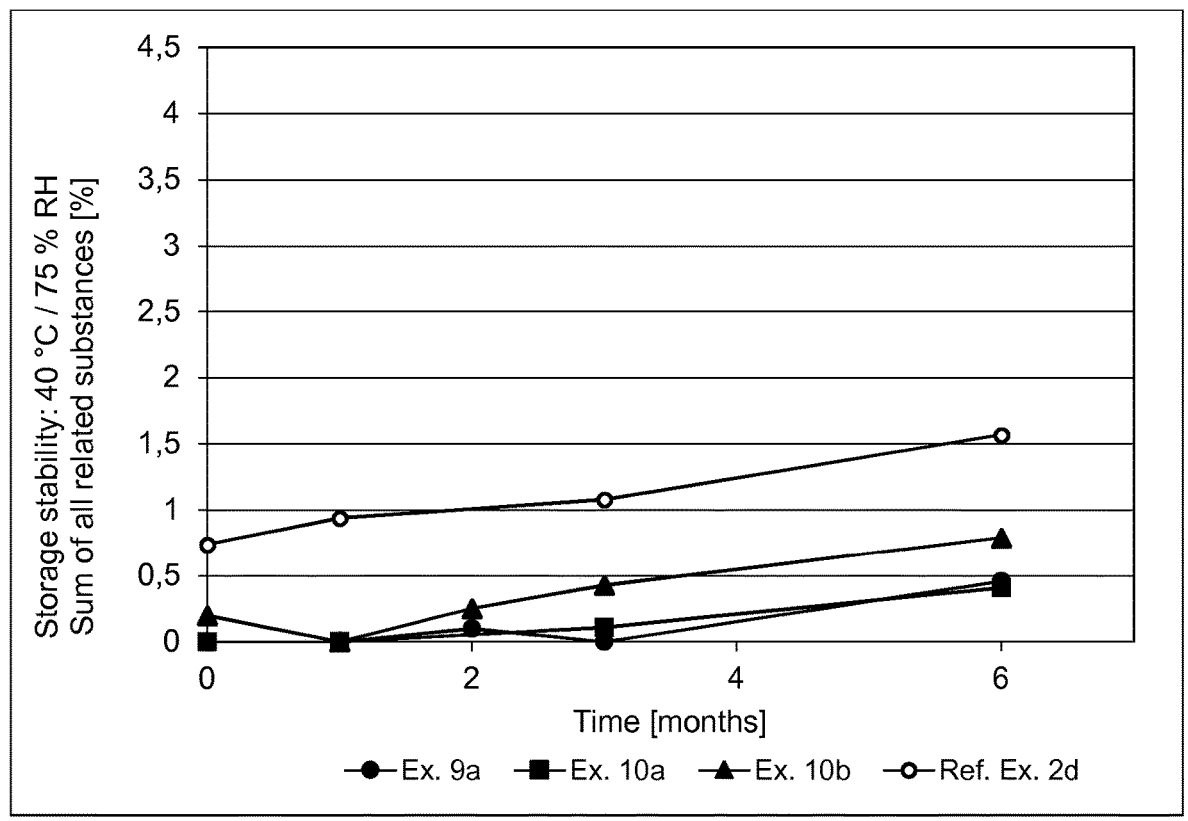
FIG. 10c depicts the sum of all related (i.e. possible degradation product) substances detected in a storage stability test at 40° C. and 75% RH over 0 to 6 months for TTS prepared according to Reference Example 2d and Examples 9a, 10a and 10b.

A long term storage stability test was conducted for Examples 10a and 10b under different test conditions, i.e. storage at 25° C. and 60% relative humidity (RH), at 30° C. and 75% RH, and at 40° C. and 75% RH. At different time points, samples were taken from the TTS, extracted with an appropriate extraction solvent and the amount of asenapine base, as well as various possible degradation substances was determined by a specific quantitative HPLC method with a UV photometric detector, based on the asenapine content calculated from the (actual) area weight of the tested TTS. The results are shown in Tables 10.2 to 10.7. A plot of the sum of all related (i.e. possible degradation product) substances is shown in FIGS. 10a to 10c in comparison to Example 9a, and in comparison to Reference Example 2d (for storage at 25° C. and 60% RH as well as at 40° C. and 75% RH).

TABLE 10.2

| Ex. 10a - 25° C./60% RH | Detected amounts [%] | | | | |
|---|---|---|---|---|---|
| | Initial | 3 months | 6 months | 9 months | 12 months |
| Asenapine base | 97 | 96 | 97 | 96 | 96 |
| Asenapine N-Oxide (Cis) | n.d. | n.d. | 0.18 | 0.16 | 0.26 |
| Asenapine N-Oxide (Trans) | n.d. | n.d. | 0.16 | 0.15 | 0.26 |
| Tetradehydro Asenapine | n.d. | <LOR | <LOR | <LOR | <LOR |
| Other related substances | n.d. | n.d. | <LOR | n.d. | <LOR |
| Sum of all related substances | 0.00 | 0.00 | 0.34 | 0.31 | 0.52 |

* n.d. = not detected, LOR = Limit of reporting (0.1%)

TABLE 10.3

| Ex. 10a - 30° C./75% RH | Detected amounts [%] | | | | |
|---|---|---|---|---|---|
| | Initial | 3 months | 6 months | 9 months | 12 months |
| Asenapine base | 97 | 95 | 96 | 96 | 96 |
| Asenapine N-Oxide (Cis) | n.d. | <LOR | 0.13 | 0.18 | 0.31 |
| Asenapine N-Oxide (Trans) | n.d. | <LOR | 0.13 | 0.16 | 0.31 |
| Tetradehydro Asenapine | n.d. | <LOR | <LOR | <LOR | <LOR |
| Other related substances | n.d. | <LOR | n.d. | n.d. | <LOR |
| Sum of all related substances | 0.00 | 0.00 | 0.26 | 0.34 | 0.62 |

* n.d. = not detected, LOR = Limit of reporting (0.1%)

TABLE 10.4

| Ex. 10a - 40° C./75% RH | Detected amounts [%] | | | |
|---|---|---|---|---|
| | Initial | 1 month | 3 months | 6 months |
| Asenapine base | 97 | 98 | 95 | 96 |
| Asenapine N-Oxide (Cis) | n.d. | n.d. | 0.11 | 0.21 |
| Asenapine N-Oxide (Trans) | n.d. | n.d. | <LOR | 0.20 |
| Tetradehydro Asenapine | n.d. | <LOR | <LOR | <LOR |
| Other related substances | n.d. | n.d. | n.d. | <LOR |
| Sum of all related substances | 0.00 | 0.00 | 0.11 | 0.41 |

* n.d. = not detected, LOR = Limit of reporting (0.1%)

TABLE 10.5

| Ex. 10b - 25° C./60% RH | Detected amounts [%] | | |
|---|---|---|---|
| | Initial | 3 months | 6 months |
| Asenapine base | 96 | 95 | 96 |
| Asenapine N-Oxide (Cis) | 0.10 | 0.17 | 0.20 |
| Asenapine N-Oxide (Trans) | 0.10 | 0.16 | 0.18 |
| Tetradehydro Asenapine | <LOR | <LOR | 0.13 |
| Other related substances | n.d. | n.d. | n.d. |
| Sum of all related substances | 0.20 | 0.33 | 0.51 |

* n.d. = not detected, LOR = Limit of reporting (0.1%)

TABLE 10.6

| Ex. 10b - 30° C./75% RH | Detected amounts [%] | | | | |
|---|---|---|---|---|---|
| | Initial | 1 month | 2 months | 3 months | 6 months |
| Asenapine base | 96 | 97 | 95 | 96 | 96 |
| Asenapine N-Oxide (Cis) | 0.10 | <LOR | 0.10 | 0.20 | 0.21 |
| Asenapine N-Oxide (Trans) | 0.10 | n.d. | <LOR | 0.19 | 0.19 |
| Tetradehydro Asenapine | <LOR | n.d. | <LOR | <LOR | 0.15 |
| Other related substances | n.d. | n.d. | <LOR | n.d. | n.d. |
| Sum of all related substances | 0.20 | 0.00 | 0.10 | 0.39 | 0.55 |

* n.d. = not detected, LOR = Limit of reporting (0.1%)

TABLE 10.7

| Ex. 10b - 40° C./75% RH | Detected amounts [%] | | | | |
|---|---|---|---|---|---|
| | Initial | 1 month | 2 months | 3 months | 6 months |
| Asenapine base | 96 | 97 | 96 | 96 | 95 |
| Asenapine N-Oxide (Cis) | 0.10 | <LOR | 0.13 | 0.22 | 0.32 |
| Asenapine N-Oxide (Trans) | 0.10 | <LOR | 0.12 | 0.21 | 0.28 |
| Tetradehydro Asenapine | <LOR | <LOR | <LOR | <LOR | 0.19 |
| Other related substances | n.d. | <LOR | <LOR | n.d. | <LOR |
| Sum of all related substances | 0.20 | 0.00 | 0.25 | 0.43 | 0.79 |

* n.d. = not detected, LOR = Limit of reporting (0.1%)

The stability data show that an improved stability and also storage stability can be achieved by a combination of α-tocopherol and ascorbyl palmitate, and that addition of a certain amount of sodium metabisulfite has a positive impact on the overall storage stability.

Example 11A and Reference Examples 11B, 11C and 11D

Coating Composition

The formulations of the asenapine-containing coating compositions of Example 11a as well as Reference Examples 11b, 11c and 11d are summarized in Table 11.1 below. The formulations are based on weight percent, as also indicated in Table 11.1.

TABLE 11.1

|  | Ex. 11a | | Ref. Ex. 11b | | Ref. Ex. 11c | | Ref. Ex. 11d | |
|---|---|---|---|---|---|---|---|---|
| Ingredient (Trade Name) | Amt [g] | Solids [%] | Amt [g] | Solids [%] | Amt [g] | Solids [%] | Amt [g] | Solids [%] |
| Asenapine base | 2.90 | 10.0 | — | — | — | — | — | — |
| Asenapine maleate | — | — | 7.50 | 50.0 | 1.80 | 12.0 | 2.12 | 13.8 |
| Sodium hydroxide (10% sol. in ethanol) | — | — | 14.9 | 9.95 | — | — | 4.20 | 2.75 |
| Sodium hydrogen carbonate | — | — | — | — | 0.75 | 5.03 | — | — |
| Acrylic adhesive in ethyl acetate, ethanol, heptanes and methanol, with a titanium cross-linking agent. Solids content ~42.4% by wt. (Duro-Tak™ 387-2516) | 47.5 | 69.5 | 14.2 | 40.1 | 29.4 | 82.9 | 23.1 | 63.9 |
| Polyvinylpyrrolidone (Povidone K30) | 2.90 | 10.0 | — | — | — | — | 1.50 | 9.80 |
| α-Tocopherol | 0.04 | 0.14 | — | — | — | — | — | — |
| Ascorbyl palmitate (10% sol. in ethanol denat, containing 1% (v/v) methyl ethyl ketone) | 0.58 | 0.19 | — | — | — | — | — | — |
| Sodium metabisulfite (30% aq. solution) | 0.10 | 0.11 | — | — | — | — | — | — |
| Medium chain triglycerides (Miglyol 812 N) | 2.90 | 10.0 | — | — | — | — | 1.50 | 9.77 |
| Ethanol denat. (1% (v/v) methyl ethyl ketone) | 12.9 | — | 15.1 | — | 4.30 | — | 4.56 | — |
| Total | 69.8 | 100.0 | 51.7 | 100.0 | 36.3 | 100.0 | 37.0 | 100.0 |
| Area weight [g/m$^2$] | 145.3 | | — | | 153.4 | | 144.3 | |
| Asenapine content [mg/cm$^2$] | 1.453 | | — | | 1.312 | | 1.417 | |

Preparation of the Coating Composition

The coating composition of Example 11a was prepared as described for Examples 9d and 10a.

For Reference Example 11b, a beaker was loaded with the asenapine maleate, the sodium hydroxide solution was added and the mixture stirred. As the mixture solidified, ethanol was added and the mixture further stirred. The acrylic pressure sensitive adhesive Duro-Tak™ 387-2516 was weighed into the reaction mixture, which was then stirred and allowed to stand, and stirred again. The resulting mixture was inhomogeneous so that coating of the composition was impossible.

For Reference Example 11c, a beaker was loaded with the asenapine maleate and the ethanol was added. The acrylic pressure sensitive adhesive Duro-Tak™ 387-2516 was weighed into the reaction mixture, which was then stirred and allowed to stand, and stirred again until a clear solution including undissolved particles was obtained.

For Reference Example 11d, a beaker was loaded with the asenapine maleate and the sodium hydrogen carbonate. The ethanol was added and the acrylic pressure sensitive adhesive Duro-Tak™ 387-2516 was weighed into the reaction mixture, which was then stirred. The polyvinylpyrrolidone was weighed in a beaker and added to the mixture under stirring. The sodium hydroxide solution and the medium chain triglycerides were added dropwise and consecutively in this order. A white, homogeneous solution was obtained.

Coating of the Coating Composition, Example 11a and Reference Examples 11c and 11d See Reference Example 1a and Reference Example 1b for the coating process. The coating thickness gave an area weight of the matrix layer of 145.3 g/m$^2$ (Example 11a), 153.4 g/m$^2$ (Reference Example 11c) and 144.3 g/m$^2$ (Reference Example 11d), respectively. The dried film was laminated with a polyethylene terephthalate backing layer (23 μm thickness) to provide an asenapine-containing self-adhesive layer structure. As outlined above, coating was impossible for Reference Example 11b. The coated matrix layer of Reference Example 11c was visibly inhomogeneous, likely due to the undissolved sodium hydrogen carbonate particles and adhesion appeared to be insufficient. The coated matrix layer of Example 11a showed excellent adhesion, while the coated matrix layer of Reference Example 11d exhibited only moderate adhesion.

Preparation of the TTS

Figure 11A:
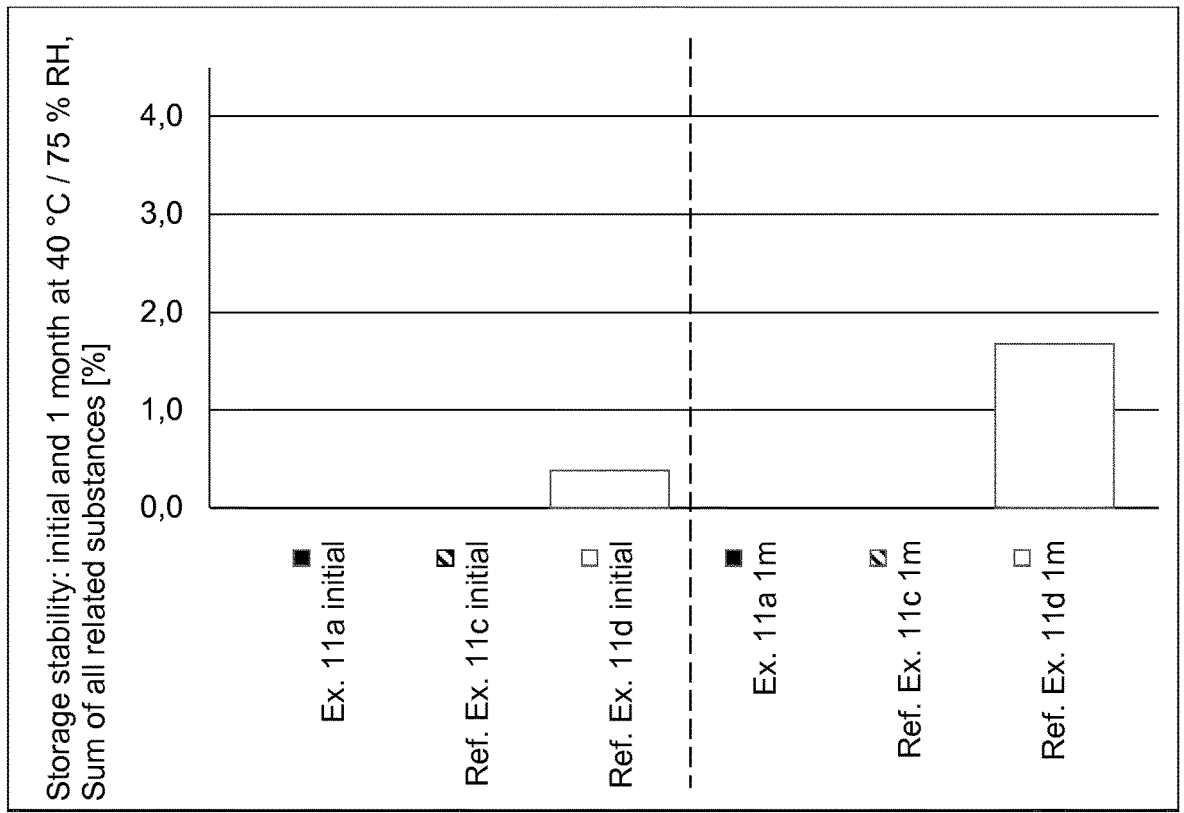
FIG. 11a depicts the sum of all related (i.e. possible degradation product) substances detected in a storage stability test at 40° C. and 75% RH initially and after 1 month for TTS prepared according to Example 11a and Reference Examples 11c and 11d.
Figure 11B:
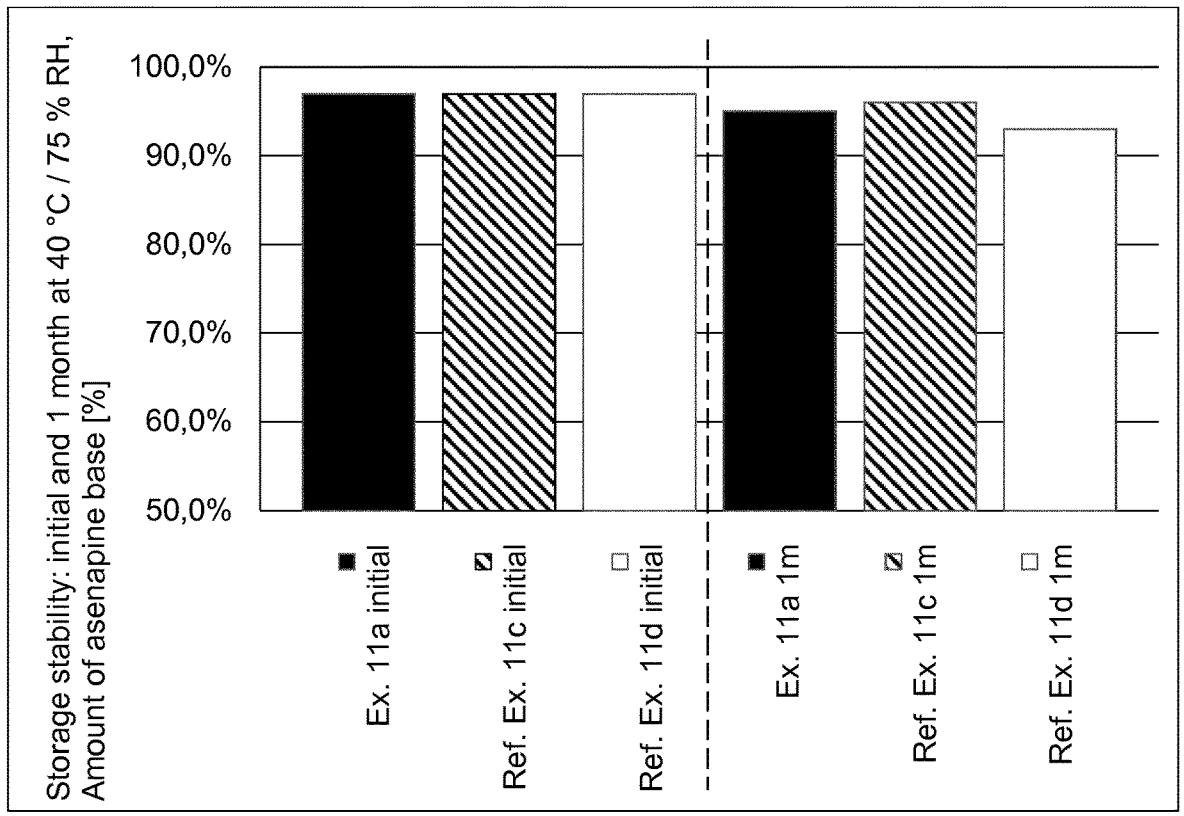
FIG. 11b depicts the amount of asenapine base detected in a storage stability test at 40° C. and 75% RH initially and after 1 month for TTS prepared according to Example 11a and Reference Examples 11c and 11d.
Figure 11C:
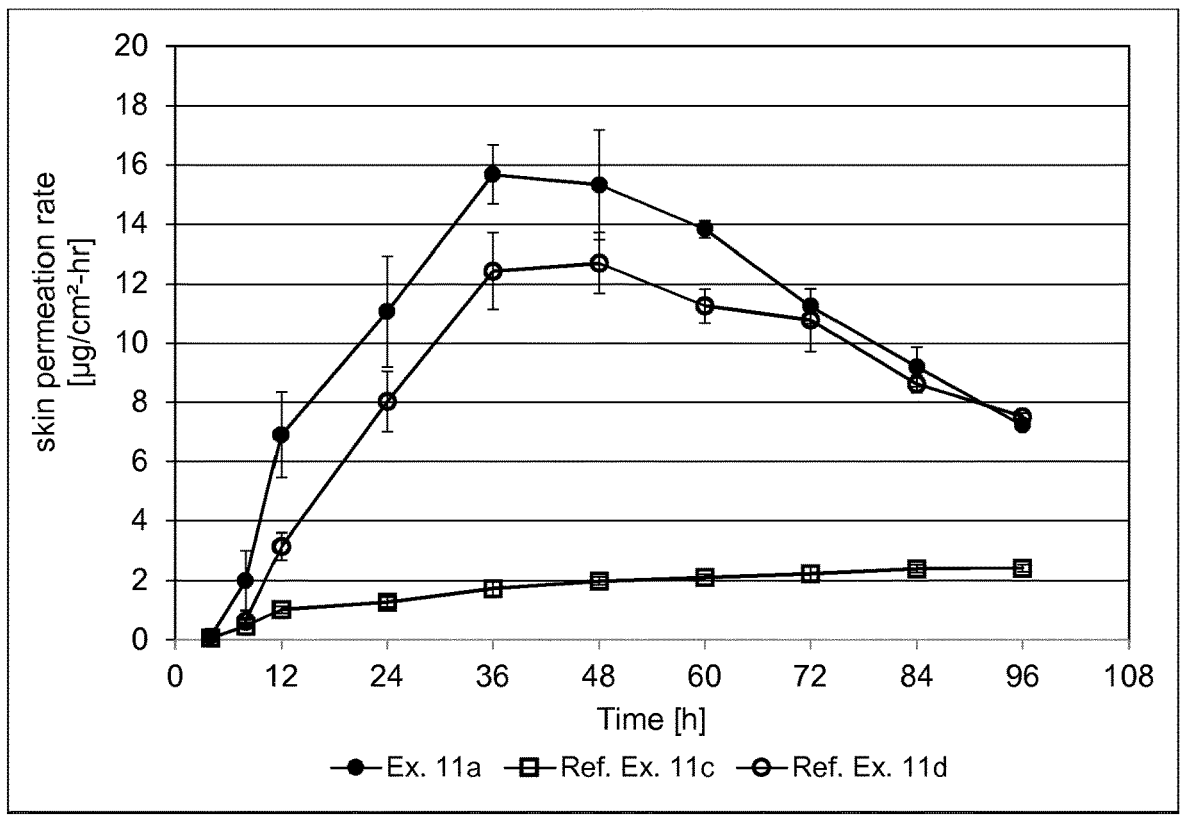
FIG. 11c depicts the asenapine skin permeation rate of TTS prepared according to Example 11a and Reference Examples 11c and 11d for hours 0 to 96.
Figure 11D:
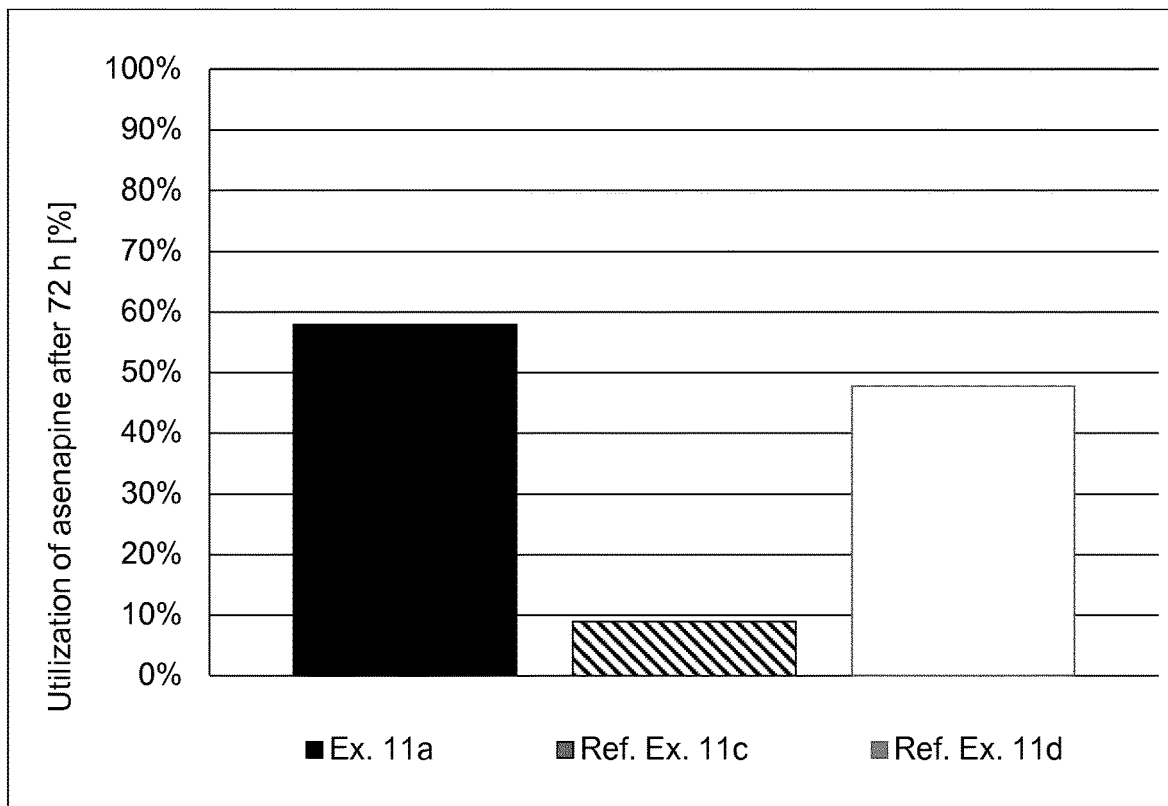
FIG. 11d depicts the utilization of asenapine of TTS prepared according to Example 11a and Reference Examples 11c and 11d after 72 hours.
Figure 11E:
FIG. 11e to 11g show pictures of the prepared TTS according to Example 11a (FIG. 11e), Reference Example 11c (FIG. 11f) and Reference Example 11d (FIG. 11g).
Figure 11F:
Figure 11G:

See Example 1. FIG. 11e to 11g show pictures of the prepared TTS according to Example 11a, Reference Example 11c and Reference Example 11d, respectively. From these figures, it can be seen that the TTS surface of Examples 11a and Reference Example 11d is smooth, while the TTS surface of Reference Example 11b is rough, suggesting an inhomogeneous matrix layer.

Stability Measurements

The initial stability as well as the stability after 1 month storage at 40° C. and 75% RH of the TTS of Example 11a as well as Reference Examples 11c and 11d was investigated. Samples were taken from the TTS immediately after preparation of the TTS and after 1 month storage time, extracted with an appropriate extraction solvent and the amount of asenapine base, as well as various possible degradation substances was determined by a specific quantitative HPLC method with a UV photometric detector, based on the asenapine content calculated from the (actual) area weight of the tested TTS. The results are shown in Tables 11.2 and 11.3 as well as in FIGS. 11a and 11b.

TABLE 11.2

| | Detected amounts [%] | | |
|---|---|---|---|
| Initial stability measurement | Ex. 11a | Ref. Ex. 11c | Ref. Ex. 11d |
| Asenapine base | 97 | 97 | 97 |
| Asenapine N-Oxide (Cis) | <LOR | <LOR | 0.18 |
| Asenapine N-Oxide (Trans) | <LOR | <LOR | 0.20 |

TABLE 11.2-continued

| Initial stability measurement | Detected amounts [%] | | |
|---|---|---|---|
| | Ex. 11a | Ref. Ex. 11c | Ref. Ex. 11d |
| Tetradehydro Asenapine | <LOR | <LOR | <LOR |
| Other related substances | n.d. | n.d. | <LOR |
| Sum of all related substances | 0.00 | 0.00 | 0.38 |

* n.d. = not detected, LOR = Limit of reporting (0.1%)

TABLE 11.3

| Stored for 1 month at 40° C./75% RH | Detected amounts [%] | | |
|---|---|---|---|
| | Ex. 11a | Ref. Ex. 11c | Ref Ex. 11d |
| Asenapine base | 95 | 96 | 93 |
| Asenapine N-Oxide (Cis) | <LOR | <LOR | 0.59 |
| Asenapine N-Oxide (Trans) | <LOR | <LOR | 0.67 |
| Deschloro Asenapine | n.d. | <LOR | <LOR |
| Tetradehydro Asenapine | <LOR | <LOR | 0.15 |
| Other related substances | <LOR | n.d. | 0.27 |
| Sum of all related substances | 0.00 | 0.00 | 1.68 |

* n.d. = not detected, LOR = Limit of reporting (0.1%)

These data demonstrate that the inventive formulation is able to stabilize the asenapine free base by using a combination of α-tocopherol and ascorbyl palmitate, and that the stability obtained in such a way is even higher than formulations relying on an in situ production of the asenapine free base from the more stable asenapine maleate salt by way of deprotonation with sodium hydroxide (Ref. Ex. 11d).

In situ production of the free base form of the active agent is believed to be disadvantageous due to the reduced permeability of the salt form, which is why the in vitro skin permeation behavior of formulations based on asenapine maleate can be lower, assumedly depending on the timing of the deprotonation reaction (see measurement of skin permeation rate below).

In addition, as Reference Examples 11b and 11c demonstrate, the use of deprotonating agents such as sodium bicarbonate or sodium hydroxide also leads to coating compositions getting difficult (see FIG. 11c) or even impossible to formulate so that no TTS can be obtained (Ref. Ex. 11b).

Measurement of Skin Permeation Rate

The permeated amount and the corresponding skin permeation rates of TTS prepared according to Example 11a as well as Reference Examples 11c and 11d were determined by in vitro experiments in accordance with the OECD Guideline (adopted Apr. 13, 2004) carried out with a 7.0 ml Franz diffusion cell. Split thickness human skin from cosmetic surgeries (abdomen, date of birth 1964) was used. A dermatome was used to prepare skin to a thickness of 800 μm, with an intact epidermis for all TTS. Diecuts with an area of 1.157 cm² were punched from the TTS. The asenapine permeated amount in the receptor medium of the Franz cell (phosphate buffer solution pH 5.5 with 0.1% saline azide as antibacteriological agent) at a temperature of 32±1° C. was measured and the corresponding skin permeation rate calculated. The results are shown in Table 11.4 and FIG. 11c.

TABLE 11.4

| | Skin permeation rate with SD [μg/(cm² h)] | | | | | |
|---|---|---|---|---|---|---|
| Elapsed | Ex. 11a (n = 3) | | Ref. Ex. 11c (n = 3) | | Ref. Ex. 11d (n = 3) | |
| time [h] | Rate | SD | Rate | SD | Rate | SD |
| 4 | 0.10 | 0.04 | 0.07 | n.a. | — | — |
| 8 | 2.00 | 0.45 | 0.48 | 0.06 | 0.64 | 0.28 |
| 12 | 6.90 | 1.02 | 1.02 | 0.12 | 3.16 | 1.00 |
| 24 | 11.07 | 1.29 | 1.28 | 0.17 | 8.02 | 1.44 |
| 36 | 15.67 | 1.02 | 1.74 | 0.25 | 12.43 | 1.87 |
| 48 | 15.32 | 0.58 | 1.99 | 0.14 | 12.70 | 1.00 |
| 60 | 13.83 | 1.06 | 2.11 | 0.10 | 11.25 | 1.86 |
| 72 | 11.24 | 0.29 | 2.25 | 0.23 | 10.78 | 0.29 |
| 84 | 9.20 | 0.13 | 2.41 | 0.13 | 8.61 | 0.58 |
| 96 | 7.22 | 0.20 | 2.43 | 0.13 | 7.51 | 0.67 |

*: Standard deviation in this Example was, as in all other Examples, calculated based on the n-method.

Utilization of Asenapine

The utilization of asenapine at 72 hours was calculated based on the cumulative permeated amount at 72 hours and the initial asenapine content. The results are shown in Table 11.5 and in FIG. 11d.

TABLE 11.5

| Utilization of asenapine after 72 hours [%] | | |
|---|---|---|
| Example 11a (n = 3) | Ref. Example 11c (n = 3) | Ref. Example 11d (n = 3) |
| 57.9 | 9.0 | 47.8 |

The in vitro experiments show that the good skin permeation rate as well as the utilization of asenapine of the previously developed reference formulations (Ref. Ex. 1b and 1c) could be surprisingly maintained for Example 11a, which represents a formulation in accordance with the present invention and which provides improved stability (see above and FIGS. 11a and 11b). While Reference Example 11d was able to provide a little lower, but still acceptable skin permeation rate, the stability for Reference Example 11d was inacceptable (see above). On the other hand, Reference Example 11c does not provide an acceptable skin permeation rate (see FIG. 11c) and the asenapine utilization is also very low (Table 11.5 above as well as FIG. 11d).

The inventive formulations are able to provide improved stability, both in terms of asenapine degradation as well as asenapine content, while maintaining an excellent skin permeation rate.

Examples 12A-C

Coating Composition

The formulations of the asenapine-containing coating compositions of Examples 12a to 12c are summarized in Table 12.1 below. The formulations are based on weight percent, as also indicated in Table 12.1.

TABLE 12.1

| Ingredient (Trade Name) | Ex. 12a Amt [g] | Ex. 12a Solids [%] | Ex. 12b Amt [g] | Ex. 12b Solids [%] | Ex. 12c Amt [g] | Ex. 12c Solids [%] |
| --- | --- | --- | --- | --- | --- | --- |
| Asenapine base | 50.0 | 10.0 | 50.0 | 10.0 | 50.0 | 10.0 |
| Acrylic adhesive in ethyl acetate. Solids content ~38.7% by wt. (Duro-Tak™ 387-4287) | 894.3 | 69.1 | 892.8 | 69.0 | 895.8 | 69.3 |
| Aluminium acetylacetonate | 2.30 | 0.46 | 2.30 | 0.46 | 2.30 | 0.46 |
| Polyvinylpyrrolidone (Povidone K30) | 50.4 | 10.0 | 49.9 | 10.0 | 50.0 | 10.0 |
| α-Tocopherol | 0.25 | 0.05 | 0.25 | 0.05 | 0.26 | 0.05 |
| Ascorbyl palmitate (10% sol. in ethanol denat, containing 1% (v/v) methyl ethyl ketone) | 10.0 | 0.20 | 20.1 | 0.40 | 10.0 | 0.20 |
| Sodium metabisulfite (30% aq. solution) | 1.86 | 0.11 | 1.90 | 0.11 | 0.46 | 0.03 |
| Medium chain triglycerides (Miglyol 812 N) | 50.2 | 10.0 | 50.0 | 10.0 | 50.0 | 10.0 |
| Ethanol denat. (1% (v/v) methyl ethyl ketone) | 241.9 | — | 226.5 | — | 247.3 | — |
| Total | 1301.2 | 100.0 | 1293.8 | 100.0 | 1306.1 | 100.0 |
| Area weight [g/m²] | 139.9-149.7 | | 142.0-147.5 | | 138.2-143.3 | |
| Asenapine content [mg/cm²] | 1.399-1.497 | | 1.420-1.475 | | 1.382-1.433 | |

Preparation of the Coating Composition

A stainless steel vessel was loaded with a part of the ethanol, the sodium metabisulfite solution was added dropwise under stirring and the mixture stirred at least 10 min. The α-Tocopherol and the ascorbyl palmitate solution were added dropwise under stirring and the resulting mixture stirred for at least 20 min. After adding the medium chain triglycerides under stirring, polyvinylpyrrolidone was weighed in a beaker and added to the mixture under stirring. The acrylic pressure sensitive adhesive Duro-Tak™ 387-4287 was weighed into the reaction mixture, the resulting mixture was stirred and allowed to stand, after which the aluminium acetylacetonate and the asenapine were each weighed in a beaker and added to the mixture with the remaining part of the ethanol. The mixture was stirred until a homogeneous solution was obtained.

Coating of the Coating Composition

See Reference Example 1a and Reference Example 1b for the coating process. Different films with an area weight of between 139.9 and 149.7 g/m² (Ex. 12a), 142.0 and 147.5 g/m² (Ex. 12b) and 138.2 and 143.3 g/m² were produced. The dried film was laminated with a polyethylene terephthalate backing layer (23 μm thickness) to provide an asenapine-containing self-adhesive layer structure.

Preparation of the TTS

See Example 1.

Stability Measurements

Figure 12A:
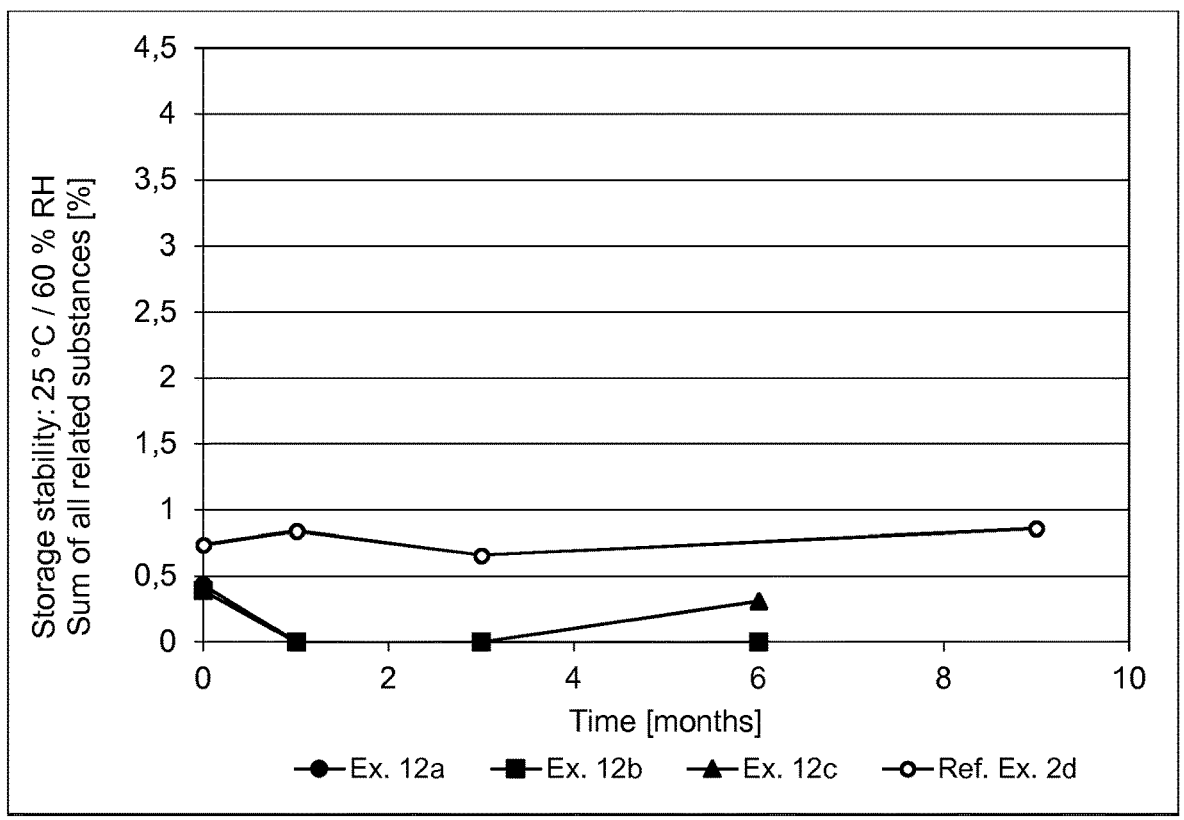
FIG. 12a depicts the sum of all related (i.e. possible degradation product) substances detected in a storage stability test at 25° C. and 60% RH over 0 to 9 months for TTS prepared according to Reference Example 2d and over 0 to 6 months for Examples 12a, 12b and 12c.
Figure 12B:
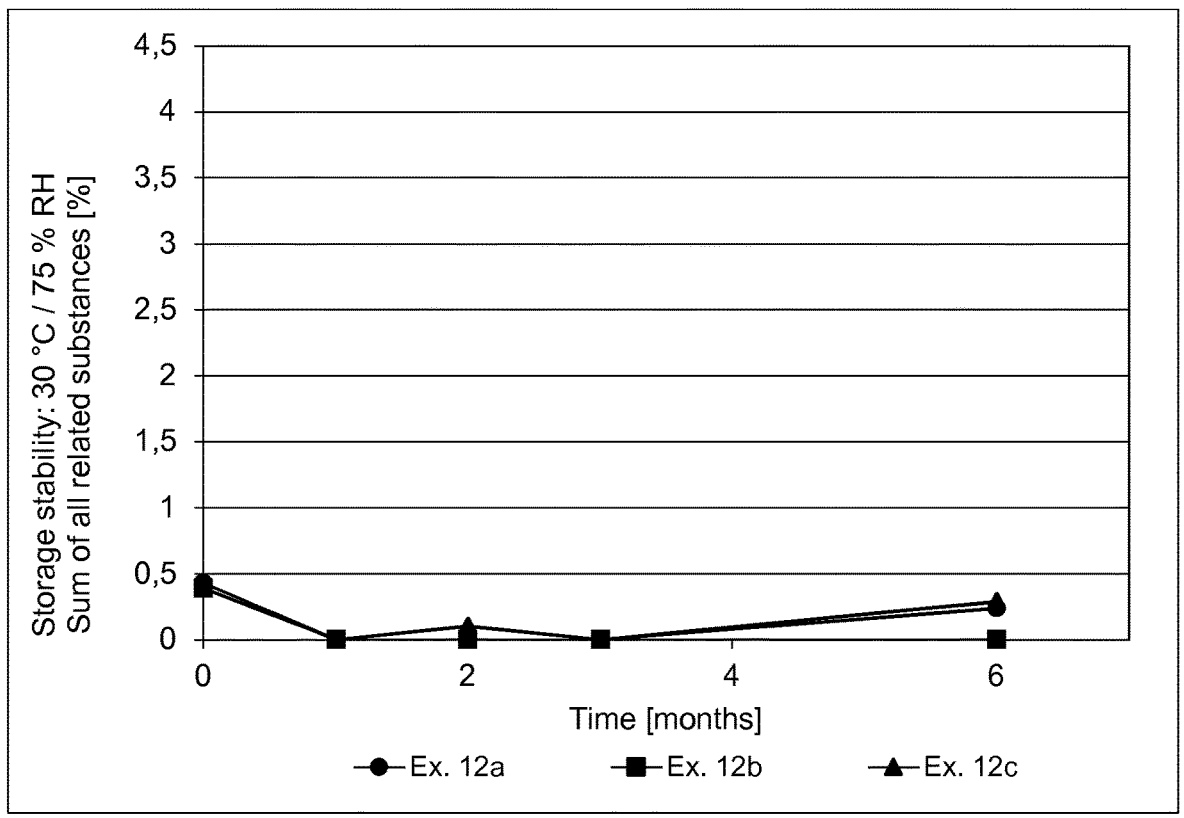
FIG. 12b depicts the sum of all related (i.e. possible degradation product) substances detected in a storage stability test at 30° C. and 75% RH over 0 to 6 months for Examples 12a, 12b and 12c.
Figure 12C:
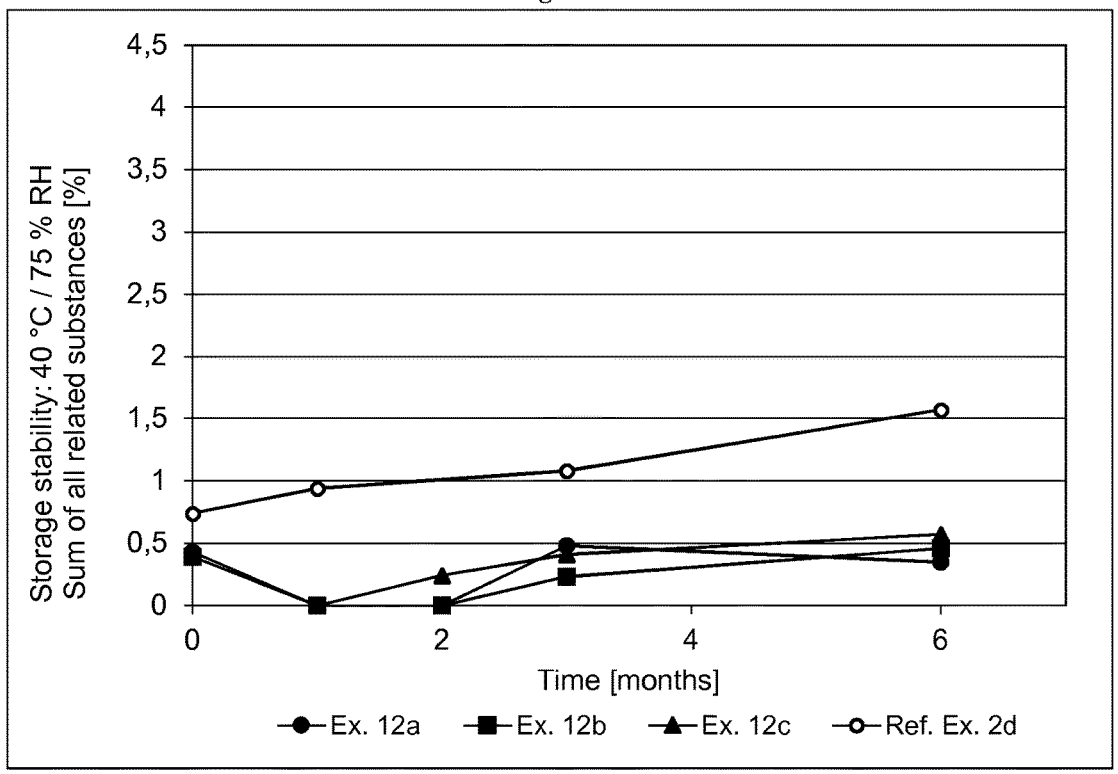
FIG. 12c depicts the sum of all related (i.e. possible degradation product) substances detected in a storage stability test at 40° C. and 75% RH over 0 to 6 months for Reference Example 2d and Examples 12a, 12b and 12c.
Figure 12D:
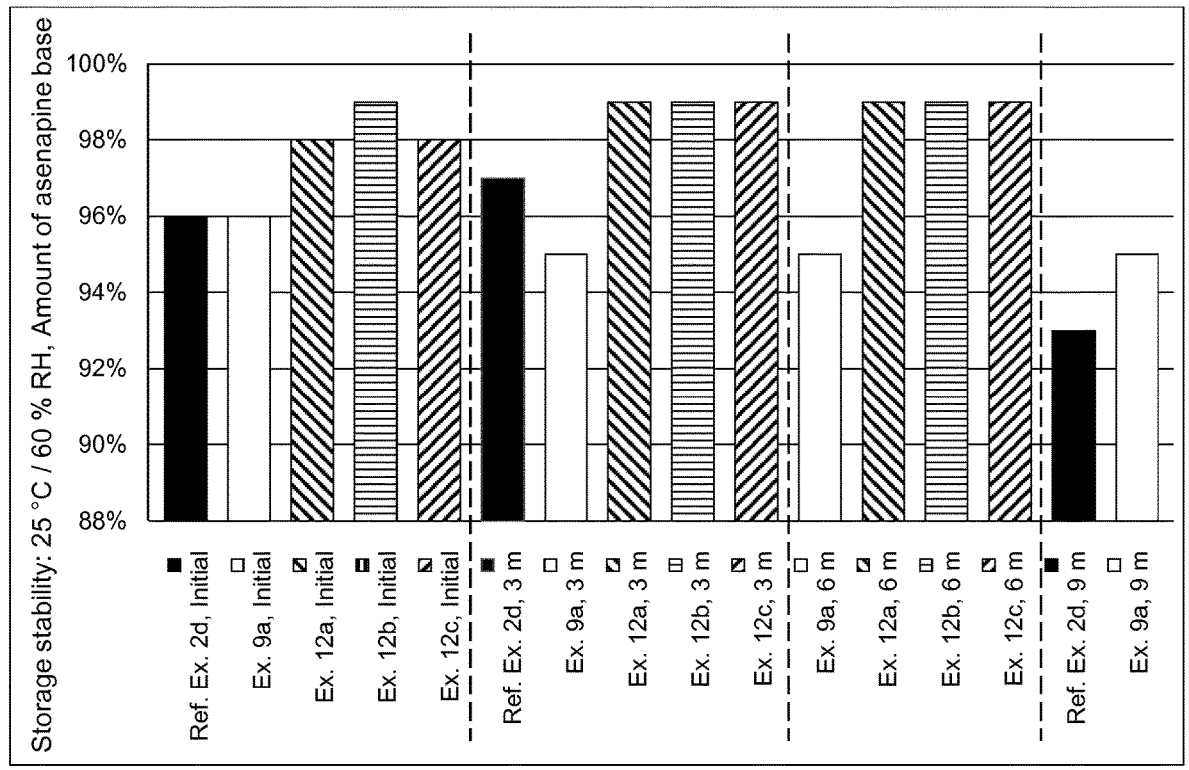
Figure 12E:
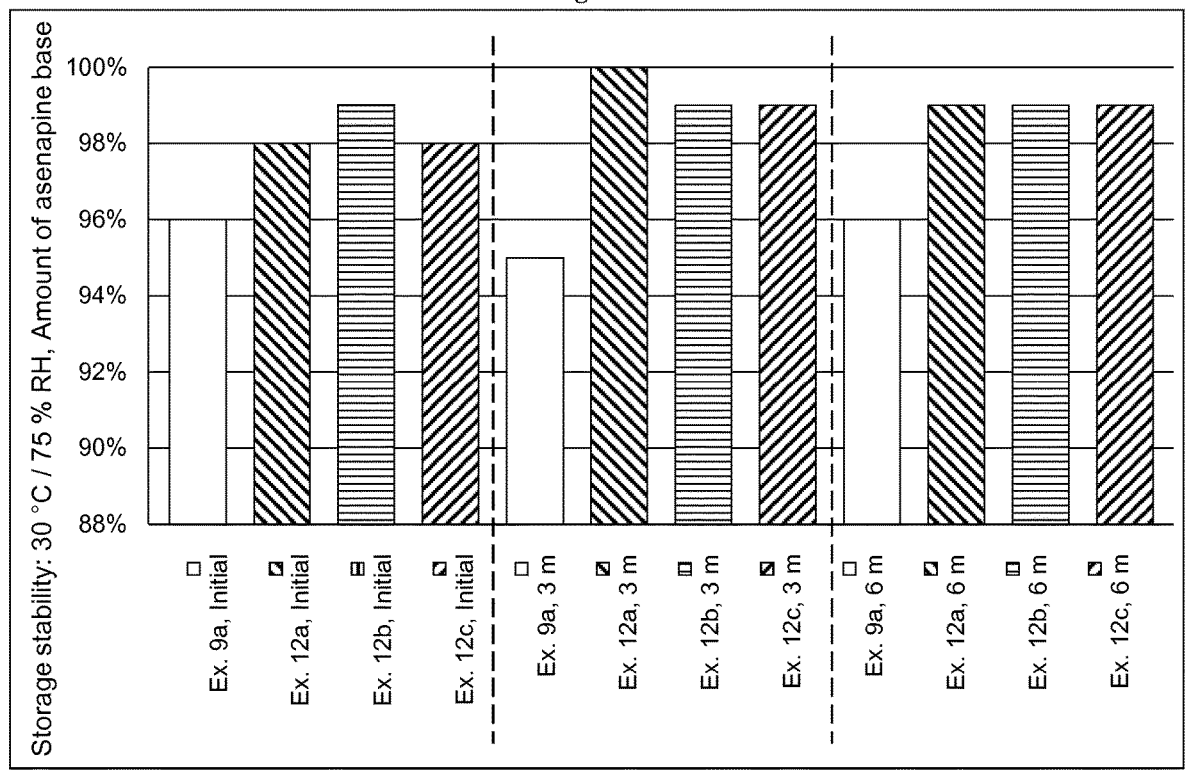
FIG. 12e depicts the amount of asenapine base detected in a storage stability test at 30° C. and 75% RH initially, after 3 months and after 6 months for TTS prepared to Examples 9a, 12a, 12b and 12c.
Figure 12F:
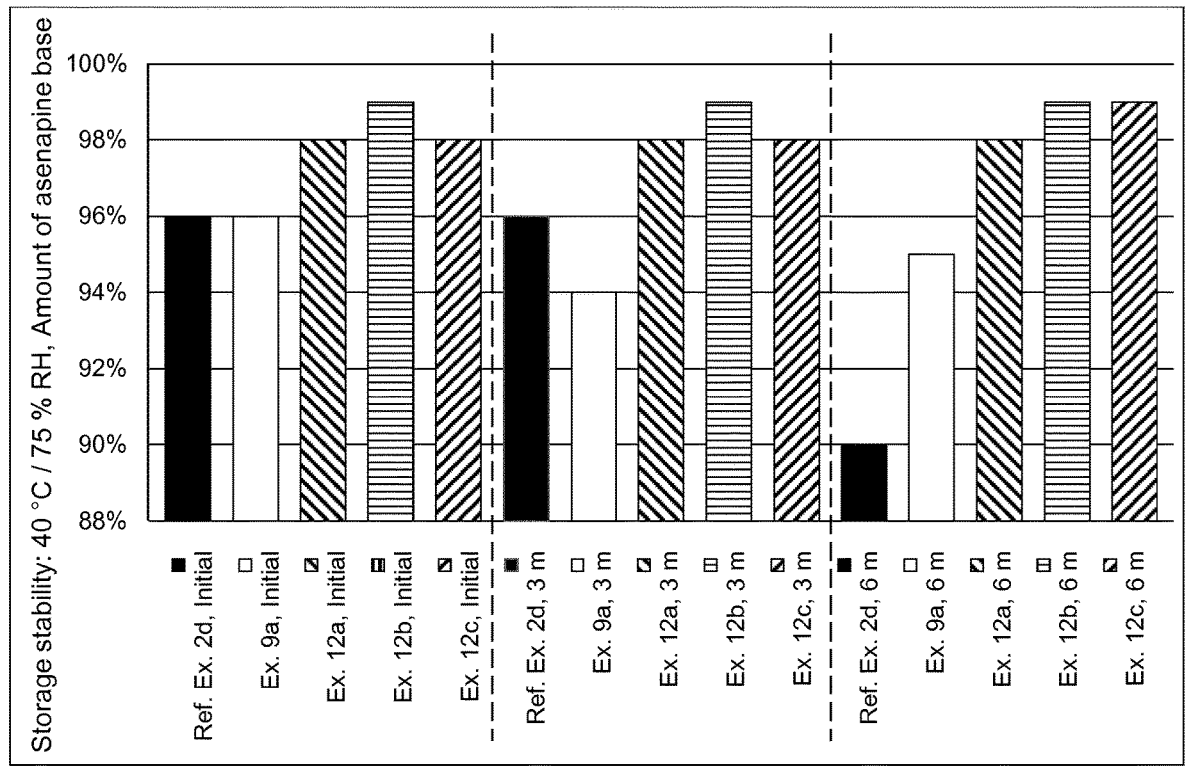
FIG. 12f depicts the amount of asenapine base detected in a storage stability test at 40° C. and 75% RH initially, after 3 months and after 6 months for TTS prepared according to Reference Example 2d and Examples 9a, 12a, 12b and 12c.

A long term storage stability test was conducted for Examples 12a to 12c under different test conditions, i.e. storage at 25° C. and 60% relative humidity (RH), at 30° C. and 75% RH, and at 40° C. and 75% RH. At different time points, samples were taken from the TTS, extracted with an appropriate extraction solvent and the amount of asenapine base, as well as various possible degradation substances was determined by a specific quantitative HPLC method with a UV photometric detector, based on the asenapine content calculated from the (actual) area weight of the tested TTS. The results are shown in Tables 12.2 to 12.10 as well as FIGS. 12a to 12f, wherein FIGS. 12a to 12c depict the sum of possible degradation substances detected in comparison to Reference Example 2d (for storage at 25° C. and 60% RH as well as at 40° C. and 75% RH), and FIGS. 12d to 12f depict the amount of asenapine base in comparison to Example 9a, and in comparison to Reference Example 2d (where data is available).

TABLE 12.2

| Ex. 12a - 25° C./60% RH | Detected amounts [%] | | | |
| --- | --- | --- | --- | --- |
| | Initial† | 1 month | 3 months | 6 months |
| Asenapine base | 98 | 99 | 99 | 99 |
| Asenapine N-Oxide (Cis) | 0.21 | n.d. | n.d. | n.d. |
| Asenapine N-Oxide (Trans) | 0.22 | n.d. | n.d. | n.d. |
| Tetradehydro Asenapine | <LOR | n.d. | <LOR | <LOR |
| Other related substances | n.d. | n.d. | n.d. | n.d. |
| Sum of all related substances | 0.43 | 0.00 | 0.00 | 0.00 |

* n.d. = not detected, LOR = Limit of reporting (0.1%)
†Due to a systematic error in the HPLC analysis (artefact peaks), the initial values are too high and not reliable

TABLE 12.3

| Ex. 12a - 30° C./75% RH | Detected amounts [%] | | | | |
| --- | --- | --- | --- | --- | --- |
| | Initial† | 1 month | 2 months | 3 months | 6 months |
| Asenapine base | 98 | 99 | 98 | 100 | 99 |
| Asenapine N-Oxide (Cis) | 0.21 | n.d. | n.d. | n.d. | 0.12 |
| Asenapine N-Oxide (Trans) | 0.22 | n.d. | n.d. | n.d. | 0.12 |
| Tetradehydro Asenapine | <LOR | <LOR | <LOR | <LOR | <LOR |

TABLE 12.3-continued

| Ex. 12a - 30° C./75% RH | Detected amounts [%] | | | | |
|---|---|---|---|---|---|
| | Initial† | 1 month | 2 months | 3 months | 6 months |
| Other related substances | n.d. | n.d. | n.d. | n.d. | <LOR |
| Sum of all related substances | 0.43 | 0.00 | 0.00 | 0.00 | 0.24 |

\* n.d. = not detected, LOR = Limit of reporting (0.1%)
†Due to a systematic error in the HPLC analysis (artefact peaks), the initial values are too high and not reliable

TABLE 12.4

| Ex. 12a - 40° C./75% RH | Detected amounts [%] | | | | |
|---|---|---|---|---|---|
| | Initial† | 1 month | 2 months | 3 months | 6 months |
| Asenapine base | 98 | 99 | 99 | 98 | 98 |
| Asenapine N-Oxide (Cis) | 0.21 | n.d. | n.d. | 0.19 | 0.17 |
| Asenapine N-Oxide (Trans) | 0.22 | n.d. | n.d. | 0.18 | 0.18 |
| Tetradehydro Asenapine | <LOR | <LOR | <LOR | <LOR | <LOR |
| Other related substances | n.d. | n.d. | n.d. | 0.11 | <LOR |
| Sum of all related substances | 0.43 | 0.00 | 0.00 | 0.48 | 0.35 |

\* n.d. = not detected, LOR = Limit of reporting (0.1%)
†Due to a systematic error in the HPLC analysis (artefact peaks), the initial values are too high and not reliable

TABLE 12.5

| Ex. 12b - 25° C./60% RH | Detected amounts [%] | | | |
|---|---|---|---|---|
| | Initial† | 1 month | 3 months | 6 months |
| Asenapine base | 99 | 99 | 99 | 99 |
| Asenapine N-Oxide (Cis) | 0.19 | n.d. | <LOR | <LOR |
| Asenapine N-Oxide (Trans) | 0.20 | n.d. | <LOR | <LOR |
| Tetradehydro Asenapine | <LOR | <LOR | <LOR | <LOR |
| Other related substances | n.d. | n.d. | n.d. | <LOR |
| Sum of all related substances | 0.39 | 0.00 | 0.00 | 0.00 |

\* n.d. = not detected, LOR = Limit of reporting (0.1%)
†Due to a systematic error in the HPLC analysis (artefact peaks), the initial values are too high and not reliable

TABLE 12.6

| Ex. 12b - 30° C./75% RH | Detected amounts [%] | | | | |
|---|---|---|---|---|---|
| | Initial† | 1 month | 2 months | 3 months | 6 months |
| Asenapine base | 99 | 99 | 99 | 99 | 99 |
| Asenapine N-Oxide (Cis) | 0.19 | n.d. | n.d. | <LOR | <LOR |
| Asenapine N-Oxide (Trans) | 0.20 | n.d. | n.d. | <LOR | <LOR |
| Tetradehydro Asenapine | <LOR | <LOR | <LOR | <LOR | <LOR |
| Other related substances | n.d. | n.d. | n.d | n.d. | <LOR |
| Sum of all related substances | 0.39 | 0.00 | 0.00 | 0.00 | 0.00 |

\* n.d. = not detected, LOR = Limit of reporting (0.1%)
†Due to a systematic error in the HPLC analysis (artefact peaks), the initial values are too high and not reliable

TABLE 12.7

| Ex. 12b - 40° C./75% RH | Detected amounts [%] | | | | |
|---|---|---|---|---|---|
| | Initial† | 1 month | 2 months | 3 months | 6 months |
| Asenapine base | 99 | 99 | 99 | 99 | 99 |
| Asenapine N-Oxide (Cis) | 0.19 | n.d. | <LOR | 0.12 | 0.17 |
| Asenapine N-Oxide (Trans) | 0.20 | n.d. | <LOR | 0.11 | 0.18 |

TABLE 12.7-continued

| Ex. 12b - 40° C./75% RH | Detected amounts [%] | | | | |
|---|---|---|---|---|---|
| | Initial† | 1 month | 2 months | 3 months | 6 months |
| Tetradehydro Asenapine | <LOR | <LOR | <LOR | <LOR | 0.11 |
| Other related substances | n.d. | n.d. | n.d | n.d. | <LOR |
| Sum of all related substances | 0.39 | 0.00 | 0.00 | 0.23 | 0.46 |

\* n.d. = not detected, LOR = Limit of reporting (0.1%)
†Due to a systematic error in the HPLC analysis (artefact peaks), the initial values are too high and not reliable

TABLE 12.8

| Ex. 12c - 25° C./60% RH | Detected amounts [%] | | | |
|---|---|---|---|---|
| | Initial† | 1 month | 3 months | 6 months |
| Asenapine base | 98 | 99 | 99 | 99 |
| Asenapine N-Oxide (Cis) | 0.21 | n.d. | <LOR | 0.15 |
| Asenapine N-Oxide (Trans) | 0.22 | n.d. | <LOR | 0.16 |
| Tetradehydro Asenapine | <LOR | <LOR | <LOR | <LOR |
| Other related substances | n.d. | n.d. | n.d. | <LOR |
| Sum of all related substances | 0.43 | 0.00 | 0.00 | 0.31 |

\* n.d. = not detected, LOR = Limit of reporting (0.1%)
†Due to a systematic error in the HPLC analysis (artefact peaks), the initial values are too high and not reliable

TABLE 12.9

| Ex. 12c - 30° C./75% RH | Detected amounts [%] | | | | |
|---|---|---|---|---|---|
| | Initial† | 1 month | 2 months | 3 months | 6 months |
| Asenapine base | 98 | 99 | 99 | 99 | 99 |
| Asenapine N-Oxide (Cis) | 0.21 | n.d. | <LOR | <LOR | 0.14 |
| Asenapine N-Oxide (Trans) | 0.22 | n.d. | 0.10 | <LOR | 0.15 |
| Tetradehydro Asenapine | <LOR | <LOR | <LOR | <LOR | <LOR |
| Other related substances | n.d. | n.d. | n.d. | n.d. | <LOR |
| Sum of all related substances | 0.43 | 0.00 | 0.10 | 0.00 | 0.29 |

\* n.d. = not detected, LOR = Limit of reporting (0.1%)
†Due to a systematic error in the HPLC analysis (artefact peaks), the initial values are too high and not reliable

TABLE 12.10

| Ex. 12c - 40° C./75% RH | Detected amounts [%] | | | | |
|---|---|---|---|---|---|
| | Initial† | 1 month | 2 months | 3 months | 6 months |
| Asenapine base | 98 | 99 | 98 | 98 | 99 |
| Asenapine N-Oxide (Cis) | 0.21 | <LOR | 0.12 | 0.21 | 0.22 |
| Asenapine N-Oxide (Trans) | 0.22 | <LOR | 0.12 | 0.20 | 0.25 |
| Tetradehydro Asenapine | <LOR | <LOR | <LOR | <LOR | 0.10 |
| Other related substances | n.d | n.d. | n.d. | <LOR | <LOR |
| Sum of all related substances | 0.43 | 0.00 | 0.24 | 0.41 | 0.57 |

\* n.d. = not detected, LOR = Limit of reporting (0.1%)
†Due to a systematic error in the HPLC analysis (artefact peaks), the initial values are too high and not reliable The stability data of Examples 12a-c show that the use of certain acrylic polymers lead to excellent initial as well as storage stability of the asenapine formulations, in particular in terms of the amount of asenapine base remaining after storage.

In Vivo Clinical Study

In Vivo Clinical Study

An in vivo clinical trial was conducted to investigate the relative bioavailability of asenapine after transdermal application of the TTS of Reference Examples 2c and 2d compared to sublingual administration. The study was performed in accordance with the ethical principles that have their origin in the Declaration of Helsinki.

Trial Design

The trial was conducted in a single center, Phase I, open-label design with 3 treatments, 3 treatment periods, a fixed treatment sequence in 16 healthy male and female subjects, comparing the relative bioavailability of asenapine in plasma after single dose transdermal application of the TTS prepared in Reference Examples 2c and 2d to the currently marketed sublingual tablets (Sycrest®, 5 mg).

For each subject, the trial consisted of:
An ambulant screening period in which informed consent was obtained and eligibility of the subjects assessed. Depending on the outcome of the screening, subjects were included in the trial.
A treatment and observation period consisting of 3 sequential treatment periods (each several days long).
An ambulant follow-up visit after the end of last treatment.

Regarding the 3 sequential treatment periods, the subjects received sublingual tablets of 5 mg asenapine b.i.d. (=twice daily) (Reference) on the first day of period 1, a single dose of the TTS prepared in Reference Example 2c (3 TTS of 10 cm² each) during period 2 and a single dose of the TTS prepared in Reference Example 2d (1 TTS of 15 cm²) during period 3.

Selection of Trial Population

Only subjects meeting all inclusion and none of the exclusion criteria were included into the treatment phase. The criteria were assessed at screening and a re-check was performed on Day −1 of Period 1.

Inclusion Criteria

Subjects had to fulfill all of the following criteria to be eligible for participation in the treatment period.
1. Subjects who are able to understand and follow instructions during the study.
2. Signed informed consent.
3. White.
4. Age ≥18 and ≤55 years.
5. Nonsmoker.
6. In general good physical health as determined by medical and surgical history, physical examination, 12-lead electrocardiogram (ECG), vital signs, and clinical laboratory tests.
7. Weight within the normal range according to accepted values for the body mass index (BMI) within 18.0 to 29.4 kg/m².
8. Normal blood pressure (Systolic Blood Pressure (SBP)≥90 ≤139 mmHg; Diastolic Blood Pressure ≥55≤89 mmHg) measured after 5 min rest in supine position.
9. A pulse rate of ≥50 and ≤99 b/min measured after 5 min rest in supine position.
10. ECG recording without clinically significant abnormalities.
11. Having had no febrile or infectious illness for at least 7 days prior to the first administration.

Exclusion Criteria

To ensure that the subjects are healthy and in a comparable status, the following exclusion criteria were applied.

Lifestyle Restrictions
1. Demonstrating excess in xanthine consumption (more than 5 cups of coffee or equivalent per day).
2. More than moderate alcohol consumption (>35 g of ethanol regularly per day or >245 g regularly per week).
3. Any history of alcohol or drug abuse.
4. Vegetarian.
5. Positive drug screen.
6. Positive alcohol breath test.
7. Consumption of xanthine-containing food or beverages as well as grapefruit juice or Seville oranges within 48 hours before first dosing.
8. Consumption of char-grilled food, broccoli, or Brussel sprouts within 72 hours before first dosing.

Prior Medication
9. Use of any medication (self-medication or prescription medication) except hormonal contraception within 4 weeks before first dosing (or at least 10 times the respective elimination half-life, whichever is longer).

Medical and Surgical History
10. Demonstrating any active physical disease, acute or chronic.
11. Any history of drug hypersensitivity, asthma, urticaria or other severe allergic diathesis as well as current hay fever.
12. Any history of hypersensitivity of any component of the investigated dosage forms.
13. Any history of chronic gastritis or peptic ulcers.
14. Any history of chronic or recurrent metabolic, renal, hepatic, pulmonary, gastrointestinal, neurological (esp. history of epileptic seizures), endocrinological (esp. diabetes mellitus), immunological, psychiatric or cardiovascular disease, myopathies, dermal diseases, and bleeding tendency.
15. Gilbert syndrome.
16. Any gastrointestinal complaints within 7 days prior to first dosing.
17. Any scars, moles, tattoos, skin irritation or excessive hair growth at the TTS application site.
18. Any suicidal ideation of type 2 to 5 on the C-SSRS (Columbia Suicidal Severity Rating Scale) in the past 12 months (i.e., active suicidal thought, active suicidal thought with method, active suicidal thought with intent but without specific plan, or active suicidal thought with plan and intent).

Laboratory Examinations
19. Laboratory values outside the reference range that are of clinical relevance (e.g., suggesting an unknown disease and requiring further clinical evaluation assessed by the investigator), especially regarding aspartate aminotransferase (AST), alanine aminotransferase (ALT), gamma glutamyl transpeptidase (GGT).
20. Positive test for human immunodeficiency virus (HIV) antibodies/p24 antigen.
21. Positive Hepatitis B-virus surface antigen (HBsAg) test.
22. Positive Anti-hepatitis C-virus antibodies (Anti-HCV) test.

Other
23. Blood donation within 30 days before signing informed consent to this trial.
24. Participation in the treatment phase of a clinical study 30 days or blocked by the follow-up period of a previous clinical trial before signing informed consent to this trial.
25. Women of childbearing potential not using a highly effective method of birth control. Highly-effective methods of birth control are defined as those which result in a low failure rate, i.e. less than 1% per year, when used consistently and correctly (e.g., combination of intrauterine device and condom). Female subjects are considered to be of childbearing potential unless surgically sterilized by hysterectomy or bilateral tubal ligation, or postmenopausal for at least 2 years.
26. Pregnant or breastfeeding women.

Treatments During the Study

The treatments administered during the study are summarised in Table 13.1 below and their characteristics are detailed below.

TABLE 13.1

| Treatment | Dose (Active amount based on label composition of the dosage form) | Formulation | Mode of administration |
|---|---|---|---|
| Reference (Period 1) | 5 mg per tablet | sublingual tablet | Two administrations b.i.d. (q12 h) |
| TTS of Ref. Ex. 2c (Period 2) | 3 * (8.4 mg/10 cm$^2$) | TTS | Single administration, TTS applied for 3.5 days |
| TTS of Ref. Ex. 2d (Period 3) | 21.0 mg/15 cm$^2$ | TTS | Single administration, TTS applied for 3.5 days | b.i.d. = twice daily; q12 h = every 12 h

The reference formulation administered in period 1 contains the active ingredient asenapine maleate and is marketed under the trade name Sycrest® 5 mg Sublingualtabletten by N.V. Organon, Oss, Netherlands. The pharmacy central number (PZN) is 07728207.

Administration of the Sublingual Tablets (Reference)

Sublingual tablets were administered in the morning and in the evening of the first day only with 12 hours in between the two administrations according to the administration instructions given in the summary of product characteristics. The subjects were instructed to place the tablets under the tongue for at least 10 min to allow dissolving of the sublingual tablet and not to chew or swallow the sublingual tablets.

Application of the TTS

The TTS were applied to intact skin on the upper chest or upper back. Hairs on the application area were trimmed with scissors (not shaved) before application, if necessary. The subjects were instructed to verify that the skin is free of detergents, oils and fat before TTS application. The TTS was placed on the desired position and pressed for at least 30 sec with fingers or the palm to fixate the TTS on the skin surface. In case of need and to avoid further detachment, the TTS was additionally fixated with an adhesive overlay free of active agent. The optional adhesive overlay was placed above the TTS in such a way that each side was equally covered by the adhesive overlay. Afterwards, to fixate the TTS, it was pressed again for at least 30 sec with fingers or the palm. The TTS were removed after 3.5 days (84 hours, Period 2 and Period 3). After removal, the used TTS (including the adhesive overlay, if applicable) were handled and stored under nitrogen in the refrigerator until they were further analyzed.

Timing of Dose for Each Subject

On the first day of Period 1, no breakfast was served; the subjects fasted overnight before morning administration. A standardized lunch was given 4 h and dinner approximately 10 hour after morning administration. Fluid intake was not allowed from 1 hour before until 1 hour after morning and evening administration. As food does not interact with the TTS, the subjects received standardized meals and beverages during in-house days at customary times during Period 2 and 3. During in-house days, the subjects were only allowed to consume food or beverages provided by the study unit.

Restrictions and Precautions

During the trial, subjects were instructed to abstain from all activities which may increase body temperature, i.e., physical exertion, sauna, environments with great heat. During the time the TTS were worn, subjects were not allowed to perform any activities which may influence adhesion of the TTS such as any activities which would increase sweating. Further restrictions on food and beverages intakes were placed e.g. in accordance with the exclusion criteria.

Sample Collection and Determination of Blood Plasma Concentrations

Blood samples for the determination of the concentration of asenapine and its metabolites in blood plasma were collected at specified time points after administration.

A validated internally standardized liquid chromatography tandem mass spectrometry method was used for the determination of the blood plasma concentration of asenapine, N-desmethyl-asenapine and asenapine-glucuronide, which was carried out by a GLP (Good Laboratory Practice)—certified laboratory. Plasma concentrations of asenapine-glucuronide were only determined for 8 subjects, which had no influence on the validity of the results, or the interpretation of the trial results. The lower limits of quantification (LLOQs) were 0.1 ng/ml for asenapine and N-desmethyl-asenapine in plasma, and 0.25 ng/ml for asenapine-glucuronide.

Adverse Events (AE)

Adverse events were ascertained by the investigator using non-leading questions, noted as spontaneously reported by the subjects to the medical staff or observed during any measurements on all study days after administration of the dosage form and rated by a study physician.

Furthermore, suicide risk was monitored. All positive reports during the trial were documented as adverse events. Suicidal ideation of type 1-3 was documented as a non-serious AE. Suicidal ideation of type 4 and 5 and all suicidal behavior during the trial were documented as a serious adverse event (SAE) and reported.

An AE was referred to the treatment and time point after which it occurred, i.e., any AE occurring before the first dosing was counted as baseline complaint/pre-treatment AE and is not included in the below analysis.

Results and Analysis

All 16 subjects completed period 1 (reference) of the trial. After period 1 (reference) and before commencing period 2 (Ref. Ex. 2c), 1 subject dropped out. Another subject dropped out during period 3 (Ref. Ex. 2d), but could be assessed for the adverse events analysis. Safety laboratory parameters, vital signs, and ECG parameters showed no medically relevant changes. The results of the study are shown in Tables 13.2 to 13.9 and FIGS. 13a to 13e.

Arithmetic Mean Blood Plasma Concentration of Asenapine

Figure 13A:
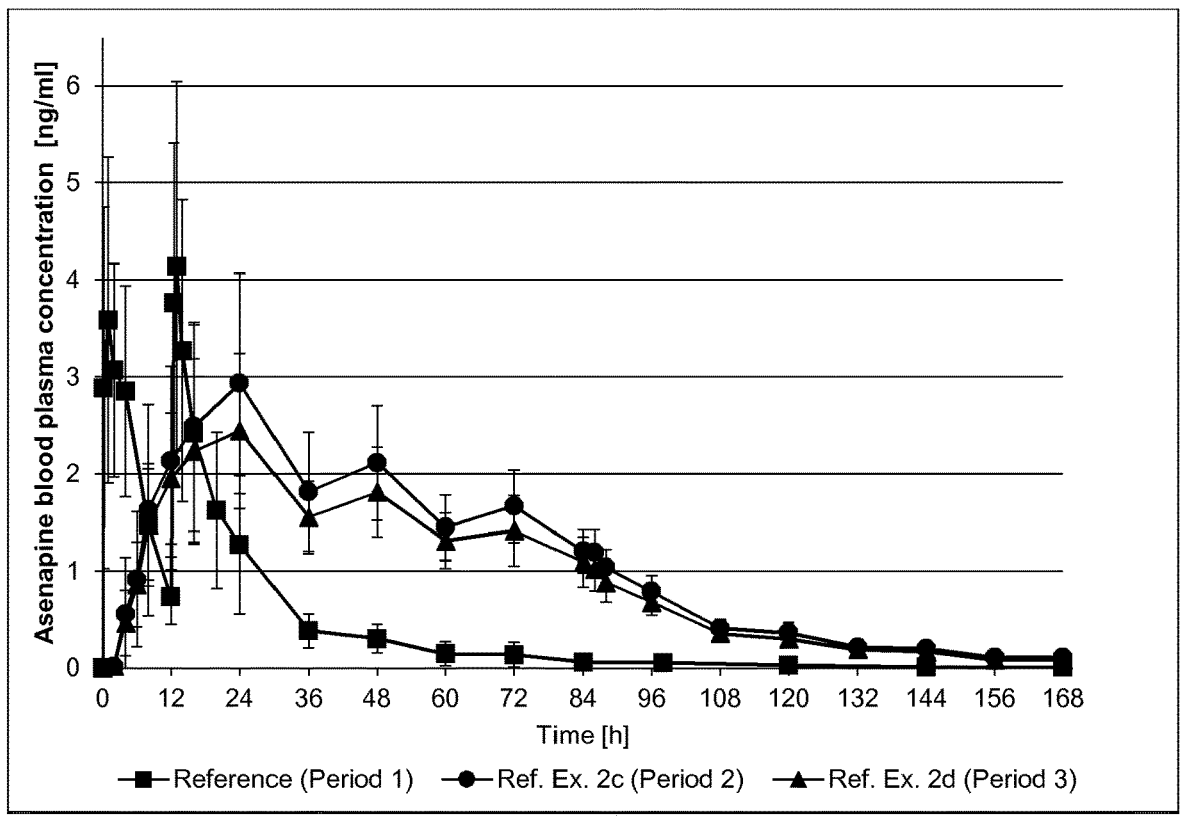
FIG. 13a depicts the asenapine blood plasma concentration (arithmetic mean values with standard deviation as error bars) obtained in an in vivo clinical study of the TTS prepared according to Reference Examples 2c and 2d for hours 0 to 168.
Figure 13B:
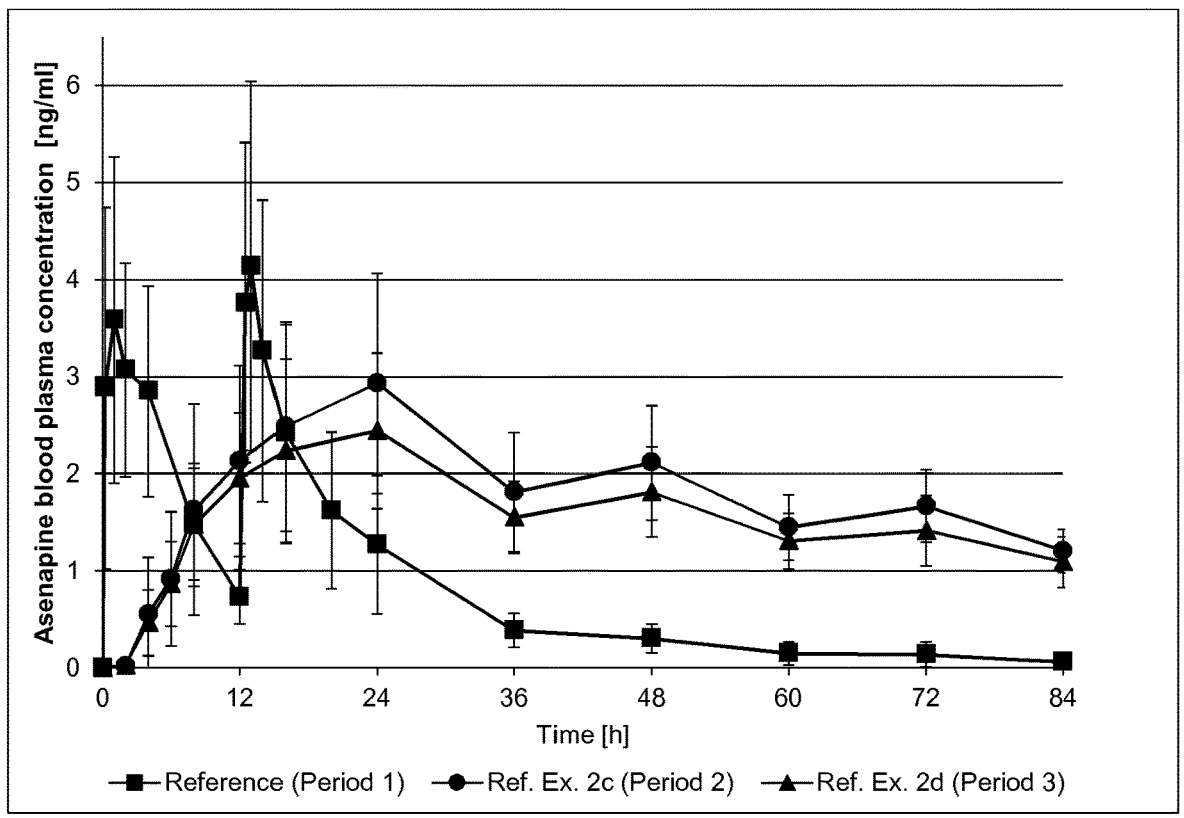
FIG. 13b depicts the asenapine blood plasma concentration (arithmetic mean values with standard deviation as error bars) obtained in an in vivo clinical study of the TTS prepared according to Reference Examples 2c and 2d for hours 0 to 84.
Figure 13C:
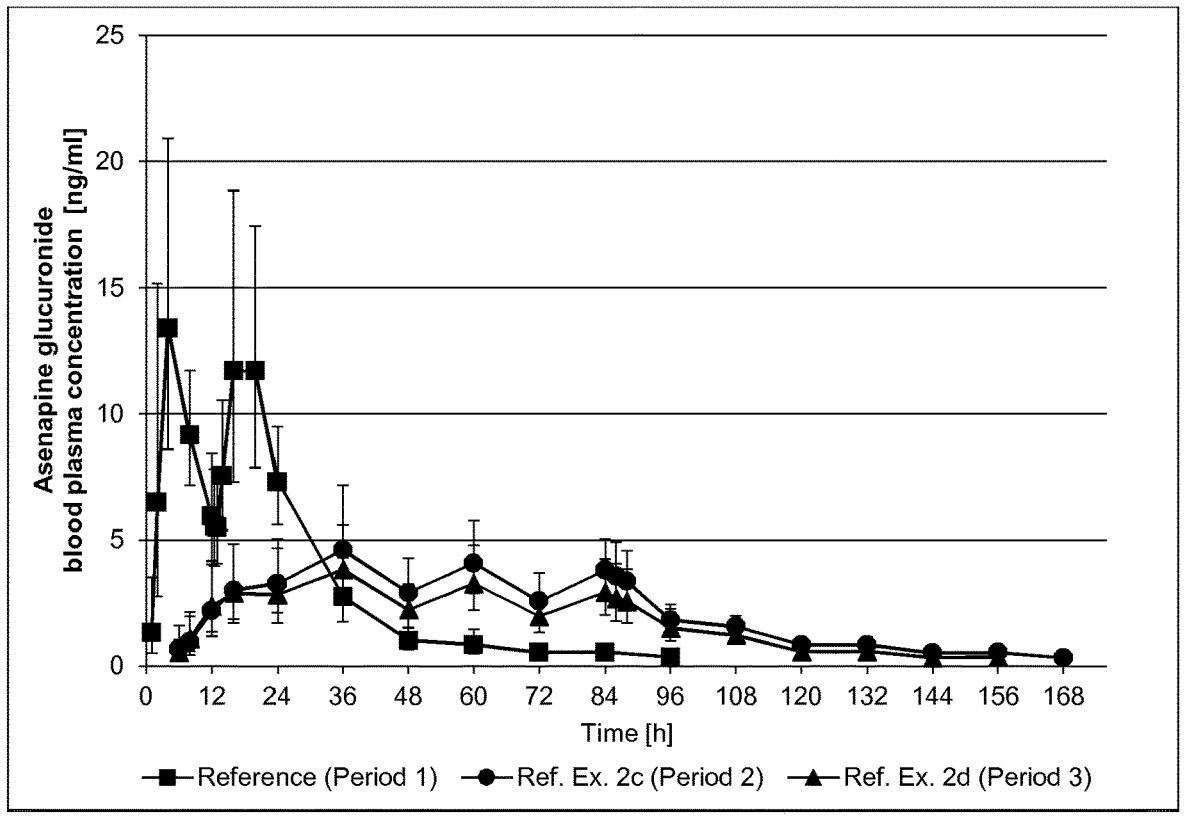
FIG. 13c depicts the asenapine-glucuronide blood plasma concentration (geometric mean values with geometric mean multiplied with/divided by the geometric standard deviation as error bars) obtained in an in vivo clinical study of the TTS prepared according to Reference Examples 2c and 2d for hours 0 to 168.
Figure 13D:
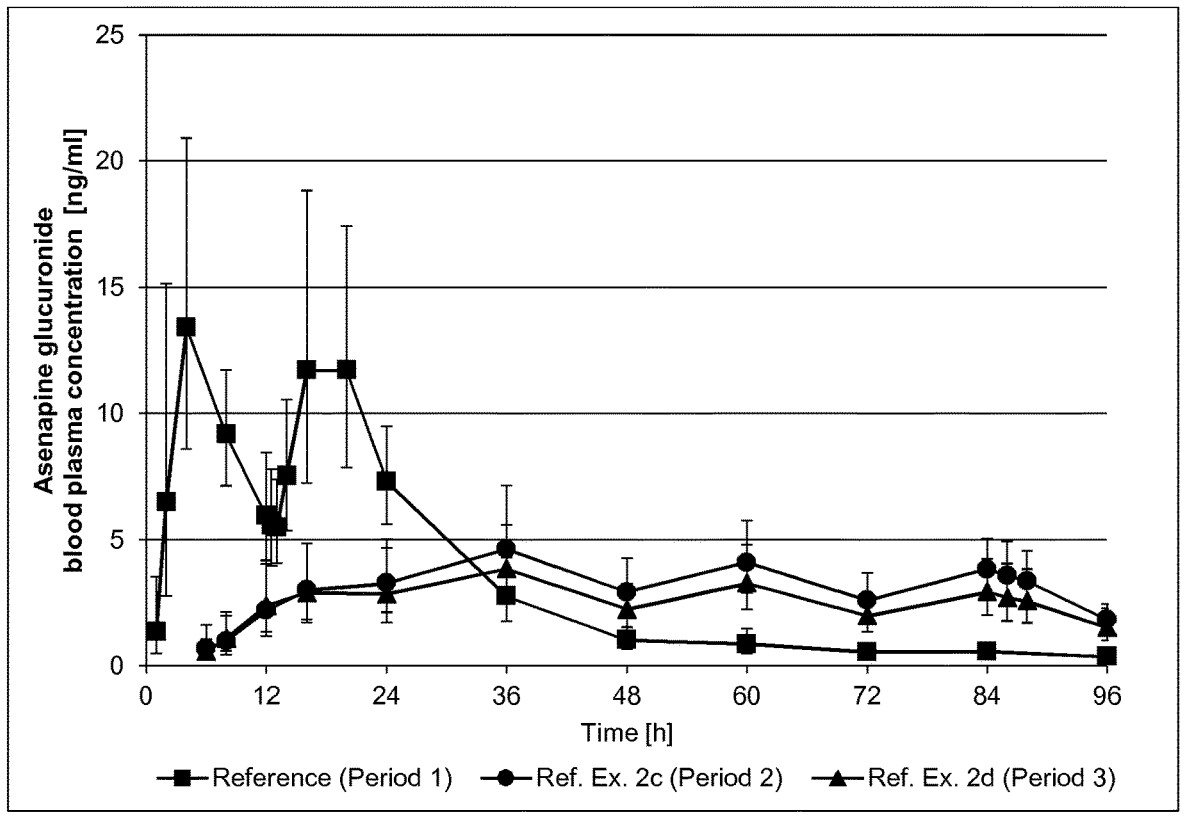
FIG. 13d depicts the asenapine-glucuronide blood plasma concentration (geometric mean values with geometric mean multiplied with/divided by the geometric standard deviation as error bars) obtained in an in vivo clinical study of the TTS prepared according to Reference Examples 2c and 2d for hours 0 to 96.
Figure 13E:
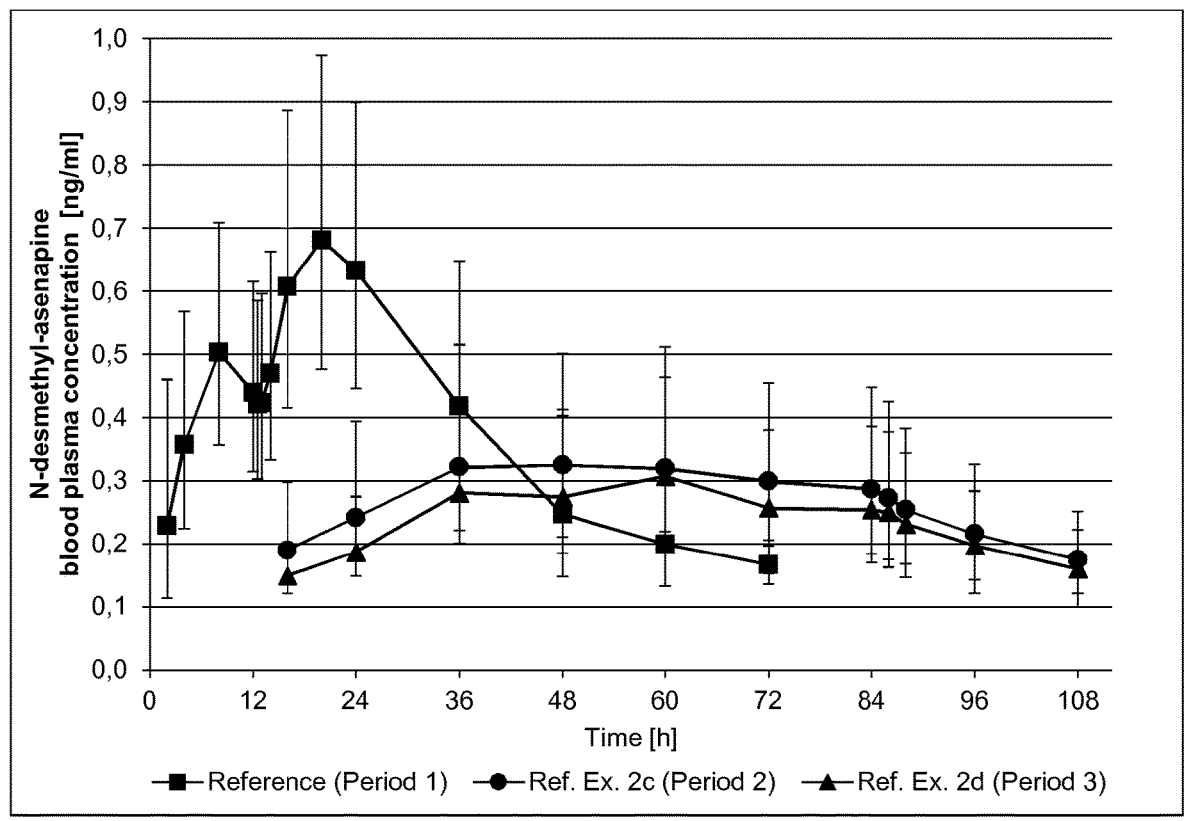
FIG. 13e depicts the N-desmethyl-asenapine blood plasma concentration (geometric mean values with geometric mean multiplied with/divided by the geometric standard deviation as error bars) obtained in an in vivo clinical study of the TTS prepared according to Reference Examples 2c and 2d for hours 0 to 108.

Arithmetic mean values of the asenapine blood plasma concentration based on all 16 subjects for period 1 and based on the 15 and 14 subjects that completed periods 2 and 3, respectively, along with the standard deviation values are presented in Table 13.2 as well as FIGS. 13a and 13b. AUC values were calculated from the blood plasma concentration. The $t_{lag}$ was calculated approximatively as the mean arithmetic value of the first point in time when a measurable (i.e. non-zero) asenapine blood plasma concentration was obtained, and the results also indicated in Table 13.2.

TABLE 13.2

| Time [h] | Asenapine blood plasma concentration [ng/ml] | | | | | |
|---|---|---|---|---|---|---|
| | Reference (n = 16) | | Ref. Ex. 2c (n = 15) | | Ref. Ex. 2d (n = 14) | |
| | mean | SD | mean | SD | mean | SD |
| 0 | 0.00 | 0.00 | 0.00 | 0.00 | 0.00 | 0.00 |
| 0.5 | 2.89 (n = 15) | 1.86 | — | — | — | — |
| 1 | 3.58 | 1.68 | — | — | — | — |
| 2 | 3.07 | 1.10 | 0.02 | 0.07 | 0.02 | 0.07 |
| 4 | 2.85 | 1.09 | 0.56 | 0.58 | 0.47 | 0.34 |
| 6 | — | — | 0.92 | 0.70 | 0.86 | 0.44 |
| 8 | 1.48 | 0.57 | 1.63 | 1.09 | 1.47 | 0.63 |
| 12 | 0.73 | 0.28 | 2.13 | 0.98 | 1.95 | 0.67 |
| 12.5 | 3.76 | 1.65 | — | — | — | — |
| 13 | 4.14 | 1.90 | — | — | — | — |
| 14 | 3.27 | 1.56 | — | — | — | — |
| 16 | 2.42 | 1.12 | 2.49 | 1.08 | 2.23 | 0.95 |
| 20 | 1.62 | 0.80 | — | — | — | — |
| 24 | 1.27 | 0.71 | 2.93 | 1.14 | 2.44 | 0.80 |
| 36 | 0.39 | 0.18 | 1.81 (n = 14) | 0.61 | 1.55 | 0.37 |
| 48 | 0.30 | 0.15 | 2.11 | 0.59 | 1.81 | 0.46 |
| 60 | 0.15 | 0.12 | 1.45 (n = 14) | 0.34 | 1.31 | 0.29 |
| 72 | 0.14 | 0.13 | 1.67 | 0.37 | 1.42 | 0.36 |
| 84 | 0.06 | 0.09 | 1.21 (n = 14) | 0.22 | 1.09 | 0.26 |
| 86 | — | — | 1.19 | 0.24 | 1.02 | 0.23 |
| 88 | — | — | 1.04 | 0.18 | 0.88 | 0.20 |
| 96 | 0.06 | 0.09 | 0.79 | 0.16 | 0.68 | 0.13 |
| 108 | — | — | 0.41 | 0.09 | 0.36 | 0.06 |
| 120 | 0.03 | 0.06 | 0.37 | 0.11 | 0.30 | 0.07 |
| 132 | — | — | 0.22 | 0.08 | 0.19 | 0.04 |
| 144 | 0.01 | 0.04 | 0.20 | 0.06 | 0.17 | 0.04 |
| 156 | — | — | 0.11 | 0.07 | 0.09 | 0.07 |
| 168 | 0.01 | 0.03 | 0.11 | 0.07 | 0.09 | 0.07 |
| 192 | — | — | 0.04 | 0.06 | 0.02 | 0.04 |
| 216 | — | — | 0.01 | 0.03 | 0.01 | 0.03 |
| 240 | — | — | 0.01 | 0.03 | 0.00 | 0.00 |
| $AUC_{(0-48)}$ [(ng/ml) h] | — | — | 95.06 | 37.20 | 82.26 | 25.65 |
| $AUC_{(0-72)}$ [(ng/ml) h] | — | — | 135.12 | 46.05 | 117.34 | 33.44 |
| $AUC_{(0-84)}$ [(ng/ml) h] | 178.44* | 63.59 | 152.36 | 48.81 | 132.38 | 36.84 |
| $C_{max}$ [ng/ml] | 4.71 | 1.68 | 2.93 | 1.14 | 2.51 | 0.90 |
| $C_{48}$ [ng/ml] | — | — | 2.11 | 0.59 | 1.81 | 0.46 |
| $C_{72}$ [ng/ml] | — | — | 1.67 | 0.37 | 1.42 | 0.36 |
| $C_{84}$ [ng/ml] | — | — | 1.21 | 0.22 | 1.09 | 0.26 |
| $t_{lag}$ [h] | 0.5 | 0 | 4.27 | 1.00 | 3.71 | 0.70 |
| Residual amount** [mg/total area of release] | | | 12.0 (3*10 cm²) | 3.3 (3*10 cm²) | 10.3 (15 cm²) | 2.3 (15 cm²) |
| Mean release rate*** [mg/day] | — | — | 3.8 | 0.9 | 3.1 | 0.6 |

*The $AUC_{(0-84)}$ value is calculated for the reference period by multiplying the $AUC_{(0-24)}$ value by 3.5.
**The residual amount is determined by extraction of the active from a sample of the used TTS with an appropriate solvent followed by determination of the active amount using a validated HPLC method with a UV photometric detector.
***The mean release rate is calculated based on the initial asenapine content in the TTS (according to the label composition) applied and on the residual amount in the TTS after 84 hours referring to the total dose administered (see Table 13.1).

Pharmacokinetic Analysis of Asenapine and Metabolites

Based on the plasma concentration time data of asenapine and metabolites, plasma pharmacokinetic parameters were calculated using non compartmental procedures and the results are presented in Tables 13.3 to 13.5, wherein $C_{av}$ represents the average concentration observed during the relevant dosing interval (12 hours for Period 1/Reference and 84 hours for Periods 2 and 3/Reference Examples 2c and 2d), and wherein $t_{lag}$ represents the time of first quantifiable concentration after administration. For $C_{av}$ and $t_{lag}$ of the Reference formulation merely the first dosing interval (0-12 hours) was considered. Further, the blood plasma concentration profile of the metabolites asenapine glucuronide and N-desmethyl-asenapine was depicted as geometric mean values and indicating the geometric mean multiplied with and divided by the geometric standard deviation as error bars in FIGS. 13c, 13d and 13e.

The biometrical evaluation was carried out using SAS software, Version 9.3 of the SAS System for windows. Pharmacokinetics calculations were carried out using Phoenix WinNonlin version 6.4 The pharmacokinetic calculation was based on all subjects who completed at least 2 treatment periods, i.e., who have evaluable data for the Reference and at least one of Reference Examples 2a or 2b for asenapine and N-desmethyl-asenapine. Thus, the subject number was n=15 for Periods 1 and 2 (Reference and Reference Example 2c) and n=14 for Period 3 (Reference Example 2d). For asenapine-glucuronide, the subject number was n=8 for all Periods. Values below LLOQ were excluded from any calculations for descriptive statistics. Descriptive statistics of concentrations were calculated if at least ½ of the individual data points were measured equal or above LLOQ.

Calculation of the pharmacokinetic characteristics were based on actual blood sampling times [h] (relative to the corresponding administration time—accepted deviations from planned blood sampling times were within 3.5%) rounded to 2 decimal digits and negative pre dose times set to zero.

At time points in the lag time between time zero and the first quantifiable concentration, concentrations below LLOQ were calculated as zero. Concentrations below LLOQ between 2 quantifiable concentrations were calculated with half the LLOQ. Trailing concentrations below LLOQ were not used in calculations.

Descriptive statistics of pharmacokinetic parameters were calculated separately for each of the Periods 1, 2 and 3. For $t_{max}$, frequency tables were drawn by treatment based on the nominal time of $t_{max}$.

For each of Reference and Reference Examples 2c and 2d, pharmacokinetic parameters of asenapine and metabolites were compared by means of an exploratory analysis of variance (ANOVA) model. Arithmetic and geometric means used for the calculation of point estimators such as differences or ratios between treatments were derived from the ANOVA as least square means (LSMEANS) or exponential transformed LSMEANS, respectively. The inclusion of a 90% confidence interval implies a value of α=0.05 for the type-I error. No α-adjustment was performed.

Based on fundamental pharmacokinetic relationships, the multiplicative model was applied for all concentration related parameters. This implied that these characteristics were rather log normally than normally distributed. The ANOVA, therefore, was performed after logarithmic transformation. Exemplary results are shown in Tables 13.6 and 13.7.

The plasma concentration profile of asenapine shows that therapeutic concentrations may be maintained over the entire wearing period of the TTS without major fluctuations. Compared to sublingual administration, maximum concentrations were lower and reached later after transdermal application. The formation of the major metabolites, N-desmethyl-asenapine and asenapine-glucuronide, is markedly reduced compared to sublingual administration.

TABLE 13.3

Descriptive statistics: geometric means and standard deviation factors of asenapine blood plasma concentration [ng/ml]

| Time [h] | Reference (n = 15) Mean | SD | Ref. Ex. 2c (n = 15) Mean | SD | Ref. Ex. 2d (n = 14) Mean | SD |
|---|---|---|---|---|---|---|
| 0.5 | 2.32 | 2.11 | — | — | — | — |
| 1 | 3.21 | 1.72 | — | — | — | — |
| 2 | 2.9 | 1.47 | — | — | — | — |
| 4 | 2.64 | 1.52 | 0.451 | 2.78 | 0.337 | 2.41 |
| 6 | — | — | 0.65 | 2.45 | 0.703 | 1.81 |
| 8 | 1.37 | 1.55 | 1.28 | 2.08 | 1.25 | 1.68 |
| 12 | 0.683 | 1.57 | 1.92 | 1.61 | 1.76 | 1.46 |
| 12.5 | 3.21 | 1.78 | — | — | — | — |
| 13 | 3.52 | 1.85 | — | — | — | — |
| 14 | 2.88 | 1.7 | — | — | — | — |
| 16 | 2.18 | 1.65 | 2.27 | 1.55 | 1.93 | 1.61 |
| 20 | 1.44 | 1.68 | — | — | — | — |
| 24 | 1.12 | 1.76 | 2.72 | 1.49 | 2.32 | 1.39 |
| 36 | 0.35 | 1.57 | 1.71 | 1.44 | 1.51 | 1.28 |
| 48 | 0.273 | 1.64 | 2.03 | 1.33 | 1.75 | 1.3 |
| 60 | 0.182 | 1.59 | 1.41 | 1.27 | 1.28 | 1.25 |
| 72 | 0.183 | 1.63 | 1.62 | 1.28 | 1.37 | 1.31 |
| 84 | — | — | 1.18 | 1.22 | 1.06 | 1.28 |
| 86 | — | — | 1.17 | 1.22 | 1 | 1.24 |
| 88 | — | — | 1.02 | 1.2 | 0.862 | 1.25 |
| 96 | — | — | 0.776 | 1.24 | 0.665 | 1.24 |
| 108 | — | — | 0.401 | 1.27 | 0.352 | 1.2 |
| 120 | — | — | 0.35 | 1.35 | 0.291 | 1.28 |
| 132 | — | — | 0.223 | 1.31 | 0.188 | 1.26 |
| 144 | — | — | 0.194 | 1.33 | 0.163 | 1.31 |
| 156 | — | — | 0.144 | 1.23 | 0.129 | 1.23 |
| 168 | — | — | 0.148 | 1.26 | 0.132 | 1.21 |

Key pharmacokinetic characteristics of Asenapine in plasma

| | Reference (n = 15) | Ref. Ex. 2c (n = 15) | Ref. Ex. 2d (n = 14) |
|---|---|---|---|
| $AUC_{(0-24)}$ * [(ng/ml) h] | 47.4 (1.51) 27.3-89.6 | 38.6 (1.61) 22.3-77.5 | 35.6 (1.46) 19.7-72.8 |
| $AUC_{(24-48)}$ * [(ng/ml) h] | 12.6 (1.66) 5.61-28.3 | 49.2 (1.41) 27.5-86.8 | 42.7 (1.31) 31.0-67.6 |
| $AUC_{(48-72)}$ * [(ng/ml) h] | — | 39.0 (1.28) 24.5-60.7 | 34.1 (1.27) 22.2-51.7 |
| $AUC_{(0-48)}$ * [(ng/ml) h] | | 88.2 (1.49) 49.7-161 | 78.6 (1.36) 51.8-140 |
| $AUC_{(0-72)}$ * [(ng/ml) h] | | 128 (1.42) 74.2-222 | 113 (1.33) 80.3-192 |
| $AUC_{(0-84)}$ * [(ng/ml) h] | — | 145 (1.39) 85.5-245 | 128 (1.32) 89.4-215 |
| $C_{max}$ [ng/ml] * | 3.47 (1.61) 1.43-6.88 | 2.72 (1.49) 1.46-5.08 | 2.37 (1.41) 1.56-4.78 |
| $C_{48}$ [ng/ml] | — | 2.03 (1.33) 1.27-3.47 | 1.75 (1.30) 1.10-2.65 |
| $C_{72}$ [ng/ml] | — | 1.62 (1.28) 1.01-2.26 | 1.37 (1.31) 0.822-2.13 |
| $C_{84}$ [ng/ml] | — | 1.18 (1.22) 0.826-1.61 | 1.06 (1.28) 0.675-1.70 |
| $C_{av}$ [ng/ml] * | 1.92 (1.52) 0.796-3.34 | 1.72 (1.39) 1.02-2.92 | 1.52 (1.32) 1.06-2.56 |
| $t_{max}$ [h] ** | 1.03 0.5-4.0 | 24.0 24.0-24.0 | 24.0 16.0-24.1 |
| $t_{lag}$ [h] ** | 0.5 0.5-1.1 | 4.0 2.0-6.0 | 4.0 2.0-4.0 |

TABLE 13.3-continued

| | | | |
|---|---|---|---|
| $t_{1/2\ \lambda z}$ [h] * | 16.5 (1.85) | 28.0 (1.38) | 27.1 (1.41) |
| | 8.18-55.5 | 16.0-42.7 | 17.5-52.7 |

* AUC, $C_{max}$, $C_{av}$ and $t_{1/2\ \lambda z}$ given as geometric mean (Standard deviation), Minimum-Maximum; Standard deviation (SD) given is the geometric standard deviation factor for both, the descriptive statistics and key PK characteristics.
** $t_{max}$ and $t_{lag}$ as Median (Minimum-Maximum)

TABLE 13.4

Key pharmacokinetic characteristics of asenapine-glucuronide in plasma

| | Reference (n = 8) | Ref. Ex. 2c (n = 8) | Ref. Ex. 2d (n = 8) |
|---|---|---|---|
| $AUC_{(0-24)}$ * [(ng/ml) h] | 221 (1.41) 147-383 | 44.0 (1.68) 22.8-115 | 42.6 (1.69) 23.0-116 |
| $AUC_{(24-48)}$ * [(ng/ml) h] | 84.4 (1.35) 51.8-131 | 92.7 (1.52) 64.0-226 | 76.6 (1.49) 54.4-166 |
| $AUC_{(0-48)}$ * [(ng/ml) h] | — | 137 (1.56) 87.6-340 | 120 (1.55) 77.4-281 |
| $AUC_{(0-72)}$ * [(ng/ml) h] | — | 220 (1.50) 152-521 | 185 (1.50) 134-418 |
| $AUC_{(0-84)}$ * [(ng/ml) h] | — | 259 (1.48) 183-593 | 214 (1.49) 158-478 |
| $C_{max}$ [ng/ml] * | 13.4 (1.56) 7.75-28.0 | 4.66 (1.54) 3.05-11.1 | 3.84 (1.45) 2.68-7.71 |
| $t_{max}$ [h] ** | 4.00 4.00-4.05 | 36.0 36.0-83.9 | 36.0 36.0-60.0 |
| $t_{lag}$ [h] ** | 1.00 1.00-1.03 | 6.01 4.00-8.00 | 6.00 4.00-8.02 |
| $t_{1/2\lambda z}$ [h] * | 15.9 (1.47) 8.12-29.2 | 27.9 (1.38) 17.3-50.0 | 21.6 (1.24) 14.4-27.4 |

* AUC, $C_{max}$ and $t_{1/2\lambda z}$ given as geometric mean (Standard deviation), Minimum-Maximum; Standard deviation given is the geometric standard deviation factor
** $t_{max}$ and $t_{lag}$ as Median (Minimum-Maximum)

TABLE 13.5

Key pharmacokinetic characteristics of N-desmethyl-asenapine in plasma

| | Reference (n = 15) | Ref. Ex. 2c (n = 15) | Ref. Ex. 2d (n = 14) |
|---|---|---|---|
| $AUC_{(0-24)}$ * [(ng/ml) h] | 11.5 (1.42) 6.34-20.1 | 1.67 (2.43) 0.452-5.79 | 1.27 (2.16) 0.420-3.87 |
| $AUC_{(0-48)}$ * [(ng/ml) h] | — | 9.10 (1.69) 4.27-24.1 | 7.51 (1.54) 3.97-16.2 |
| $AUC_{(0-72)}$ * [(ng/ml) h] | — | 16.8 (1.62) 8.27-42.9 | 14.4 (1.51) 7.79-30.8 |
| $AUC_{(0-84)}$ * [(ng/ml) h] | — | 20.3 (1.59) 10.1-51.5 | 17.5 (1.50) 9.31-38.0 |
| $C_{max}$ [ng/ml] * | 0.514 (1.43) 0.259-0.969 | 0.351 (1.58) 0.173-0.846 | 0.310 (1.49) 0.165-0.634 |
| $t_{max}$ [h] ** | 8.00 4.00-11.9 | 48.0 36.0-84.1 | 60.0 36.0-72.0 |
| $t_{lag}$ [h] ** | 2.02 1.00-4.05 | 16.0 8.00-24.0 | 16.0 12.0-24.1 |

* AUC and $C_{max}$ given as geometric mean (Standard deviation), Minimum-Maximum; Standard deviation given is the geometric standard deviation factor
** $t_{max}$ and $t_{lag}$ as Median (Minimum-Maximum)

TABLE 13.6

90% confidence intervals for log transformed pharmacokinetic characteristics of asenapine-glucuronide

| | Comparison | Point estimate (%) | Lower limit of 90% CI (%) | Upper limit of 90% CI (%) |
|---|---|---|---|---|
| $AUC_{(0-48)}$ | Period 2/Reference | 44.70 | 37.04 | 53.93 |
| | Period 3/Reference | 39.04 | 32.35 | 47.10 |
| | Period 2/Period 3 | 114.49 | 94.90 | 138.14 |
| $C_{max}$ | Period 2/Reference | 34.87 | 27.01 | 45.03 |
| | Period 3/Reference | 28.74 | 22.26 | 37.11 |
| | Period 2/Period 3 | 121.34 | 93.97 | 156.70 |

TABLE 13.7

90% confidence intervals for log transformed pharmacokinetic characteristics of N-desmethyl-asenapine

| | Comparison | Point estimate (%) | Lower limit of 90% CI (%) | Upper limit of 90% CI (%) |
|---|---|---|---|---|
| $AUC_{(0-48)}$ | Period 2/Reference | 41.47 | 34.95 | 49.21 |
| | Period 3/Reference | 33.13 | 27.80 | 39.47 |
| | Period 2/Period 3 | 125.18 | 105.05 | 149.17 |
| $C_{max}$ | Period 2/Reference | 68.34 | 58.52 | 79.80 |
| | Period 3/Reference | 58.77 | 50.14 | 68.90 |
| | Period 2/Period 3 | 116.28 | 99.19 | 136.31 |

Adverse Events (AE)

Tables 13.8 and 13.9 reflect the number of adverse events reported in the different categories.

Although treatment duration for the sublingual tablet (Reference) was only 12 h (i.e., 2 administrations) compared to 3.5 days TTS application (Reference Examples 2c and 2d), common systemic side effects of asenapine treatment, such as fatigue and dizziness, were observed less frequently after TTS application and, in case of fatigue, only with mild intensity. In comparison to the sublingually administered treatment (Reference), the frequency and intensity of fatigue was notably lower after transdermal administration, and dizziness occurred with lower frequency.

Oral discomfort symptoms, such as hypoaesthesia and dry mouth, as observed following the administration of the reference treatment, were not observed under TTS application (Reference Examples 2c and 2d).

Local tolerance at the application site was good, only mild reactions were observed occasionally (five AEs) which subsided without intervention.

The dysmenorrhea reported during period 3, which was moderate in intensity, had no relationship to the TTS of Reference Example 2d administered.

No SAE was reported and none of the subjects had suicidal ideations.

Overall, transdermal application of asenapine was safe and well tolerated. The AEs observed after administration of either TTS (Periods 2 and 3) were mostly mild and transient, resolved without intervention, and the frequency of AEs was lower compared to the reference period 1.

TABLE 13.8

Adverse events (AE) and serious adverse events (SAE) reported during the study

|  | Period 1 (Reference) (n = 16) | Period 2 (Ref Ex. 2c) (n = 15) | Period 3 (Ref. Ex. 2d) (n = 15) | total |
|---|---|---|---|---|
| Mild (AE) | 41 | 26 | 17 | 84 |
| Moderate (AE) | 13 | 1 | 2 | 16 |
| Severe (AE) | 3 | 0 | 1 | 4 |
| Serious (SAE) | 0 | 0 | 0 | 0 |
| total | 57 | 27 | 20 | 104 |
| Outcome: Number of subjects recovered | 57 | 27 | 20 | 104 |

TABLE 13.9

Adverse events (AE) by type of AE

|  | Period 1 (Reference) (n = 16) | Period 2 (Ref Ex. 2c) (n = 15) | Period 3 (Ref. Ex. 2d) (n = 15) | total |
|---|---|---|---|---|
| Fatigue* | 21 (8/11/2) | 12 (11/1/0) | 11 (10/1/0) | 44 |
| Dizziness | 11 | 2 | 2 | 15 |
| Hypoaesthesia oral | 12 | 0 | 0 | 12 |
| Gastrointestinal disorders (Abdominal pain upper, constipation, diarrhoea, dry mouth) | 5 | 1 | 0 | 6 |
| Other general disorders and administration site conditions | 1 | 6 | 2 | 9 |
| Musculoskeletal and connective tissue disorders (pain in extremity) | 1 | 0 | 0 | 1 |
| Other nervous system disorders (akathisia, head discomfort, headache, paraesthesia, presyncope) | 6 | 6 | 4 | 16 |
| Dysmenorrhoea | 0 | 0 | 1 | 1 |
| total | 57 | 27 | 20 | 104 |

*Numbers in parentheses indicate incidences by intensity (mild/moderate/severe)

The invention relates in particular to the following further items:

1. Transdermal therapeutic system for the transdermal administration of asenapine comprising a self-adhesive layer structure containing a therapeutically effective amount of asenapine, said self-adhesive layer structure comprising:
   A) a backing layer;
   B) an asenapine-containing matrix layer consisting of a matrix layer composition comprising:
      1. asenapine;
      2. a polymer selected from acrylic polymers;
      3. an additional polymer; and
      4. α-tocopherol in an amount of from 0.01 to 2% of the matrix layer composition and ascorbyl palmitate in an amount of at least 0.01% of the matrix layer composition as stabilizers.

2. Transdermal therapeutic system according to item 1, wherein the matrix layer composition further comprises sodium metabisulfite in an amount of from 0 to 0.5%, preferably from 0.01 to 0.2%, and more preferably from 0.05 to 0.15% of the matrix layer composition as stabilizer.

3. Transdermal therapeutic system according to item 2, wherein the matrix layer composition further comprises sodium metabisulfite in an amount of about 0.1% of the matrix layer composition as stabilizer.

4. Transdermal therapeutic system according to any one of items 1 to 3,
wherein the matrix layer composition comprises α-tocopherol in an amount of at least 0.025% of the matrix layer composition, and/or
wherein the matrix layer composition comprises α-tocopherol in an amount of up to 1.5% or 0.75%, preferably up to 0.5%, and more preferably up to 0.1% of the matrix layer composition.

5. Transdermal therapeutic system according to item 4, wherein the matrix layer composition comprises α-tocopherol in an amount of about 0.05% of the matrix layer composition.

6. Transdermal therapeutic system according to any one of items 1 to 5,
wherein the matrix layer composition comprises ascorbyl palmitate in an amount of at least 0.02%, preferably at least 0.08%, and more preferably at least 0.15% of the matrix layer composition, and/or
wherein the matrix layer composition comprises ascorbyl palmitate in an amount of up to 2.0 or 1.0%, and preferably up to 0.6% of the matrix layer composition.

7. Transdermal therapeutic system according to item 6, wherein the matrix layer composition comprises ascorbyl palmitate in an amount of from 0.2% to 0.4% of the matrix layer composition.

8. Transdermal therapeutic system according to any one of items 1 to 7,
wherein the additional polymer is selected from polymers which provide for an improved water and/or moisture absorption of the matrix layer, and more preferably from polyvinylpyrrolidones, and most preferably from soluble polyvinylpyrrolidones.

9. Transdermal therapeutic system according to item 8, wherein the additional polymer is a polyvinylpyrrolidone having a K-Value within a range selected from the group of ranges consisting of
9 to 15, and preferably 10.2 to 13.8,
15 to 20, and preferably 15.3 to 18.4,
20 to 27, and preferably 22.5 to 27.0,
27 to 35, and preferably 27.0 to 32.4, and
75 to 110, and preferably 81.0 to 97.2,
or any mixtures thereof, and preferably is a polyvinylpyrrolidone having a K-Value within a range of 27.0 to 32.4 or of 81.0 to 97.2 or any mixtures thereof, and more preferably is a polyvinylpyrrolidone having a K-Value within range of 27.0 to 32.4.

10. Transdermal therapeutic system according to item 8 or 9, wherein the matrix layer composition comprises an additional polymer selected from polyvinylpyrrolidones, and preferably from soluble polyvinylpyrrolidones, in an amount of from 0 to 20% of the matrix layer composition, preferably from 5 to 15% of the matrix layer composition and more preferably in an amount of about 10% of the matrix layer composition.

11. Transdermal therapeutic system according to any one of items 1 to 10,
wherein the transdermal therapeutic system contains at least 0.70 mg/cm$^2$, preferably at least 0.80 mg/cm$^2$, more preferably at least 0.82 mg/cm$^2$ and most preferably at least 0.83 mg/cm$^2$ asenapine.

12. Transdermal therapeutic system according to any one of items 1 to 11,
wherein the transdermal therapeutic system contains from 0.70 mg/cm$^2$ to 4.0 mg/cm$^2$, preferably from 0.80 mg/cm$^2$ to 3.0 mg/cm$^2$, more preferably from 0.82 mg/cm$^2$ to 2.0 mg/cm$^2$ and most preferably from 0.83 mg/cm$^2$ to 1.7 mg/cm$^2$ asenapine.

13. Transdermal therapeutic system according to any one of items 1 to 12,
wherein the area weight of the matrix layer ranges from 90 to 230 g/m$^2$, preferably from 110 to 210 g/m$^2$, and most preferably from 120 to 170 g/m$^2$.

14. Transdermal therapeutic system according to any one of items 1 to 13,
wherein the transdermal therapeutic system provides by transdermal delivery a mean release rate of 0.5 to 20 mg/day over at least 48 hours, preferably over 72 hours, and more preferably over 84 hours of administration.

15. Transdermal therapeutic system according to item 14, wherein the transdermal therapeutic system provides by transdermal delivery a mean release rate of 0.5 to 20 mg/day, preferably 1.0 to 15 mg/day, more preferably of 2.0 to 10 mg/day over at least 48 hours of administration, or
wherein the transdermal therapeutic system provides by transdermal delivery a mean release rate of 0.5 to 20 mg/day, preferably 1.0 to 15 mg/day, more preferably of 2.0 to 10 mg/day over at least 72 hours of administration, or
wherein the transdermal therapeutic system provides by transdermal delivery a mean release rate of 0.5 to 20 mg/day, preferably 1.0 to 15 mg/day, more preferably of 2.0 to 10 mg/day over 84 hours of administration.

16. Transdermal therapeutic system according to any one of items 1 to 15,
wherein the transdermal therapeutic system provides by transdermal delivery an $AUC_{0-48}$ from 20 to 300 (ng/ml) h or from more than 300 to 450 (ng/ml) h, and preferably provides by transdermal delivery an $AUC_{0-48}$ from 30 to 200 (ng/ml) h.

17. Transdermal therapeutic system according to any one of items 1 to 16,
wherein the transdermal therapeutic system provides by transdermal delivery an $AUC_{0-72}$ from 30 to 400 (ng/ml) h or from more than 400 to 600 (ng/ml) h, and preferably provides by transdermal delivery an $AUC_{0-72}$ from 50 to 300 (ng/ml) h.

18. Transdermal therapeutic system according to any one of items 1 to 17,
wherein the transdermal therapeutic system provides by transdermal delivery an $AUC_{0-84}$ from 35 to 450 (ng/ml) h or from more than 450 to 700 (ng/ml) h, and preferably provides by transdermal delivery an $AUC_{0-84}$ from 60 to 350 (ng/ml) h.

19. Transdermal therapeutic system according to any one of items 1 to 18,
wherein the transdermal therapeutic system provides by transdermal delivery a $C_{max}$ to $C_{48}$ ratio of less than 2.0, preferably of less than 1.5 and more preferably of less than 1.3.

20. Transdermal therapeutic system according to any one of items 1 to 19,
wherein the transdermal therapeutic system provides by transdermal delivery a $C_{max}$ to $C_{72}$ ratio of less than 3.0, preferably of less than 2.5 and more preferably of less than 2.0.

21. Transdermal therapeutic system according to any one of items 1 to 20,
wherein the transdermal therapeutic system provides by transdermal delivery a $C_{max}$ to $C_{84}$ ratio of less than 3.5, preferably of less than 3.0, more preferably of less than 2.5 and most preferably of less than 2.0.

22. Transdermal therapeutic system according to any one of items 1 to 21,
wherein the asenapine-containing matrix layer does not comprise isopropyl palmitate in an amount of 10% of the matrix layer composition, preferably does not comprise isopropyl palmitate in an amount of 5 to 15% of the matrix layer composition and most preferably does not comprise isopropyl palmitate.

23. Transdermal therapeutic system according to any one of items 1 to 22,
wherein the matrix layer composition does not comprise any of polysiloxanes and polyisobutylenes in an amount of more than 50% of the matrix layer composition.

24. Transdermal therapeutic system according to any one of items 1 to 23,
wherein the transdermal therapeutic system has an area of release of from 5 to 100 cm$^2$.

25. Transdermal therapeutic system according to any one of items 1 to 24,
wherein the asenapine-containing matrix layer does not comprise isopropyl myristate in an amount of 5% of the matrix layer composition, preferably does not comprise isopropyl myristate in an amount of 1 to 10% of the matrix layer composition and most preferably does not comprise isopropyl myristate.

26. Transdermal therapeutic system according to any one of items 1 to 25,
wherein the asenapine-containing matrix layer does not comprise ethyl cellulose in an amount of 10-20% of the matrix layer composition and preferably does not comprise ethyl cellulose.

27. Transdermal therapeutic system according to any one of items 1 to 26,
wherein the asenapine-containing matrix layer does not comprise hydrogen chloride.

28. Transdermal therapeutic system according to any one of items 1 to 27,
wherein the asenapine-containing matrix layer does not comprise toluene.

29. Transdermal therapeutic system according to any one of items 1 to 28,
wherein the asenapine-containing matrix layer is obtainable by drying a coated coating composition wherein no hydrochloric acid has been included in the coating composition.

30. Transdermal therapeutic system according to any one of items 1 to 29,
wherein the asenapine-containing matrix layer is obtainable by drying a coated coating composition comprising no toluene.

31. Transdermal therapeutic system according to any one of items 1 to 30,
wherein the asenapine in the matrix layer composition is included in the form of the free base.

32. Transdermal therapeutic system according to any one of items 1 to 31,
wherein the matrix layer composition is obtainable by incorporating the asenapine in the form of the free base.

33. Transdermal therapeutic system according to any one of items 1 to 32,
wherein at least 90 mol %, preferably at least 95 mol %, more preferably at least 98 mol % and most preferably at least 99 mol % of the asenapine in the matrix layer is present in the form of the free base.

34. Transdermal therapeutic system according to any one of items 1 to 33,
wherein the asenapine in the matrix layer is completely dissolved.

35. Transdermal therapeutic system according to any one of items 1 to 34,
wherein the matrix layer composition contains asenapine particles, preferably constituted of asenapine free base.

36. Transdermal therapeutic system according to any one of items 1 to 35,
wherein the amount of asenapine in the matrix layer composition ranges from 2 to 20%, preferably from 3 to 15% and more preferably from 4 to 12% of the matrix layer composition.

37. Transdermal therapeutic system according to any one of items 1 to 36,
wherein the asenapine has a purity of at least 95%, preferably of at least 98% and more preferably of at least 99% as determined by quantitative HPLC.

38. Transdermal therapeutic system according to any one of items 1 to 37,
wherein the matrix layer composition is a pressure-sensitive adhesive composition.

39. Transdermal therapeutic system according to any one of items 1 to 38,
wherein the polymer is selected from pressure-sensitive adhesive polymers.

40. Transdermal therapeutic system according to any one of items 1 to 39,
wherein the polymer is selected from acrylic polymers comprising functional groups.

41. Transdermal therapeutic system according to item 40,
wherein the functional groups are selected from hydroxyl groups, carboxylic acid groups, neutralized carboxylic acid groups and mixtures thereof.

42. Transdermal therapeutic system according to item 41,
wherein the functional groups are limited to hydroxyl groups.

43. Transdermal therapeutic system according to any one of items 1 to 42,
wherein the polymer is selected from acrylic polymers which do not comprise carboxylic acid groups or neutralized carboxylic acid groups or both groups.

44. Transdermal therapeutic system according to any one of items 1 to 43,
wherein the polymer is selected from acrylic polymers which do not comprise acidic groups.

45. Transdermal therapeutic system according to any one of items 1 to 44,
wherein the polymer is selected from acrylic polymers comprising hydroxyl groups and no carboxylic acid groups.

46. Transdermal therapeutic system according to item 45,
wherein the polymer is a copolymer based on vinyl acetate, 2-ethylhexyl-acrylate, 2-hydroxyethyl-acrylate and glycidyl-methacrylate or a copolymer based on vinyl acetate, 2-ethylhexyl-acrylate and 2-hydroxyethyl-acrylate.

47. Transdermal therapeutic system according to any one of items 39 to 46,
wherein the polymer is cross-linked by a cross-linking agent and preferably is cross-linked by an aluminium or a titanium cross-linking agent.

48. Transdermal therapeutic system according to any one of items 39 to 46,
wherein the polymer is not cross-linked by a cross-linking agent.

49. Transdermal therapeutic system according to any one of items 1 to 48,
wherein the polymer is selected from acrylic polymers comprising no hydroxyl groups and no carboxylic acid groups.

50. Transdermal therapeutic system according to item 49,
wherein the polymer is selected from acrylic polymers comprising no functional groups.

51. Transdermal therapeutic system according to item 50,
wherein the polymer is a copolymer based on methyl acrylate, 2-ethylhexyl acrylate and t-octyl acrylamide, or a copolymer based on 2-ethylhexyl-acrylate and vinyl acetate.

52. Transdermal therapeutic system according to any one of items 1 to 51,
wherein the amount of the polymer ranges from 50 to 90%, preferably from 60 to 85% and more preferably from 65 to 80% of the matrix layer composition.

53. Transdermal therapeutic system according to any one of items 1 to 52,
wherein the total polymer content in the matrix layer composition ranges from 60 to 95%, preferably from 70 to 90% and more preferably from 75 to 85% of the matrix layer composition.

54. Transdermal therapeutic system according to any one of items 1 to 53,
wherein the transdermal therapeutic system has an area of release of from 5 to 100 cm$^2$, preferably from 5 to 80 cm$^2$, and more preferably from 10 to 50 cm² or from 50 to 80 cm², from 10 to 40 cm² or from 10 to 30 cm² or from 55 to 65 cm².

55. Transdermal therapeutic system according to any one of items 1 to 54,
wherein the amount of asenapine contained in the transdermal therapeutic system ranges from 5 to 100 mg, preferably from 10 to 80 mg, and most preferably from 15 to 60 mg.

56. Transdermal therapeutic system according to any one of items 1 to 55,
wherein the transdermal therapeutic system has an area of release of from 5 to 100 cm², and the amount of asenapine contained in the transdermal therapeutic system ranges from 5 to 100 mg.

57. Transdermal therapeutic system according to any one of items 1 to 56,
wherein the matrix layer composition comprises further excipients or additives selected from the group consisting of additional polymers, cross-linking agents, solubilizers, fillers, tackifiers, plasticizers, stabilizers, softeners, substances for skincare, permeation enhancers, pH regulators, and preservatives.

58. Transdermal therapeutic system according to item 57,
wherein the tackifier is selected from polyethylene glycols, triglycerides, dipropylene glycol, resins, resin esters, terpenes and derivatives thereof, ethylene vinyl acetate adhesives, dimethylpolysiloxanes and polybutenes, and mixtures thereof.

59. Transdermal therapeutic system according to item 58,
wherein the matrix layer composition comprises medium chain triglycerides as tackifier.

60. Transdermal therapeutic system according to item 59,
wherein the matrix layer composition comprises medium chain triglycerides as tackifier in an amount of from 0.1 to 14% of the matrix layer composition, preferably from 1 to 13% of the matrix layer composition, more preferably from 3 to 12% of the matrix layer composition, and most preferably from 5 to 12% of the matrix layer composition.

61. Transdermal therapeutic system according to item 60,
wherein the matrix layer composition comprises medium chain triglycerides as tackifier in an amount of about 10% of the matrix layer composition.

62. Transdermal therapeutic system according to any one of items 59 to 61,
wherein the fatty acid composition of the medium chain triglycerides consists of one or more of
  (i) Hexanoic acid,
  (ii) Octanoic acid,
  (iii) Decanoic acid,
  (iv) Dodecanoic acid, and
  (v) Tetradecanoic acid.

63. Transdermal therapeutic system according to any one of items 59 to 62,
wherein the fatty acid composition of the medium chain triglycerides consists of
  (i) 0 to 5% hexanoic acid,
  (ii) 40.0 to 90.0% octanoic acid,
  (iii) 10.0 to 55.0% decanoic acid,
  (iv) 0 to 5% dodecanoic acid, and
  (v) 0 to 2% tetradecanoic acid.

64. Transdermal therapeutic system according to any one of items 59 to 63,
wherein the fatty acid composition of the medium chain triglycerides consists of
  (i) 0 to 2% hexanoic acid,
  (ii) 50.0 to 80.0% octanoic acid,
  (iii) 20.0 to 45.0% decanoic acid,
  (iv) 0 to 2% dodecanoic acid, and
  (v) 0 to 1% tetradecanoic acid.

65. Transdermal therapeutic system according to any one of items 59 to 64,
wherein the fatty acid composition of the medium chain triglycerides consists of
  (i) 0 to 2% hexanoic acid,
  (ii) 50.0 to 65.0% octanoic acid,
  (iii) 30.0 to 45.0% decanoic acid,
  (iv) 0 to 2% dodecanoic acid, and
  (v) 0 to 1% tetradecanoic acid.

66. Transdermal therapeutic system according to any one of items 59 to 64,
wherein the fatty acid composition of the medium chain triglycerides consists of
  (i) 0 to 2% hexanoic acid,
  (ii) 65.0 to 80.0% octanoic acid,
  (iii) 20.0 to 35.0% decanoic acid,
  (iv) 0 to 2% dodecanoic acid, and
  (v) 0 to 1% tetradecanoic acid.

67. Transdermal therapeutic system according to any one of items 59 to 66,
wherein the acid value of the medium chain triglycerides is 0.5 mg KOH/g or less, preferably 0.2 mg KOH/g or less and most preferably 0.1 mg KOH/g or less.

68. Transdermal therapeutic system according to any one of items 59 to 67,
wherein the peroxide value of the medium chain triglycerides is 5.0 mequi O/kg or less, preferably 2.0 mequi O/kg or less and most preferably 1.0 mequi O/kg or less.

69. Transdermal therapeutic system according to any one of items 59 to 68,
wherein the hydroxyl value of the medium chain triglycerides is 10 mg KOH/g or less, preferably 8.0 mg KOH/g or less and most preferably 5.0 mg KOH/g or less.

70. Transdermal therapeutic system according to item 57,
wherein the stabilizer is selected from sodium metabisulfite, ascorbic acid and ester derivatives thereof, butylated hydroxytoluene, tocopherol and ester derivatives thereof such as tocopheryl acetate and tocopheryl linoleate, as well as any combination thereof.

71. Transdermal therapeutic system according to item 57,
wherein the permeation enhancer is selected from diethylene glycol monoethyl ether, diisopropyl adipate, isopropyl myristate, isopropyl palmitate, lauryl lactate, dimethylpropylene urea and a mixture of propylene glycol monoesters and diesters of fatty acids.

72. Transdermal therapeutic system according to any one of items 1 to 71,
wherein the matrix layer composition does not comprise a permeation enhancer selected from oleic acids, triglycerides, oleic alcohols, and mixtures thereof.

73. Transdermal therapeutic system according to any one of items 1 to 72,
wherein the matrix layer composition does not comprise a permeation enhancer.

74. Transdermal therapeutic system according to any one of items 1 to 73, providing a cumulative skin permeation rate of asenapine at hour 48 or at hour 72 as measured in a Franz diffusion cell with dermatomed human skin of 1 μg/(cm² h) to 20 μg/(cm² h), preferably of 2 μg/(cm² h) to 15 μg/(cm² h) and more preferably of 4 μg/(cm² h) to 12 μg/(cm² h).

75. Transdermal therapeutic system according to any one of items 1 to 74,
providing a skin permeation rate of asenapine as measured in a Franz diffusion cell with dermatomed human skin of
0 μg/(cm² h) to 10 μg/(cm² h) in the first 8 hours,
2 μg/(cm² h) to 20 μg/(cm² h) from hour 8 to hour 24,
3 μg/(cm² h) to 20 μg/(cm² h) from hour 24 to hour 32,
3 μg/(cm² h) to 20 μg/(cm² h) from hour 32 to hour 48,
2 μg/(cm² h) to 15 μg/(cm² h) from hour 48 to hour 72.
76. Transdermal therapeutic system according to any one of items 1 to 75,
providing a cumulative permeated amount of asenapine as measured in a Franz diffusion cell with dermatomed human skin of 0.05 mg/cm² to 1.0 mg/cm², preferably of 0.1 mg/cm² to 0.7 mg/cm² over a time period of 48 hours.
77. Transdermal therapeutic system according to any one of items 1 to 76,
providing a cumulative permeated amount of asenapine as measured in a Franz diffusion cell with dermatomed human skin of 0.1 mg/cm² to 2.0 mg/cm², preferably 0.2 mg/cm² to 1.0 mg/cm² over a time period of 72 hours.
78. Transdermal therapeutic system according to any one of items 1 to 77,
wherein the matrix layer contains initially an amount of asenapine of at least 95%, preferably of at least 96%, more preferably of at least 97% and even more preferably of at least 98% of the theoretical amount of asenapine included in the matrix layer.
79. Transdermal therapeutic system according to any one of items 1 to 78,
wherein the matrix layer contains, after having been stored at 25° C. and 60% relative humidity for at least 2 months, preferably at least 3 months, an amount of asenapine of at least 90%, preferably of at least 92%, more preferably of at least 94% and even more preferably of at least 95% of the theoretical amount of asenapine included in the matrix layer.
80. Transdermal therapeutic system according to any one of items 1 to 79,
wherein the matrix layer contains, after having been stored at 40° C. and 75% relative humidity for at least 2 months, preferably at least 3 months, an amount of asenapine of at least 88%, preferably of at least 90%, more preferably of at least 91% and even more preferably of at least 92% of the theoretical amount of asenapine included in the matrix layer.
81. Transdermal therapeutic system according to any one of items 1 to 80,
wherein the matrix layer contains initially a total amount of asenapine-related degradation substances of less than 0.7%, preferably of less than 0.5%, more preferably of less than 0.3% and even more preferably of less than 0.2%.
82. Transdermal therapeutic system according to any one of items 1 to 81,
wherein the matrix layer contains, after having been stored at 25° C. and 60% relative humidity for at least 2 months, preferably at least 3 months, a total amount of asenapine-related degradation substances of less than 1.0%, preferably of less than 0.7%, more preferably of less than 0.5% and even more preferably of less than 0.4%.
83. Transdermal therapeutic system according to any one of items 1 to 79,
wherein the matrix layer contains, after having been stored at 40° C. and 75% relative humidity for at least 2 months, preferably at least 3 months, a total amount of asenapine-related degradation substances of less than 3.0%, preferably of less than 2.0%, more preferably of less than 1.5% and even more preferably of less than 0.7%.
84. Transdermal therapeutic system according to any one of items 1 to 83,
further comprising a release liner.
85. Transdermal therapeutic system according to any one of items 1 to 84,
further comprising an adhesive overlay or comprising no adhesive overlay, and preferably comprising no adhesive overlay.
86. Transdermal therapeutic system according to any one of items 1 to 85,
wherein the backing layer is substantially asenapine-impermeable.
87. Transdermal therapeutic system according to any one of items 1 to 86,
wherein the self-adhesive layer structure does not comprise an additional skin contact layer.
88. Transdermal therapeutic system according to any one of items 1 to 87,
wherein the self-adhesive layer structure comprises an additional skin contact layer.
89. Transdermal therapeutic system according to item 88,
wherein the self-adhesive layer structure comprises a membrane which is located between the matrix layer and the additional skin contact layer, wherein the membrane is preferably a rate controlling membrane.
90. Transdermal therapeutic system according to any one of items 1 to 89,
wherein the self-adhesive layer structure comprises an additional reservoir layer which is located between the backing layer and the matrix layer, and a further rate controlling membrane which is located between the additional reservoir layer and the matrix layer.
91. Transdermal therapeutic system according to any one of items 1 to 90,
wherein the transdermal therapeutic system is a matrix-type TTS.
92. Transdermal therapeutic system according to any one of items 1 to 91
for use in a method of treatment, preferably for use in a method of treating psychosis and more preferably for use in a method of treating one or more conditions selected from schizophrenia, bipolar disorder, posttraumatic stress disorder, major depressive disorder, dementia related psychosis, agitation and manic disorder.
93. Transdermal therapeutic system according to item 92
for use in a method of treating schizophrenia and/or bipolar disorder.
94. Transdermal therapeutic system according to item 92
for use in a method of treating bipolar disorder, in particular acute manic or mixed episodes of bipolar disorder.
95. Transdermal therapeutic system according to any one of items 92 to 94
for use in a method of treatment with a dosing interval of at least 24 hours or 1 day, at least 48 hours or 2 days, or at least 72 hours or 3 days.
96. Transdermal therapeutic system according to any one of items 92 to 95
for use in a method of treatment with a dosing interval of up to 168 hours or 7 days, up to 120 hours or 5 days, or up to 96 hours or 4 days.
97. Transdermal therapeutic system according to item 95
for use in a method of treatment with a dosing interval of 24 hours or 1 day.
98. Transdermal therapeutic system according to item 95
for use in a method of treatment with a dosing interval of 48 hours or 2 days.

99. Transdermal therapeutic system according to item 95 for use in a method of treatment with a dosing interval of 84 hours or 3.5 days.
100. Transdermal therapeutic system according to any one of items 92 to 99
for use in a method of treating a patient,
wherein the transdermal therapeutic system provides a reduction in at least one asenapine-related side effect relative to an equivalent dose of sublingual asenapine.
101. Transdermal therapeutic system according to item 94 for use in a method of treating a patient, wherein
the patient is a human patient suffering from fatigue, somnolence, dizziness, or any combination thereof, or
the at least one asenapine-related side effect is fatigue, somnolence, dizziness, oral hypoaesthesia, or any combination thereof, or
the incidence of the at least one asenapine-related side effect relative to an equivalent dose of sublingual asenapine is reduced by at least about 30%, at least about 40%, at least about 70% or at least about 80%, and/or the intensity of the at least one asenapine-related side effect relative to an equivalent dose of sublingual asenapine is reduced, or
the at least one asenapine-related side effect is fatigue and the incidence of fatigue relative to an equivalent dose of sublingual asenapine is reduced by at least about 30% or at least about 40% and/or the intensity of fatigue relative to an equivalent dose of sublingual asenapine is reduced, or
the at least one asenapine-related side effect is dizziness, and the incidence of dizziness relative to an equivalent dose of sublingual asenapine is reduced by at least about 30%, at least about 40%, at least about 70% or at least about 80%.
102. Transdermal therapeutic system according to any one of items 1 to 101
for use in a method of reducing, in a patient, at least one asenapine-related side effect relative to an equivalent dose of sublingual asenapine.
103. Transdermal therapeutic system according to item 102 for use in a method of reducing, in a patient, at least one asenapine-related side effect relative to an equivalent dose of sublingual asenapine, wherein
the patient is a human patient suffering from fatigue, somnolence, dizziness, or any combination thereof, or
the at least one asenapine-related side effect is fatigue, somnolence, dizziness, oral hypoaesthesia, or any combination thereof, or
the incidence of the at least one asenapine-related side effect relative to an equivalent dose of sublingual asenapine is reduced by at least about 30%, at least about 40%, at least about 70% or at least about 80%, and/or the intensity of the at least one asenapine-related side effect relative to an equivalent dose of sublingual asenapine is reduced, or
the at least one asenapine-related side effect is fatigue and the incidence of fatigue relative to an equivalent dose of sublingual asenapine is reduced by at least about 30% or at least about 40% and/or the intensity of fatigue relative to an equivalent dose of sublingual asenapine is reduced, or
the at least one asenapine-related side effect is dizziness and the incidence of dizziness relative to an equivalent dose of sublingual asenapine is reduced by at least about 30%, at least about 40%, at least about 70% or at least about 80%.
104. A method of treatment, and in particular a method of treating psychosis and more preferably a method of treating one or more conditions selected from schizophrenia, bipolar disorder, posttraumatic stress disorder, major depressive disorder, dementia related psychosis, agitation and manic disorder
including applying a transdermal therapeutic system according to any one of items 1 to 91 to the skin of a patient.
105. A method of treating schizophrenia and/or bipolar disorder
including applying a transdermal therapeutic system according to any one of items 1 to 91 to the skin of a patient.
106. A method of treating bipolar disorder and in particular acute manic or mixed episodes of bipolar disorder
including applying a transdermal therapeutic system according to any one of items 1 to 91 to the skin of a patient.
107. A method of treatment according to any one of items 104 to 106
including applying a transdermal therapeutic system according to any one of items 1 to 91 for at least 24 hours or 1 day, at least 48 hours or 2 days, or at least 72 hours or 3 days to the skin of a patient.
108. A method of treatment according to any one of items 104 to 106
including applying a transdermal therapeutic system according to any one of items 1 to 91 for up to 168 hours or 7 days, up to 120 hours or 5 days, or up to 96 hours or 4 days to the skin of a patient.
109. A method of treatment according to any one of items 104 to 106
including applying a transdermal therapeutic system according to any one of items 1 to 91 for 24 hours or 1 day to the skin of a patient.
110. A method of treatment according to any one of items 104 to 106
including applying a transdermal therapeutic system according to any one of items 1 to 91 for 48 hours or 2 days to the skin of a patient.
111. A method of treatment according to any one of items 104 to 106
including applying a transdermal therapeutic system according to any one of items 1 to 91 for 84 hours or 3.5 days to the skin of a patient.
112. The method of treatment according to any one of items 104 to 111,
wherein the transdermal therapeutic system provides a reduction in at least one asenapine-related side effect relative to an equivalent dose of sublingual asenapine.
113. The method of treatment according to item 112,
wherein the patient is a human patient suffering from fatigue, somnolence, dizziness, or any combination thereof.
114. The method of treatment according to item 112 or 113,
wherein the at least one asenapine-related side effect is fatigue, somnolence, dizziness, oral hypoaesthesia, or any combination thereof.
115. The method of treatment according to any one of items 112 to 114,
wherein the incidence of the at least one asenapine-related side effect relative to an equivalent dose of sublingual asenapine is reduced by at least about 30%, at least about 40%, at least about 70% or at least about 80%, and/or wherein the intensity of the at least one asenapine-related side effect relative to an equivalent dose of sublingual asenapine is reduced.
116. The method of treatment according to item 115, wherein
the at least one asenapine-related side effect is fatigue and the incidence of fatigue relative to an equivalent dose of sublingual asenapine is reduced by at least about 30% or at least about 40% and/or the intensity of fatigue relative to an equivalent dose of sublingual asenapine is reduced, or
the at least one asenapine-related side effect is dizziness and the incidence of dizziness relative to an equivalent dose of sublingual asenapine is reduced by at least about 30%, at least about 40%, at least about 70% or at least about 80%.

117. A method of reducing, in a patient, at least one asenapine-related side effect relative to an equivalent dose of sublingual asenapine, the method comprising administering a transdermal therapeutic system according to any one of items 1 to 91.

118. The method according to item 117,
wherein the patient is a human patient suffering from fatigue, somnolence, dizziness, or any combination thereof.

119. The method according to item 117 or 118,
wherein the at least one asenapine-related side effect is fatigue, somnolence, dizziness, oral hypoaesthesia, or any combination thereof.

120. The method according to any one of items 117 to 119 wherein the incidence of the at least one asenapine-related side effect relative to an equivalent dose of sublingual asenapine is reduced by at least about 30%, at least about 40%, at least about 70% or at least about 80%, and/or wherein the intensity of the at least one asenapine-related side effect relative to an equivalent dose of sublingual asenapine is reduced.

121. The method according to item 120, wherein
the at least one asenapine-related side effect is fatigue and the incidence of fatigue relative to an equivalent dose of sublingual asenapine is reduced by at least about 30% or at least about 40% and/or the intensity of fatigue relative to an equivalent dose of sublingual asenapine is reduced, or
the at least one asenapine-related side effect is dizziness and the incidence of dizziness relative to an equivalent dose of sublingual asenapine is reduced by at least about 30%, at least about 40%, at least about 70% or at least about 80%.

122. A method of reducing at least one asenapine-related side effect in a patient being treated with sublingual asenapine therapy, the method comprising:
 a) discontinuing sublingual asenapine therapy; and
 b) administering a transdermal therapeutic system according to any of items 1 to 91 to the skin of the patient, wherein the transdermal therapeutic system provides a reduction in at least one asenapine-related side effect relative to an equivalent dose of sublingual asenapine.

123. The method of item 122, wherein the transdermal therapeutic system delivers an amount of asenapine equivalent to the amount of asenapine originally provided by the sublingual asenapine therapy.

124. Process of manufacture of a matrix layer for use in a transdermal therapeutic system according to any one of items 1 to 103 comprising the steps of:
 1) combining at least the components asenapine, acrylic polymer, additional polymer, α-tocopherol and ascorbyl palmitate, in a solvent to obtain a coating composition;
 2) coating the coating composition onto a backing layer or a release liner or any intermediate liner; and
 3) drying the coated coating composition to form the matrix layer.

125. The process according to item 124,
wherein in step 1) at least the components asenapine, acrylic polymer, additional polymer, α-tocopherol, ascorbyl palmitate and sodium metabisulfite are combined in a solvent to obtain the coating composition.

126. The process according to item 124 or 125,
wherein in step 1) the asenapine is dissolved to obtain a coating composition.

127. The process according to any one of items 124 to 126, wherein preferably the solvent is selected from alcoholic solvents, in particular methanol, ethanol, isopropanol and mixtures thereof, and from non-alcoholic solvents, in particular ethyl acetate, hexane, n-heptane, heptanes, petroleum ether, toluene, and mixtures thereof, and more preferably is selected from ethanol and ethyl acetate.

128. The process according to any one of items 124 to 127, wherein the polymer is an acrylic polymer and preferably a copolymer based on vinyl acetate, 2-ethylhexyl-acrylate, 2-hydroxyethyl-acrylate and glycidyl-methacrylate or a copolymer based on vinyl acetate, 2-ethylhexyl-acrylate and 2-hydroxyethyl-acrylate, which is provided as a solution and preferably as a solution in ethyl acetate, n-heptane, heptanes, methanol, ethanol, or any mixtures thereof, with a solids content of from 30 to 60% by weight.

129. The process according to any one of items 124 to 128, wherein the polymer is an acrylic polymer and wherein the polymer is cross-linked.

130. The process according to item 123,
wherein no additional cross-linking agent is used in step 1) to obtain the coating composition.

131. The process according to any one of items 124 to 128, wherein the polymer is an acrylic polymer and wherein the polymer is not cross-linked.

132. The process according to item 131,
wherein an additional cross-linking agent is used in step 1) to obtain the coating composition,
wherein the cross-linking agent preferably is an aluminium or a titanium cross-linking agent.

133. The process according to any one of items 124 to 132, wherein drying is performed in one or more cycles at room temperature and/or at a temperature of from 65 to 100° C., more preferably from 70 to 90° C.

134. Transdermal therapeutic system for the transdermal administration of asenapine comprising a self-adhesive layer structure comprising:
 A) a backing layer;
 B) an asenapine-containing matrix layer consisting of a matrix layer composition comprising:
  1. asenapine included in the form of the free base;
  2. a copolymer based on vinyl acetate, 2-ethylhexyl-acrylate, 2-hydroxyethyl-acrylate and glycidyl-methacrylate or a copolymer based on vinyl acetate, 2-ethylhexyl-acrylate and 2-hydroxyethyl-acrylate;
  3. medium chain triglycerides in an amount of from 5 to 12% of the matrix layer composition;
  4. soluble polyvinylpyrrolidone in an amount of from 5 to 15% of the matrix layer composition; and
  5. α-tocopherol in an amount of from 0.025 to 0.1% of the matrix layer composition, ascorbyl palmitate in an amount of from 0.15 to 0.5% of the matrix layer composition, and sodium metabisulfite in an amount of from 0.05 to 0.15% of the matrix layer composition, as stabilizers;

The invention claimed is:
1. A transdermal therapeutic system for the transdermal administration of asenapine comprising a self-adhesive layer structure containing a therapeutically effective amount of asenapine, said self-adhesive layer structure comprising:
 A) a backing layer;
 B) an asenapine-containing matrix layer consisting of a matrix layer composition comprising:
  a) asenapine;
  b) a polymer selected from acrylic polymers;
  c) an additional polymer; and
  d) α-tocopherol in an amount of from 0.01 to 2% of the matrix layer composition, and ascorbyl palmitate in an amount of at least 0.01% of the matrix layer composition as stabilizers.

2. The transdermal therapeutic system according to claim 1, wherein the matrix layer composition further comprises a detectable amount of sodium metabisulfite to 0.5% sodium metabisulfite, from 0.01 to 0.2% sodium metabisulfite, from 0.05 to 0.15% sodium metabisulfite, or about 0.1% sodium metabisulfite.

3. The transdermal therapeutic system according to claim 1, wherein the matrix layer composition comprises at least 0.025% α-tocopherol, up to 1.5% α-tocopherol, up to 0.75% α-tocopherol, up to 0.5% α-tocopherol, up to 0.1% α-tocopherol, or about 0.05% α-tocopherol.

4. The transdermal therapeutic system according to claim 1, wherein the matrix layer composition comprises at least 0.02% ascorbyl palmitate, at least 0.08% ascorbyl palmitate, at least 0.15% ascorbyl palmitate, a detectable amount of ascorbyl palmitate up to 2.0% ascorbyl palmitate, a detectable amount of ascorbyl palmitate up to 1.0% ascorbyl palmitate, a detectable amount of ascorbyl palmitate up to 0.6% ascorbyl palmitate, or from 0.2 to 0.4% ascorbyl palmitate.

5. The transdermal therapeutic system according to claim 1, wherein the additional polymer is a polyvinylpyrrolidone.

6. The transdermal therapeutic system according to claim 5, wherein the polyvinylpyrrolidone is a soluble polyvinylpyrrolidone, and wherein the matrix layer composition comprises the soluble polyvinylpyrrolidone in a detectable amount up to 20%, from 5 to 15%, or about 10% soluble polyvinylpyrrolidone by weight.

7. The transdermal therapeutic system according to claim 1, wherein the transdermal therapeutic system contains at least 0.70 mg/cm² asenapine, at least 0.80 mg/cm² asenapine, at least 0.82 mg/cm² asenapine, or at least 0.83 mg/cm² asenapine.

8. The transdermal therapeutic system according to claim 1, wherein the asenapine in the matrix layer composition is included in the form of asenapine free base.

9. The transdermal therapeutic system according to claim 1, wherein the matrix layer composition comprises from 2 to 20 asenapine by weight, from 3 to 15% asenapine by weight, or from 4 to 12% asenapine by weight.

10. The transdermal therapeutic system according to claim 1, wherein the polymer is selected from pressure-sensitive adhesive polymers, and acrylic polymers comprising hydroxyl groups and no carboxylic acid groups.

11. The transdermal therapeutic system according to claim 1, wherein the matrix layer composition comprises from 50 to 90% polymer by weight, from 60 to 85% polymer by weight, or from 65 to 80% polymer by weight.

12. The transdermal therapeutic system according to claim 1, wherein the matrix layer composition comprises a tackifier, and wherein the tackifier is selected from the group consisting of polyethylene glycols, triglycerides, dipropylene glycol, resins, resin esters, terpenes and derivatives thereof, ethylene vinyl acetate adhesives, dimethylpolysiloxanes, polybutenes, medium chain triglycerides, and mixtures thereof.

13. The transdermal therapeutic system according to claim 12, wherein the tackifier is medium chain triglycerides, and
wherein the matrix layer composition comprises the medium chain triglycerides in an amount of from 0.1 to 14%, from 1 to 13%, from 3 to 12%, from 5 to 12%, or of about 10% medium chain triglycerides by weight.

14. The transdermal therapeutic system according to claim 1, wherein the transdermal therapeutic system provides a skin permeation rate of asenapine as measured in a Franz diffusion cell with dermatomed human skin of
0 μg/(cm² h) to 10 μg/(cm² h) in the first 8 hours,
2 μg/(cm² h) to 20 μg/(cm² h) from hour 8 to hour 24,
3 μg/(cm² h) to 20 μg/(cm² h) from hour 24 to hour 32,
3 μg/(cm² h) to 20 μg/(cm² h) from hour 32 to hour 48, and
2 μg/(cm² h) to 15 μg/(cm² h) from hour 48 to hour 72.

15. The transdermal therapeutic system according to claim 1, wherein the matrix layer composition contains an initial amount of asenapine, and wherein the asenapine-containing matrix layer has an asenapine content selected from the group consisting of:
at least 95%, at least 96%, at least 97%, or at least 98% to of the initial amount of asenapine after manufacture of the asenapine-containing matrix layer;
at least 90%, at least 92%, at least 94%, or at least 95% of the initial amount of asenapine after having been stored at 25° C. and 60% relative humidity for at least 2 months;
at least 88%, at least 90%, at least 91%, or at least 92% of the initial amount of asenapine after having been stored at 40° C. and 75% relative humidity for at least 2 months;
and combinations thereof.

16. The transdermal therapeutic system according to claim 1, wherein the matrix layer composition contains a total amount of asenapine-related degradation substances selected from:
less than 0.7%, less than 0.5%, less than 0.3% or less than 0.2% shortly after manufacture, and
less than 1.0%, less than 0.7%, less than 0.5%, or less than 0.4% after having been stored at 25° C. and 60% relative humidity for at least 2 months.

17. A method of treating one or more conditions selected from schizophrenia, bipolar disorder, posttraumatic stress disorder, major depressive disorder, dementia related psychosis, agitation and manic disorder, and acute manic or mixed episodes of bipolar disorder in a human patient,
the method comprising applying the transdermal therapeutic system according to claim 1 to the skin of a patient in need thereof.

18. A process of manufacturing the asenapine-containing matrix layer of claim 1, the process comprising the steps of:
a) combining at least asenapine, an acrylic polymer, an additional polymer, α-tocopherol, and ascorbyl palmitate, in a solvent to obtain a coating composition;
b) coating the coating composition onto a backing layer or a release liner, or an intermediate liner; and
c) drying the coated coating composition to form the asenapine-containing matrix layer.

19. The transdermal therapeutic system according to claim 1, wherein the polymer is a copolymer based on vinyl acetate, 2-ethylhexyl-acrylate, 2-hydroxyethyl-acrylate, and glycidyl-methacrylate or a copolymer based on vinyl acetate, 2-ethylhexyl-acrylate and 2-hydroxyethyl-acrylate.

20. The transdermal therapeutic system according to claim 19, wherein the polymer is cross-linked by an aluminium or a titanium cross-linking agent.

* * * * *

UNITED STATES PATENT AND TRADEMARK OFFICE
CERTIFICATE OF CORRECTION

PATENT NO. : 11,648,213 B2
APPLICATION NO. : 17/250163
DATED : May 16, 2023
INVENTOR(S) : Mohr et al.

It is certified that error appears in the above-identified patent and that said Letters Patent is hereby corrected as shown below:

In the Claims

Claim 2, Column 88, Line 37, "to 0.5%" should read -- up to 0.5% --.

Claim 9, Column 101, in the beginning of Line 39, "20" should read -- 20% --.

Claim 13, Column 101, Line 62, "or of about 10%" should read -- or about 10% --.

Claim 15, Column 102, in the beginning of Line 17, "to" should be deleted.

Signed and Sealed this
Fifth Day of September, 2023

Katherine Kelly Vidal
*Director of the United States Patent and Trademark Office*